US011521714B1

(12) United States Patent
Jain et al.

(10) Patent No.: US 11,521,714 B1
(45) Date of Patent: Dec. 6, 2022

(54) INCREASING DIVERSITY OF PARTICIPANTS IN HEALTH RESEARCH USING ADAPTIVE METHODS

(71) Applicant: Vignet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/177,153

(22) Filed: Feb. 16, 2021

Related U.S. Application Data

(63) Continuation-in-part of application No. 17/166,899, filed on Feb. 3, 2021, now Pat. No. 11,196,656, and
(Continued)

(51) Int. Cl.
*G06F 40/253* (2020.01)
*G06F 40/289* (2020.01)
(Continued)

(52) U.S. Cl.
CPC .......... *G16H 10/20* (2018.01); *G06F 40/253* (2020.01); *G06F 40/289* (2020.01); *G16H 10/60* (2018.01); *H04L 67/60* (2022.05)

(58) Field of Classification Search
CPC ........ G16H 10/20; G16H 10/60; H04L 67/32; G06F 40/289; G06F 40/253
See application file for complete search history.

(56) References Cited

U.S. PATENT DOCUMENTS 5,547,878 A 8/1996 Kell
5,832,474 A 11/1998 Lopresti et al.
(Continued)

FOREIGN PATENT DOCUMENTS

WO WO1995012812 5/1995
WO WO2013144769 10/2013
WO WO2016110804 7/2016

OTHER PUBLICATIONS

Cancer.gov [online], "NCI Dictionary of Cancer Terms," Jan. 9, 2020, retrieved on Mar. 13, 2020, retrieved from URL<https://www.cancer.gov/publications/dictionaries/cancer-terms/def/research-study>, 1 page.
(Continued)

*Primary Examiner* — Stephen S Hong
*Assistant Examiner* — Ahamed I Nazar
(74) *Attorney, Agent, or Firm* — Fish & Richardson P.C.

(57) ABSTRACT

Methods, systems, and apparatus, including computer programs encoded on a computer storage medium, for adapting communications and interactions to enhance monitoring using remote devices. In some implementations, a system communicates with remote devices that are each configured to perform monitoring. The system generates records that specify outcomes or responses obtained after sending the messages. The generated records are used to create or update profiles for different categories of users. Each profile has a set of inclusion criteria defining the category corresponding to the profile, and stores data that characterizes effects of message attributes on outcomes or responses for users in the category corresponding to the profile. The system selects a profile for each member of a group of users involved in a particular monitoring program, then adapts communication for each user based on the profile selected for the user.

22 Claims, 22 Drawing Sheets

Related U.S. Application Data a continuation-in-part of application No. 17/166,777, filed on Feb. 3, 2021, now Pat. No. 11,361,846.

(51) Int. Cl.
*G16H 10/20* (2018.01)
*G16H 10/60* (2018.01)
*H04L 67/60* (2022.01)

(56) References Cited

U.S. PATENT DOCUMENTS

| | | | |
|---|---|---|---|
| 6,029,144 | A | 2/2000 | Barrett et al. |
| 6,514,200 | B1 | 2/2003 | Khouri |
| 6,574,622 | B1 | 6/2003 | Miyauchi et al. |
| 6,663,846 | B1 | 12/2003 | McCombs et al. |
| 6,879,970 | B2 | 4/2005 | Shiffman et al. |
| 7,054,782 | B2 | 5/2006 | Hartlaub |
| 7,113,917 | B2 | 9/2006 | Jacobi et al. |
| 7,251,609 | B1 | 7/2007 | McAlindon et al. |
| 7,415,447 | B2 | 8/2008 | Shiffman et al. |
| 7,752,059 | B2 | 7/2010 | Sweeney et al. |
| 7,809,601 | B2 | 10/2010 | Shaya et al. |
| 7,809,660 | B2 | 10/2010 | Friedlander et al. |
| 7,930,262 | B2 | 4/2011 | Friedlander et al. |
| 7,937,275 | B2 | 5/2011 | Schoenberg |
| 8,032,545 | B2 | 10/2011 | Setimi |
| 8,065,180 | B2 | 11/2011 | Hufford et al. |
| 8,157,730 | B2 | 4/2012 | LeBouef et al. |
| 8,316,020 | B1 * | 11/2012 | Kleinmann ............ G06Q 30/02 707/734 |
| 8,380,531 | B2 | 2/2013 | Paty et al. |
| 8,433,605 | B2 | 4/2013 | Hufford et al. |
| 8,527,486 | B2 | 9/2013 | Wittig et al. |
| 8,533,029 | B2 | 9/2013 | Hufford et al. |
| 8,583,453 | B2 | 11/2013 | Plummer et al. |
| 8,606,595 | B2 | 12/2013 | Udani |
| 8,684,922 | B2 | 4/2014 | Tran |
| 8,707,392 | B2 | 4/2014 | Birtwhistle et al. |
| 8,966,548 | B2 | 2/2015 | Busse et al. |
| 8,990,250 | B1 | 3/2015 | Chowdry et al. |
| 9,020,971 | B2 | 4/2015 | Bayliss et al. |
| 9,286,442 | B2 | 3/2016 | Csoma et al. |
| 9,495,651 | B2 | 11/2016 | O'Sullivan et al. |
| 9,514,655 | B1 | 12/2016 | Nusbaum et al. |
| 9,659,254 | B2 | 5/2017 | Achin et al. |
| 9,753,618 | B1 | 9/2017 | Jain et al. |
| 9,813,318 | B2 | 11/2017 | Iyoob et al. |
| 9,848,061 | B1 | 12/2017 | Jain et al. |
| 9,858,063 | B2 | 1/2018 | Jain et al. |
| 9,928,230 | B1 | 3/2018 | Jain et al. |
| 9,983,775 | B2 | 5/2018 | Jain et al. |
| 10,069,934 | B2 | 9/2018 | Jain et al. |
| 10,095,688 | B1 | 10/2018 | Jain et al. |
| 10,231,622 | B2 | 3/2019 | Soyao et al. |
| 10,255,274 | B1 * | 4/2019 | Schilling ............ G06F 16/2455 |
| 10,304,000 | B2 | 5/2019 | Birnbaum et al. |
| 10,452,816 | B2 | 10/2019 | Kidd et al. |
| 10,455,262 | B2 | 10/2019 | Rieger et al. |
| 10,510,438 | B2 | 12/2019 | Frazier et al. |
| 10,521,557 | B2 | 12/2019 | Jain et al. |
| 10,546,339 | B2 | 1/2020 | Jiao et al. |
| 10,565,894 | B1 | 2/2020 | Jain et al. |
| 10,580,531 | B2 | 3/2020 | Jiao et al. |
| 10,628,553 | B1 | 4/2020 | Murrish et al. |
| 10,636,525 | B2 | 4/2020 | Jiao et al. |
| 10,650,474 | B2 | 5/2020 | Jiao et al. |
| 10,672,519 | B2 | 6/2020 | Jiao et al. |
| 10,756,957 | B2 | 8/2020 | Jain et al. |
| 10,762,990 | B1 | 9/2020 | Jain et al. |
| 10,775,974 | B2 | 9/2020 | Jain et al. |
| 10,938,634 | B1 | 3/2021 | Cruise |
| 10,938,651 | B2 | 3/2021 | Jain et al. |
| 11,056,242 | B1 | 7/2021 | Jain et al. |
| 11,061,798 | B1 | 7/2021 | Jain et al. |
| 11,082,487 | B1 | 8/2021 | Jain et al. |
| 11,102,304 | B1 | 8/2021 | Jain et al. |
| 11,127,506 | B1 | 9/2021 | Jain et al. |
| 11,151,462 | B2 | 10/2021 | Jain et al. |
| 11,153,156 | B2 | 10/2021 | Jain et al. |
| 11,157,823 | B2 | 10/2021 | Jain et al. |
| 11,158,423 | B2 | 10/2021 | Jain et al. |
| 11,196,656 | B1 | 12/2021 | Jain et al. |
| 11,240,329 | B1 | 2/2022 | Jain et al. |
| 11,296,971 | B1 | 4/2022 | Jain et al. |
| 11,316,941 | B1 | 4/2022 | Jain et al. |
| 2002/0099570 | A1 | 7/2002 | Knight |
| 2002/0143595 | A1 | 10/2002 | Frank et al. |
| 2003/0065669 | A1 | 4/2003 | Kahn et al. |
| 2003/0130871 | A1 | 7/2003 | Rao et al. |
| 2004/0059697 | A1 | 3/2004 | Forman |
| 2004/0172447 | A1 | 9/2004 | Miller |
| 2004/0175700 | A1 | 9/2004 | Geesaman |
| 2004/0210457 | A1 | 10/2004 | Sameh |
| 2005/0165626 | A1 | 7/2005 | Karpf |
| 2005/0182664 | A1 | 8/2005 | Abraham-Fuchs |
| 2006/0184493 | A1 | 8/2006 | Shiffman et al. |
| 2007/0179361 | A1 | 8/2007 | Brown et al. |
| 2007/0250429 | A1 | 10/2007 | Walser et al. |
| 2007/0294110 | A1 | 12/2007 | Settimi |
| 2008/0010945 | A1 | 1/2008 | McKenna et al. |
| 2008/0109455 | A1 | 5/2008 | Katz |
| 2008/0140444 | A1 | 6/2008 | Karkanias |
| 2008/0294459 | A1 | 11/2008 | Angell et al. |
| 2009/0163183 | A1 | 6/2009 | O'Donoghue et al. |
| 2009/0299766 | A1 | 12/2009 | Friedlander et al. |
| 2010/0088245 | A1 | 4/2010 | Harrison et al. |
| 2010/0218132 | A1 | 8/2010 | Soni et al. |
| 2010/0250285 | A1 | 9/2010 | Shelton |
| 2012/0035954 | A1 | 2/2012 | Yeskel |
| 2012/0059735 | A1 | 3/2012 | Su et al. |
| 2012/0065987 | A1 | 3/2012 | Farooq et al. |
| 2012/0310670 | A1 | 12/2012 | Pruitt |
| 2013/0030836 | A1 | 1/2013 | Ackerson |
| 2013/0262140 | A1 | 10/2013 | Friedlander et al. |
| 2014/0067596 | A1 | 3/2014 | McGovern et al. |
| 2014/0195297 | A1 | 7/2014 | Abuelsaad et al. |
| 2014/0278474 | A1 | 9/2014 | McClure et al. |
| 2014/0297311 | A1 | 10/2014 | Jackson |
| 2014/0310398 | A1 | 10/2014 | Zhou |
| 2014/0316793 | A1 | 10/2014 | Pruit |
| 2014/0350954 | A1 | 11/2014 | Ellis et al. |
| 2015/0073830 | A1 | 3/2015 | Hill et al. |
| 2015/0178473 | A1 | 6/2015 | Hufford et al. |
| 2015/0178474 | A1 | 6/2015 | Hufford et al. |
| 2015/0193588 | A1 | 7/2015 | Nemoto et al. |
| 2015/0228041 | A1 | 8/2015 | Naley et al. |
| 2015/0294090 | A1 | 10/2015 | Kodiyan |
| 2015/0347682 | A1 | 12/2015 | Chen et al. |
| 2015/0356582 | A1 | 12/2015 | Turner, Jr. |
| 2016/0086505 | A1 | 3/2016 | Hanlon |
| 2016/0098541 | A1 | 4/2016 | Haskell et al. |
| 2016/0140322 | A1 | 5/2016 | Menon et al. |
| 2016/0180053 | A1 | 6/2016 | Fuertinger et al. |
| 2016/0267238 | A1 | 9/2016 | Nag |
| 2016/0314257 | A1 | 10/2016 | Nolan et al. |
| 2016/0357944 | A1 | 12/2016 | Iyer et al. |
| 2016/0378950 | A1 | 12/2016 | Reiner |
| 2017/0020444 | A1 | 1/2017 | Lurie |
| 2017/0039324 | A1 | 2/2017 | Francois et al. |
| 2017/0039341 | A1 | 2/2017 | Shklarski et al. |
| 2017/0071671 | A1 | 3/2017 | Neumann |
| 2017/0076049 | A1 | 3/2017 | Miller |
| 2017/0085444 | A1 | 3/2017 | Hart |
| 2017/0235912 | A1 | 8/2017 | Moturu et al. |
| 2017/0293538 | A1 | 10/2017 | Seenappa |
| 2017/0372348 | A1 | 12/2017 | Baluja |
| 2018/0025125 | A1 | 1/2018 | Crane et al. |
| 2018/0036591 | A1 | 2/2018 | King |
| 2018/0039726 | A1 | 2/2018 | Boissel |
| 2018/0056130 | A1 | 3/2018 | Bitran et al. |
| 2018/0068083 | A1 | 3/2018 | Cohen et al. |
| 2018/0089159 | A1 * | 3/2018 | Jain ...................... G06F 40/186 |
| 2018/0089376 | A1 | 3/2018 | Tucker et al. |
| 2018/0121605 | A1 | 5/2018 | Allen |

(56) References Cited

U.S. PATENT DOCUMENTS

| | | | |
|---|---|---|---|
| 2018/0150523 | A1 | 5/2018 | Shiffman et al. |
| 2018/0176331 | A1* | 6/2018 | Jain .................. H04L 67/63 |
| 2018/0189046 | A1 | 7/2018 | Kunisetty |
| 2018/0242860 | A1 | 8/2018 | LeBouef et al. |
| 2018/0301205 | A1 | 10/2018 | Mao |
| 2018/0359281 | A1 | 12/2018 | Ng |
| 2018/0367560 | A1 | 12/2018 | Mahaffey |
| 2018/0373462 | A1 | 12/2018 | Childress |
| 2019/0000349 | A1 | 1/2019 | Narayan et al. |
| 2019/0006025 | A1 | 1/2019 | Li |
| 2019/0012434 | A1 | 1/2019 | Frazier |
| 2019/0080785 | A1 | 3/2019 | Li |
| 2019/0122266 | A1 | 4/2019 | Ramer et al. |
| 2019/0138656 | A1 | 5/2019 | Yang et al. |
| 2019/0140892 | A1* | 5/2019 | Jain .................. H04L 41/16 |
| 2019/0206521 | A1 | 7/2019 | Walpole et al. |
| 2019/0227528 | A1 | 7/2019 | Abbott et al. |
| 2019/0272925 | A1* | 9/2019 | Barrett ................ G16H 50/80 |
| 2020/0058382 | A1 | 2/2020 | Birnbaum et al. |
| 2020/0065879 | A1 | 2/2020 | Hu et al. |
| 2020/0105380 | A1 | 4/2020 | Ennist |
| 2020/0131581 | A1 | 4/2020 | Jain et al. |
| 2020/0145308 | A1 | 5/2020 | Al Ramady |
| 2020/0211679 | A1 | 7/2020 | Pellini et al. |
| 2020/0211680 | A1 | 7/2020 | Sablinski et al. |
| 2020/0243167 | A1 | 7/2020 | Will |
| 2020/0319877 | A1 | 10/2020 | Glazer |
| 2020/0321116 | A1 | 10/2020 | Neumann |
| 2020/0342352 | A1 | 10/2020 | Neumann |
| 2020/0350041 | A1 | 11/2020 | Li |
| 2020/0357490 | A1 | 11/2020 | Kartoun et al. |
| 2020/0387810 | A1 | 12/2020 | Hodgson |
| 2020/0410090 | A1 | 12/2020 | Baker |
| 2020/0411199 | A1 | 12/2020 | Shrager et al. |
| 2021/0004537 | A1 | 1/2021 | Sapugay |
| 2021/0044579 | A1 | 2/2021 | Nelson-Gal |
| 2022/0076822 | A1 | 3/2022 | Liu et al. |

OTHER PUBLICATIONS

DeAngelis, "Patient Monitoring, Big Data, and the Future of Healthcare," Wired.com, Aug. 6, 2014, retrieved at URL<https://www.wired.com/insights/2014/08/patient-monitoring-big-data-future-healthcare/>, 6 pages.

Dias et al., "Wearable Health Devices—Vigtal Sign Monitoring, Systems and Technologies," Sensors, Jul. 25, 2018, 18(8):2414.

Ekonomou et al., "An Integrated Cloud-based Healthcare Infrastructure", IEEE Third International Conference on Cloud Computing Technology and Science, 2011, pp. 532-536.

FDA.gov [online], "FDA Offers Guidance to Enhance Diversity in Clinical Trials, Encourage Inclusivity in Medical Product Development", published on Nov. 9, 2020, retrieved on Mar. 11, 2021, retrieved from URL<https://www.fda.gov/news-events/press-announcements/fda-offers-guidance-enhance-diversity-clinical-trials-encourage-inclusivity-medical-product>, 3 pages.

Flatiron.com [online], "OncoTrials," May 14, 2018, retrieved on Mar. 13, 2020, retrieved from URL <https://flatiron.com/oncology/clinical-trials/>, 4 pages.

Flatiron.com [online], "Press Release: Flatiron Health Announces Three Publications Studying a Feasible, Reliable, Scalable and Meaningful Real-World Progression Endpoint for Oncology Research," Aug. 22, 2019, retrieved on Mar. 13, 2020, retrieved from URL<https://flatiron.com/press/press-release/real-world-progression-2019/>, 4 pages.

Foxnews.com [online], "FDA Issues Final Guidance to Improve Diversity in Clinical Trials", published on Nov. 9, 2020, retrieved on Mar. 11, 2021, retrieved from URL<https://www.foxnews.com/health/fda-issues-final-guidance-improve-diversity-clinical-trials>, 7 pages.

Grilo et al. "Pretreatment Patient Factors Predicting Attrition From a Multicenter Randomized Controlled Treatment Study for Panic Disorder," Comprehensive Psychiatry, Nov./Dec. 1998, 39(6):323-332.

Hammond et al., "Connecting Information to Improve Health", Health Affairs, Feb. 2010, 7 pages.

Hayhurst, "How Network Monitoring Keeps Healthcare Devices and Patients Safe," HealthTech, May 7, 2020, retrieved at URL<https://healthtechmagazine.net/article/2020/05/how-network-monitoring-keeps-healthcare-devices-and-patients-safe>, 8 pages.

Kakria, "A Real-Time Health Monitoring System for Remote Cardiac Patients Using Smartphone and Wearable Sensors," International Journal of Telemedicine and Applications, Nov. 12, 2015, vol. 2015, Article ID 373474, 11 pages.

Komen.org [online], "Types of Research Studies," Mar. 11, 2015, retrieved on Mar. 13, 2020, retrieved from URL<https://ww5.komen.org/BreastCancer/DifferentTypesofResearchStudies.html>, 5 pages.

Lenane, "Continuous Heart Monitoring Key to Identifying Cause of Cryptogenic Stroke," Diagnostic and Interventional Cardiology, Nov. 16, 2015, retrieved at URL<https://www.dicardiology.com/article/continuous-heart-monitoring-key-identifying-cause-cryptogenic-stroke>, 4 pages.

Med.Standford.edu [online], "Cohort Discovery," retrieved on Mar. 13, 2020, retrieved from URL <https://med.stanford.edu/starr-tools/cohort-discovery.html>, 3 pages.

Michaeljfox.org [online], "Fox Trial Finder," retrieved on Mar. 13, 2020, retrieved from URL<https://www.michaeljfox.org/trial-finder>, 4 pages.

Miksad et al., "Small But Might: The Use of Real-World Evidence to Inform Precision Medicine," Clinical Pharmacology & Therapeutics, Jul. 2019, 106(1):87-90.

Mixpanel.com [online], "What is cohort analysis?," retrieved on Mar. 13, 2020, retrieved from URL <https://mixpanel.com/topics/cohort-analysis/>, 11 pages.

Murphy et al., "Visual Query Tool for Finding Patient Cohorts from a Clinical Data Warehouse of the Partners Healthcare System," Presented at Proceedings of AMIA Symposium, 2000:1174.

Nickelled.com [online], "Chapter 5: Top cohort analysis tools and resources," Dec. 12, 2018, retrieved on Mar. 13, 2020, retrieved from URL<https://www.nickelled.com/cohort-analysis/tools/>, 17 pages.

Opb.org [online], "OHSU's COVID-19 Study Accused of Racial Bias", Published on Jun. 6, 2020, retrieved on Mar. 11, 2021, retrieved from URL<https://www.opb.org/news/article/key-to-oregon-ohsu-covid-19-study-accused-of-racial-bias/>, 8 pages.

Oregonlive.com [online], "OHSU ends massive coronavirus study because it underrepresented minorities, university says", published on Aug. 27, 2020, retrieved on Mar. 11, 2021, retrieved from URL<https://www.oregonlive.com/coronavirus/2020/08/ohsu-drops-massive-coronavirus-study-because-minorities-didnt-sign-up-university-says.html>, 4 pages.

PaloAltoNetworks.com, "Monitor Device Health," Panorama Administrator's Guide Version 8.1, last updated Jun. 17, 2020, retrieved at URL<https://docs.paloaltonetworks.com/panorama/8-1/panorama-admin/manage-firewalls/device-monitoring-on-panorama/monitor-device-health.html>, 3 pages.

Pennic, "Life Image, Medel.ai Integrates to Support AI-Driven Clinical Trails," Nov. 6, 2018, retrieved from URL<https://hitconsultant.net/2018/11/06/life-image-medel-ai-partner-ai-driven-clinical-trails/#.Xmr7yqhKhZc>, 4 pages.

Phaneuf, "Latest Trends in Medical Monitoring Devices and Wearable Health Technology," BusinessInsider.com, Jan. 31, 2020, retrieved at URL<https://www.businessinsider.com/wearable-technology-healthcare-medical-devices>, 8 pages.

Rogers et al., "Composer: Visual Cohort Analysis of Patient Outcomes," Applied Clinical Informatics, Mar. 2019, 10(2):278-285.

Smith et al., "Performance Measurement for Health System Improvement: Experiences, Challenges and Prospects," Proceedings of WHO European Ministerial Conference on Health Systems, Jun. 25-27, 2008, Tallinn, Estonia, 28 pages.

Statsoft, "Neural Networks", published in 2002, retrieved on Apr. 14, 2004, retrieved from URL<http://www.obgyn,cam.ac.uk/cam-only/statsbook/stneunet.html>.

Tucker, "Five of the Best Health Monitoring Devices," TheGuardian.com, Aug. 21, 2016, retrieved at URL<https://www.theguardian.com/technology/2016/aug/21/five-best-cardio-health-monitoring-devices>, 9 pages.

(56) References Cited

OTHER PUBLICATIONS

Wikipedia.org [online], "Clinical trial," Feb. 17, 2020, retrieved on Mar. 13, 2020, retrieved from URL<https://en.wikipedia.org/wiki/Clinical_trial>, 18 pages.
Wikipedia.org [online], "Observational study," Feb. 17, 2020, retrieved on Mar. 13, 2020, retrieved from URL<https://en.wikipedia.org/wiki/Observational_study>, 4 pages.
Wikipedia.org [online], "Research," Mar. 7, 2020, retrieved on Mar. 13, 2020, retrieved from URL<https://en.wikipedia.org/wiki/Research>, 17 pages.
Coravos et al., "Modernizing and designing evaluation frameworks for connected sensor technologies in medicine", Digital Medicine 3, Mar. 2020.
Ctti-clinicaltrials.org [online], "Clinical Trials Transformation Initiative (CTTI) Recommendations: Advancing the Use of Mobile Technologies for Data Capture and Improved Clinical Trials", published in Jul. 2018, [retrieved on Jan. 7, 2021], retrieved from URL<https://www.ctti-clinicaltrials.org/sites/www.ctti-clinicaltrials.org/files/mobile-devices-recommendations.pdf#Pg2Ln13>.
Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.
Obgyn.com [online], "Neural Networks", published in 2002, retrieved on Jan. 19, 2021, 34 pages.
U.S. Non Final Office Action in U.S. Appl. No. 17/166,899, dated Apr. 19, 2021, 25 pages.
U.S. Non Final Office Action in U.S. Appl. No. 17/324,098, dated Aug. 2, 2021, 19 pages.
U.S. Non Final Office Action in U.S. Appl. No. 17/166,777, dated Apr. 27, 2021, 26 pages.
Atan et al., "Sequential Patient Recruitment and Allocation for Adaptive Clinical Trials" Proceedings of the 22nd International Conference on Artificial Intelligence and Statistics, 2019, 89:1-10.
Berry, "Adaptive Clinical Trials in Oncology", Nature Reviews, Apr. 2012, 9:199-207.
Bothwell et al., "Adaptive Design Clinical Trials: A Review of the Literature and ClinicalTrials.gov", BMJ Open, 2018, 11 pages.
Branch-Elliman et al., "Pragmatic, Adaptive Clinical Trials: Is 2020 the Dawning of a New Age?", Contemporary Clinical Trials Communications, 2020, 19:1-3.
Chow et al., "Adaptive Design Methods in Clinical Trials—A Review", Orphanet Journal of Rare Diseases, May 2, 2008, 13 pages.
FDA.gov [online], "Enhancing the Diversity of Clinical Trial Populations—Eligibility Criteria, Enrollment Practices, and Trial Designs", published in Nov. 2020, retrieved on Jan. 31, 2022, 21 pages.
FDA.gov [online], "FDA Takes Action for Failure to Submit Required Clinical Trial Results Information to ClinicalTrials.gov", published on Apr. 28, 2021, retrieved on Apr. 31, 2022, 3 pages.
FDA.gov [online], "FDA's Role: ClinicalTrials.gov Information", published on Apr. 28, 2021, retrieved on Jan. 31, 2022, 4 pages.
Forbes.com [online], "How Digital Technology Can Increase Diversity, Equity and Inclusion In Medical Research", published on May 12, 2021, retrieved on Oct. 28, 2021, retrieved from URL<https://www.forbes.com/sites/forbestechcouncil/2021/05/12/how-digital-technology-can-increase-diversity-equity-and-inclusion-in-medical-research/?sh=1dfa75252f7a>, 5 pages.
Gaydes et al., "Good Practices for Adaptive Clinical Trials in Pharmaceutical Product Development", Drug Information Journal, 2009, 43:539-556.
Korn et al., "Adaptive Clinical Trials: Advantages and Disadvantages of Various Adaptive Design Elements", JNCI J Natl. Cancer Inst., 2017, 109(6):1-6.
NPR.org [online], "Scientists Say The Rush To Do COVID Research Led To A Whole Lot Of Waste", published on Apr. 23, 2021, retrieved on Feb. 1, 2022, 9 pages.
Pallmann et al., "Adaptive Designs in Clinical Trials: Why Use Them, and How to Run and Report Them", BMC Medicine, 2018, 16:29.
Park et al., "Critical Concepts in Adaptive Clinical Trials", Clinical Epidemiology, 2018, 10:343-351.
Shen et al., "Learning for Dose Allocation in Adaptive Clinical Trials with Safety Constraints", Proceedings of the 37th International Conference on Machine Learning, 2020, 11 pages.
Simon et al., "Adaptive Enrichment Designs for Clinical Trials", Biostatistics, 2013, 14(4):613-625.
Thorlund et al., "Key Design Considerations for Adaptive Clinical Trials: A Primer for Clinicians", BMJ, 2017, 5 pages.
Grants.nih.gov [online], "Amendment: NIH Policy and Guidelines on the Inclusion of Women and Minorities as Subjects in Clinical Research", published on Nov. 28, 2017, retrieved on Mar. 3, 2022, retrieved from URL<https://grants.nih.gov/grants/guide/notice-files/NOT-OD-18-014.html>, 3 pages.
Grants.nih.gov [online], "NIH Policy and Guidelines on The Inclusion of Women and Minorities as Subjects in Clinical Research", published on Dec. 6, 2017, retrieved on Mar. 3, 2022, retrieved from URL<https://grants.nih.gov/policy/inclusion/women-and-minorities/guidelines.html>, 17 pages.
Ispor.com [online], "How mHealth technology is revolutionizing clinical research," Sep./Oct. 2018, retrieved on Apr. 1, 2022, retrieved from URL<https://www.ispor.org/docs/default-source/publications/value-outcomes-spotlight/september-october-2018/ispor-vos-october-2018-toc-mhealth.pdf?sfvrsn=5822a619_2>, 4 pages.
U.S. Final Office Action in U.S. Appl. No. 17/166,777, dated Aug. 5, 2021, 9 pages.
U.S. Non-Final Office Action in U.S. Appl. No. 17/592,440, dated Apr. 26, 2022, 58 pages.
U.S. Notice of Allowance in U.S. Appl. No. 17/166,777, dated Feb. 4, 2022, 14 pages.
U.S. Notice of Allowance in U.S. Appl. No. 17/166,899, dated Aug. 4, 2021, 11 pages.
U.S. Notice of Allowance in U.S. Appl. No. 17/324,098, dated Dec. 15, 2021, 6 pages.
U.S. Notice of Allowance in U.S. Appl. No. 17/378,643, dated Nov. 10, 2021, 30 pages.

\* cited by examiner

| Study Criteria | 510a |
|---|---|

- Cohort Size: 100  _511_
- Study Length: 45 days  _512_
- Study Region: Virginia  _513_
- Requirements:  _514_
  (1) Must make 3 Medical Office Visits per Month
  (2) Must have a Smartphone
- Inclusion Criteria:  _515a_
  (1) Must be between 30 and 50 years old
  (2) Must be Diagnosed with High Blood Pressure
- Exclusion Criteria:  _516_
  (1) Can't have Diabetes
  (2) Can't be Pregnant
- Target Date: April, 2024  _517_
- ...

Diversity Analysis Results (Cohort Selection/Invitation) _520a_

- Reference Population: _521_ VA (2024 Estimated) – 49% (Group 1) / 24% (Group 2) / 24% (Group 3)
- Target Group Composition for Cohort: _522_ 50% (Group 1) / 25% (Group 2) / 25% (Group 3)
- Previous Participants: _523_ 915 (Group 1); 220 (Group 2); 200 (Group 3) - No Warning. Required Invitation Acceptance Rate is < 15%

Recommended Actions – Selecting Cohort _530a_

Option 1 – (1) Send invitations to all previous study participants in _532_ Groups 1-3; (2) remove Inclusion Criteria 1
- Diversity Score: 0.91
- Target Group Composition: 50% / 25% / 25%
- Predicted Group Composition at Enrollment: 43% / 30% / 27%
- Predicted Group Composition at Study Completion: 51% / 23% / 26%

Option 2 - (1) Send invitations to all previous study participants; and _534_ (2) invite 20% more participants from Group 2 than Group 3
- Diversity Score: 0.85
- Target Group Composition: 50% / 25% / 25%
- Predicted Group Composition at Enrollment: 43% / 30% / 24%
- Predicted Group Composition at Study Completion: 54% / 23% / 23%

FIG. 5A

Study Criteria _510b_

- Cohort Size: 100 _511_
- Study Length: 45 days _512_
- Study Region: Virginia _513_
- Requirements: _514_
  (1) Must make 3 Medical Office Visits per Month
  (2) Must have a Smartphone
- Inclusion Criteria: _515b_
  (1) Must be Diagnosed with High Blood Pressure
- Exclusion Criteria: _516_
  (1) Can't have Diabetes
  (2) Can't be Pregnant
- Target Date: April, 2024 _517_
- ...

Diversity Analysis Results (Enrollment) _520b_

- Target Group Composition: _522_    50% / 25% / 25%
- Enrolled Group Composition: _524_    48% / 27% / 24%
- Predicted Group Composition at Completion: _525_   55% / 20% / 25%
- Anticipated Diversity Level at Completion: _526_   0.87
- Warning: _527_ Group Composition Outside of Target Composition Range!

Adjust Enrollment _540_

| Recommended Users to Improve Diversity | Recommended Users for Removal or Replacement |
|---|---|
| User S:<br>- Group(s): Group 2 (Underrepresented)<br>- Expected Participation Level: 76%<br>- Anticipated Diversity Level if Added: 0.91<br><br>[INVITE] | User D:<br>- Group(s): Group 1 (Overrepresented)<br>- Participation Level: 51%<br>- Anticipated Diversity Level if Removed: 0.90<br><br>[REMOVE / REPLACE] |
| User R:<br>- Group(s): Group 2 (Underrepresented)<br>- Expected Participation: 71%<br>- Anticipated Diversity Level if Added: 0.90<br><br>INVITE | User B:<br>- Group(s): Group 1 (Overrepresented)<br>- Participation Level: 59%<br>- Anticipated Diversity Level if Removed: 0.89<br><br>REMOVE / REPLACE |

INCREASING DIVERSITY OF PARTICIPANTS IN HEALTH RESEARCH USING ADAPTIVE METHODS

CROSS REFERENCE TO RELATED APPLICATIONS

This application is a Continuation-in-Part of U.S. application Ser. No. 17/166,899, filed Feb. 3, 2021 and is also a Continuation-in-Part of U.S. application Ser. No. 17/166,777, filed Feb. 3, 2021.

FIELD OF INVENTION

This application generally relates to adapting communications and interactions during the course of monitoring programs that involve collection of data from remote devices over communication networks.

BACKGROUND

There are many different types of devices that people use on a regular basis, e.g., phones, laptops, desktop computers, appliances, wearable devices, etc. There is also a large variety of types of users, with differing attributes and preferences. As a result, a single type of communication or interaction often is not effective for large groups of devices and users.

SUMMARY

In some implementations, a computer system provides a platform for administering monitoring programs that involve customized data collection from groups of remote devices. The system enables different parties, e.g., organizations, administrators, third-parties, etc., to create or register monitoring programs to be distributed and managed by the system. For example, a server system can provide a multi-tenant system that provides functionality to create monitoring programs each tenant organization, select groups of devices and users to participate in the monitoring programs, and distribute the monitoring programs (e.g., including items such as software modules, configuration data, data collection instructions, interactive content, etc. so that groups of remote devices carry out the monitoring). The system can thus administer many different monitoring programs on behalf of different tenant organizations, with the system including servers that collect and process data from the remote devices as the monitoring programs are carried out over time. The system can also monitor the effectiveness of the various monitoring programs, and can recommend adaptations to the monitoring programs and the monitoring groups if the system determines that compliance with program requirements is low or is predicted to be low. Many of the monitoring programs involve consistent, repeated interactions and data collection actions over a period of time (e.g., weeks, months, or even years).

As discussed below, the present system provides management functions for that are superior to typical application stores and other systems that provide interactions over the Internet. A typical application store providing software for mobile phones, for example, provides as many software applications as users desire, but does not track subsequent use of the applications and whether the usage and data provided meets standards and criteria for the applications, much less take actions to improve the usage rates and data quality. Nor is a typical application store configured to track and achieve different application-specific goals, such as targeted levels of diversity among devices and users using different applications, or to adjust applications to avoid or compensate for biases or flaws that disproportionately affect different devices or users. By contrast, the present system does track the extent that users and devices in the monitoring group for a monitoring program comply with the requirements of the monitoring program over time. Each monitoring program can have a defined group of devices and users involved in monitoring programs are often committed to ongoing participation in the monitoring program (e.g., subscribed, enrolled, or otherwise registered). While a monitoring group can change over time, the system can evaluate each monitoring group continually to ensure that the group's current composition and projected future composition (as well as data quality, compliance with requirements, etc.) all meet the overall goals for the monitoring program.

The participation in a monitoring program typically requires a set of actions, both for data collection and separate from data collection, that need to be performed to comply with the requirements of the monitoring program. The success of the monitoring program as a whole can depend on having a monitoring group with at least a minimum level of diversity (e.g., variation or variety in different attributes or categories), where devices and/or users for each of different profiles or contexts each comply with the required actions over time. The system can determine whether the usage and data collected meets the particular standards and criteria for each monitoring program, as well as take actions to improve the usage rates and data quality for the monitoring group. The system stores data indicating the goals and requirements for a monitoring program as a whole, such as a need to achieve a targeted level of diversity among devices and users. The system can detect elements of monitoring programs that disproportionately affect different devices or users, and can identify changes to adjust the monitoring programs to avoid or compensate for those biases. The system can also select a monitoring group, or determine changes to a monitoring group, to achieve compliance with the monitoring program requirements by at least the needed minimum of participants from each of the different groups or categories.

These and other functions make the present system more effective by raising the percentage of participating devices and users that are retained in and comply with requirements of a monitoring program. This also improves the efficiency in the allocation of computational resources, because the rate of successful completion of monitoring programs increases significantly, limiting the additional time, processing, network bandwidth, and other resources that would be needed to re-start a failed program or extend a monitoring program that has not acquired sufficient data. The system can define target characteristics for the composition of a monitoring group, including the level of diversity or distribution among different groups or backgrounds. The system can repeatedly verify, for each monitoring program, whether successful monitoring is occurring for sufficient numbers of devices or users for the respective groups of backgrounds, and use various actions (e.g., monitoring program changes, monitoring group changes, changed communication, etc.) as feedback to bring the level of diversity. This allows the system to manage each monitoring program at the aggregate level, to achieve desired characteristics (e.g., diversity or distribution of characteristics) in the monitoring group as a whole and consequently for the aggregate data set that will result from the monitoring program. Beyond monitoring the compliance of individual members of a monitoring group, the system detects changes or risks to completion of the objective of the monitoring program (including potential lack of diversity or representation among some subjects to be monitored) recommends and carries out actions to proactively avoid those risks.

The system provides interfaces that provide the functionality to design and update monitoring programs that involve collection of sensor data, user input, and other interactions using remote devices. The various monitoring programs that the system administers can each have their own respective characteristics and requirements. For example, different monitoring programs may have different objectives or purposes, and so may very different parameters, e.g., duration of the program (e.g., 1 month, three months, etc.), frequency of data collection (e.g., hourly, daily, weekly, etc.), latency for sending results, types of data to be collected, types of sensors to be used, types of user interactions or user inputs needed during monitoring, and so on. The system can concurrently manage the data collection and data processing for different monitoring programs, generating separate data sets for each monitoring program and performing individual communications with each remote device for the specific monitoring program(s) that the remote device is involved in.

One of the important aspects of a monitoring program is the set of devices and users that participate in the monitoring program, referred to generally as the "monitoring group" for a monitoring program. In many situations, the monitoring group for a monitoring program must have certain size and composition characteristics in order for the monitoring to be effective. If the monitoring group is too small or has a composition that is too homogenous, the monitoring results may be inaccurate or incomplete. Even worse, in many cases, if the composition of the monitoring group deviates significantly from required characteristics, the results of the monitoring program may be unusable, meaning that the computing resources of client devices and servers (e.g., processing capability, storage capacity, power, network bandwidth, etc.) expended in in monitoring over weeks, months, or years has been wasted. Systems and users that rely on effective monitoring may expect that monitoring is being performed appropriately (perhaps due to a large number of monitored devices and users), only to find later that monitoring was ineffective due to a skewed composition of the monitoring group, which may have failed to detect and quantify many contexts, situations, and events that should have been monitored.

The present system manages monitoring programs in a way that improves on previous systems with the ability to evaluate the composition of monitoring groups and actually improve the composition of and compliance of monitoring groups to meet the needs of their associated monitoring programs. The system does this in several ways, such as by guiding the initial selection of subjects to include in the monitoring group, adaptively adding and adjusting membership in the monitoring group, adjusting the characteristics of a monitoring program to avoid or remove bias against compliance by certain groups, and predicting the resulting compliance, retention, and data quality that will be achieved by the end of a monitoring program (e.g., at a scheduled end date or at a certain amount of time in the future. It is not sufficient to simply enroll a group that has the proper size and composition (including diversity), the needed number of participants and diversity of participants need to comply with monitoring program requirements, provide sufficiently complete and accurate data, and be retained until the end of the monitoring program. To assist with this, the system can predict, for individuals or groups, the level or extent of compliance with requirements, data quality for collected data, retention to the end of a predetermined time period, and other properties, and use those predictions for updating user interfaces as well as to adjust monitoring programs and monitoring groups that the system manages.

Each monitoring program may have a set of selection criteria that are used to determine the eligibility of devices and/or users to participate in a monitoring program. The selection criteria can include inclusion criteria that specify characteristics that are needed in order to participate, as well as exclusion criteria that specify characteristics that disqualify a user or device from participating. The selection criteria can be applied by the system to identify candidates or confirm that participants should be added to the monitoring group for a monitoring program (e.g., enrolled in the monitoring program and remote monitoring initiated). However, even if the devices and users selected for a monitoring group each individually meet the selection criteria, that does not ensure that the monitoring group as a whole has the characteristics needed for the monitoring program to be successful (e.g., to provide a predetermined minimum level of statistical validity or confidence). Accordingly, the systems and techniques describes herein allow more sophisticated evaluation and adaptation of monitoring programs (e.g., required actions, data collection, monitoring groups, etc.) so that the system guides the monitoring program to achieve not only data collection by a minimum number of participants, but also to have valid data collection over the course of the monitoring program from at least the minimum numbers for participants corresponding to each of various different profiles or backgrounds.

The system is configured to distribute software for monitoring programs to devices that are used to perform the monitoring. The monitoring program may specify parameters for monitoring, such as times when data is to be obtained from, requested from, or sent to the devices. The monitoring program may also indicate the type of data or the specific data that is to be obtained from, requested from, or sent to the devices. The data obtained or requested from the devices may include sensor data collected using sensors of the devices or from other devices (e.g., connected through wired or wireless links). The data that the system sends to the remote devices may include instructions to collect sensor data, or updates to the monitoring program or a portion of the monitoring program on the devices. In updating software used to implement a monitoring program on the remote devices, the configuration of the remote devices can be adjusted, for example, to change what data is collected, change how the data is collected, change communication network settings, etc.

In some implementations, the computer system adjusts individual monitoring programs and distributes changes to devices for each program's monitoring group. Even within the monitoring group of a single monitoring program, the system may select different settings, interactions, or content to provide to different devices. In some cases, the interactions vary depending which of various profiles the devices correspond to. The computer system may assign each of the device to at least one profile based on attributes of the devices or their users. For example, a first profile may be used for devices that include a GPS unit and a heartrate monitor, and that have a user that lives in an urban environment and is between 25 and 30 years of age. If a first device meets the device requirements of the profile and has a user that meets the user requirements of the profile, the system may classify the first device as corresponding to the first profile and the system interacts with that device using the information in that profile.

In some implementations, the system generates the profiles based on previously observed outcomes for devices and users in other monitoring programs. For example, the system may generate profiles based on observed outcomes of currently ongoing and/or previously completed monitoring programs. The observed outcomes may include the compliance of the devices or their users with the requirements of the monitoring program, and the retention of the devices or their users in the monitoring program. As another example, the system may generate profiles based on attributes of devices and/or users in a set, such as a set of devices and/or users that have participated in one or more monitoring programs. The attributes may include, for example, sensors that the devices include, sensor devices that are compatible with the devices, models of the devices, operating systems of the devices, etc. The attributes may also include demographic or non-demographic information that describes the users. The users may include, for example, users that have previously participated in a monitoring program, that are currently participating in a monitoring program, have indicated that they want to participate in a monitoring program, or that are eligible for a monitoring program.

In some implementations, the system generates the profiles using a machine learning model or a group of machine learning models. As an example, the computer system may using a clustering machine learning model to cluster different devices or users based on observed outcomes. Similarly, as another example, the system may use a clustering model to cluster different groups of devices or users based on attributes of the devices or users. The model may use any or all attributes available to the model in performing the clustering. Alternatively, the model may use a subset of attributes corresponding to key attributes to perform the clustering. These key attributes may be determined using another machine learning model or a group of other machine learning models, using a static algorithm or group of static algorithms, or based on input from an administrator or researcher.

In some implementations, the system uses the profiles to create or adjust the monitoring group for a monitoring program. As an example, in response to determining that a monitoring group has less than a minimum threshold number of devices corresponding to a first profile, the system may add a device or user that meets the criteria for the first profile. The profiles can provide a way for the system to diversify a monitoring group or achieve a better distribution of monitored devices and users across different profiles or sets of characteristics. Adjusting the monitoring group may be based on the level of diversity in a monitoring group. The profiles, or a subset of the profiles, may correspond to different groups or categories that are assessed during diversity analysis. The system may determine that criteria specifying minimum or target levels of diversity for the monitoring program are not met when, for example, the monitoring group does not include any members from a certain group or profile, or if there is an insufficient amount (e.g., number, proportion, etc.) of members that correspond to the group or profile. For example, the system may determine that one or more profiles or categories of devices or users are not represented in or are underrepresented in a monitoring group, and, in response, the system can adjust the monitoring group to include additional device(s) that correspond to the one or more profiles or categories.

The system may analyze diversity at one or more points during the lifecycle of a monitoring program (e.g., defining the program, selecting the initial monitoring group, while data collection is ongoing, etc.). As an example, in a research study, if a device corresponding to a first group fails to provide the needed data, the system may determine whether the diversity targets for the research study are still met through data that is successfully collected from other devices. For example, the diversity criteria may specify that at least a minimum number or percentage of the participants should be from a first category, and the system can verify that the minimum is still satisfied by other devices and users that are providing data in compliance with the study's requirements. If the diversity criteria are not met, the system may generate a recommendation to correct or improve the diversity of the monitored group, or may automatically perform another action. For example, the system may automatically select an additional device of user corresponding to the first category to add to the monitoring group, and may transmit the software, configuration data, content, or other elements needed for the additional device to begin the needed monitoring.

In some implementations, the system is configured to perform a diversity assessment for a monitoring program and perform actions such as providing alerts, providing recommendations, and changing the monitoring program in response. In performing the diversity assessment, the computer system may identify the breakdown of a monitoring group among different categories or profiles, e.g., determining the numbers or proportions of each of different categories or profiles in the monitoring group. This information is referred to below as the "group composition" for a monitoring group, which can include data indicating which groups (e.g., categories, profiles, etc.) make up the monitoring group and in which amounts or proportions they occur (e.g., 10% in group 1, 30% in group 2, 0% in group 3, etc.). The groups or categories can be defined using many different attributes, including demographic and non-demographic characteristics. For example, different categories or profiles can be defined based on combinations of attribute values in different ranges, for example, for device types, device capabilities, user demographic characteristics (e.g., age, sex, race, occupation, educational level, etc.), geographic location, health status (e.g., diseases, physiological measurements, etc.).

After identifying the group composition for a monitoring group, the computer system may compare the group composition to a composition target to determine if the group composition is deviates from the composition target and to what extent. When a deviation of at least a predetermined amount is detected, the computer system may generate a warning for a researcher or administrator associated with the monitoring program, determine an action to correct the group composition, and/or generate a recommendation to perform the action or automatically perform the action. The system may proceed to generate a diversity report that it transmits to a client device over a communication network.

In some implementations, the diversity report may include the identified group composition (e.g., identifying groups represented, as well as warnings, recommended actions, and/or an indication of actions automatically performed by the system to better align to the diversity target. A researcher may use the information in the diversity report to make changes to the study, such as by changing the study parameters, adding or removing study criteria, inviting additional subjects to enroll in the study, enrolling additional participants Similarly, the system may make these changes automatically or in response to receiving a confirmation from the researcher. The changes made to the study may be targeted to or customized for to certain groups of a population, such as certain groups within a candidate pool, enrolled participants, and/or enrolled and active participants.

In some implementations, a computer system is configured to manage multiple monitoring programs corresponding to different groups of enrolled subjects. Each of the monitoring programs can have a set of elements that, for example, outline the requirements for the respective monitoring program. The groups of enrolled subjects each include multiple subjects that participate in the same monitoring program or in a monitoring program having the same set of requirements. The subjects within each of the groups can belong to different categories of subjects that interact with the computer system differently or that otherwise have different needs that require adjusted interaction. To promote high compliance with the monitoring programs' requirements among the diverse groups of participants, the computer system can adapt its interactions so that they are tailored to the needs of each category of subjects present among the monitoring program participants.

As an example, the computer system may manage a monitoring program for conducting a clinical trial for a new pharmaceutical. The monitoring program may require obtaining measurements of a physical attribute twice a day for a period of one month. The enrolled subjects of the monitoring program may include a first subgroup of participants that belong to a first category of subjects, and a second subgroup of participants that belong to a second category of subjects. Using information related to the first category, the computer system can determine that the first subgroup responds well to in-application services. In contrast, information related to the second category can indicate that second subgroup responds well to video calls or audio calls, and responds poorly to in-application services. As a result, the computer system can adapt the manner in which it interacts with the different subgroups of participants to achieve high data quality and high compliance with the requirements of the monitoring program. One of the ways this can be done is by converting or translating a message into different forms or styles depending on the information associated with the different categories of subjects. This information may include subject attributes, behaviors associated with the subjects in the categories, and anticipated effects of different monitoring program elements on the actions of the subjects in the categories, and may be stored as part of profiles that represents the different categories of subjects.

With respect to the first subgroup, the system may send reminder notifications to devices belonging to participants in the first subgroup, where the reminder notification will be displayed as an in-app notification in an application for the monitoring program. In contrast, the system may call the devices belonging to participants in the second subgroup and provided an automated message reminding the participants to provide the measurements.

In some implementations, the computer system determines different categories of subjects using collected information. The computer system may collect attribute information, such a demographic and non-demographic information, on each of the participants that enrolls in a monitoring program. Additionally or alternatively, the computer system may collect other information, such response information, that the computer system uses to determine outcomes for the participants, such as if participants are compliant with the requirements of the monitoring program or are providing data of sufficient data quality. After collecting enough data, the computer system can group subjects, such as past and currently enrolled participants, based on at least one of their attributes and their outcomes. These groups may each represent a different category of subjects.

In some implementations, after determining the groups that represent the different categories of subjects, the computer system can generate profiles for each of the categories of subjects using the groups. The profiles can include inclusion criteria for each of the categories of subjects. The inclusion criteria may include a set of attributes that are used by the system to determine which subjects belong to which categories of subjects. As an example, the computer system may determine the inclusion criteria using the groups by identifying the attributes that are shared by all subjects in those groups or that are common among the subjects in those groups. When identifying what categories of subjects are present among a set of enrolled participants in a monitoring program, the computer system may obtain attribute information for the different participants and compare it to the inclusion criteria for the different categories of subjects. Additionally or alternatively, if a participant has been previously associated with a particular category of subjects, the computer system may look up the participant to determine which category of subjects they belong to. In some cases, a participant may belong to multiple categories of subjects.

In some implementations, the profiles generated by the computer system contain other information. The computer system can analyze the collected information and outcomes of the different subjects in the different groups of subjects to determine anticipated behaviors of the subjects in the groups and the predicted effects of different monitoring program elements on the subjects. For example, the computer system may use the collected information to determine that a first group of subjects demonstrates higher compliance when messages are sent before 11:00 am when compared to messages sent at different times. The computer system can include the different anticipated behaviors and effects for a particular group in the corresponding profile. The anticipated behaviors and effects can indicate preferences for interactions between the subjects in the different categories of subjects and the computer system. For example, the anticipated behaviors and effects can indicate preferences for certain communication attributes over other communication attributes.

As an example, the computer system may collect, for each subject user, information such as response times, notification compliance rates, user retention rates, user data quality indications, etc. The computer system may assign this information to different profiles based on comparing attributes of the users to profile member parameters. That is, for each user, the computer system may determine what profile the user is associated with using known attributes of the user and inclusion criteria for the profiles, and proceed to assign the information collected from the user to at least one particular profile. The computer system may use the collective information assigned to the profile to identify behaviors that exist among the associated users. For example, the behaviors may indicate a preference for a particular communication channel, communication time, communication frequency, communication formality, etc.

As another example, the computer system may generate a profile that represents a first category of users who tend to communicate primarily through SMS text message or prefer to communicate through SMS text message. Accordingly, a known behavior associated with this profile is that this category of users tends to respond more positively to messages sent by SMS text message. When the computer system determines that there exists a group of devices among the monitored devices that are associated with this profile, the computer system may update the communication channel to SMS text message for a single, multiple, or all event messages that are to be sent to the monitored devices.

In some implementations, the computer system is configured to distribute software for a monitoring program to devices that are to be monitored. The monitoring program may indicate times when data is to be obtained from, requested from, or sent to the monitored devices. The monitoring program may also indicate the type of data or the specific data that is to be obtained from, requested from, or sent to the monitored devices. The data obtained or requested from the monitored devices may include sensor data collected using sensors of the monitored devices or sensor devices electronically connected to the monitored devices. The data sent to the monitored devices may include messages that request the users of the monitored devices to perform one or more actions. These actions may include a request to perform an action such a request to take a blood pressure test, a request to permit the access of sensor data, a request to respond to the notification using one or more preselected responses provided in the notification or freestyle responses, etc.

In some implementations, the computer system adjusts interactions by modifying messages that it sends to subjects enrolled in monitoring programs. As an example, the computer system may determine one or more categories of users that the users of the monitored devices belong to. The computer system may proceed to access profiles that represent these categories of users, and use the profiles to customize the messages for the different groups of monitored devices. In more detail, if a first group of the monitored devices are associated with a first profile and a second group of the monitored devices are associated with a second profile, the computer system may customize and send a first notification to the first group of monitored devices having a first set of notification or message attributes, and a second notification to the second group of monitored devices having a second set of notification or message attributes that are different from the first set. The computer system may customize the messages to adjust, for example, the time of that the notification is sent, a deadline for providing a response or performing an action associated with a notification, the channel of communication, the formality of the communication such as word choice and sentence structure, the frequency of communication, etc.

In some implementations, the computer system makes these adjustments to interactions to achieve one or more goals. For example, the computer system may adjust how to communicate with the different categories of users to achieve improved user retention in the monitoring program, to improve user compliance, and/or to improve the data quality collected. The computer system may make these adjustments to achieve or improve the likelihood of achieving one or more monitoring program requirements.

In one general aspect, a method includes communicating, by a server system, with multiple remote devices that are each configured to perform monitoring according to at least one of a plurality of monitoring programs administered by the server system, where the communicating involves sending messages with different message attributes to remote devices over a communication network; generating, by the server system, records that specify outcomes or responses obtained after sending the messages, the records indicating (i) characteristics of messages sent to the remote devices and (ii) characteristics of users of the remote devices that received the messages; using, by the server system, the generated records to create or update profiles for different categories of users, each profile having a set of inclusion criteria defining the category of users corresponding to the profile, where each profile stores data that characterizes effects of message attributes on outcomes or responses for users in the category corresponding to the profile; for a group of users involved in a particular monitoring program, selecting, by the server system, a profile for each member of the group from among the profiles; and customizing, by the server system, interactions of the server system with remote devices of users in the group based on the profiles, where the server system customizes the interactions using the profiles to select different message attributes to increase a likelihood of a target outcome of the monitoring program.

Implementations include one or more of the following features. For example, in some implementations, generating records indicating characteristics of the messages sent includes generating records indicating one or more of the following: a time that the messages were sent; a channel of communication that the messages were sent by; content of the messages; an indication of formality associated with the messages; an indication of word choice associated with the messages; an indication of sentence structure associated with the messages; a response time associated with the messages; an indication of compliance associated with the messages; or an indication of data quality associated with the messages.

In some implementations, generating records indicating characteristics of users of the devices that received the messages includes generating records indicating one or more of the following: a demographic attribute of the user; a physiological attribute of the user; or a behavioral attribute of the user.

In some implementations, selecting a profile for each member of the group from among the profiles includes: identifying characteristics for each member of the group; determining that the characteristics satisfy a first set of inclusion criteria of the sets of inclusion criteria defining the categories that correspond to the profiles; and selecting the profile that corresponds to the first set of inclusion criteria.

In some implementations, customizing interactions of the server system with remote devices of users in the group based on the profiles includes, for each category of users in the group, adjusting a communication to remove, add, or modify one or more message attributes using the stored data of the corresponding profile.

In some implementations, adjusting the communication to remove, add, or modify one or more message attributes includes adjusting the communication to modify one or more of the following: a time for the communication to take place; a channel of communication; content of a message to be sent in communication; a formality of communication; word choice of message to be sent in communication; or sentence structure of message to be sent in communication.

In some implementations, customizing interactions of the server system with remote devices of users in the group based on the profiles includes: generating updated configuration data for software installed on the remote devices of the users in the group; distributing the updated configuration data to a subset of the remote devices of the users in the group, where the subset of the remote devices corresponds to a particular profile of the profiles; and interacting with subset of the remote devices differently than other remote devices of the users in the group in accordance with the updated configuration data.

In some implementations, customizing the interactions with the remote devices to increase the likelihood of the target outcome includes customizing interactions with remote devices to increase the likelihood of one or more of the following: retention of users involved in the monitoring program; compliance of users involved in the monitoring program; obtaining sufficient data quality corresponding to users involved in the monitoring program; or obtaining improved data quality corresponding to users involved in the monitoring program.

In some implementations, the method includes: accessing an event schedule corresponding to the monitoring program; identifying a particular event from the event schedule based on at least one of a time, date, or completed performance of an action; and retrieving or generating a message that corresponds to the event, where customizing interactions of the server system with remote devices of users in the group based on the profiles includes, for each category of users in the group, customizing the message using the stored data of the corresponding profile.

In some implementations, the method includes: detecting an event corresponding to the monitoring program; and retrieving or generating a message that corresponds to the event, where customizing interactions of the server system with remote devices of users in the group based on the profiles includes, for each category of users in the group, customizing the message using the stored data of the corresponding profile.

In some implementations, the method includes receiving, from a remote computing device of a program manager of the monitoring program and over the communication network, a message corresponding to the monitoring program and designated for the users in the group, where customizing interactions of the server system with remote devices of users in the group based on the profiles includes, for each category of users in the group, customizing the message using the stored data of the corresponding profile.

In some implementations, customizing interactions of the server system with remote devices of users in the group based on the profiles includes: selecting a first set of message attributes for users in the group that belong to a first category of the different categories of users; using the first set of message attributes to generate or modify a first message for the users in the group that belong to the first category; selecting a second set of message attributes for users in the group that belong to a second category of the different categories of users; and using the second set of message attributes to generate or modify a second message for the users in the group that belong to the second category, where at least one attribute in the first set of message attributes is not shared in the second set of message attributes, and at least one attribute in the second set of message attributes is not shared in the first set of message attributes.

In some implementations, the method includes sending, over the communication network and in accordance with the first set of message attributes, the first message to a first group of remote devices, the first group of remote devices belonging to users in the group that belong to the first category of the different categories of users; and sending, over the communication network and in accordance with the second set of message attributes, the second message to a second group of remote devices, the second group of remote devices belonging to users in the group that belong to the second category of the different categories of users.

In one general aspect, a method includes: extracting, from a subject database, at least one of (i) subject attribute data describing characteristics of the subjects or (ii) subject outcome data including results from monitoring programs that involved the subjects; grouping the subjects, based on the extracted data from the database, into different groups according to levels of similarity among attributes of the subjects or monitored outcomes for the subjects; constructing a profile for each of the groups, where constructing the profile for a group includes defining inclusion criteria for the group based on aggregate data for the subjects in the group; using data sets in the subject database to characterize, for each profile, differing effects of elements of monitoring programs on program compliance outcomes for subjects that satisfy the criteria of the profile; and using the characterization data to create or adjust a monitoring program involving communicating with a selected set of remote devices over a communication network.

Implementations include one or more of the following features. For example, in some implementations, grouping the subjects into the different groups according to the levels of similarity among the attributes of the subjects or the monitored outcomes for the subjects using at least one machine learning model includes: providing at least one of the attributes of the subjects or the monitored outcomes for the subjects as input to a machine learning model; and using the machine learning model to cluster the subjects based on at least one of the attributes of the subjects or the monitored outcomes for the subjects, where the resulting clusters corresponds to the different groups of subjects.

In some implementations, the machine learning model includes a clustering model.

In some implementations, the clustering model is a k-means clustering model.

In some implementations, the clustering model is a density clustering model, a connectivity clustering model, a centroid clustering model, distribution clustering model, a subspace clustering model, a group clustering model, a graph clustering model, signed-based clustering model, or a neural network model.

In some implementations, using the characterization data to create or adjust the monitoring program includes: identifying a set of elements of the monitoring program; identifying a subset of profiles corresponding to the set of remote devices; using the set of elements and the subset of profiles to determine one or more negative effects on program compliance outcomes of the monitoring program; and based on the one or more negative effects, determining an adjustment to at least one of the monitoring program or to the set of remote devices to counter the one or more negative effects.

In some implementations, determining the adjustment to at least one of the monitoring program or to the set of remote devices includes determining to adjust the monitoring program by adding a study element to the monitoring program to compensate for a predicted impact of at least one element in the set of elements.

In some implementations, determining the adjustment to at least one of the monitoring program or to the set of remote devices includes determining to adjust the monitoring program by removing or modifying a study element to the monitoring program to compensate for a predicted impact of at least one element in the set of elements.

In some implementations, determining the adjustment to at least one of the monitoring program or to the set of remote devices includes determining to (i) add one or more remote devices to the set of remote devices, or (ii) switching out one or more of the remote device in the set of remote devices for one or more other remote devices.

In some implementations, determining the adjustment to at least one of the monitoring program or to the set of remote devices includes, for each profile in the subset of profiles, generating a new version of the monitoring program that is applicable to corresponding subsets of devices in the set of remote devices.

In another general aspect, a method includes: accessing, by the one or more computers, subject data in a database for subjects that have been involved in one or more monitoring programs, the subject data includes attribute data indicating attributes of subjects and outcome data indicating monitored outcomes for the subjects monitored during one or more monitoring programs that involve collection of data for each subject over a communication network; determining, by the one or more computers, subsets of the subjects based on a degree of similarity in at least attributes of the subjects or monitored outcomes for the subjects; defining, by the one or more computers, a plurality of profiles based on the determined subsets, where each of the profiles represents a different class of subjects having attributes that satisfy criteria specified in the profile; generating, by the one or more computers, impact characterization data indicating different levels of impact that elements of monitoring programs have on outcomes for subjects that satisfy the criteria of different profiles, the impact characterization being generated based on analysis of the outcome data for different groups of subjects that correspond to different profiles; and using, by the one or more computers, the plurality of profiles and the generated impact characterization data to create a monitoring program or adjust a monitoring program involving communicating with a selected set of remote devices over the communication network.

In some implementations, the method includes adding a study element to the monitoring program based on the impact characterization data, where the study element is added to compensate for a predicted impact of at least one other element in the monitoring program.

In some implementations, the method includes: generating a new version of the monitoring program for a particular profile of the different profiles; and adding a study element to a monitoring program or modifying a study element in the monitoring program, where the study element is added or modified to compensate for a predicted impact of at least one other element in the monitoring program based on a portion of the impact characterization data associated with the particular profile of the different profiles.

In some implementations, customizing the monitoring program for each of the different profiles based on portions of the impact characterization data corresponding to each of the different profiles.

In some implementations, storing portions of the impact characterization data corresponding to the different profiles in each of the profiles.

In some implementations, generating the impact characterization data includes generating at least one of scores, likelihoods, and percentage rates, where the scores, likelihoods, and percentages correspond to determined impacts that the elements of monitoring programs have on outcomes for subjects that satisfy the criteria of different profiles.

In some implementations, generating the at least one of scores, likelihoods, and percentage rates includes: generating a set of scores for each of the profiles; generating a set of likelihoods for each of the profiles; or generating a set of percentage rates for each of the profiles.

In some implementations, determining subsets of the subjects includes using at least one machine learning model to determine the subsets of the subjects based on at least one of the attributes of the subjects or the monitored outcomes for the subjects.

In some implementations, using at least one machine learning model to determine the subsets of the subjects includes: providing at least one of the attributes of the subjects or the monitored outcomes for the subjects as input to a machine learning model of the at least one machine learning model; and using the at least one machine learning model to cluster the subjects based on at least one of the attributes of the subjects or the monitored outcomes for the subjects, where each of the resulting clusters corresponds to a subset of the subjects.

In one general aspect, a method includes determining, by the one or more computers, a target composition for a group of devices to be monitored in a monitoring program, where the monitoring program involves collecting data from geographically distributed devices over a network, where the target composition is determined based on the composition of a heterogeneous reference set of devices in a geographical area, the target composition providing a target level of diversity among the devices in the group for each of multiple attributes; determining, by the one or more computers, a group composition for a group of devices that includes at least one of candidate devices for the monitoring program or enrolled devices that are enrolled to be monitored in the monitoring program; determining, by the one or more computers, that the group composition differs from the target composition in a manner that the group composition does not achieve target level of diversity for at least one attribute of the multiple attributes; in response to determining that the group composition provides lower diversity than the target composition for the at least one attribute, selecting, by the one or more computers, one or more actions that are configured to adjust the composition of the group to achieve the target level of diversity for the at least one attribute; and providing, by the one or more computers, output indicating the selected one or more actions that are selected to adjust the composition of the group to achieve the target level of diversity in the group.

Implementations may include one or more of the following aspects. For example, in some implementations, the group of devices include computer network infrastructure devices including one or more of routers, firewalls, switches, servers, load-balancers, intrusion detection systems, and storage area networks.

In some implementations, the target composition provides a target level of diversity across each of geographical location, device load level, hardware configuration, and software configuration.

In some implementations, the method includes: carrying out the selected one or more actions to adjust the composition of the group toward the target composition; and monitoring the adjusted group by performing repeated communications with each of the devices in the adjusted group over a period of time to collected predetermined data from the devices in the adjusted group.

In some implementations, the one or more actions are selected based on output from a machine learning model that is configured to predict, where the machine learning model includes a trained neural network or a trained classifier.

In another general aspect, a method includes: determining, by the one or more computers, a target level of diversity for a monitoring program based on a composition of a reference group, where the monitoring program involves collecting data from a set of geographically distributed devices over a network; determining, by the one or more computers, a group level of diversity for a group based on the composition of the group, where the group includes at least one of candidates or participants for the monitoring program; determining, by the one or more computers, that the group level of diversity does not provide the target level of diversity; in response to determining that the group level of diversity does not provide the target level of diversity, selecting, by the one or more computers, one or more actions that are configured to adjust the composition of the group to achieve the target level of diversity in the group; and providing, by the one or more computers, output data that indicates the selected one or more actions to adjust the composition of the group toward the target level of diversity for the group.

Implementations may include one or more of the following aspects. For example, in some implementations, the one or more actions are selected based on output of a machine learning model.

In some implementations, the target level of diversity is based on a projected future composition of the reference group.

In some implementations, the reference group is a group in a particular geographic area.

In some implementations, the reference group is a group that has a particular health condition or a risk of developing the particular health condition.

In some implementations, the target level of diversity indicates levels of composition for one or more age, sex, race, or ethnicity.

In some implementations, the selected one or more actions includes providing support or interaction to a subset of the group, the support or interaction being customized for the needs of the subset.

In some implementations, the selected one or more actions includes and action to broaden inclusion criteria for the cohort to encompass more of individuals having background that improves the diversity of the group.

In some implementations, the selected one or more actions includes and action to remove or narrow exclusion criteria for the cohort.

In some implementations, the method includes identifying an element of the monitoring program that results in a bias in the group, where the selected one or more actions are configured to reduce or eliminate the bias.

In some implementations, the one or more actions are configured to adjust the composition of the group to achieve the target level of diversity in the group.

The described techniques can be used to realize various advantages. The system provides active evaluation of the progress of monitoring programs over time, ensuring that the data collection and compliance with program requirements are sufficient to meet the objectives of the monitoring program. This enables the system to verify that not only the nominal size and composition of the monitoring group is sufficient, but that the realized compliance, retention, and data collection quality will result in a successful monitoring program. For example, a monitoring program begins with 100 enrolled participants, 50 in group 1 and 50 in group 2, where the program needs a minimum of 40 active participants in each of the two groups at the end of the three-month monitoring period. The system stores data specifying these requirements and then on a regular basis, for example, daily, check whether the data collection and participant actions yield the characteristics that would meet the requirements for the study as a whole. Even if all 100 participants nominally remain in the study, the system may determine that in the first month 7 of the participants in group 1 provided incomplete or inaccurate data. Detecting this trend or pattern of decreasing compliance in group 1, the system can predict that this presents above a threshold likelihood that the minimums for group 1 will not be met at the end of the three-month program period. The system can take various actions to address the issue, including: alerting a researcher associated with the program, changing the interaction some or all members of group 1, adding or recommending to add additional members of group 1, changing the data collection actions for members of group 1 to increase compliance, changing elements of the program (e.g., substituting a requirement for an in-person visit with one for a phone call), and so on. These changes may ensure or, at least, improve the likelihood that the one or more set goals for the monitoring program are achieved.

For example, the system can manage monitoring programs by using subject responses to determine that a subset of subjects are failing to comply with at least one requirement of the monitoring program. In response, the system may add a subset of new subjects to the monitoring program, or replace the low compliance subjects with a new subset of subjects. Similarly, the management and distribution system may, at an outset of a new monitoring program, modify the requirements of the monitoring program for a particular group of subjects if it determines that one or more requirements are likely to result in one or more group of subjects failing to achieve particular outcomes and, therefore, the monitoring program failing to meet the one or more set goals. As an example, the management and distribution system may use a profile for a group of subjects to determine that a group of subjects is unlikely to have access to a sensor that can obtain data with sufficient accuracy or consistency for the requirements of the monitoring program and, based on this, that the monitoring program is anticipated to fail to obtain viable results. In response to this determination, the management and distribution system may modify the monitoring program for the group of subjects to include additional events for data requests so that additional data can be obtained from the group of subjects during the monitoring program to counter the data inaccuracies or inconsistencies.

This active management and verification is a significant improvement over other systems. For example, even if other systems begin with an appropriate set of subjects, they generally do not have the capability to check on an ongoing basis whether a monitoring program is still viable, or the capability to predict whether the monitoring program will be successful or its results viable by a completion time.

The system also improves the ability of monitoring programs to reach their objectives by the system selecting individuals for monitoring groups that, together, form a monitoring group predicted to meet the defined goals for the monitoring program. In more detail, the system may select a diverse group of subjects to enroll in or invite to the monitoring program such that the composition of the group meets predetermined diversity requirements (e.g., which may be inferred by the system from analysis of other monitoring programs or may be specified by a user). By including a diverse group of subjects at the outset of the monitoring program, the management and distribution system can start the monitoring program in track to obtain a viable monitoring data set from the monitoring program. This is a much needed feature today, as many medical studies today fail to produce viable results or produce results having severely limited applicability due to a failure to include or maintain a diverse set of participants. As discussed below, diversity is not limited to demographic attributes such as age, sex, race, socioeconomic status, and so on, but can also encompass diversity among physical characteristics, medical histories, genetic profiles, geographic locations, and many other attributes that are not demographic in nature.

The disclosed systems may also take into account other attributes of the subjects when selecting a group of subjects to enroll or invite to a monitoring program. For example, the systems may take into account historical data, trends in the historical data, and, optionally, trends among certain populations to select subjects that are likely to meet the requirements of the study. The historical data or trends may indicate past or anticipated retention rates for subjects or groups of subjects, past or anticipated compliance rates for subjects or groups of subjects, or past or anticipated data quality obtained from subjects or groups of subjects. For example, the historical data may indicate that a particular subset of subjects is likely to have low compliance with a particular requirement of a monitoring program. In response to this determination, the management and distribution systems may avoid enrolling or inviting those subjects to the monitoring program. More significantly, to ensure that members of these groups are still represented and participate successfully, the system can increase the number of participants from that group to account for higher expected attrition. More efficiently, the system can identify the elements that are correlated to low compliance for that group, and change those elements or include additional supports to boost compliance, specifically providing supports that the historical data has shown to have been effective in prior monitoring programs with that specific group. For example, those subjects may be needed to achieve certain minimum diversity criteria or other goals for the monitoring program. The system may modify the elements of the monitoring program for that particular subset of subjects to improve compliance. Modifying the elements may include modifying or removing requirements of the monitoring program, or adding remedial elements. For example, if the particular subset of subjects is determined by the management and distribution system to generally not have access to a vehicle and, as a result, have low compliance with required medical office visits, the system may add taxi credit to a new version of the monitoring program for those subjects as a remedial measure to improve compliance rates for those subjects with respect to office visits.

In selecting subjects at an outset of a monitoring program or determining how to modify the elements of a monitoring program to improve, the disclosed systems may use various profiles that represent categories of subjects. These profiles may be used to determine how particular subjects are likely to respond to certain monitoring program requirements, and, therefore, to determine if they should be enrolled to the monitoring program or if the monitoring program needs to be adjusted for one or more particular groups of subjects. These profiles may additionally or alternatively be used to improve the diversity of a monitored group or to determine if a monitored group has a sufficient diversity. For example, the management and distribution system may identify the profiles corresponding to a monitoring group and use the profiles to determine if there is sufficient diversity, at the outset or predicted diversity at completion of the monitoring program. If diversity is insufficient, the management and distribution system may use the profiles to identify unrepresented or underrepresented profiles, and proceed to enroll or invite subjects from categories represented by those unrepresented or underrepresented profiles.

By selecting at the outset of a monitoring program a group of subjects that will likely provide the overall set of data and the diverse context to be able to capture the variety of data needed for the monitoring program, the management and distribution systems are able to significantly reduce computational inefficiencies. Notably, this selection improves the likelihood of obtaining viable results and otherwise successfully completing the monitoring program, which reduces, on average, the time to complete the monitoring programs and/or eliminates, or at least significantly reduces, the need to repeat monitoring programs and the waste resulting from having to cancel or discard results from a monitoring study that fails to achieve participation from the needed categories of subjects.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIGS. 5A-5C are diagrams that illustrate example diversity assessment and action selection interfaces.

Like reference numbers and designations in the various drawings indicate like elements.

DETAILED DESCRIPTION

Figure 1:
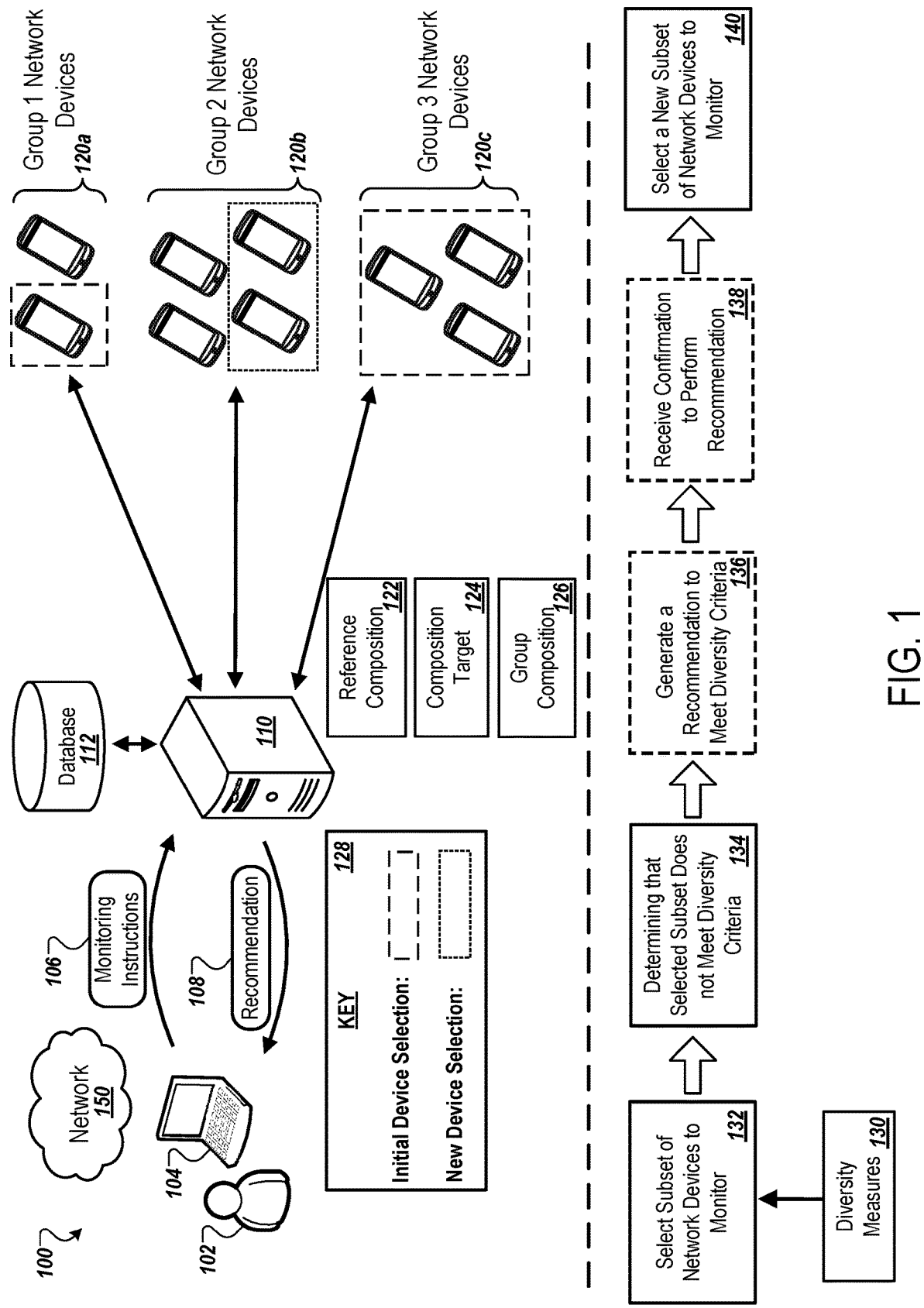
FIG. 1 is a diagram that illustrates an example system for assessing and selecting technologies to meet diversity requirements.

FIG. 1 is a diagram that illustrates an example system 100 for assessing and selecting technologies to meet diversity requirements. Among other uses, the system 100 can be used to identify and/or select devices and/or software to monitor to ensure that certain diversity criteria is being met. Similarly, the system 100 can be used to analyze device and/or software selections made by a user, and perform an action such as generating a recommendation to adjust the analyzed devices if the selected devices and/or software does not meet the diversity criteria or would not be expected to meet the diversity criteria by the end of a monitoring period. For example, if the selections made by the user would result in an insufficient number of devices associated with a particular group from being monitored, the system 100 may generate a warning to send to an administer with a recommendation to add a device from the underrepresented group, remove a device from one of the overrepresented groups, to add a device from the underrepresented group and remove a device form one of the overrepresented groups, or to perform one or more other actions such as to adjust the criteria for making a device and/or software selection.

Monitoring a set of devices or particular software running on a set of devices may include the system 100 collecting data from a distributed group of devices over a network. Data may be collected over a predetermined amount of time, until a goal is achieved, and/or until an event is detected. The frequency of data collection may be predetermined such that data is collected (e.g., requested and/or received) at predetermined intervals. Alternatively, data may be collected as it is produced, in response to certain goals or milestones being met, in response to certain events occurring or being detected, etc.

The system 100 can be used to, for example, identify (e.g., calculate) a target diversity level for a group of devices to be monitored (or a group of devices that are used to run software to be monitored), assess the current diversity of the group of devices (e.g., that have been selected for monitoring), and generate recommendations to reach or approach the target diversity level. The system 100 includes a client device 104 and a computer system 110 that includes functionality to make diversity assessments of devices and/or software selected for monitoring. The computer system 110 may further include functionality to select corresponding actions to perform or recommend in order to achieve the target diversity level.

It may be important to achieve and/or maintain a target diversity level for monitored devices to ensure the viability of data or results obtained during the monitoring period. For example, the computer system 110 may monitor how particular software performs on a variety of devices associated with different groups to determine how the software will perform when publicly released. If however, the monitored devices are not representative of the devices used by the general population, then data or results obtained from the monitoring of the devices may lack utility or otherwise have only limited applicability. For example, the data or results may fail to identify incompatibility between the monitored software and devices associated with a particular group when those devices are not included in the monitoring or are unrepresented (e.g., when compared to the use of those devices in the general population) to the point that statistically significant results regarding those groups of devices cannot be obtained or are sufficiently unlikely to be obtained.

Accordingly, in identifying a target diversity level and working to achieve or maintain the target diversity level, the computer system 110 can obtain improved data or results from the monitoring of multiple devices or software running on those devices. The improved data or results may be more comprehensive in that they correspond to a more diverse device pool.

In addition, in identifying a target diversity level and working to achieve or maintain the target diversity level, the computer system 110 can more efficiently conduct monitoring of multiple devices or software running on those devices. For example, the computer system 110 may determine that based on a reference population of devices (e.g., devices used in target region), the target diversity level should provide that no devices (or a very limited number of devices) that are Group 4 devices should be monitored. This may be based on, for example, the reference population of devices not including any (or a very limited number of) Group 4 devices. As such, the computer system 110 can improve efficiency by limiting the enrollment and monitoring of devices to those devices that are not Group 4 devices. That is, the computer system 110 can limit the enrollment and monitoring of devices to only those devices that will produce useful results (e.g., as may be indicated by the target diversity level). This has the added benefit of reducing computational burden on the computer system 110, reducing the amount of computing resources (e.g., CPU hours, RAM, etc.) that would have been otherwise spent monitoring the unnecessary devices (e.g., Group 4 devices), freeing up computing resources to perform other tasks, etc.

As illustrated in FIG. 1, the computer system 110 has access to a database 112 and also communicates with the client device 104 over a network 150. The computer system 110 can receive data from the client device 104 and can send data to the client device 104 as will be described in more detail below. For example, the computer system 110 can receive monitoring instructions 106 from the client device 104 indicating monitoring criteria and/or criteria for device selection, an indication of devices to select for monitoring, and/or an indication of software to monitor that is to be run on a cohort of devices. The computer system 110 may store the monitoring instructions 106, e.g., the criteria and/or device selections, in the database 112, perform a diversity analysis using the monitoring instructions 106, generate analysis results and/or recommendation(s) for the monitoring program, and/or transmit the analysis results and/or recommendation(s) to the client device 104. The computer system 110 may additionally or alternatively automatically perform one or more actions based on the results of the diversity assessment. For example, the computer system 110 may automatically adjust monitoring parameters, add or remove inclusion criteria for devices, add or remove exclusion criteria for devices, enroll or remove from enrollment one or more devices, etc.

Eligibility criteria such as inclusion criteria which dictates the minimum requirements that devices must meet to be enrolled in the monitoring program and exclusion criteria which dictates which devices must be excluded (e.g., even if they meet the inclusion criteria) may be used to determine which devices to enroll and, therefore, which devices to monitor. Sometimes eligibility criteria can have a detrimental effect on diversity as certain eligibility criterion may disproportionately impact certain groups of devices, e.g., a particular model of device, devices running a particular operating system (OS), devices running a particular OS version, a particular model or series of devices, devices having a particular hardware component, etc.

The client device 104 may be used by an administrator 102 to perform various actions with respect to the monitoring of devices. For example, the administrator 102 can use the client device 104 to create a new monitoring program (e.g., to test new software or a new version of software, such as a particular software module, a new operating system version, etc.), update a monitoring program (e.g., update parameters of a monitoring program, add or remove inclusion criteria for the devices, add or more exclusion criteria for the devices, enroll or remove devices from monitoring, etc.), and/or monitor the devices (e.g., monitor the performance of devices while running particular software, monitor the devices for errors or malfunctions, monitor the devices activity of participants, data collected from participants, review recommendations from the computer system 210, etc.). The client device 204 may be a computing device, such as a desktop computer, a laptop computer, a smartphone, a tablet, a cell phone, etc.

The computer system 110 may monitor a cohort of devices to, for example, test new or existing software. For example, the computer system 110 may, based on the monitoring instructions 106, determine that a new software program, Program A is to be tested on a cohort of devices to determine if minimum performance can be achieved across a variety of devices, to identify errors that are caused or might be caused as a result of running the Program A on a variety of devices such as system crashes, to determine if Program A causes any devices to overheat or experience other malfunctions, etc. The administrator 102 may initiate the monitoring of devices through the client device 104, e.g., in order to determine if new software is ready for release (e.g., to the public, to a particular country, to a particular region, to personnel of a particular business, to a particular group of persons, etc.), to determine if new or existing software is sufficient to meet the needs of a client (e.g., a particular business, a government entity, a particular group of persons, etc.), to determine if the new or existing software meets performance criteria (e.g., minimum loading times, minimum response times such as a render response time or a server response time, maximum battery life drain on underlying device, minimum throughput performance, minimum concurrency performance, maximum load times, latency requirements, maximum error rates, etc.).

The computer system 110 may monitor a cohort of devices to, for example, test the performance of the devices and/or test the hardware components of devices. For example, the computer system 110 may, based on the monitoring instructions 106, determine that devices with the latest CPU B should be tested to identify the performance benefits provided by CPU B. The administrator 102 may initiate the monitoring of devices through the client device 104, e.g., in order to start the monitoring of devices having CPU B during performance testing. The monitoring instructions 106 may indicate, for example, that the inclusion criteria for the monitoring program includes a requirement that all enrolled devices have the CPU B. Based on this, the computer system 110 may select a subset of available devices for performance testing, where each of the selected devices includes the CPU B. The computer system 110 may perform a diversity analysis on the selected subset of devices. The diversity analysis may reveal, for example, that one more additional devices should be included in the performance testing, such as one or more devices from varying groups of devices (e.g., the groups of devices corresponding to particular manufactures, particular hardware components, particular operating systems or other software, etc.).

The computer system 110 may communicate with the client device 104 and various devices, such as devices in a first group of network devices 120a, in a second group of network devices 120b, and/or in a third group of network devices 120c over a network 150. The network 150 can include public and/or private networks and can include the Internet. The network 150 may include wired networks, wireless networks, cellular networks, local area networks, wide area networks, etc.

The devices in the first group of network devices 120a, the second group of network devices 120b, and the third group of network devices 120c may include devices that may optionally be monitored. These candidate devices may be, for example, specifically used for testing, e.g., software and/or performance testing. For example, these devices may be part of a mobile device farm. These devices may include, for example, network-enabled computing devices, such as one or more desktop computers, laptop computers, smartphones, cell phones, tablets, etc.

A reference composition 122 is the group composition for a particular population of devices and is used by the computer system 110 to determine a composition target 124. That is, the reference composition 122 may reflect group diversity for a particular set of devices (e.g., the set of devices used by the general public, used by a particular government agency, used by a particular business, used by a particular group of individuals that meet certain selection criteria such as being recently released or having particular hardware components, etc.). The reference composition 122 may be selected by the administrator 102, or determined by the computer system 110 based on information provided by the administrator 102 (e.g., provided in the monitoring instructions 106). For example, if the administrator 102 provides in the monitoring instructions 106 that a new software module is to be tested for a particular government agency, the computer system 110 may determine that the devices currently in use for the personnel of the government agency should be used as a reference population of devices. Based on this the computer system 110 may determine the reference composition 122 by, for example, accessing data from the database 112 or from remote storage that indicates that 70% of the personnel of the government agency use smartphones running OS A, and 30% of the personnel of the government agency use smartphones running OS B.

The computer system 210 may use the reference composition 122 to determine a composition target 124 for the set (e.g., cohort) of devices to be monitored. For example, the composition target 124 may be determined by removing one or more group of devices from the reference composition 122, by adjusting the reference composition 122 to account for trends (e.g., to estimate a new composition for a population of devices at a future point in time), etc. The composition target 124 may indicate the sought device diversity for monitoring, e.g., at an enrollment stage of monitoring or, more likely, at the conclusion of the conclusion of monitoring. As an example, if a selected set of devices to be monitored for performance over a period of one month is being performed for new devices that have not previously undergone performance tests, the computer system 110 may determine the composition target 124 by limiting the device population of the reference composition 122 to only those devices in the device population that are new models released in the last year and/or are models that have not previously undergone performance tests. The computer system 110 may use the reference composition 122 to identify the different group percentages for the composition target 124. The computer system 110 may similarly determine what devices to enroll in monitoring based on the cohort composition target 224, e.g., in an effort to have an observed/enrolled group composition 126 of devices at the end of the monitoring program match the composition target 124.

The composition target 124 may additionally or alternately indicate a quota that needs to be met for the different groups of devices. For example, the composition target 124 may additionally or alternatively indicate that there needs to be at least two devices from the Group 3 network devices 120c and at least one device from the Group 1 network devices 120a.

Continuing the earlier example, if the reference composition 122 provides for 70% Group 3 devices 120c and 30% Group 1 devices 120a and trend data (e.g., previously determined by the computer system 110 and stored in the database 112) indicates that there is a trend of a growing population of percent of Group 3 devices 120c relative to the population of Group 1 devices 120a, then the computer system 110 may calculate the composition target 124 based on the trend data as 75% Group 3 devices 120c and 25% Group 1 devices 120a.

The group composition 126 may represent the current composition of a relevant population of devices to be monitored. For example, at a time of enrollment, the group composition 126 may refer to the composition of a group of devices that have been enrolled by the computer system 110 in the monitoring program. Similarly, during the monitoring program, the group composition 126 may refer to the composition of a group of devices that are still undergoing monitoring. Some devices that were initially enrolled may no longer be monitored at this time due to, for example, errors, crashes, hardware failures, etc. As another example, some devices that were initially enrolled may have been removed by the computer system 110 from enrollment to meet diversity criteria. Accordingly, the computer system 110 may determine the group composition 126 multiple times through the monitoring program, e.g., at fixed time intervals, in response to errors or warnings being detected, when certain monitoring milestones are reached (e.g., tests regarding a particular performance parameter are completed).

The computer system 110 can also be used to automatically determine devices and/or software eligible for monitoring or to enroll in monitoring based on information provided by the administrator 102. For example, the administrator 102 may provide selection criteria that indicates parameters for monitoring (e.g., as part of the monitoring instructions 106), such as a length of time that the monitoring will take place for, a time of day that the monitoring will take place for, frequency of data requests to the monitored devices and/or data transmissions from the monitored devices, inclusion requirements for the devices or software that are used to determine eligibility, exclusion criteria for the devices or software that may dictate the automatic removal of any devices or software that meet one of the exclusion criterion (e.g., even if the devices or software meet the inclusion requirements), etc.

Where the selection criteria has or is predicted by the computer system 110 to have a disproportionately adverse effect on a particular group of devices (e.g., such that it is predicted that the diversity of devices at an end of the monitoring period will be outside of a target diversity device composition), the system 100 may generate a warning and/or a recommendation to adjust the selection criteria. In some cases, instead of generating a recommendation, the system 100 may perform one or more actions automatically.

The devices or software to be monitored may include, for example, computer devices, such as network enabled smartphones, tablet computers, laptop computers, desktop computers, etc. The devices or software may additionally or alternatively include particular software that is running on device, a virtual machine, a container, a network environment, a virtual network environment, etc. For example, the computer system 110 may be used to monitor a particular type of OS software that it would like to test on multiple different devices (e.g., of different manufacturers, models, hardware specifications, CPU types, RAM amounts, etc.). The computer system 110 may receive an indication from the administrator 102 of the software to be monitored and selection criteria for the devices that are to run the software. The computer system 110 may determine a diverse group of devices to run the software, or determine that a group of devices selected by the administrator 102 does not meet diversity criteria (or is unlikely to meet the diversity criteria).

As illustrated in FIG. 1, the overall process of creating and carrying out a monitoring program may be broken down into different stages 132-140. In the first stage 132, the administrator 102 can select through the client device 104 a set of devices (e.g., cohort of devices) to monitor or the computer system 110 can select the set of devices based on the monitoring instructions 106. Continuing the earlier example, the computer system 110 may select three devices from Group 3 devices 120c and one device from the Group 1 devices 120a to monitor based on the monitoring instructions 106 and previously determined trend data. In response to the selection of the set of devices that are to be monitored, the computer system 110 may calculate diversity measures 130 to determine if the selected set of devices meets diversity criteria. The diversity measures 130 may include, for example, the current group composition 126 determined using the selected devices. For example, the computer system 110 may determine that group composition is 75% Group 3 devices 120c and 25% Group 1 devices 120a as indicated by the key 128. The diversity measures 130 may include the reference composition 122 or an update to the reference composition 122, the composition target 124 or an update to the composition target 124, and/or the results of a comparison of the group composition 126 (or a predicted group composition 126 for the end of the monitoring program) to the composition target 124. The diversity measures 130 may also include the calculation of new trend data or the updating of existing of trend data using new information.

As an example, in generating the diversity measures 130, the computer system 110 may determine, based on trends in one or more devices populations, that Group 2 devices have a fast growing population. Based on this, the computer system 110 may determine that the results of the monitoring program will have limited applicability if Group 2 devices are unrepresented or not included. As such, the computer system 110 may calculate a new composition target 124 that accounts for the growing use of Group 2 devices. For example, the computer system 110 may determine that the composition target 124 should be 20% Group 1 devices 120a, 40% Group 2 devices 120b, and 40% Group 3 devices 120c.

In the second stage 134, the computer system 110 determines that the selected subset (e.g., the initial device selection) does not meet diversity criteria. For example, the computer system 110 may determine that the diversity criteria is not met if the group composition 126 does not include or is predicted not to include by the end of the monitoring program a device from a device group in the composition target 124. Similarly, the computer system 110 may determine that the diversity criteria is not met if the group composition 126 deviates a threshold percent (e.g., for any one group of devices) or predicted to deviate by a threshold percent by the end of the monitoring program from the composition target 124. As another example, the computer system 110 may determine that the diversity criteria is not met if the group composition 126 or the predicted group composition at the end of the monitoring program is not within range (e.g., for any one group of devices) of a target diversity range (e.g., calculated based on the composition target 124).

In an optional third stage 136, the computer system generates a recommendation to meet the diversity criteria. For example, the computer system 110 may generate a recommendation 108 that it transmits to the client device 104. The recommendation may be to add a device from an underrepresented group of devices, remove a device from enrollment that is in an overrepresented group of devices, remove inclusion an inclusion criterion so that more devices may qualify for enrollment, remove an exclusion criterion so that less devices will be rejected from enrollment, etc. For example, if the inclusion criteria indicated that the device had to be one of a set of specific device models, the computer system 110 may recommend that the inclusion criteria be removed (e.g., as it may be overly restrictive for failing to account for new device models). Similarly, continuing the earlier example, the computer system 110 may recommend for two devices from the Group 2 devices 120b to be added and for one of the Group 1 devices 120c to be removed.

In an optional fourth stage 138, the computer system 110 receives confirmation from the client device 104 to perform the actions specified in the recommendation 108.

In some cases, the computer system 110 receives instructions to perform one or more different or modified actions compared to the actions in the recommendation 108.

In the fifth stage 140, the computer system 110 selects a new subset of devices to monitor. For example, in response to receiving a confirmation to perform the recommended actions provided in the recommendation 108, the computer system 110 may enroll two devices from the Group 2 devices 120b as indicated by the key 128. By doing this, the computer system 110 can update the group composition 126 so that the current group composition 126 or a predicted group composition at the end of the monitoring program will match (or be sufficiently close to) the composition target 124 and/or so that a minimum number of Group 2 devices 120b can be enrolled in the monitoring program. This would indicate that sufficient device diversity is predicted to be met based on the updates to the enrolled devices.

Other changes or modifications to the enrolled devices may be performed at other stages of the monitoring program. These changes or modifications may be made for diversity purposes based on newly determined diversity measures. These changes or modifications may be based on changes to the enrolled devices, a warning generated in response to new data indicating that the composition target 124 is unlikely to be met by the end of the monitoring program (e.g., new trend data, data indicating the a number of devices from a particular group of devices have been unenrolled, etc.), etc.

Figure 2:
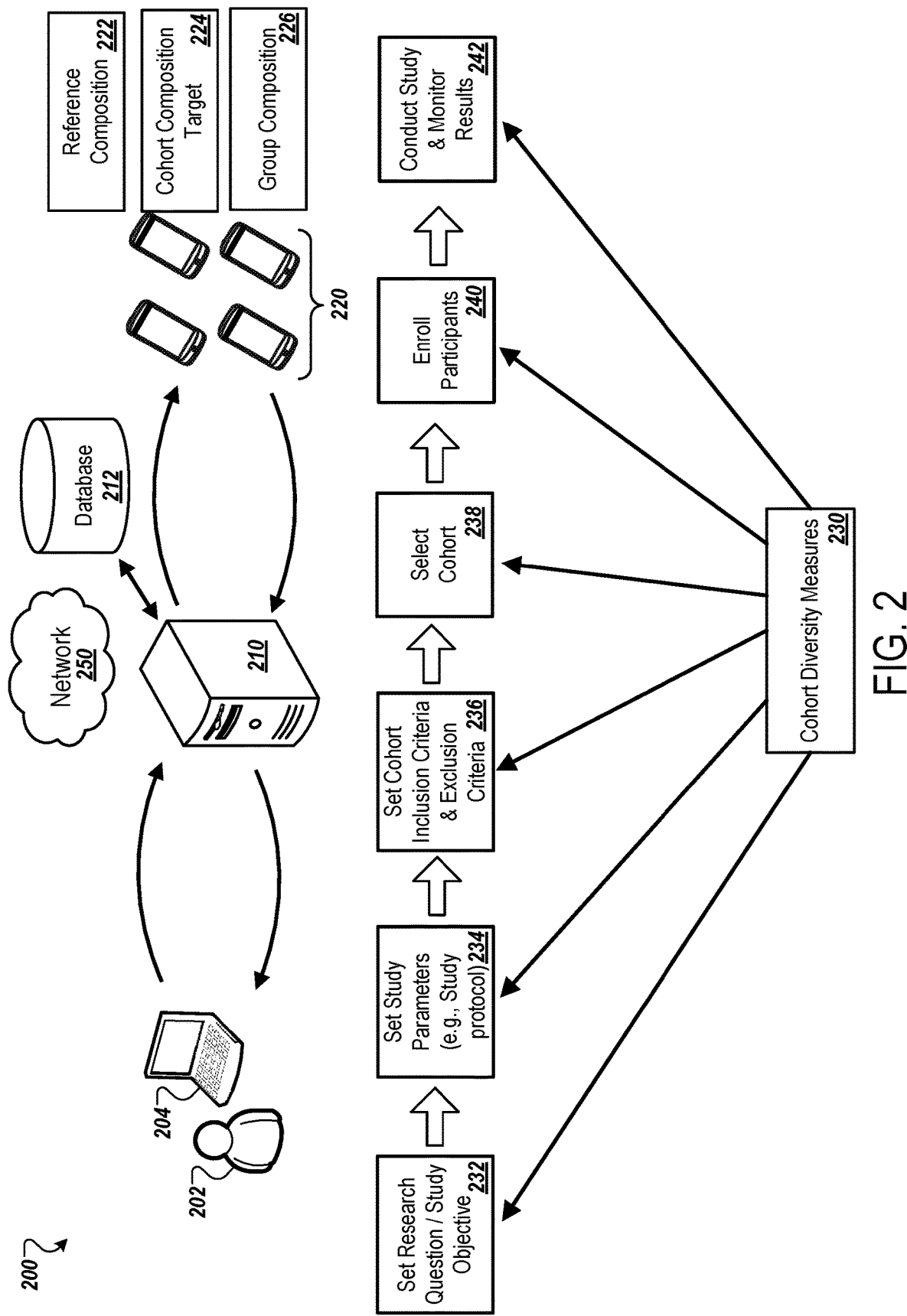
FIG. 2 is a diagram that illustrates an example system for performing diversity assessment and action selection.

FIG. 2 is a diagram that illustrates an example system 200 for performing diversity assessment and action selection. Among other uses, the system 200 can be used to assist in the creation and implementation of research studies (e.g., clinical trials, experimental studies, longitudinal studies, correlational studies, case studies, etc.). Specifically, the system 200 can be used to, for example, identify a target diversity level for a research study (e.g., based on one or more goals for the research study), assess the current diversity of the research study, and generate recommendations to reach or approach the target diversity level. The system 200 includes a client device 204 and a computer system 210 that includes functionality to make diversity assessments of one or more research studies and to select corresponding actions to perform or recommend. The numerous benefits discussed above with respect to the computer system 110 are applicable to the computer system 210.

The systems discussed herein, including the computer system 210, can be used to create, manage, adapt, and evaluate monitoring programs in many fields, including manufacturing quality control, environmental monitoring, health research, and many other areas where sampling is used to monitor a subset of a population. In the case of health research in particular, the system can be a multi-tenant system for administering clinical trials through remote devices. The system can create and adapt clinical trials that involve many users remotely collecting user input and sensor data through mobile devices. The system can create and administer studies for various different organizations, allowing the system to efficiently administer many clinical trials concurrently, each with their own separate monitoring groups (e.g., cohorts of participants with associated devices), objectives for monitoring, data collection and reporting procedures, and requirements for diversity in the monitoring groups.

The techniques described can be used to achieve various benefits. For example, by taking into account diversity at the onset and multiple times throughout a clinical study, numerous health benefits can be achieved. Notably, diversity in a research study can be monitored and actions performed in an effort to maintain a target level of diversity such that the results of the study are applicable to typically unrepresented segments of a population. With respect to new medications and treatments, the applicability of these new medication and treatments may be extended such that those belonging to the underrepresented segments can be safely administered the medications/treatments where there otherwise would have been significant doubt due to, for example, there being no data collected for these groups and/or an insufficient amount of data for the results to be statistically relevant for these groups. Similarly, negative interactions and side effects of new medications/treatments for those belonging to the underrepresented segments are more likely to be identified, thereby reducing the risk of injury or death.

As an example, many recent COVID-19 vaccine trials excluded pregnant women due to pregnant women being a high risk group. Unfortunately, by eliminating this group of participants from the vaccine trials, there is insufficient data to determine if many of the vaccines can be safely administered to pregnant women. The disclosed system may identify pregnant women as a group that should be included for a vaccine or medical trial as an underrepresented or excluded group of participants. This may be especially true for medications that are likely to be taken by pregnant women, such as those that are meant to address pregnancy issues, illness that commonly arise during pregnancy, medications that are typically taken by women between the ages 18 and 54, etc. The disclosed system may further account for the increased risks by, for example, making a researcher aware of the increased risks, recommending additional or more comprehensive monitoring during the study for this particular group of participants, recommending a lower dose of the medication or vaccine being tested for this particular group of participants, etc. In this way, important data can be collected on the underrepresented or excluded group of pregnant women while steps can be taken to reduce the risk presented to this group. The collected data may indicate whether it is safe to administer the vaccine to pregnant women, whether there are any side effects unique to pregnant women, whether there are any reactions to the vaccine associated with medications typically taken by pregnant women, etc. Accordingly, in recommending that this group of typically excluded or underrepresented participants be included in the study, the disclosed system can improve the safety afforded to those in the group.

In general, diversity may refer to the variety of groups or attributes represented in a set (e.g., a monitoring group for a monitoring program, a candidate pool, etc.). One way to assess diversity is to assess distribution of members of a monitoring group across different groups, e.g., to determine whether the distribution of members into the different groups is sufficiently similar to the distribution of those groups among a reference population. This population may be a current population at a geographical region or an expected future population, a group that has been invited to participate in a research study, a group (e.g., cohort) that has enrolled in a research study, a group that has enrolled and remains active in a research study, etc. This population may additionally or alternatively be a subset of a larger reference population.

The categories or profiles used as different groups to assess diversity may be defined using one or more attributes, including demographic and non-demographic characteristics. In many cases it is important to obtain diversity not only in demographics, but also in health status, lifestyle, location, context, medical history, and other factors to obtain a broad and effective monitoring. As an example, groups to be assessed during a research study may be defined to have certain combinations of attributes, with one group having a first set of attributes, a second group having a second set of attributes, and so on. The attributes used to define groups can include race, ethnicity, nationality (or nationality of relatives such as parents or grandparents), residence in a certain region (e.g., city, county, state, country, etc.), genomics data (e.g., having a particular gene variant or not having a particular gene variant), state of health (e.g., a body fat percentage of less than 25%), physiological attributes (e.g., weighing more than a threshold amount, weighing less than a threshold amount, having a RHR within a particular range, etc.), psychological attributes, and so on. The attributes can include behavior factors such as sleep, diet, exercise, and other behavior factors.

Other examples of characteristics that can be used to define a group may include ages, age ranges, medical conditions, medicines (e.g., that have been prescribed and/or are being taken by individuals), treatments (e.g., that individuals are undergoing), etc. For example, a first group of a particular population may correspond to all those in the population that have been diagnosed with diabetes, while a second group of the population may correspond to all those in the population that have not been diagnosed with diabetes, and a third group of the population may correspond to all those in the population between the ages of 20-40 regardless of whether they are diagnosed with diabetes It may be important to achieve and/or maintain a target diversity level for participants in a study to ensure the viability of data or results obtained during the study. For example, the computer system 210 may want to perform a research study to determine the effectiveness and safety of a new pharmaceutical. If however, the study participants are not representative of a reference population that is to use the new pharmaceutical, then data or results obtained from the study may lack utility or otherwise have only limited applicability. For example, if a target group composition cannot be achieved by the end of the study (or the target group composition cannot be achieved within a margin of error), the results of the study may fail to identify side effects of those in groups that are typically excluded from studies due to the higher risk they present (e.g., pregnant women, elderly persons, those with particular diseases or other serious ailments, etc.), of those in groups that are typically less likely to join or complete a study, those in groups that have difficulty meeting the requirements of a study (e.g., due to residential location, access to vehicles, access to computing devices, etc.), etc. Similarly, the data may be insufficient to determine if the medication can be safely administered to those groups.

The computer system 210 may access data corresponding to a particular reference population, such as a list of persons in the reference population. The computer system 210 may filter the reference population to those that have the characteristics corresponding to a particular group, and proceed to sample from the filtered list, e.g., in order to identify a manageable list of persons associated with first group. As will be described in more detail below, the computer system 210 can use this sampled list in a variety of ways. For example, the computer system 210 may simply invite the persons in the sample list. As another example, the computer system 210 may analyze the other characteristics of the persons in the sample list and use these characteristics to identify persons to be invited/enrolled in the study, and/or removed from consideration or enrollment for the study. In this way, the computer system 210 can enroll participants who more accurately represent the larger reference set (e.g., the reference population).

In general, study parameters may include the information that defines the protocol for a study. The study parameters may include, for example, one or more locations where the study is to be conducted, an expected number of participants for the study, a length of the study, an age range of participants for the study, a budget for the study, a target date for the release of a medication or treatment being studied, etc. The study parameters may also include requirements of the participants and/or for how the study is to be conducted. For example, a first parameter for a new research study may provide that participants will be required to attend three medical office visits per month, and a second parameters may provide that participants are required to have or obtain a smartphone. The study parameters may be set by a researcher 202 through the client device 204, by the computer system 210, or by a combination of the researcher 202's inputs and the computer system 210.

In general, eligibility criteria (also referred to as selection criteria) are used to identify devices and users that can appropriately participate in a monitoring study. The criteria may include inclusion criteria and exclusion criteria described in more detail below. Eligibility criteria may also refer to other requirements provided in the study parameters. For example, there may be an eligibility criterion that participants have access to a smartphone, laptop, or other network-enabled computing device due to the study parameters requiring the participants to make frequent telehealth visits. The system 210 ensures not only that eligibility criteria are satisfied for participants in a monitoring program, but that the desired level of diversity is present across the monitoring group as a whole, with diversity being tracked and achieved for each of the different types of attributes that are important for achieving the outcome of the monitoring program.

In general, inclusion criteria may refer to the minimum requirements that candidates must meet in order to be enrolled in study. The inclusion criteria may be based on the question (e.g., goal) of the study, e.g., provided by the researcher 202. For example, if a new study is designed to research the side effects of a new Drug X for the treatment of high cholesterol, then the inclusion criteria for the study may include a requirement that participants have high cholesterol. The inclusion criteria may be set by the researcher 202 using the client device 204. The computer system 210 may additionally or alternatively set the inclusion criteria. For example, based on information sent to the computer system 210 from the client device 204 indicating that the goal of the researcher study is to identify the side effects of a new Drug X for the treatment of high cholesterol, the computer system 210 may, based on this information, add a requirement that each participant have high cholesterol to the inclusion criteria or may generate a recommendation for the researcher 202 to add this criterion or confirm its inclusion. Other examples of inclusion criteria may include a particular age or age range (e.g., corresponding to a particular group of persons that are most likely to take Drug X).

In general, exclusion criteria may refer to attributes of candidates that prevent them from being enrolled in the study (e.g., even if they meet the inclusion criteria). The exclusion criteria may be based on and/or otherwise take into consideration risk factors. For example, the exclusion criteria may prevent those who are pregnant or over a certain age from participating in the study. The exclusion criteria may be based on the question (e.g., goal) of the study, e.g., provided by the researcher 202. For example, if a new study is designed to research the side effects of a new Drug X for the treatment of high cholesterol, then the exclusion criteria may include attributes that have known negative effects with Drug X. For example, the computer system 210 may refer to previous studies stored in a database 212 that indicates that Drug X cannot be safely administered to those with diabetes. In response, the computer system 210 may automatically add diabetes as an exclusion criterion for the research study, or generate a recommendation to add diabetes as an exclusion criterion and send the recommendation to the client device 204 to present to the researcher 202.

As illustrated in FIG. 2, the computer system 210 has access to the database 212 and also communicates with the client device 204 over a network 250. The computer system 210 can receive data from the client device 204 and can send data to the client device 204 as will be described in more detail below. For example, the computer system 210 can receive data from the client device 204 indicating a question and/or requirements for a study (e.g., to initiate a new research study). The computer system 210 may store questions and/or requirements in the database 212, perform a diversity analysis using the questions and/or requirements, generate analysis results and/or recommendation(s) for the new study, and/or transmit the analysis results and/or recommendation(s) to the client device 204. The computer system 210 may additionally or alternatively automatically perform one or more actions based on the results of the diversity assessment. For example, the computer system 210 may automatically adjust study parameters, add or remove inclusion criteria, add or remove exclusion criteria, enroll or remove one or more participants, send invitations to enroll to one or more participants, etc.

The client device 204 may be used by a researcher 202 to perform various actions with one or more research studies. For example, the researcher 202 can use the client device 204 to create a research study, update a research study (e.g., update parameters of a research study, add or remove inclusion criteria of a research study, add or more exclusion criteria of a research study, enroll or remove participants of a research study, etc.), and/or monitor a research study (e.g., monitor activity of participants, data collected from participants, review recommendations from the computer system 210, etc.). The client device 204 may be a computing device, such as a desktop computer, a laptop computer, a smartphone, a tablet, a cell phone, etc.

The computer system 210 may communicate with the client device 204 and the participant devices 220 over a network 250. The network 250 can include public and/or private networks and can include the Internet. The network 250 may include wired networks, wireless networks, cellular networks, local area networks, wide area networks, etc.

The computer system 210 can also communicate with participant devices 220. The participant devices 220 may belong to users who have been invited to enroll in a research study, have enrolled in the research study, and/or are enrolled and active in the research study. The participant devices 220 may be computing devices. For example, the participant device 220 may include one or more desktop computers, laptop computers, smartphones, cell phones, tablets, etc.

A reference composition 222 is the group composition for a particular population and is used by the computer system 210 to determine a cohort composition target 224. That is, the reference composition 222 may reflect group diversity for a particular population (e.g., for a particular region, a particular region at a future point in time, those having a particular medical condition, those taking a certain medication, those belonging to a particular age group, etc.). The reference composition 222 may be selected by the researcher 202, or determined by the computer system 210 based on information provided by the researcher 202. For example, if the researcher 202 provides that a study regarding a new cholesterol medication is to take place in Virginia and does not specifically indicate a reference population, the computer system 210 may use Virginia as a reference population. The computer system 210 may proceed to identify the group composition of the reference population. For example, the computer system 210 may look up and/or estimate the percentage of Virginia's population that have or are likely to experience high cholesterol, percentages corresponding to particular races or ethnicities, percentages corresponding to particular age ranges, etc.

The computer system 210 may use the reference composition 222 to determine a cohort composition target 224. For example, the cohort composition target 224 may be determined by removing one or more groups from the reference composition 222 (e.g., if you want to focus the study on only persons suffering from a particular medication), by adjusting the reference composition 222 to account for trends (e.g., to estimate a new composition for a population at a future point in time), etc. The cohort composition target 224 may indicate the sought group diversity for a new research study, e.g., at enrollment or, more likely, at the conclusion of the research study. As an example, if a new research study is to study the effects of a new cholesterol medication, the computer system 210 may determine the cohort composition target 224 by limiting the population of the reference composition 222 to only those in the population that are suffering from high cholesterol or are likely to suffer from high cholesterol. The computer system 210 may use the reference composition 222 to identify the different group percentages for the cohort composition target 224. The computer system 210 may determine what candidates to invite and/or enroll based on the cohort composition target 224, e.g., in an effort to have a group composition 226 at the end of the study match the cohort composition target 224.

As an example, the reference composition 222 may indicate for a corresponding population that a first group corresponding to those of a first ethnicity makes up 55% of the population, that a second group corresponding to a second ethnicity makes up 20% of the population, that a third group corresponding to third ethnicity makes up 15% of the population, and that a fourth group corresponding to those that have or are likely to from high cholesterol makes up 43% of the population. In determining the cohort composition target 224, the computer system 210 may refer to the reference composition 222 to determine percentages for the first three groups when the population is limited to the fourth group. For example, the computer system 210 may use the reference composition 222 to determine that 52% of the individuals in the fourth group also belong to the first group, that 25% of the individuals in the fourth group also belong to the second group, and that 12% of the individuals in the fourth group also belong to the third group. The computer system 210 may proceed to set the cohort composition target 224 to 52% for the first group, 25% for the second group, 12% for the third group, and 11% to one or more other groups.

The group composition 226 may represent the current composition of a relevant population of the study. For example, the group composition 226 may refer to the composition of a group of candidates that were invited to enroll in a study and/or to a cohort of enrolled participants. The computer system 210 may determine the group composition 226 multiple times through the study, e.g., once for each stage of the research study. The group composition 226 may be calculated using different populations. For example, the group composition 226 may initially be calculated for the candidate pool of potential participants, to a group of candidates that were invited to enroll, to the cohort of enrolled participants (e.g., at one or more points throughout the study), etc.

As illustrated in FIG. 2, a research study may be broken down into different stages 232-242. In the first stage 232, the researcher 202 can use the client device 204 to set a research question or study objective. For example, the researcher 202 can initiate a new study through the client device 204 by submitting a study objective to study the side effects of a new Drug X for treating high cholesterol. In the second stage 234, the researcher 202 and/or the computer system 210 set parameters for the study, such as a study size, a region where the study is to take place, devices and/or sensors needed for the study, etc. As an example, the computer system 210 may generate one or more recommendations for study parameters, such as a recommended study size. In the third stage 236, the researcher 202 and/or the computer system 210 set cohort inclusion criteria and/or exclusion criteria. In the fourth stage 238, the researcher 202 and/or the computer system 210 select the cohort. Selecting the cohort may include identifying a group of candidates send enrollment invitation to. Alternatively, selecting the cohort may include identifying a group of candidates from an applicant pool to enroll. In the fifth stage 240, the cohort participants are enrolled. The computer system 210 may generate and send a notification to the participant devices 220 indicating that they have been enrolled. In the sixth stage 242, the study is conducted and the results are monitored. Data may be obtained from the participants through the participant devices 220. The data may be used to identify an activity or participation level of the participants, participants who are inactive, participants who have unenrolled, etc.

Each of the stages 232-242 of the research study may be based on cohort diversity measures 230. That is, the cohort diversity measures 230 may be used by the computer system 210 to confirm or modify how the research study is to proceed from one stage to the next. The cohort diversity measures 230 may include results of one or more diversity analyses, e.g., which may differ depending on the present stage of the research study. For example, with respect to the first stage 232, the cohort diversity measures 230 may include an indication of biases associated with the research question/study objective, or type of research question/study objective. Specifically, if the research study objective is set to study the effects of Drug X for the treatment of high cholesterol, the computer system 210 may access historical data and/or remote data of previous cholesterol research studies that shows that persons of Asian ethnicity are often unrepresented by 20% in cholesterol research studies. There may be relevant reasons for this, such as the possibility of persons of Asian ethnicity being significantly less likely to have high cholesterol. However, despite this, it may be critical to accurately represent the Asian ethnicity segment of the cohort composition target 224 to ultimately determine if Drug X can be safely administered to those of Asian ethnicity and/or to identify dangerous side effects which may disproportionately affect those of Asian ethnicity. More generally, the cohort diversity measures 230 may show that persons of a certain group are consistently underrepresented in clinical trials involving a new medication, such as pregnant persons, persons older than 70 years of age, persons with immune system disorders, etc.

The cohort diversity measures 230 may include one or more diversity levels calculated by the computer system 210. These diversity levels may correspond to a current level of diversity, e.g., present among previous participants (e.g., potential candidates), those invited to enroll in the study (e.g., candidates), those that have accepted to be enrolled in the study and/or are enrolled in the study (e.g., participants), etc. Additionally or alternatively, these diversity levels may correspond to a predicted level of diversity at a future point in time, such as the study completion.

A determined diversity level may indicate how close the predicated group composition at study completion is to the cohort composition target 224. The diversity level may be expressed as, for example, a diversity score. That is, the diversity level may be expressed a value (e.g., a number, a classification, etc.) that is indicative of how close the predicted group composition at study completion is to the cohort composition target 224 (e.g., a target group composition). In some cases, the score can indicate a magnitude of how far the distribution or composition of members of the cohort varies from the target distribution or composition. As an example, a diversity score of 1.0 may indicate that the predicted group composition at study completion matches the cohort composition target 224. Lower scores can indicate increasing differences from the target level, e.g., a score of 0.9 may indicate that the composition varies from the target by at least 5% in at least one category or attribute, a score of 0.8 may indicate that the composition varies from the target by at least 10% in one target or attribute, etc. The scoring can change linearly or nonlinearly with the amount of deviation from the target.

The diversity score for a monitoring group may be determined as an aggregate or composite of separate scores for different categories or profiles for which composition is tracked. For example, if there are 5 different types of participants needed, and only four of the 5 meet the requirements for the minimum number of participants, then the diversity score can be 80%. Separate scores may be determined for each category or group to be included, and those scores can be averaged (e.g., if group 1 has 100% of needed members, group 2 has 90% of needed members, and group 3 has 60% of needed members, the average of 83% can be used as a diversity score for the monitoring group as a whole).

The diversity score may be based on absolute measures, such as the numbers of participants in each group, or it may be relative measures, such as the amount in one group relative to the amount in another category or to the monitoring group as a whole (e.g., a ratio, proportion, fraction, percentage, etc.). A diversity score can also be determined relative to other references, such as a previously predicted group composition, a previously determined diversity score, a predicted group composition corresponding to one or more recommendations (e.g., predicated based on an assumption that the recommended actions will be performed), etc.

Diversity scores can be generated and provided for each of the different categories or attributes that are relevant to the monitoring program. For example, the system can determine, for each of various groups to be represented in the monitoring group, how close the subset representing that group is to the target level for the group. This can help indicate, for example, the specific groups or categories of devices and users where additional representation is needed in the monitoring group.

Additionally or alternatively, the diversity level may be expressed as a probability or confidence score indicating the expected results for the study, such as a likelihood that a minimum amounts or proportions of the different groups represented in the monitoring group will achieve compliance with the requirements until the end of the monitoring program. Because there are multiple different groups or categories of members in the monitoring group, set of probabilities or confidence scores can be determined, with one for each of the different groups or categories. In addition, multiple versions of the scores can be determined for different scenarios, e.g., one for the current state of the monitoring program and the current monitoring group, and others representing the expected likelihood(s) of success that would result after performing different actions corresponding to different recommendations.

The diversity level may indicate a level of confidence in achieving the cohort composition target 224, and/or achieving a group composition that is with an acceptable range (e.g., percent range or value range) of the cohort composition target 224. For example, a diversity score of 0.91 may indicate that the computer system 210 has determined that there is 91% possibility of the group composition at study completion being within a threshold percentage (e.g., 5%, 3%, 1%, etc.) of the cohort composition target 224. Or, if the cohort composition target 224 is expressed as one or more ranges, the score can indicate the likelihood of the composition having representation of groups that falling within the target ranges.

Diversity level may also or alternatively describe a group composition (e.g., a predicted group composition), or the difference between a group composition (e.g., current or predicted) and the cohort composition target 224. For example, a predicted group composition at study enrollment may be a first diversity level, a predicted group composition at study completion may be a second diversity level, and a difference (e.g., difference between two sets of values, absolute value of the difference between the two sets of values, etc.) the group composition at study completion and the cohort composition target 224 as a third diversity level.

In some cases, there are multiple diversity metrics used to assess the level of diversity. For example, a first diversity level may include a diversity distribution indicating different likelihoods of achieving the cohort composition target 224, and a diversity score may be second diversity level identified from the diversity distribution (e.g., as the value associated with the highest probability out of the all of the values).

The target diversity level described above and elsewhere may refer to a single diversity level or to a group of multiple diversity levels or metrics. For example, a target diversity level may require as a first level or metric a requirement that a cohort (e.g., monitored group) meets certain enrollment minimums (e.g., at least one subject from each diversity group). For example, the enrollment minimums may provide that for each medical condition in a list of particular medical conditions, there are at least two corresponding subjects that have the medical condition. The target diversity level may further require a diversity score metric. For example, the monitoring program may require a diversity score of 0.7 or greater by the end of the monitoring program. This diversity score may be calculated using a target group composition of subjects and an observed or anticipated (e.g., at the end of the monitoring program) composition of subjects (e.g., determined from the current or anticipated enrollment of subjects in the monitoring program). This diversity score can, for example, represent the difference between the actual (e.g., observed or anticipated) composition of subjects and the target composition (e.g., a composition having sufficient or ideal diversity). For example, the diversity score may be a value between 0 and 1. Here, 0 may correspond to complete or maximum divergence or difference between a vector (or array) representing an actual composition of subjects and a second vector (or array) representing the target composition of subjects. Similarly, 1 may correspond to no or minimum divergence or difference between the two vectors or the two arrays. The computer system 210 may, therefore, calculate a diversity score and/or a target diversity level by calculating the difference or divergence between two or more vectors. Similarly, the computer system 210 may, therefore, calculate a diversity score and/or a target diversity level by calculating the difference or divergence between two or more arrays.

In determining a diversity level such as a diversity score, the computer system 210 may sample from a larger reference set to obtain a makeup that is representative of the larger reference set (e.g., replicating, within a predetermined tolerance, the distribution of certain attributes or characteristics that are relevant to the monitoring program). That is, the computer system 210 may sample from a larger reference set so that the sample reflects the characteristics across the reference group. For example, the computer system 210 may access from the database 212 or from an external data storage, data that corresponds to persons having characteristics that define a first group, such as being of a specific race, being of a specific ethnicity, being of a specific nationality, living in a certain region (e.g., city, county, state, country, etc.), having particular genomics data (e.g., particular gene variant), having a particular state of health, having particular physiological attributes (e.g., weighing more than a threshold amount, weighing less than a threshold amount, having a RHR within a particular range, etc.), having a particular diet or having particular eating habits (e.g., vegetarian, vegan, etc.), having a particular occupation, having a particular level of education (e.g., high school diploma, two years of college, four years of college, graduate degree, etc.), etc. The computer system 210 may access this data, such as a list of persons in the reference population (e.g., used to determine the reference composition 222) that belong to this first group, and proceed to sample the data (e.g., in order to identify a manageable list of persons associated with first group).

The computer system 210 can use this sampled list in a variety of ways. For example, the computer system 210 may simply invite the persons in the sample list, or a subset of persons in the sampled list, to participate in the study. As another example, the computer system 210 may analyze the other characteristics of the persons in the sample list and use these characteristics to identify persons to be invited/enrolled in the study, and/or removed from consideration or enrollment for the study. For example, if the sample data indicates that 95% of users associated with Group 1 also have characteristic B and none of the users associated with Group 1 have characteristic C, the computer system 210 may set characteristic B as inclusion criteria for Group 1 participants, and characteristic C as exclusion criteria for Group 1 participants. In this way, the computer system 210 can enroll participants who more accurately represent the larger reference set (e.g., the reference population).

The computer system 210 may make various recommendations or take various actions based on the determined diversity level(s). These diversity measures may be, for example, compared by the computer system 210 to one or more thresholds that correspond to particular recommendations and/or actions.

As another example with respect to the first stage 232, the cohort diversity measures 230 may also include an indications of determinations made by the computer system 210 with respect to whether the question/objective is too limited. For example, the computer system 210 may generate a warning if it determines that a study objective set by the researcher 202 will result in a restrictive FDA label. The computer system 210 may also generate a recommendation or identify an action to perform as part of the cohort diversity measures 230. For example, if the objective is to study the effects of a particular treatment on a small population segment, the computer system 210 may generate a recommendation to modify the objective to take into account other population segments, such as similar population segments.

As another example, with respect to the second stage 234, the cohort diversity measures 230 may include indications of particular study parameters that disproportionately affect certain groups of the cohort composition target 224. For example, the computer system 210 may generate a warning for a study parameter that requires that participants have or use a smartphone upon determining that the study parameter is predicated to significantly reduce the enrollment of users belonging to an example Group A. The cohort diversity measures 230 may also include a recommendation for a revised study parameter, a replacement study parameter, a removal of the study parameter, or an addition of a study parameter (e.g., the providing a smartphone to users in Group A as part of the study). The recommendations may be specific to particular population groups. Instead of a recommendation, one or more of the actions may be automatically performed by the computer system 210. The cohort diversity measures 230 may additionally or alternatively include the reference composition 222 determined by the computer system 210 based on the study parameters.

As another example, with respect to the third stage 236, the cohort diversity measures 230 may include indications of particular study criteria that disproportionately affect certain groups of the cohort composition target 224. For example, the computer system 210 may generate a warning for an exclusion criterion that prevents those older than 65 years old from enrolling in the study upon determining that the majority of persons belonging to Group B that are likely to enroll are older than 65 years old and/or upon determining that persons belonging to Group B that are older than 65 years old are much more likely to be retained than those in Group B under 65 years old. Accordingly, the exclusion criterion may prevent or make it exceedingly difficult for the group composition 226 to reach the cohort composition target 224 by the end of the research study. The cohort diversity measures 230 may also include a recommendation for a revised inclusion criterion or exclusion criterion, a replacement inclusion criterion or exclusion criterion, a removal of an inclusion criterion or exclusion criterion, or an addition of an inclusion criterion or exclusion criterion. The recommendation may be specific to particular population groups. Continuing the earlier example, the computer system 210 may generate a recommendation to remove the age exclusion criterion for only those belonging to Group B (e.g., to account for the particular conduct of Group B participants while limiting the amount of risk introduced that comes from enrolling those of advanced age). The cohort diversity measures 230 may additionally or alternatively include the reference composition 222 determined by the computer system 210 based on the study parameters, the inclusion criteria, and/or the exclusion criteria.

As another example, with respect to the fourth stage 238, the cohort diversity measures 230 may include recommendations as to what candidates should be invited for enrollment in the study, and/or what candidates should be accepted for enrollment if there are a group of applicant candidates. The cohort diversity measures 230 may also include a determined group composition for the recommended invitees/applicants, for the predicted cohort of enrolled participants at the start of the study (e.g., based on a prediction of what percentage of invitees from the different groups are expected to enroll), and for the predicted cohort of enrolled participants at the end of the study (e.g., based on a prediction of what percentage of the invitees from the different groups are expected to enroll and expected to be retained/remain active). The recommendation may be specific to particular population groups. As an example, the computer system 210 may generate a recommendation to invite 25% more candidates from Group B than from Group A based on historical data indicating that those from Group A are 20% more likely to enroll than those from Group B. Instead of generating a recommendation to send to the client device 204, the computer system 210 may perform one or more actions automatically. For example, the computer system 210 may automatically determine which candidates from an applicant pool to enroll, and/or which candidates from a candidate pool (e.g., previous study participants, previous study applicants, previous study participants that completed their respective studies, etc.) to invite.

As another example, with respect to the fifth stage 240, the cohort diversity measures 230 may include an updated group composition 226 based on the enrolled participants and an updated prediction for the group composition 226 at the end of the study (e.g., based on the past behaviors and/or trends of the different groups). The cohort diversity measures 230 may include an indication of the results of a comparison between the updated prediction for the group composition 226 at the end of the study and the cohort composition target 224. For example, the cohort diversity measures 230 may include warning that indicates too many persons from Group A have enrolled relative to the number of persons from Groups B and C that have enrolled. The cohort diversity measures 230 may also include recommendations corresponding to the enrolled participants. For example, if more candidates from Group A enrolled than was anticipated, the recommendations may include removing one or more of the participants from Group A (e.g., those that have been identified as the least reliable/active from historical data and/or stored user profile information in the database 212), to send new invites to candidates of Groups B and C, and/or to revise the study parameters, the inclusion criteria, and/or the exclusion criteria in order to increase the retention of those in Groups B and C. As an example, due to a low enrollment of Group C participants and trend of poor retention of Group C participants when they are required to visit medical offices, the computer system 210 may determine as a recommendation a support option to account for the identified problem. For example, the computer system 210 may determine a first recommendation to provide Group C participants taxi fare to counter the known cause of the poor Group C retention, and a second recommendation to allow Group C participants to make their appointments through telehealth services.

In some cases, the fourth stage 238 and the fifth stage 240 are part of the same stage. For example, if there are pool of candidates who have applied, selecting the cohort from the applicant pool may include enrolling those selected as participants for the study.

As another example, with respect to the sixth stage 242, the cohort diversity measures 230 may include an updated group composition 226 based on the remaining enrolled participants and an updated prediction for the group composition 226 at the end of the study. For example, the computer system 210 can take into account participants that have left the study or that are no longer active. The cohort diversity measures 230 may include an indication of the results of a comparison between the updated prediction for the group composition 226 at the end of the study and the cohort composition target 224. For example, the cohort diversity measures 230 may include warning that indicates too many persons from Group B are at risk of being removed from the study due to low activity, and/or that it is unlikely that the cohort composition target 224 can be reached based on observed data for Group B and previously determined trends for Group B. The cohort diversity measures 230 may also include recommendations corresponding to the enrolled participants. For example, the computer system 210 may recommend adding one or more study parameters specific to participants in Group B that have previously worked to increase participation.

Many different research studies are conducted every year, including clinical studies for new treatments and medications. However, health care disparities are an issue plaguing various research studies that can arise due to a failure to take into account certain segments of a population. Particular segments of the population, such as older adults, pregnant women, children, and racial and ethnic minorities are affected in different ways but are often underrepresented in research studies. As a consequence, the results of these research studies may have limited applicability, particularly for those in the underrepresented segments of the population. This often leads to health care disparities such that there is incomplete or unreliable information as to how those segments of the population will be affected, which can prevent, for example, new medications and treatments from being safely administered to those segments of the population. Moreover, many current studies fail to take into account behavioral variation among the different segments of the population. This often leads to lower enrollment and retention of some segments of the population.

The techniques discussed herein enable the computer system 210 to detect and correct for bias and underrepresentation of different population segments at many stages throughout the research study process. As noted above, the computer system 210 can calculate diversity metrics and impacts of different factors in a study on different segments, when defining a research question (232), when setting study parameters (234), when setting cohort inclusion and exclusion criteria (236), when selecting members of cohorts (238), enrolling participants (240), and when conducting a research study and monitoring results (242). At each stage, the computer system 210 can assess levels of representation to verify that the needed diversity is present both for the current study data and cohort, as well as for the ultimate outcomes for the study (e.g., for the group within the cohort that is retained to completion of the study, and the data set obtained by the end of the study). At each stage, the computer system 210 can assess diversity and alert a study administrator if the composition deviates from a target composition by more than a predetermined amount (e.g., exceeds a threshold level of difference for at least one segment of interest). The computer system 210 can also identify and recommend actions, e.g., changes to the study parameters or group of individuals selected as a cohort that will improve the distribution or composition of the cohort toward target levels representing the desired level of diversity.

Figure 3:
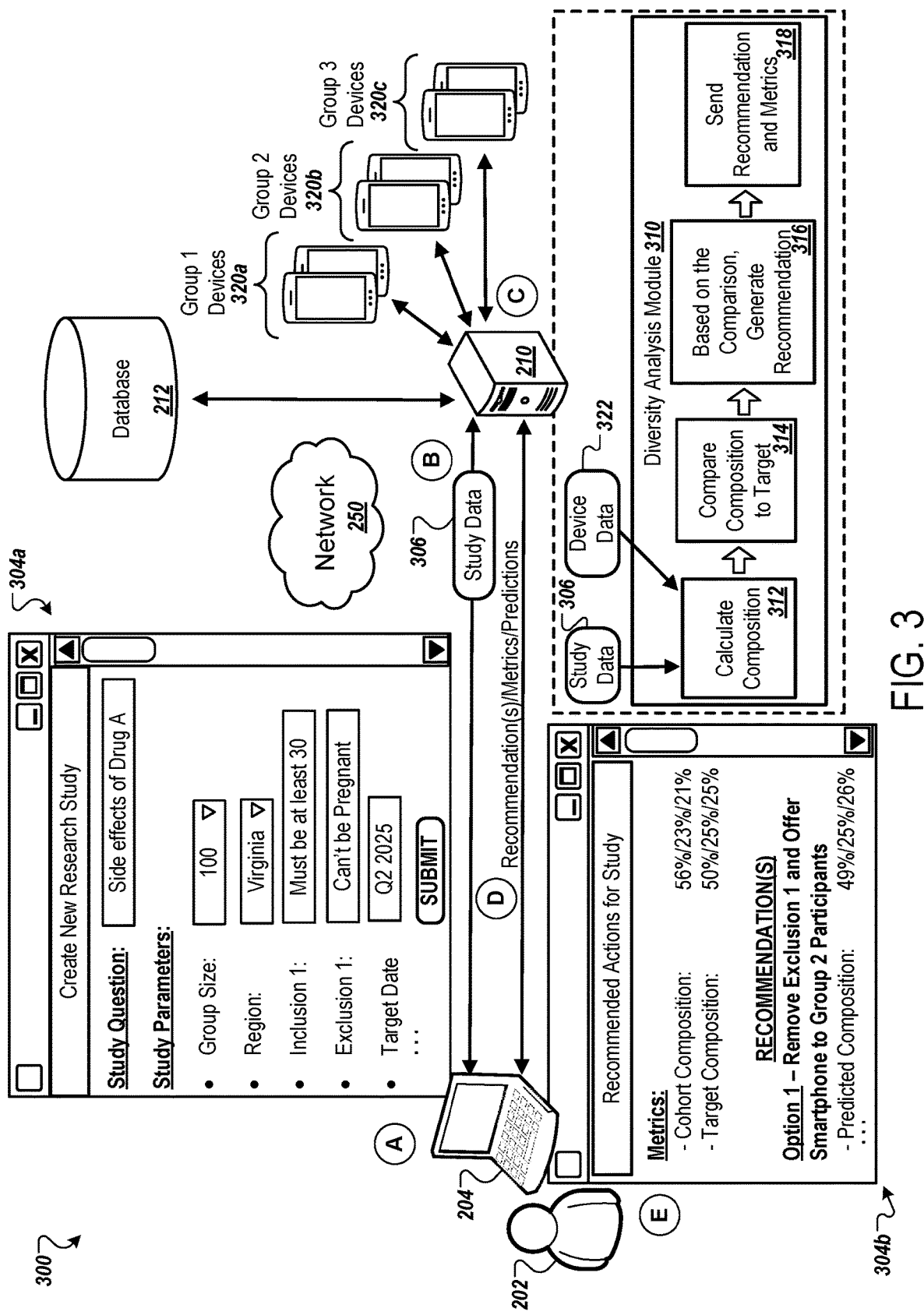
FIG. 3 is a diagram that illustrates an example system and process for performing diversity assessment and action selection for a new research study.

FIG. 3 is a diagram that illustrates one or more components of the system 200 and a process for performing diversity assessment and action selection for a new research study.

In general, FIG. 3 illustrates the researcher 202 initiating a research study through the client device 204. The computer system 210 can use the information received from the client device 204 to calculate one or more diversity measures, such as the reference population for the study, the reference composition, and the target composition. The computer system 210 may also invite users to enroll in the study and/or enroll users in the study based on the received information. Based on the users that enrolled and their associated groups, the computer system 210 may generate and transmit to the client device 204 a recommendation to improve the diversity of the study participants.

FIG. 3 illustrates various operations and flows of data represented as stages (A)-(E), which can be performed in the order shown or in a different order. For example, one or more of the stages (A)-(E) can occur concurrently.

As illustrated, in stage (A), the researcher 202 may be presented an interface 304a of the client device 204 to create a new research study and/or to set a new research question. The researcher 202 may interact with one or more interface elements in the interface 304a to set a study question, to set study parameters, to set inclusion criteria, and/or to set exclusion criteria.

In stage (B), after providing the study question and/or the corresponding study parameters, the researcher 202 may submit the new study to the computer system 210. For example, in response to receiving an indication that the researcher 202 has selected a "Submit" interface element, the client device 204 may generate and transmit study data 306 to the computer system 210 over the network 250.

The study data 306 may include, for example, a study question or research objective, study parameters, inclusion criteria, and/or exclusion criteria. In some cases, the study data 306 may only include the study question or research objective. The computer system 210 may automatically select the study parameters, inclusion criteria, and/or exclusion criteria based on the study question/research objective and/or based on default values. Alternatively, the researcher 202 may set the study parameters, the inclusion criteria, and/or the exclusion criteria at a later time, e.g., after the computer system 210 has performed a diversity analysis of the study question or research objective.

In stage (C), in response to receiving the study data 306, the computer system 210 may perform a diversity analysis using the study data 306. In performing the diversity analysis, the computer system 210 may calculate the cohort diversity measures 230 discussed above with respect to FIG. 2. The computer system 210 may, for example, use a diversity analysis module 310 to perform the diversity analysis based on the study data 306 and/or device data 322, to generate recommendations based on the diversity analysis, and/or to perform one or more actions based on the diversity analysis. The device data 322 may include data received from or generated for Group 1 devices 320a that correspond to a first group of users (e.g., candidates or enrolled participants), Group 2 devices 320b that correspond to a second group of users (e.g., candidates or enrolled participants), and/or Group 3 devices 320c that correspond to a third group of users (e.g., candidates or enrolled participants). The Group 1 devices 320a, the Group 2 devices 320b, and the Group 3 devices 320c may represent three groups of devices whose corresponding users are candidate participants for the study. As an example, these devices may represent all users (e.g., previous study participants; previous study applications; current study applications; etc.) who meet the inclusion criteria and do not meet the exclusion criteria. Similarly, these devices may represent users who the computer system 210 has invited to enroll in the study. As another example, these devices may represent the users who have enrolled in the study.

The device data 322 may indicate, for example, data received from at least a subset of the Group 1 devices 320a, the Group 2 devices 320b, and/or the Group 3 devices 320c. For example, the device data 322 may include response to invitations to enroll in the study. The device data 322 may, therefore, indicate each of the users that have been invited to enroll in the study and have agreed to enroll in the study. Similarly, the device data 322 may include data indicating which users have enrolled in the study. The device data 322 may also or alternatively indicate other information such as which invitations to enroll have successfully been transmitted to the users (e.g., to their corresponding device), which users have viewed an invitation to enroll (e.g., but have not yet responded), the percent of users by group that have responded positively to an invitation to enroll, the percent of users by group that have responded negatively to an invitation to enroll, etc.

As part of the diversity analysis, the diversity analysis module 310 of the computer system 210 may perform an operation 312 of calculating a composition to use for the study based on the study data 306 and/or the device data 322. The composition may be current group composition or a predicted composition at a future point in time, such as at the end of the study (e.g., determined based on machine learning models or statistical data indicating the predicted compliance or retention levels for different groups). The composition may be, for example, the group composition 226 shown in FIG. 2. As an example, the diversity analysis module 310 may use the device data 322 indicating which devices (and their corresponding users) have responded positively to an invitation to enroll in the study. That is, the device data 322 may indicate which users have enrolled in the study. The diversity analysis module 310 may use the device data 322 to determine the current group composition (e.g., participants who are currently enrolled), or a predicted group composition (e.g., at the time of enrollment, or at the time of study completion).

In some cases, the diversity analysis module 310 may use the device data 322 to update the database 212. For example, the diversity analysis module 310 may simply store the device data 322 on the database 212. As another example, as explained in more detail below with respect to FIG. 4 and FIGS. 6A-6B, the diversity analysis module 310 may use the device data 322 to update trend data associated with different user groups. This trend data may be stored in the database 212, and used by the diversity analysis module to make predictions and/or recommendations. For example, the diversity analysis module 310 may update trend data in the database 212 corresponding to the likelihood of a Group 1 users accepting invitations to enroll in a study based on the number of invitations successfully transmitted to the Group 1 devices 320a and the number of positive responses received from the Group 1 devices 320a as provided in the device data 322.

The diversity analysis module 310 performs a second operation 314 of comparing the group composition to a composition target, such as the cohort composition target 224 shown in FIG. 2. The composition target may be set by the researcher 202 and be part of the study data 306. Alternatively, the computer system 210 may determine the cohort composition target based on the study data 306. For example, the computer system 210 may first determine a reference composition based on the study data 306. As an example, the computer system 210 may use the region parameter (Virginia) and the target date parameter (Q2 2025) to determine the reference composition. Specifically, the computer system 110 may use the two parameters and corresponding data stored in the database (e.g., trend data, population data, etc.) to estimate the population composition in the region at the target date (e.g., the ethnic population composition of Virginia in the year 2025). The computer system 110 may proceed to set this estimated population composition as the reference composition.

From the reference composition, the diversity analysis module 310 may determine the cohort composition target. For example, the diversity analysis module 310 may use the inclusion criteria of must be at least 30 and the exclusion criteria of cant be pregnant to limit the population of the reference composition to only those who are over 30 and/or are not pregnant. The diversity analysis module 310 may calculate the cohort composition target 224 from the reference composition using the identified subset of the population. In some cases, the diversity analysis module 310 may detect diversity issues, such as that the inclusion criteria and/or the exclusion criteria are too limiting (e.g., to specific groups). For example, the diversity analysis module 310 of the computer system 210 may generate a warning if the updated population to use for the cohort composition target 224 excludes or significantly reduces the representation of certain segments in the reference population.

In comparing the group composition to the composition target, the diversity analysis module 310 may determine if the group composition matches the composition target, is within a threshold percent (e.g., for any one group) of the composition target, and/or falls within an acceptable target diversity range (e.g., calculated based on the composition target).

The diversity analysis module 310 performs a third operation 316 of generating a recommendation to send to the client device 204 based on the results of the comparison. In generating a recommendation, the diversity analysis module 310 may perform a statistical analysis to identify one or more actions to include in the recommendation. The statistical analysis may be based on identified correlations between different parameters, criteria, and/or actions and certain participant groups and/or group trends. For example, historical data may indicate that past participants associated with Group C have a very low percentage of attending medical appointments, and that previously performed actions of providing taxi credits was typically effective at improving the visit attendance of participants in this group. Accordingly, if the diversity analysis module 310 identifies an issue where participants of Group C are not attending medical appointments, the computer system 210 may recommend that the researcher 202 provide the Group C participants with a taxi credit. The computer system 210 may also make this recommendation prior to any attendance issue being observed, to prevent such an issue from arising.

Additionally or alternatively, in generating the recommendation, the diversity analysis module 310 may use one or more machine learning models to select one or more actions to recommend. As an example, the diversity analysis module 310 may provide an input vector describing the characteristics of the study, such as the cohort composition target, as input to a machine learning model. The diversity analysis module 310 may additionally or alternatively provide a second input vector describing the current characteristics of the cohort, such as the group composition 226, as input to the machine learning model. The output of the machine learning model may be a vector containing a series of values. Each value may correspond to a particular action such that a relatively higher value indicates that a particular action corresponding to the value is better suited for recommendation and/or performance given the input data.

As an example, the diversity analysis module 310 may determine that the exclusion criterion of preventing those who are pregnant from joining the study will be too detrimental to certain population groups. If reference population of the calculated composition may correspond to persons who are likely to take "Drug A" for the treatment of a certain condition and the diversity analysis module 310 determines that a large percentage of persons who are anticipated to take Drug A are pregnant women, then the diversity analysis module 310 may generate update the cohort composition target to include pregnant women as a first group. The diversity analysis module 310 may proceed to generate a diversity warning based on a comparison of the group composition containing no pregnant women to the updated cohort composition target that now includes pregnant women as a group. In response to the warning, the diversity analysis module 310 may provide an input vector describing the characteristics of the study, the updated cohort composition target, and the group composition to a set of machine learning models. The output of the machine learning models may indicate one or more recommended actions to perform in order to achieve the cohort composition target. For example, the output of the machine learning models may correspond to a an action of removing the exclusion criterion of preventing pregnant women from joining the study, as this has the most significant and detrimental effect on the group composition 226 with respect to pregnant women and prevents the cohort composition target from being achieved. Be removing this exclusion criterion, pregnant women will be permitted to join the research study which may allow the cohort composition target that includes pregnant women to be achieved.

The diversity analysis module 310 may also calculate metrics corresponding to a recommendation. For example, the diversity analysis module 310 may calculate the potential effects of the recommendation on group enrollment (e.g., likelihood of enrollment), of group composition (e.g., at start of study, at the end of the study, etc.), on the likelihood of reaching the cohort composition target, etc.

In stage (D), the diversity analysis module 310 performs a fourth operation 318 of generating instructions for the computer system 210 to send the recommendation and corresponding metrics to the client device 204 over the network 250. The metrics may also include the calculated reference composition, the cohort composition target, a current group composition, and/or a predicated group composition at a future point in time (e.g., at the end of the study).

In stage (E), the client device 204 presents a recommendation interface 304b to the researcher 202. The recommendation interface 304b may depict the diversity metrics such as the cohort/group composition and the cohort composition target. The recommendation interface 304b may also present one or more recommendations, and their corresponding effects on cohort diversity. If multiple recommendations are presented, the recommendations may be presented in an order corresponding to what actions or groups of actions are most likely to succeed in reaching the cohort composition target 224, or most likely to get sufficiently close to the cohort composition target 224.

As discussed in some detail above, the diversity analysis module 310 may use one or more algorithms to perform the diversity analysis, generate the diversity measures 130, and/or generate recommendations. For example, the diversity analysis module 310 may use one or more static algorithms to calculate the group composition at a future point in time using previously obtained data or previously determined trends (e.g., generated using previously obtained data) for those groups of users (e.g., indicating the expected or average percentage of users in a particular group completing a study). The diversity analysis module 310 may additionally or alternatively use one or more machine learning algorithms trained to predict the group composition at a future point in time, and/or trained to select actions to perform and/or predict the diversity effects of those actions. The one or more machine learning algorithms may be trained using historical data that indicates the behavior of past study participants (e.g., an indication as to whether they completed or unenrolled from a study, an activity level of the participant during the study, etc.), the groups that the participants belong to, and/or the study parameters (e.g., inclusion criteria, exclusion criteria, other requirements or study parameters).

As input (e.g., an input vector), the one or more machine learning algorithms may receive an indication of the participants currently enrolled in the study and/or the group composition (e.g., group composition 226), and the current study parameters (e.g., including inclusion criteria and exclusion criteria). Other input may include an indication of the observed activity levels of users and/or groups for this study, and/or an enrollment trend of users and/or groups for this study.

With respect to machine learning algorithms configured to predict the group composition at the end of the study, the output (e.g., an output vector) of the machine learning algorithm may include a vector of values that correspond to different group composition possibilities. The highest value may indicate the most likely group composition that will be observed at the end of the study.

With respect to machine learning algorithms configured to select actions and/or predict the effects of actions, the output (e.g., an output vector) of the machine learning algorithms may include a vector of values corresponding to different actions and/or different combinations of actions. The highest value may indicate the highest recommended action or combination of actions, corresponding to the action or combination of actions that is most likely to result in achieving the cohort composition target, getting sufficiently close to the cohort composition target, and/or getting closer to the cohort composition target than other actions or combinations of actions.

Figure 4:
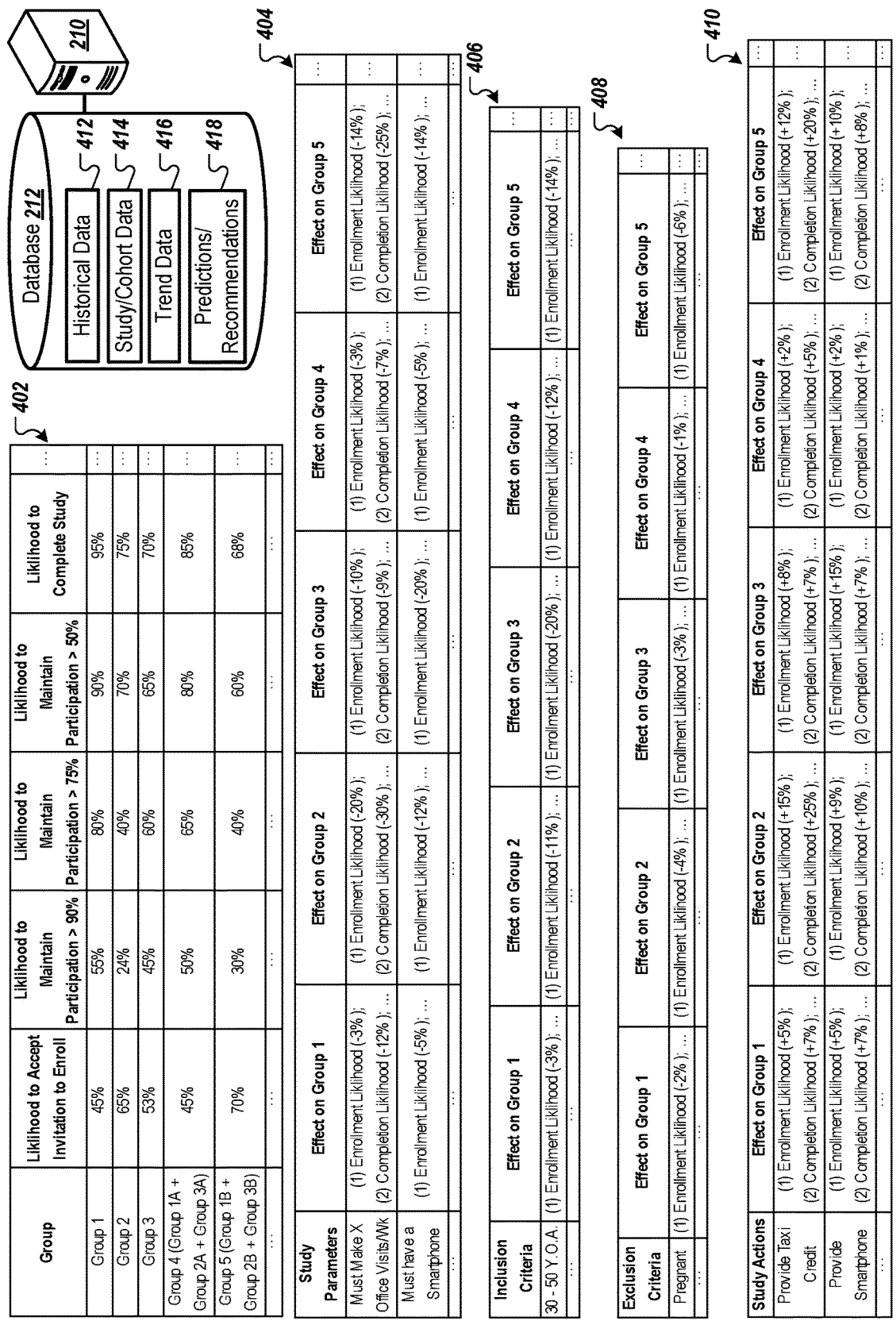
FIG. 4 is a diagram that illustrates example tables used for diversity assessment and action selection.

FIG. 4 is a diagram that illustrates example tables 402-410 used for diversity assessment and action selection. The tables 402-410 may be generated, updated, and referenced by the computer system 210. The computer system 210 may use the information in the tables 402-410 to perform a diversity analysis, calculate diversity measures (e.g., including diversity levels), and generate recommendations. The computer system 210 may store the tables 402-410 in the database 212.

Importantly, the tables 402-410 indicate the different effects that different monitoring program parameters have on the actions of individuals in different groups. For example, one element, such as a requirement of an in-person visit, may have a high negative effect on enrollment or compliance of members of one group but may have a less negative effect, or a neutral or positive effect on enrollment or compliance of members of another group. The computer system 210 analyzes the records of prior actions to characterize or profile the correlations between different factors and the resulting observed outcomes. This allows the system to quantify the potential bias that different factors cause on enrollment, compliance, and retention. It also provides the source data that the system 210 can use to trace the causes of low enrollment, compliance and retention in monitoring programs and signals to the system 210 the opportunities to address factors that may be harming monitoring program outcomes. For example, the system 210 can detect that compliance among a particular group is low, identify from the tables a data collection action that is correlated with low compliance, and then select an alternative method of collecting the data that the tables indicate has a higher likelihood of compliance As an example, the tables 402-410 may be generated by the computer system 210 using historical data 412 and study/cohort data 414 (e.g., data collected from study participants, diversity analyses during a study, etc.). The tables 402-410 may represent determined trend data 416 and/or predictions/recommendations 418 corresponding to different participant groups.

As illustrated, different groups of participants may be associated with different behaviors during a research study, and/or are likely to react differently to particular actions, study parameters, inclusion criteria, and/or exclusion criteria. By identifying how different groups are likely to behave and/or react, a study can be generated and conducted in a manner to ensure (or significantly increase the likelihood) of achieving a set cohort composition target by the end of the study.

A first table 402 indicates example trends in activities levels and study completion rates for different groups. The computer system 210 may generate the first table 402 using historical data 412. The historical data 412 may include, for example, enrollment data from one or more past studies, participation data from one or more past studies, participant profiles corresponding to participants in one or more past studies, etc. The participant profiles may include data that indicates one or more groups associated with the participants, such as demographic and/or non-demographic information of the participants. The participant profiles may include enrollment data (e.g., an indication of how many studies that the participant has been invited to join, has applied for, has enrolled in, etc.) and/or participation data (e.g., average participation level of the participant, how often the participant remained an active participant, etc.). The computer system 210 may update the table 402 using study/cohort data, which may include, for example, data measured, observed, or received during a research study such as one currently being conducted.

The first table 402 may be part of trend data 416 that is generated by the computer system 210 based on the historical data 412 and/or the study/cohort data 414. The computer system 210 may refer to the table 402 in order to generate predictions and/or recommendations 418.

A second table 404 indicates the predicted effects of particular study parameters on different groups. The effects may include, for example, anticipated changes to study enrollment, participation, and/or completion likelihood for each group. The second table 404 may be generated by the computer system 210 using the historical data 412. The second table 404 may be updated by the computer system 210 using the study/cohort data 414.

The second table 404 may be part of trend data 416 that is generated by the computer system 210 based on the historical data 412 and/or the study/cohort data 414. The computer system 210 may refer to the table 404 in order to generate the predictions and/or recommendations 418.

A third table 406 indicates the predicted effects of particular inclusion criteria on different groups. The effects may include, for example, anticipated changes to study enrollment, participation, and/or completion likelihood for each group. The third table 406 may be generated by the computer system 210 using the historical data 412. The third table 406 may be updated by the computer system 210 using the study/cohort data 414.

The third table 406 may be part of trend data 416 that is generated by the computer system 210 based on the historical data 412 and/or the study/cohort data 414. The computer system 210 may refer to the third table 406 in order to generate the predictions and/or recommendations 418.

A fourth table 408 indicates the predicted effects of particular exclusion criteria on different groups. The effects may include, for example, anticipated changes to study enrollment, participation, and/or completion likelihood for each group. The fourth table 408 may be generated by the computer system 210 using the historical data 412. The fourth table 408 may be updated by the computer system 210 using the study/cohort data 414.

The fourth table 408 may be part of trend data 416 that is generated by the computer system 210 based on the historical data 412 and/or the study/cohort data 414. The computer system 210 may refer to the fourth table 408 in order to generate the predictions and/or recommendations 418.

A fifth table 410 indicates the predicted effects of particular study actions on different groups. The effects may include, for example, anticipated changes to study enrollment, participation, and/or completion likelihood for each group. The fifth table 410 may be generated by the computer system 210 using the historical data 412. The fourth table 408 may be updated by the computer system 210 using the study/cohort data 414.

The fifth table 410 may be part of trend data 416 that is generated by the computer system 210 based on the historical data 412 and/or the study/cohort data 414. The computer system 210 may refer to the fifth table 410 in order to generate the predictions and/or recommendations 418.

The computer system 210 may generate the predictions and/or recommendations 418 for a particular study by applying the trend data 416 to the measured study/cohort data 414. For example, based on the likelihood of Group 2 participants enrolling in a study being higher than Group 3 participants, the computer system 210 may recommend that less Group 2 participants be invited to enroll in the study if the same number of participants from Groups 2 and 3 are being sought.

Figure 5B:
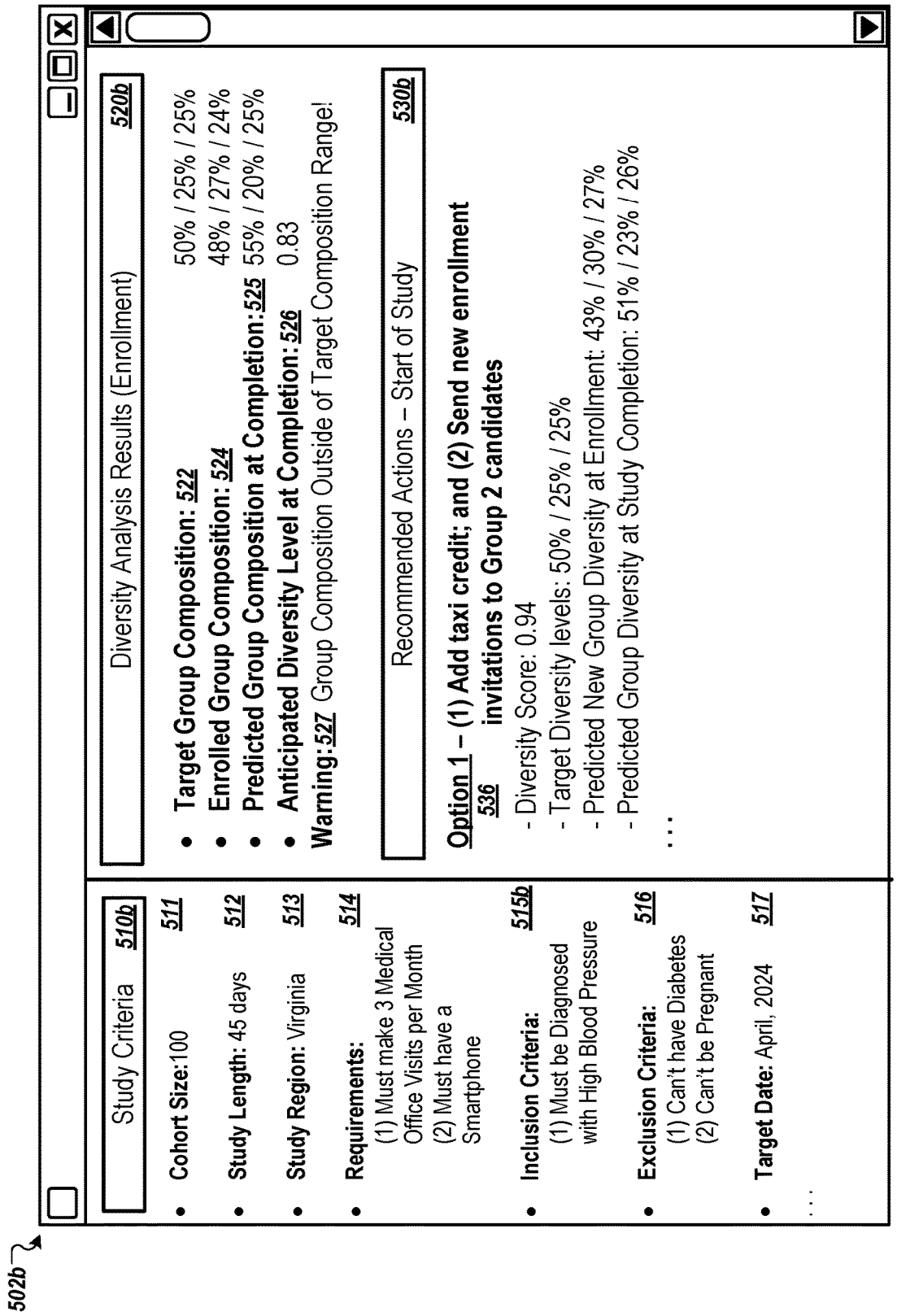

FIGS. 5A-5B are diagrams that illustrate example diversity assessment interface and action selection interfaces 502a-502c. These interfaces 502a-502c may be presented on the client device 204 of the researcher 202. The client device 204 may present the interfaces 502a-502c at one or more stages of the study based on information received from the computer system 210. As will be described in more detail below, the interfaces 502a-502c may present diversity measures calculated by the computer system 210, the results of a diversity analyses performed by the computer system 210, and/or recommendations generated by the computer system 210. The researcher 202 can interact with the interfaces 502a-502c to make various selections, such as the selections of recommendations, to make modifications (e.g., modifications to a recommendation), or to initiate one or more actions to take (e.g., one or more actions that were not recommended by the computer system 210 that the researcher 202 indicates that the computer system 210 should perform).

As will be discussed in more detail below, the recommendations may be ranked and presented in an order corresponding to their rank. The researcher 202 may interact with the interface 502a to select actions to finalize a monitoring program, adjust a monitoring program, select recommended actions to adjust a monitoring group, or make other adjustments.

FIG. 5A illustrates example diversity assessment and action selection interface 502a during a cohort selection stage of a study. The interface 502a may be presented on the client device 204. As an example, the interface 502a may be presented on the client device 204 after (e.g., in response to) the researcher 202 submitting a research question or study objective (e.g., optionally along with other study information initially submitted by the researcher 202). The interface 502a may present various diversity metrics calculated by the computer system 210 and recommendations generated by the computer system 210. The researcher 202 may interact with the interface 502a to, for example, select a recommendation for the computer system 210 to perform, adjust study parameters, select users to enroll in a study, select users to be invited to the study, etc.

The interface 502a includes a study criteria section 510a, a diversity analysis results section 520a, and a recommendation section 530a. The researcher 202 may, for example, use the interface 502a to review recommendations generated by the computer system 210 at a beginning stage of the study. The researcher 202 may, through the interface 502a, select one or more recommended actions to be performed.

The researcher 202 may be able to also use the interface 502a to indicate one or more actions to be performed, e.g., that may not have been recommended. For example, the researcher 202 may, through the interface 502a, add or remove an exclusion criterion to or from the exclusion criteria 516.

As shown, the study criteria section 510a may include various parameters for a given study. For example, the study criteria section 510a may include a cohort size 511, a study length 512, a study region 513, study requirements 514, and a target data 517.

In addition to study parameters, the study criteria 510a may also include inclusion criteria 515a that enrolled participants are required, at a minimum, to meet, and exclusion criteria 516. If a candidate happens to meet any of the exclusion criteria 516, that candidate is automatically excluded from consideration, e.g., even if they meet the inclusion criteria 515a and any other requirements in the study criteria 510a. Similarly, if new information is obtained that indicates that an enrolled participant meets an exclusion criterion, the computer system 210 may automatically remove the participant from enrollment.

However, in some cases, the computer system 210 generates a warning indicating the problem, and transmit the warning to the client device 204. The computer system 210 may refrain from removing the participant until it receives a confirmation or instructions to do so from the client device 204. The computer system 210 may, however, change how it interacts with the participant. For example, if the study involves taking a new drug, the computer system 210 may send a notice to the participant to immediately stop taking the drug, to contact their doctor, to go to the hospital, etc. Depending on the possible severity associated with the exclusion criteria (e.g., increased likelihood of a serious allergic reaction by 500%), the computer system 210 may contact a doctor for the participant and/or emergency services for the participant (e.g., if the participant does not respond to an initial message with a threshold amount of time).

The study criteria may be set by the researcher 202, the computer system 210, or a combination of the researcher 202 and the computer system 210.

The diversity analysis results section 520a depicts the results of a diversity analysis performed by the computer system 210 at the start of a study. The diversity analysis presented may be based on a research question provided by the researcher 202 and/or the study criteria 510a. This diversity analysis may reflect a diversity analysis performed before any participants have been enrolled in the study, and/or before any candidates have been invited to participate in the study.

As shown, the diversity analysis may include a determined reference population 521, a target group composition 522 (e.g., for the enrolled participant at the completion of the study), and identified previous participants 535. The identified previous study participants 523 may be all participants that are relevant to the study. For example, if the study calls for monitoring participants from Group 1, Group 2, and Group 3, the previous study participants 523 may include all previous participants of those groups. As another example, the previous study participants 523 may include only those participants that meet the study criteria 510*a*, e.g., meet the requirements 514, meet the inclusion criteria 515*a*, don't meet any of the exclusion criteria 516, live in or sufficiently near the study region 513, etc.

In some cases, the previous study participants 523 may also include participants who have registered for a study (e.g., registered for this current study) but have not necessarily participated in or completed a previous study.

The recommendation section 530*a* may include one or more recommendations generated by the computer system 210 using the diversity analysis results. The computer system 210 may generate one or more recommendations using the diversity analysis results in order to achieve the target group composition 522.

As shown, a first recommendation option 532 is displayed in the interface 502*a* and has been selected (e.g., by the researcher 202). This recommendation option 532 includes a modification to the study criteria 510*a*. Specifically, the recommendation option 532 provides for removing one of the inclusion criterion from the inclusion criteria 515*a*. The recommendation option 532 also provides that invitations to enroll will be sent to all previous study participants 523, which includes, for example, 915 participants from Group 1, 211 participants from Group 2, and 201 participants from Group 3. The previous study participants 523 may be limited to those participants that have successfully completed a study, that completed a study with an average activity level that meets a threshold activity level, that maintained an activity level above a threshold activity level, that participated in a threshold number of previous studies, that completed a threshold number of previous studies, etc.

The recommendation section 530*a* also includes a second recommendation option 534. The computer system 210 may provide for presenting the recommendation option 532 above the recommendation option 534 based on an anticipated diversity level associated with the recommendation option 532 being greater than an anticipated diversity level associated with the recommendation option 534. That is, the computer system 210 may rank the different recommendation options and display the different recommendations options in accordance with their respective ranks.

The diversity level may indicate how close the predicated group composition at study completion is to the target group composition. The diversity level may be, for example, a diversity score. That is, the diversity level may be a single value that is indicative of how close the predicted group composition at study completion is to the target group composition. As an example, a diversity score of 1.0 may indicate that the predicted group composition at study completion matches the target group composition 522. The diversity score may be absolute, or it may be relative, e.g., relative to a previously predicted group composition at study completion or relative to the predicted group composition at study completion of one or more other recommendation options. Additionally or alternatively, the diversity level may be, for example, a calculated distribution (e.g., probability distribution). This diversity distribution may, for example, indicate probabilities of achieving the target group composition 522 (e.g., after performing actions corresponding to a particular recommendation option) and/or probabilities associated with different possible group compositions at study completion.

The diversity level may indicates a level of confidence in achieving the target group composition 522, and/or achieving a group composition that is with an acceptable range (e.g., percent range or value range) of the target group composition 522. For example, a diversity score of 0.91 may indicate that the computer system 210 has determined that there is 91% possibility of the group composition at study completion being within a threshold percent (e.g., 5%, 3%, 1%, etc.) of the target group composition 522 provided that the actions corresponding to the recommendation option 532 are performed.

Diversity level may also or alternatively describe a group composition, or the difference between a group composition (e.g., current or predicted) and the target group composition 522. For example, a predicted group composition at study enrollment may be a first diversity level, a predicted group composition at study completion may be a second diversity level, and a difference (e.g., difference between two sets of values, absolute value of the difference between the two sets of values, etc.) the group composition at study completion and the target group composition 522 as a third diversity level.

In some cases, there are multiple diversity levels (e.g., diversity metrics) that include both one or more singular values, and one or more distributions. For example, a first diversity level may include a diversity distribution indicating different likelihoods of achieving the target group composition 522, and a diversity score may be second diversity level identified from the diversity distribution (e.g., as the value associated with the highest probability out of the all of the values).

As discussed above, the computer system 210 may rank the recommendations based on one or more diversity metrics (e.g., diversity levels) calculated for the recommendations. For example, the computer system 210 may rank the recommendations presented in the recommendation section 530*a* according to a calculated anticipated diversity score for each of the recommendations (e.g., that indicates the anticipated diversity of the cohort at the end of the study should the actions in the corresponding recommendation be performed). The anticipated diversity score is likely to be higher if the actions in a recommendation are predicted to produce a group composition that matches or gets sufficiently close (e.g., with respect to the performance of actions in other recommendations) to the target group composition 522. The computer system 210 may provide instructions to the client device 204 to have the recommendations presented on the interface 502*c* according to their rank. For example, the computer system 210 may provide instructions to the client device 204 to present the recommendation option 532 above the recommendation option 534 based on the anticipated diversity score (e.g., at the end of the study) associated with the recommendation option 532 being greater than the anticipated diversity score associated with recommendation option 534. By ranking the recommendations according to their influence in achieving the target group composition 522 and, therefore, their influence in on the study's ability to produce viable data, the computer system 210 can (i) more efficiently present its recommendations to the researcher, and/or (ii) take greater advantage of the limited screen space available on the client device 204 (or a display connected to the client device 204).

In some implementations, computer system 210 may only recommend a threshold number of recommendation options (e.g., for display on the client device 204) and/or only send a threshold number of recommendation options to the client device 204. For example, the computer system 210 may only recommend the two, three, or four highest ranking recommendation options for display on the client device 204. The threshold may be selected by the researcher 202 or may be automatically determined by the computer system 210. As an example, the computer system 210 may determine the threshold based on diversity scores associated with the different recommendations, and/or based on the difficulty of the actions in the recommendation options. In more detail, the computer system 210 may generate instructions to present less recommendation options if there are significant diversity score differences (e.g., greater than 5%, 10%, or 20% divergence with respect to the top three, four, or five highest ranking recommendation options) between the different recommendation options such that there are recommendation options that are clearly superior to other recommendation option, or may present more recommendation options if there are insignificant diversity score differences between the different recommendation options (e.g., less than 2%, 5%, or 10% divergence with respect to the top three, four, or five highest ranking recommendation options) such that there are multiple recommendation options that are likely to produce similar diversity results. By presenting only a subset of recommendations, the computer system 210 can (i) more efficiently present the key recommendations to the researcher, and/or (ii) take greater advantage of the limited screen space available on the client device 204 (or a display connected to the client device 204) by removing the need to devote screen space to recommendations that are unlikely or less likely to achieve the diversity needs of the study.

Prior to recommending a set of actions, the computer system 210 may first ensure that the corresponding prospective recommendation meets certain criteria. For example, the computer system 210 may first apply a minimum anticipated diversity level threshold to the recommendation before it can be presented on a display of the client device 204 and/or sent to the client device 204. For example, the computer system 210 may apply a static threshold of 0.90 to the anticipated diversity level. This would have the effect of permitting only the first recommendation option 532 from being displayed in the interface 502a. The diversity level threshold may instead be dynamic, e.g., based on a current anticipated diversity level, based on historical data for the groups being invited to participate in the study, based on the trends for the groups being invited to participate in the study, etc. For example, the computer system 210 may only allow recommendations that result in the anticipated diversity level improving by at least 5% with respect to a current anticipated diversity level at completion. By presenting only a subset of recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

The recommendations determined by the computer system 210 may also include recommendations to mitigate risks presented by the inclusion of high risk groups in the study. The inclusion of these high risks groups can benefit the diversity of the study so that the study can achieve its diversity needs (e.g., the target group composition 522, a minimum number of participants from Group 1, a minimum number of participants from Group 2, a minimum number of participants from Group 3, a minimum activity level for each of the participants or minimum average activity level for each group of participants, etc.). However, the inclusion of these high risk groups can also present additional risks that may need to be mitigated in other ways, such as through the addition, removal, or modification of study parameters (or for the provision other study actions) for those participants in these at risk groups.

The computer system 210 may identify a group of persons as at risk based on the group being tagged or preprogramed as at risk in the database 212 (e.g., tagged by the researcher 202 or tagged by a previous researcher) such as elderly persons, based on historical data showing disproportionately high incidents (e.g., side effects from pharmaceuticals, hospitalizations, death, etc.) for those in the at risk group, etc. After determining that one or more participants in the at risk group are to be enrolled in the study or invited to enroll in the study, the computer system 210 may generate one or more recommendations to mitigate the risks presented to these groups, such as a recommendation to provide additional monitoring for those in the at risk group, a recommendation for more frequent data collection for those in the at risk group, a recommendation to reduce the medication dosage for those in the at risk group to spread the vaccine administration over a longer period of time for those in the at risk group, a recommendation for the medication or vaccine to be administered only by a doctor, a recommendation for the medication or vaccine to be administered only by a doctor in a hospital, etc.

FIG. 5B illustrates example diversity assessment and action selection interface 502b during a participant enrollment stage of a study. The interface 502b may be presented on the client device 204. As an example, the interface 502b may be presented on the client device 204 at an enrollment stage of the study. Specifically, the interface 502b may be presented after (e.g., in response to) all or threshold percent of users have responded to enrollment invitations, after a threshold amount of time has passed since enrollment invitations were sent out, after a threshold number of users have enrolled, etc. The interface 502b may present various diversity metrics calculated by the computer system 210 and recommendations generated by the computer system 210 for this stage of the study. The researcher 202 may interact with the interface 502b to, for example, select a recommendation for the computer system 210 to perform, adjust study parameters, select new users to enroll in a study, select new users to be invited to the study, select users to remove from enrollment, select users to have their invitations revoked, etc.

The interface 502b includes an updated study criteria section 510b, a diversity analysis results section 520b, and a recommendation section 530b. The researcher 202 may, for example, use the interface 502b to review recommendations generated by the computer system 210 at an enrollment stage of the study. The researcher 202 may, through the interface 502b, select one or more recommended actions to be performed.

The researcher 202 may be able to also use the interface 502b to indicate one or more actions to be performed, e.g., that may not have been recommended. For example, the researcher 202 may, through the interface 502b, add or remove an inclusion criterion to or from the inclusion criteria 515b.

As shown, the study criteria section 510b may include various parameters for a given study. For example, the study criteria section 510b may include a cohort size 511, a study length 512, a study region 513, study requirements 514, and a target data 517.

In addition to study parameters, the study criteria 510b also include updated inclusion criteria 515b and exclusion criteria 516. The inclusion criteria 515b has been updated based on a selected recommendation so that an inclusion criterion has been removed. This has the effect of increasing the candidate pool of potential participants.

The diversity analysis results section 520b depicts the results of a diversity analysis performed by the computer system 210 at an enrollment stage the study. The diversity analysis presented may be based on a research question provided by the researcher 202, the study criteria 510b, the candidates invited to enroll and/or the candidates that have applied to enroll, and/or the actual enrollment of the study.

As shown, the diversity analysis results section 520b may include the target group composition 522 (e.g., for the enrolled participant at the completion of the study), an enrolled group composition 524 (e.g., indicating the diversity of participants who have actually enrolled in the study), and a predicted group diversity at completion 525. The computer system 210 may determine the predicted group diversity at completion 525 based on, for example, a combination of historical data or trends determined from historical data, and the enrolled group composition 524.

The computer system 210 may compare the predicted group diversity at completion 525 to the target group composition 522. If the predicted group composition 525 falls outside of a target composition range (e.g., based on the target group composition 522), then the computer system 210 may generate a warning 527 indicating that it is anticipated that the target group composition 522 will not be achieved.

As another example, the warning 527 may be generated by the computer system 210 in response to determining that the diversity level 526 does not meet a threshold diversity level. For example, the computer system 210 may compare the diversity level 526 to a threshold diversity level of 0.90. Based on the diversity level 526 being below the threshold diversity level, the computer system 210 may generate the warning 527 or a similar warning (e.g., indicating low diversity level and/or that the target group composition is unlikely to be achieved by study completion), and transmit the warning to the client device 204.

In some cases, the computer system 210 may compare the diversity level 526 to multiple thresholds. These thresholds may correspond to different actions performed by the computer system 210. For example, if the diversity level does not meet a first threshold but does meet a second threshold, the computer system 210 may generate a low priority warning and transmit it to the client device 204. However, if the diversity level does not meet the first threshold and the second threshold, the computer system 210 may generate a high priority warning, transmit the warning to the client device 204, and automatically perform one or more actions to account for the low diversity level. For example, the computer system 210 may determine one or more actions to take to improve the diversity level, such as invite persons to enroll from an underrepresented group, remove persons from an overrepresented group, remove or modify inclusion or exclusion criteria, adjust the study parameters, etc.

The recommendation section 530b may include one or more recommendations generated by the computer system 210 using the diversity analysis results indicated in the diversity analysis results section 520b. The computer system 210 may generate one or more recommendations using the diversity analysis results in order to achieve the target group composition 522. Specifically, the computer system 210 may determine a first recommendation option 536 based on or in response to the warning 527. The first recommendation option 536 may be a recommendation to perform one or more actions so that the predicated group diversity at completion 525 will match the target group composition 522 or will be within a target diversity range (e.g., that is based on the target group composition 522).

FIG. 5C illustrates example diversity assessment and action selection interface 502c during a participant enrollment stage of a study. The interface 502c may be presented on the client device 204. As an example, the interface 502c may be presented on the client device 204 at an enrollment stage of the study. Specifically, the interface 502c may be presented after (e.g., in response to) all or threshold percent of users have responded to enrollment invitations, after a threshold amount of time has passed since enrollment invitations were sent out, after a threshold number of users have enrolled, etc. The interface 502c may present various diversity metrics calculated by the computer system 210 and recommendations to adjust enrollment generated by the computer system 210 for this stage of the study. The interface 502c may include various interface elements that allow a user to quickly consider and act on recommendations to invite or enroll new users in the study, remove users from enrollment, or replace users who are currently enrolled. The researcher 202 may interact with the interface 502c to, for example, select new users recommended by the computer system 210 to enroll in a study, select new users recommended by the computer system 210 to be invited to the study, select users recommended by the computer system 210 for removal from enrollment, select users recommended by the computer system 210 for replacement, select users recommended by the computer system 210 for having their invitations revoked, etc.

As another example, the interface 502c may be presented on the client device 204 at one or more later stages of the study (e.g., after some of study data has been obtained from the participant devices). Specifically, the interface 502c may be presented after (e.g., in response to) a participant leaving the study, a participant's activity level dropping below a threshold activity level, a diversity score falling below a diversity score threshold, etc.

The interface 502c includes the updated study criteria section 510b, the diversity analysis results section 520b, and an enrollment section 540. The researcher 202 may, for example, use the interface 502c to adjust the enrollment for the study at the start of the study or at one or more later points in time during the study.

As shown, the study criteria section 510b may include various parameters for a given study. For example, the study criteria section 510b may include a cohort size 511, a study length 512, a study region 513, study requirements 514, and a target data 517. In addition to study parameters, the study criteria 510b also include updated inclusion criteria 515b and exclusion criteria 516.

The diversity analysis results section 520b depicts the results of a diversity analysis performed by the computer system 210 at an enrollment stage the study. The diversity analysis presented may be based on a research question provided by the researcher 202, the study criteria 510b, the candidates invited to enroll and/or the candidates that have applied to enroll, and/or the actual enrollment of the study.

As shown, the diversity analysis may include the target group composition 522 (e.g., for the enrolled participant at the completion of the study), the enrolled group composition 524 (e.g., indicating the diversity of participants who have actually enrolled in the study), and the predicted group diversity at completion 525. The computer system 210 may determine the predicted group diversity at completion 525 based on, for example, a combination of historical data or trends determined from historical data, and the enrolled group composition 524.

As discussed above, using the target group composition 522 and at least one of the enrolled group composition 524 and the predicted group composition 525, the computer system 210 calculates a diversity level 526. As shown, the diversity level 526 is an anticipated diversity level at study completion, e.g., that is indicative of the difference (e.g., actual or percent difference) between the predicted group composition 525 and the target group composition 522.

The computer system 210 may compare the predicted group diversity at completion 525 to the target group composition 522. If the predicted group composition 525 falls outside of a target composition range (e.g., based on the target group composition 522), then the computer system 210 may generate the warning 527 indicating that it is anticipated that the target group composition 522 will not be achieved.

As another example, the warning 527 may be generated by the computer system 210 in response to determining that the diversity level 526 does not meet a threshold diversity level. For example, the computer system 210 may compare the diversity level 526 to a threshold diversity level of 0.90. Based on the diversity level 526 being below the threshold diversity level, the computer system 210 may generate the warning 527 or a similar warning (e.g., indicating low diversity level and/or that the target group composition is unlikely to be achieved by study completion), and transmit the warning to the client device 204.

In some cases, the computer system 210 may compare the diversity level 526 to multiple thresholds. These thresholds may correspond to different actions performed by the computer system 210. For example, if the diversity level does not meet a first threshold but does meet a second threshold, the computer system 210 may generate a low priority warning and transmit it to the client device 204. However, if the diversity level does not meet the first threshold and the second threshold, the computer system 210 may generate a high priority warning, transmit the warning to the client device 204, and automatically perform one or more actions to account for the low diversity level. For example, the computer system 210 may determine one or more actions to take to improve the diversity level, such as invite persons to enroll from an underrepresented group, remove persons from an overrepresented group, remove or modify inclusion or exclusion criteria, adjust the study parameters, etc.

The enrollment section 540 may present more detail information on the currently enrolled participants, and/or may present options, such as recommended options, for adjusting the enrollment of the study. As shown, the enrollment section 540 may include a table 542 that includes a first column the displays that displays users that the computer system 210 recommends to be invited for enrollment and/or added to enrollment, and a second column that displays users that the computer system 210 has marked for possible removal or replacement.

Factors for recommending users for invitation, addition, removal, or replacement may include the group(s) associated with the user and an expected participation for the user. The computer system 210 may recommend the addition of users that are associated with an unrepresented group or a group that is anticipated to be unrepresented at study completion. Similarly, the computer system 210 may recommend the remove or replacement of users that are associated with an overrepresented group or a group that is anticipated to be overrepresented at study completion. As an example, the computer system 210 may be more likely to recommend Group 2 users based on the predicted group composition 525 indicating that the anticipated enrollment of Group 2 participants will be significantly lower than that indicated in the target group composition 522. The computer system 210 may also recommend users that have a higher expected participation as they will be more likely to provide data and/or consistently provide data required for a study, and/or more likely to complete the study.

The table 542 may also indicated the predicted effect that the addition, removal, or replacement of the specific users may have on the study. As an example, the computer system 210 may determine the anticipated diversity level at study completion should the corresponding user be added, removed or replaced. For example, the addition of the User S to the study is anticipated to raise the diversity level from 0.87 to 0.91.

The researcher 202 may interact with the table 542 to select one or more users to add/invite. Similarly, the researcher 202 may interact with the table 542 to select one or more users to remove or replace. If the researcher 202 select to replace a user, they the client device 204 may prompt the researcher 202 to select a replacement user to invite/add.

The recommendation for the addition, invitation, removal, or replacement of participants may further be based on the past studies that the participants have previously been a part of. For example, candidates may be more likely to be recommended for invitation and/or addition (e.g., addition may be an option if the participant has already agreed to enrolled or applied to enroll) if the participants have enrolled in a previous research study, have completed a previous research study, have enrolled in a relatively high number of research studies (e.g., compared to other candidates, enrolled participants, etc.), have completed a relatively high number of research studies, and/or have completed a threshold percent of research studies that they previously enrolled in. In contrast, enrolled participants may be more likely to be marked for removal or replacement if, for example, they have not enrolled or completed a previous research study (e.g., which would introduce a great deal of uncertainty such that there may be, for example, insufficient information to anticipate whether the participant will complete the study and/or the expected participation of the participant), have enrolled in or completed a relatively low number of studies, and/or have a low study completion percentage.

The expected participation of the candidates and the enrolled participants may be determined using information obtained from past studies. For example, the computer system 210 may access a previously calculated expected participation for an enrolled participant from a user profile for the participant. As another example, the computer system 210 may access study data stored and associated with a user, and calculated, based on the study data, an expected participation level of the user. The expected participation level may be based on, for example, a user's task completion percentage, task completion time, inquiry response time, data upload consistency, etc.

The computer system 210 may rank the users that it recommends for invitation, enrollment, removal, or replacement. For example, the users may be ranked based on the anticipated diversity level calculated by the computer system 210 should the recommendation be acted on. The effects of a user being added or invited to a study on the anticipated diversity level are likely to increase more significantly if the user belongs to a currently underrepresented group or anticipated unrepresented group (e.g., anticipated to be unrepresented by the end of the study, such as the Group 2 participants that are currently overrepresented but are anticipated to be underrepresented) than if the user belongs to a currently overrepresented or anticipated overrepresented group (e.g., Group 1 participants that are currently underrepresented but anticipated to be overrepresented by the end of the study). Additionally or alternatively, the users may be ranked based on their expected activity level in the study (e.g., based on historical data indicating their past activity levels, past study completion rates, etc.). This however may be taken into account by the anticipated diversity level since the anticipated diversity level may correspond to the predicted group composition 522 at the end of the study and a lower expected activity level associated with a user would indicate a higher likelihood of the user not completing the study and/or not producing sufficient data needed for the study.

The computer system 210 may provide instructions to the client device 204 to have the recommended users presented in the interface 502c according to their rank. For example, as shown, User S may be presented above User R based on the anticipated diversity level of 0.94 (e.g., by the end of the study) for inviting or enrolling User S being greater than the anticipated diversity level of 0.93 for inviting or enrolling User R. By ranking the user recommendations according to their influence in achieving the target group composition 522 and, therefore, their influence in on the study's ability to produce viable data, the computer system 210 can (i) more efficiently present its recommendations to the researcher, and/or (ii) take greater advantage of the limited screen space available on the client device 204 (or a display connected to the client device 204).

In some cases, the client device 204 may present the user recommendations as a list that is not necessarily organized by the recommended action. The list may instead be ordered based on the anticipated diversity level and/or the expected participation level. For example, the client device 204 may present a list of user recommendations starting with inviting User S (e.g., based on being associated with the highest diversity level), followed by inviting User R (e.g., based on being associated with the second highest diversity level), followed by removing or replacing User D (e.g., based on being associated with the third highest diversity level), and followed by removing or replacing User B (e.g., based on being associated with the fourth highest diversity level).

Similarly, the computer system 210 may only recommend a subset of the available users based on their determined ranks. For example, the computer system 210 may only recommend a threshold number of user recommendations (e.g., a total of only three, four, or six user recommendations are initially presented to the researcher 202 on the client device 204 unless the researcher 202 requests additional recommendations) or a threshold number of user recommendations for each specific action (e.g., a maximum of three invitation or enrollment recommendations are presented on the client device 204, and a maximum of two removal or replacement recommendation are presented on the client device 204) selected accordingly to their respective ranks. The thresholds may be selected by the researcher 202 or may be automatically determined by the computer system 210. As an example, the computer system 210 may determine the thresholds based on the total number of participants currently enrolled in the study and/or on a target number of participants for the study. By presenting only a subset of user recommendations, the computer system 210 can (i) more efficiently present the key recommendations to the researcher, and/or (ii) take greater advantage of the limited screen space available on the client device 204 (or a display connected to the client device 204) by removing the need to devote screen space to recommendations that are unlikely or less likely to achieve the diversity needs of the study.

The computer system 210 may apply additional criteria to the user recommendations. For example, the computer system 210 may apply one or more thresholds that indicate the maximum number of recommendations presented on the interface 502c. However, the computer system 210 may first apply a minimum anticipated diversity level threshold to the recommendation before it can be presented on a display of the client device 204 and/or sent to the client device 204. For example, the computer system 210 may apply a static threshold of 0.90 to the anticipated diversity level. This would have the effect of only the recommendations of inviting User S, inviting User R, and removing or replacing User D being displayed on the interface 502c. The diversity level threshold may instead be dynamic, e.g., based on the current anticipated diversity level at completion 526, based on historical data for the groups and/or participants enrolled in study, based on the trends for the groups and/or participants enrolled in the study, etc. For example, the computer system 210 may only allow user recommendations that result in the anticipated diversity level improving by at least 5% with respect to the current anticipated diversity level at completion 526. By presenting only a subset of user recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

The computer system 210 may apply similar thresholds to the expected participation level. For example, the computer system 210 may apply a first static or dynamic threshold (e.g., relative to the activity level of other candidates, of currently enrolled users, activity level of other candidates in the same group as the recommended user, of currently enrolled users in the same group as the recommended user, etc.) that indicates a minimum expected participation level to be recommended by the computer system 210 for an invitation to enroll in the study or to be enrolled in the study. Similarly, the computer system 210 may apply a second static or dynamic threshold (e.g., relative to the activity level of other candidates, of currently enrolled users, activity level of other candidates in the same group as the recommended user, of currently enrolled users in the same group as the recommended user, etc.) that indicates a maximum expected participation level to be recommended by the computer system 210 for removal or replacement. Again, by presenting only a subset of user recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

In some cases, a similar interface to the interface 502c is presented at one or more points throughout the study. For example, a similar interface may be presented at the user's request to modify an enrollment of participants in the study. As another example, a similar interface may be prepared and/or presented in response to certain research milestones being met, in response to a diversity warning or error being generating (e.g., due to participants associated with particular groups leaving the study; participants of particular groups not being sufficiently active in the study; etc.

Although various examples described throughout this disclosure provide for a target group composition or target group diversity including one or more target percentages for one or more groups of devices or users, the target group composition or target group diversity may alternatively provide, for each of multiple categories or types of devices or users, a target number for that category or type (e.g., a quota representing a total or minimum number to include). For example, the target group composition 522 may include a first quota of at least five-hundred users from Group 1, a second quota of at least two-hundred and fifty users from Group 2, and a third quota of at least two-hundred and fifty users from Group 3. In these examples, the relative composition of the group populations may not matter or may be a secondary factor when compared to the goal of meeting the quotas.

In some cases, there is a target group composition and one or more quotas that must be met. For example, the computer system 210 may set the target group composition 522 to 50% for Group 1 participants, 25% for Group 2 participants, and 25% for Group 3 participants, and set an acceptable target composition range as 48-52% Group 1 participants; 24-26% Group 2 participants, and 24-26% Group 3 participants. However, the computer system 210 may also set quotas for each of the groups. The target group composition and the quotas may be set in order to ensure the viability of the study results. For example, the target group composition and the quotas may be set in order to ensure (or significantly increase the likelihood) that statistically relevant results can be obtained from the study.

In some cases, the interfaces 502a-502c present different options and/or functionality depending on the current stage of the study, detected events, and/or obtained data. For example, the interface 502a may be presented at a study parameter stage of the study (e.g., the second stage 234 shown in FIG. 2), an inclusion and exclusion criteria stage of the study (e.g., the third stage 236), or a select cohort stage of the study (e.g., the fourth stage 238). In contrast, the interface 502b and/or the interface 502c may be presented at an enroll participants stage of the study (e.g., fifth stage 240). Based on the different stages associated with the interfaces, the client device 204 may present (e.g., based on instructions provided by the computer system 210) different options for the researcher 202 to interact with. For example, the client device 204 may present options in the interface 502a for the researcher 202 to select, modify, add, and/or remove study parameters. In contrast, in the client devices 204 may not immediately present these options in the interfaces 502b and 502c (e.g., although the researcher 202 may be able to still access them). Instead, the client device 204 may present in the interfaces 502b and 502c different options to view details of those currently enrolled in the study, to invite or enroll new users, to remove or replace enrolled users, to view details of candidates such as historical data of previous study participants, to view in real-time or substantially real-time the effects of different user selection scenarios (e.g., to see the effects on a calculated diversity score, on the anticipated group composition 522 at the end of the study, on anticipated participation level by group by the end of the study, on an anticipated participation level by group over the course of the study, on an anticipated group composition over the course of the study, etc.), etc.

Figure 6A:
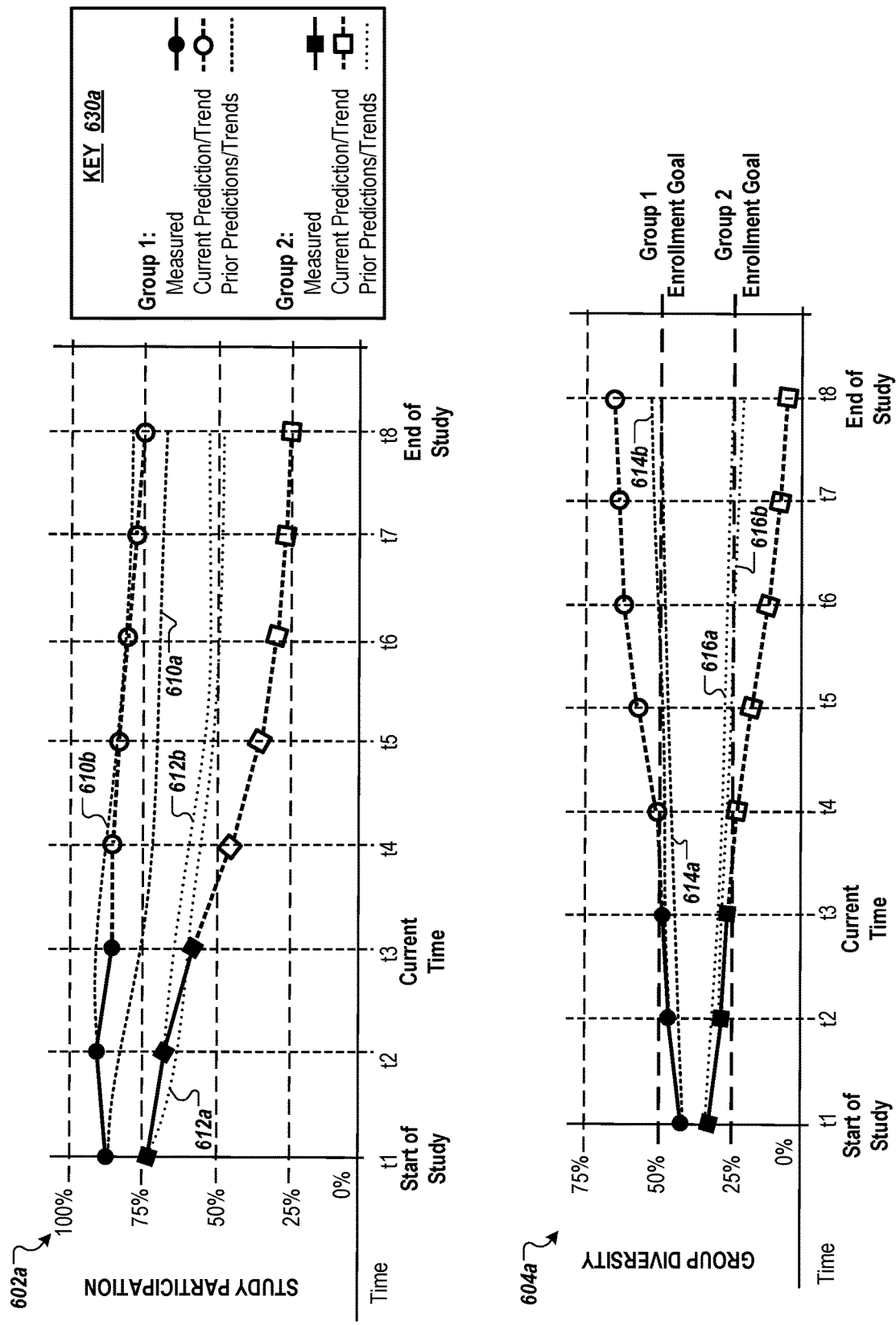
FIGS. 6A-6B are diagrams that illustrate group predictions for a research study.
Figure 6B:
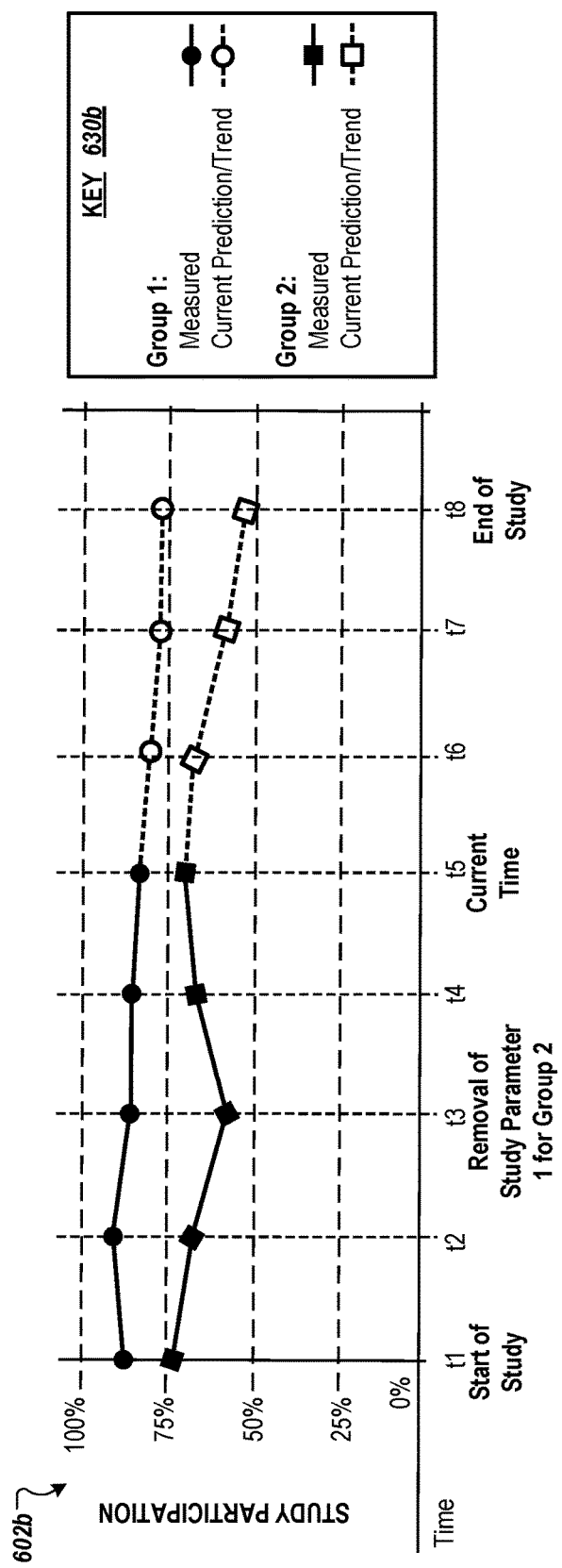
Figure 6B:
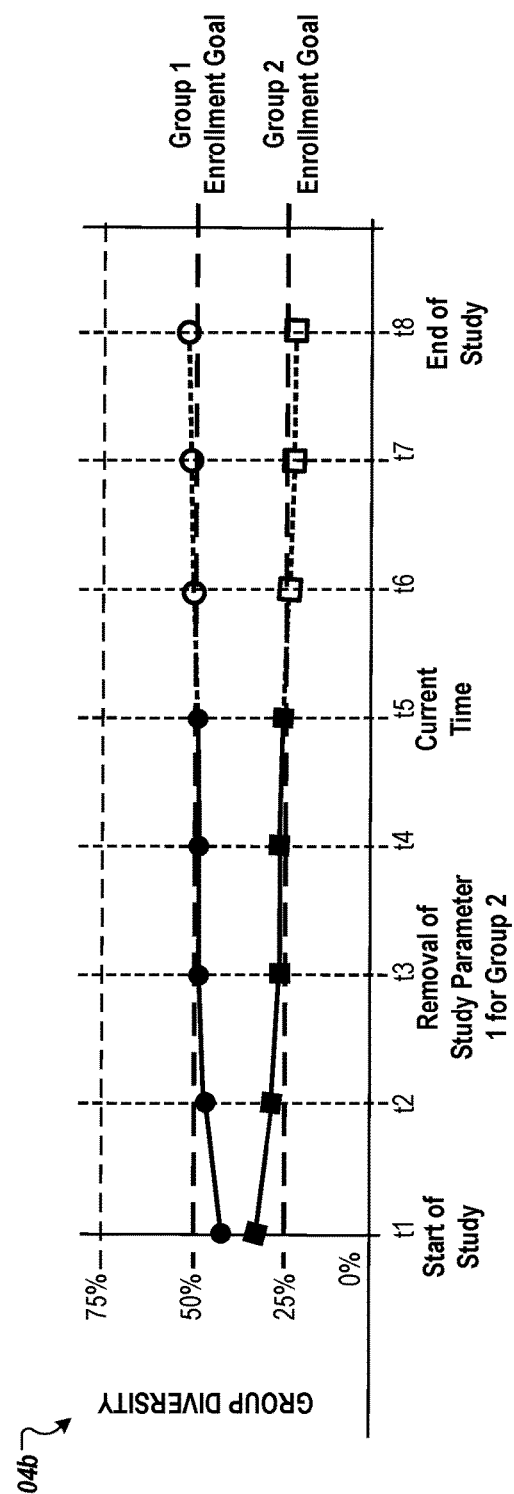

FIGS. 6A-6B are diagrams that illustrate group predictions for a research study. These predications may be generated by the computer system 210 during the performance of diversity analyses. In generating the predictions, the computer system 210 may access the table data shown and described above with respect to FIG. 4. Specifically, the computer system 210 may use previously determined trend data to make predications regarding specific groups of participants. The computer system 210, may also make predications for specific participants. These predictions can be used to update or modify the predications or the predication calculations for the groups that the specific participants belong to.

FIG. 6A is a diagram that illustrates group predictions for a research study, such as a clinical trial, or other monitoring program. The predictions may be made by the computer system 210 described above with respect to FIGS. 2-4. The computer system 210 may use the predications to determine the predicted group composition at a future time, such as at study completion.

A first graph 602a indicates measured and predicted group participation levels. As illustrated by a key 630a, the graph 602a depicts measured or observed study participation levels, previous predictions made or trends corresponding to a time before the current time (t3), and a current prediction or trend corresponding to the current time (t3). For example, the computer system 210 may have, based on one or more data points corresponding to a start of study time (t1) and known trends for Group 1 participants (e.g., as indicated in the trend data 416 shown in FIG. 4, such as the table 402), generated a prediction 610a corresponding to the start of study time (t1). The prediction 610a indicates, for example, that anticipated study participation levels of Group 1 participants at one or more future points in time with respect to the start of study time (t1). For example, the prediction 610a indicates that the Group 1 participants are most likely to have a study participation level of 66% by the end of the study (t8). The prediction 610a may be a trend line for Group 1 that is applied to one or more observed data points, such as a measured participation level of 87% at the start of the study.

Similarly, the computer system 210 may have, based on one or more data points corresponding to a start of study time (t1) and known trends for Group 2 participants (e.g., as indicated in the trend data 416 shown in FIG. 4, such as the table 402), generated a prediction 612a corresponding to the start of study time (t1). The prediction 612a indicates, for example, that anticipated study participation levels of Group 2 participants at one or more future points in time with respect to the start of study time (t1). For example, the prediction 612a indicates that the Group 2 participants are most likely to have a study participation level of 49% by the end of the study (t8). The prediction 612a may be a trend line for Group 1 that is applied to one or more observed data points, such as a measured participation level of 74% at the start of the study.

The computer system 210 may have, based data measured (e.g., received, observed, and/or collected) over the time range of t1-t2 and known trends for Group 1 participants (e.g., as indicated in the trend data 416 shown in FIG. 4, such as the table 402), generated a second prediction 610b corresponding to a second time (t2). The prediction 610b indicates, for example, that anticipated study participation levels of Group 1 participants has significantly changed such that the Group 1 participants are now anticipated to have a study participation level of 78% by the end of the study (t8). The computer system 210 also determines an updated prediction 612b for the Group 2 participants indicating a new anticipated participation level of Group 2 participants of 55% by the end of the study.

Finally, the computer system 210 may have, based on data measured from the start of the study (t1) to the current time (t3) generated a current study prediction for the Group 1 participants and the Group 2 participants. The new prediction for the Group 1 participants indicates modest changes to the anticipated study participation levels that does not raise any alarms. In contrast, a significant dip in the measured study participation levels for the Group 2 participants (and/or other indicators) has resulted in the predicted study participation levels of Group 2 participants to drop significantly. The computer system 210 may generate a warning in response to the current prediction for the Group 2 participants. For example, the computer system 210 may generate a warning based on a slope of a current prediction trend line, based on anticipated participation levels of the Group 2 participants dropping below one or more threshold study participation levels that correspond to one or more different times, etc.

As an example, participants may be automatically unenrolled from a study if there participation drops below a certain threshold (e.g., 40%). As such, because the most recent prediction for the Group 2 participants indicates an average study participation level below 40% at one or more points (e.g., before or at the end of the study), the computer system 210 may, in response, generate a warning to transmit to the client device 204. The warning may be accompanied with one or more recommendations on how to address the low study participation of Group 2 participants. Alternatively, the computer system 210 may automatically perform one or more actions in attempt to address the identified issues. As will be discussed in more detail with respect to FIG. 6B, the computer system 210 may remove a study parameter from the study for Group 2 participants that, for example, the historical data 412 has shown to have a negative effect on the participation levels (e.g., and therefore the enrollment) of Group 2 participants. This cause and effect may be depicted, for example, in table 404 of FIG. 4. The study actions recommended or performed by the computer system 210 may be depicted for example, in table 410 of FIG. 4.

In general, trend lines determined and/or applied to make predictions for group participants based on various factors. For example, a trend line applied for a particular group may be determined for and/or otherwise specific to a particular time or stage of a study (e.g., particular percentage of the study that is complete), such that there may be multiple different or possible trend lines for a given group of participants. Similarly, different group trend lines may additionally or alternatively correspond to different ranges of observed or measured values. For example, the computer system 210 may apply a first trend line for study participation of Group 1 participants if a measured data point for the start of study time falls between 80% and 90% participation, and a second trend line if the measured data point for the start of study time falls between 70% and 80% participation. Accordingly, here, the computer system 210 may apply the first trend line to the Group 1 start of study measured data point(s) to generate the prediction 610a.

The computer system 210 may make new predictions at different points throughout the study. For example, the computer system 210 may make a new prediction after a threshold amount of time has passed, after a particular study completion percentage is reached or added since a last prediction was made (e.g., prediction is made every time is determined that the current study completion percentage is 5% closer to 100% from a prior study completion percentage corresponding to when an immediately preceding prediction was made), in response to new data being collected or received (e.g., from the study participants), after a milestone in the study is reached, and/or after a stage or phase of the study changes. For example, the graphs 602a and 604a may be generated in response to receiving measuring new data from the study participants, and/or weekly based on data received and/or collected from study participants over the last week.

A second graph 604a indicates measured and predicted group diversity levels (e.g., diversity of enrolled participants). As shown, the most recent group diversity predictions indicate very low retention of Group 2 participants such that it is very unlikely that the target cohort diversity will be achieved. This low retention of Group 2 may be based, at least in part, on the low study participation levels observed and/or predicted. As an example, the computer system 210 may generate the group diversity prediction based, at least in part, on the measured and/or predicted study participation of the different groups.

As an example, the computer system 210 may have, based on one or more data points corresponding to a start of study time (t1) and known trends for Group 1 participants (e.g., as indicated in the trend data 416 shown in FIG. 4, such as the table 402), generated a prediction 614a corresponding to the start of study time (t1). The prediction 614a indicates, for example, an anticipated Group 1 enrollment relative to one or more other groups in the study. For example, the prediction 614a indicates that the Group 1 participants are most likely to make up about 50% of the study enrollment by the end of the study (t8), e.g., which is in line with a Group 1 enrollment goal to achieve the cohort composition target 224 by the end of the study. The prediction 614a may be a trend line for Group 1 that is applied to one or more observed data points, such as a measured enrollment percentage of Group 1 participants of 42% at the start of the study.

Similarly, the computer system 210 may have, based on one or more data points corresponding to a start of study time (t1) and known trends for Group 2 participants (e.g., as indicated in the trend data 416 shown in FIG. 4, such as the table 402), generated a prediction 616a corresponding to the start of study time (t1). The prediction 616a indicates, for example, an anticipated Group 2 enrollment relative to one or more other groups in the study. For example, the prediction 616a indicates that the Group 2 participants are most likely to make up about 25% of the group composition 225 by the end of the study (t8), e.g., which is in line with a Group 2 enrollment goal to achieve the cohort composition target 224 by the end of the study. The prediction 616a may be a trend line for Group 2 that is applied to one or more observed data points, such as a measured enrollment percentage of Group 2 participants of 33% at the start of the study.

The computer system 210 may have, based data measured (e.g., received, observed, and/or collected) over the time range of t1-t2 and known trends for Group 1 participants (e.g., as indicated in the trend data 416 shown in FIG. 4, such as the table 402), generated a second prediction 614b corresponding to a second time (t2). The prediction 614b indicates, for example, that anticipated study participation levels of Group 1 participants has modestly changed such that the Group 1 participants are now anticipated to make up roughly 53% of the group composition 226 by the end of the study. The computer system 210 also determines an updated prediction 616*b* for the Group 2 participants that the Group 2 participants are now anticipated to make up 23% of the group composition 226 by the end of the study. These changes may, in some cases, be enough to trigger the computer system 210 to generate a warning, to determine one or more recommendations, and/or to automatically perform one or more actions.

Finally, the computer system 210 may have, based on data measured from the start of the study (t1) to the current time (t3) generated a current study prediction for the Group 1 participants and the Group 2 participants. The new predictions for the Group 1 and Group 2 participants indicates significant changes to the group composition 226, such that the computer system 210 may, in response, generate a warning. Notably, the current prediction indicates that the enrollment of Group 2 participants is expected to deviate significantly from the Group 2 enrollment goal of 25%, and that, relatedly, the enrollment of Group 1 participants is expected to deviate significantly from the Group 1 enrollment goal. The computer system 210 may generate a warning in response to the current prediction for the Group 1 and Group 2 participants. For example, the computer system 210 may generate a warning based on a slope of a current prediction trend line, based on an anticipated group composition 226 at the end of the study (t8), based on the enrollment percentage of the Group 2 participants dropping below a threshold at one or more current and/or future points in time, based on the enrollment percentage of the Group 1 participants exceeding a threshold at one or more current and/or future points in time, etc.

FIG. 6B is a diagram that illustrates updated group predictions for a research study. The predictions may be made by the computer system 210 described above with respect to FIGS. 2-4. The computer system 210 may use the predications to determine the predicted group composition at a future time, such as at study completion.

As illustrated in FIG. 6B and by the key 630*b*, time has elapsed and the predictions have been updated accordingly when compared to FIG. 6A. The updated prediction may have been made by the computer system 210. During the elapsed time, (e.g., at the time t3) a study action of removing "Study Parameter 1" for the Group 2 participants has been performed. This study action may have been automatically performed by the computer system 210, or may have been part of a recommendation generated by the computer system 210 that was accepted by a researcher of the study. As shown, the performance of the study action has had a significant effect on the observed and predicted data (e.g., diversity related data) for the study with respect to Group 2 participants.

The first graph 602*b* indicates updated measured and predicted participation levels of study participants by group last updated at a time t5. As shown, the performance of the study action to remove a study parameter for Group 2 participants has had a significant effect (here an improvement) on the participation levels of Group 2 participants.

A second graph 604*a* indicates updated measured and predicted group diversity levels (e.g., diversity of enrolled participants). The measured and predicated group diversity levels were in this example last updated at a time t5. As shown, the most recent group diversity predictions indicate a significantly improved group diversity predictions such that the expected group diversity at the end of the study is now expected to be within 3% of the target cohort diversity.

Figure 8A:
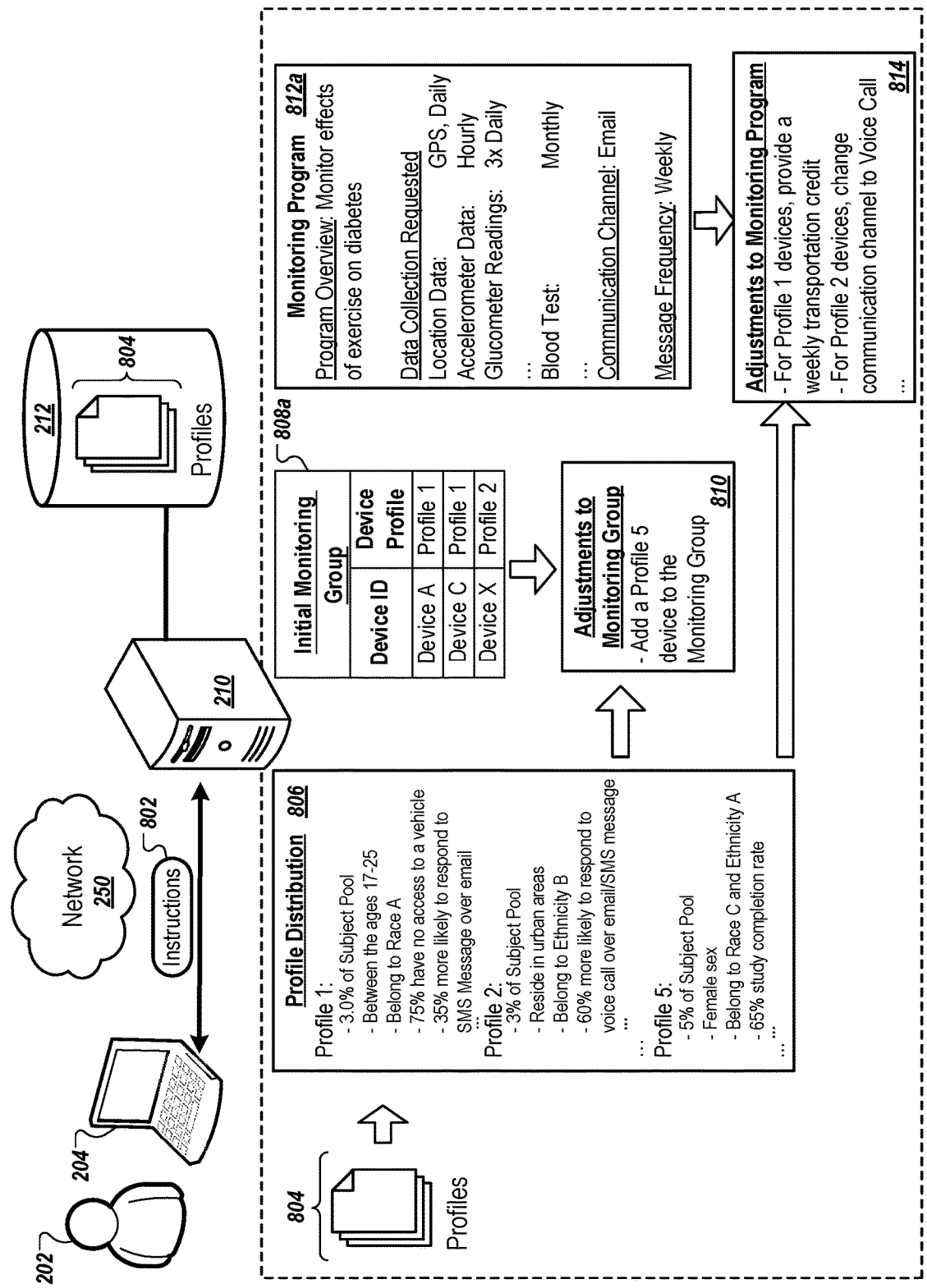
FIGS. 8A-8B are diagrams that illustrate an example system for customizing monitoring programs involving remote devices.
Figure 8B:
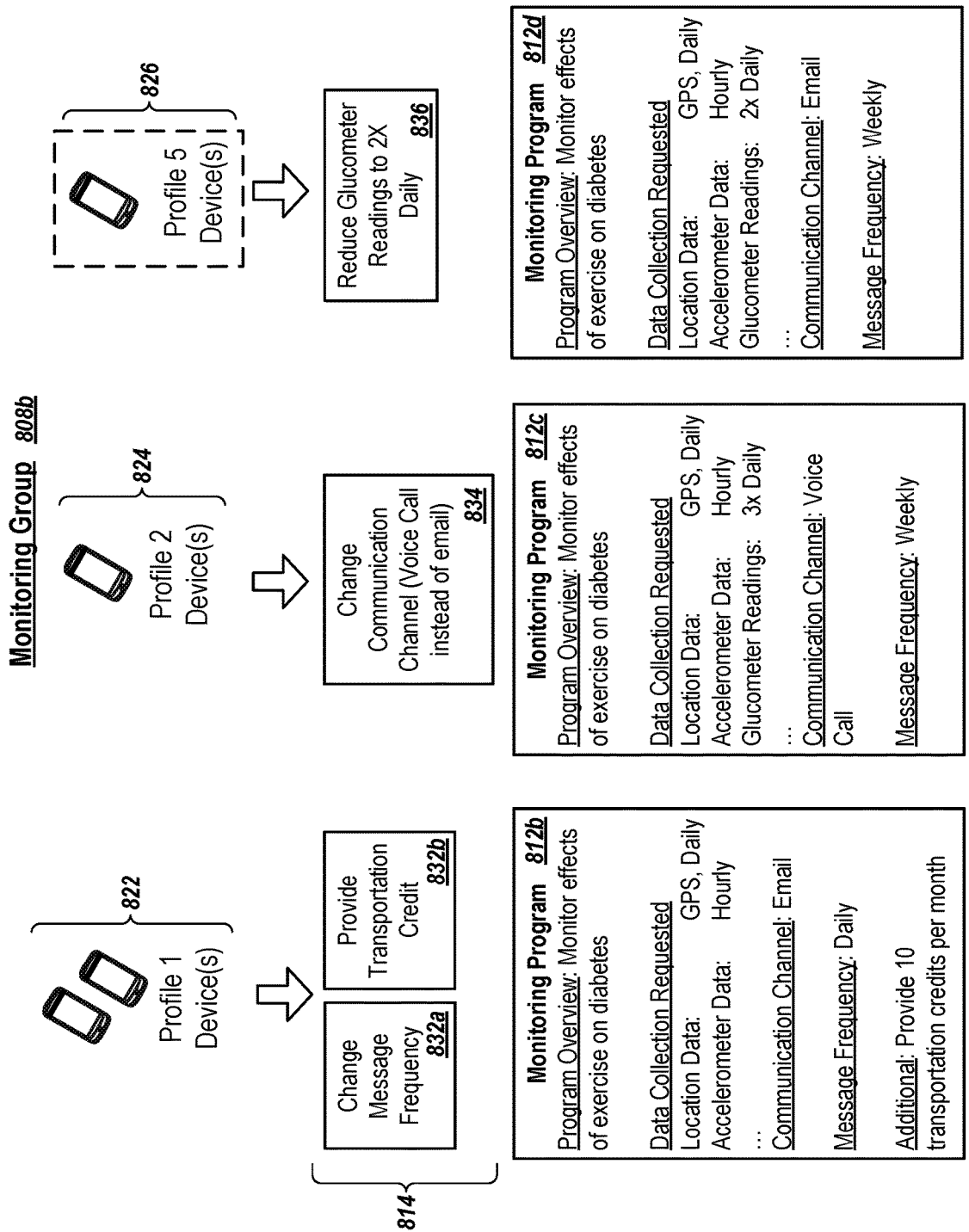

FIGS. 8A-8B are diagrams that illustrate one or more components of the system 200 and a process for customizing monitoring programs involving remote devices. In customizing monitoring program, the computer system 210 of the system 200 can assess and adjust the composition of groups for a monitoring program 812*a* or the monitoring program 812*a* using a set of profiles 804. The computer system 210 may distribute adjusted monitoring program 812 to multiple remote devices.

The computer system 210 may be configured to distribute software for a monitoring program to devices that are to be monitored. The monitoring program may indicate times when data is to be obtained from, requested from, or sent to the monitored devices. The monitoring program may also indicate the type of data or the specific data that is to be obtained from, requested from, or sent to the monitored devices. The data obtained or requested from the monitored devices may include sensor data collected using sensors of the monitored devices or sensor devices electronically connected to the monitored devices. The data sent to the monitored devices may include instructions to collect sensor data, or updates to the monitoring program or a portion of the monitoring program on the devices. In updating the monitoring program or a portion of the monitoring program on the devices, a configuration of the monitored devices can be adjusted to, for example, change what data is monitored or how the data is monitored.

The computer system 210 can adjust the monitoring program for particular groups of devices or users. These groups may correspond to different profiles generated by the computer system 210. The computer system 210 may assign each of the monitored devices to at least one profile based on attributes of the devices or attributes of users of the devices. For example, a first profile may indicate that a device must include a GPS unit and a heartrate monitor, and that the user of the device must live in an urban environment and must be between the ages of 25 and 30 years of age. If a first device of the group of device meets the device requirements of the profile criteria and has a user that meets the user requirements of the criteria, the computer system 210 may classify the first device as belonging to the first profile.

The computer system 210 may generate the profiles based on previously observed outcomes. For example, the computer system 210 may generate profiles based on observed outcomes of a currently running and/or previously performed monitoring programs. The observed outcomes may include the compliance of the devices or their users with the requirements of the monitoring program, and the retention of the devices or their users in the monitoring program. As another example, the computer system 210 may generate profiles based on attributes of devices or users in a candidate pool. The attributes may include, for example, sensors that the devices include, sensor devices that are compatible with the devices, models of the devices, operating systems of the devices, etc. The attributes may also include demographic or non-demographic information that describes the users. The users may include, for example, users that have previously participated in a monitoring program, that are currently participating in a monitoring program, have indicated that they want to participate in a monitoring program, or that are eligible for a monitoring program.

The computer system 210 may generate the profiles using a machine learning model or a group of machine learning models. As an example, the computer system 210 may using a clustering machine learning model to cluster different devices or users based on observed outcomes. Similarly, as another example, the computer system 210 may use a clustering model to cluster different groups of devices or users based on attributes of the devices or users. The model may use all attributes available to the model in performing the clustering. Alternatively, the model may use a subset of attributes corresponding to key attributes to perform the clustering. These key attributes may be determined using another machine learning model or a group of other machine learning models, using a static algorithm or group of static algorithms, or based on input from an administrator or researcher.

In general, a monitoring program refers to a set of elements that define how to conduct a monitoring program of multiple devices and/or persons. The elements may include parameters for the monitoring program. These parameters may, for example, define inclusion criteria for persons or devices in the monitoring program, and/or exclusion criteria for persons or devices in the monitoring program. The elements may also include a definition of the monitoring program or an indication of what type of studies the monitoring program has (i) previously been used for, and/or (ii) is applicable to. The elements may also include an indication of the particular data that is to be requested and/or received during a program, a schedule that indicates when data is to be requested and/or received, and/or a frequency of data collection or reception. The elements may further define one or more conditions for determining the end of the monitoring program. For example, an element may indicate that the monitoring program is to be run for six months. As another example, an element may in dictate that multiple sessions of the monitoring program are to be run until a set of particular conditions are met (e.g., enough data is collected from each of the participants). Similarly, the elements may define conditions for determining one or more milestones of the monitoring program.

The elements may define or otherwise indicate other information of the monitoring program, including other communication information. For example, the elements may indicate a default communication channel, a default word choice (e.g., vocabulary) for communication, a default sentence structure (e.g., formal, semi-formal, informal, etc.).

Figure 7:
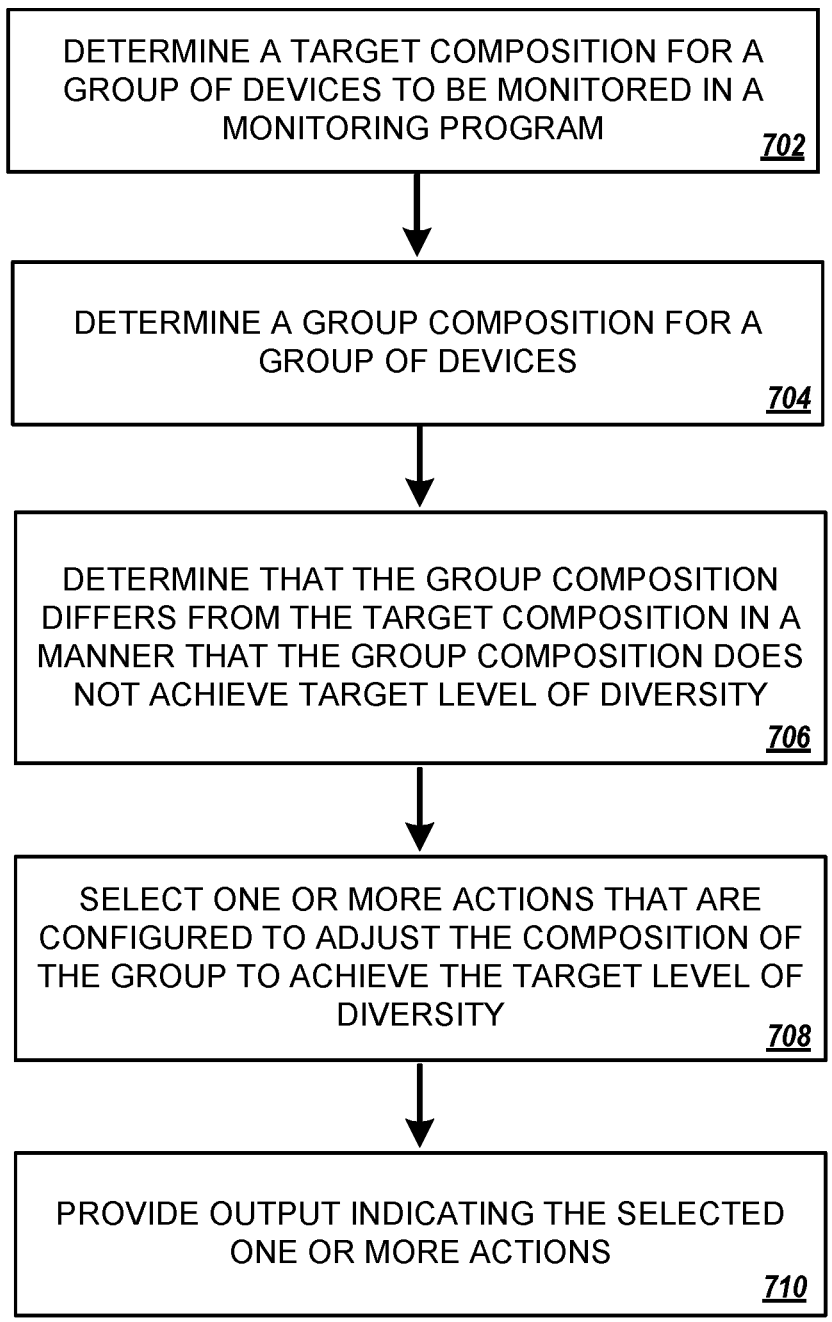
FIG. 7 is a flowchart diagram that illustrates an example process for diversity assessment and action selection.

FIG. 7 is a flowchart diagram that illustrates an example process for diversity assessment and action selection. The process 700 may be performed by the computer system 110 shown in FIG. 1. The process 700 may be performed by the computer system 210 shown in FIGS. 2-4.

In many cases, the administrator of a monitoring program, such as a researcher conducting a clinical trial, cannot determine whether the monitoring group provide sufficient diversity to achieve the needs of the monitoring program. Beyond simply whether a sufficient total number of participants are enrolled, it is difficult to determine whether the makeup of the monitoring group provides the right variety in participant backgrounds. Further, the effective level of diversity can be diminished through the lack of compliance that disproportionately affects some groups over others. The process 700 helps the system determine and inform an administrator whether a monitoring group has sufficient diversity, as well as to indicate what adjustments should be made to obtain the proper diversity representation level if it is not present.

Briefly, the system can identify a reference population for the monitoring program (e.g., population at large, or a group most likely to use a drug or product) and determine a diversity goal that reflects the characteristics of the reference population. The system can also determine diversity metrics for a monitoring group (e.g., a clinical trial cohort) and provide the diversity metrics to the administrator, indicating whether the current and expected future monitoring group characteristics will meet the target level of diversity. For example, the system can compare the diversity metrics for the cohort to the goal levels (e.g., thresholds, ranges, minimums, etc.), determine that the diversity metrics are outside a desired range, and then select actions to improve diversity in the monitoring group.

The process 700 includes determining a target composition for a group to be monitored in a monitoring program (702). In some cases, the system provides a user interface through which a researcher or other administrator can specify the target composition. In other cases, the system determines the target composition, calculating an appropriate target from data describing a reference population and other data.

As discussed above, the target composition can be based on a reference population, such as a set of devices or users in a particular geographical area. The target composition can be based on other populations or subgroups. For example, for a research study about diabetes, the target composition may be based on the set of people in the United States that have diabetes, and so the target composition represents the characteristics of that population rather than the general population. The system can receive input indicating the location or general population of interest, and then retrieve population data (e.g., census data, survey data, etc.) specifying the makeup of the population. The system then sets the target composition to have characteristics (distribution of profiles or attributes) that are the same as or are based on the characteristics in the population data.

The target composition can be defined with respect to attributes that are specified by a user as relevant to the study or as inferred by the system as relevant to the study. The dimensions used for assessing composition and diversity can be different from one monitoring program to another. Some monitoring programs may define composition in terms of a desired distribution across each of age, sex, and race. Other monitoring programs may additionally or alternatively use other attributes, such as whether a person has a certain health status or not (e.g., high blood pressure, obesity, diabetes, cancer history, etc.), a certain genetic profile, or whether the user has a certain behavior pattern. Thus, the dimensions for which diversity can be assessed and achieved can be well beyond simple demographics.

The target composition can be expressed in different ways, and even with multiple types of constraints for a single monitoring program. One is a relative measure for different groups or profiles (e.g., 10% from group 1, 20% from group 2, etc.). Another is a set of minimums or quotas for each of different groups (e.g., at least 10 from group 1, at least 25 from group 2, etc.). Another is a set of ranges, thresholds, or constraints. For example, the target may be expressed as amounts or percentages of the monitoring group for each of different attribute values (e.g., a minimum of 40% male, a minimum of 40% female, a minimum of 30 individuals that have diabetes and a minimum of 30 individuals that do not have diabetes, no more than 40% Caucasian participants, at least 15% for each of multiple different racial backgrounds, etc.)

The process 700 includes determining a group composition for a group of devices or users for the monitoring program (704). The group can be a monitoring group of enrolled devices or users that have registered or subscribed to participate in the monitoring program. As another example, the group can be a group of candidates selected to invite to participate, or a candidate pool from which candidate participants can be selected. In health research studies, the group can be an actual cohort of individuals enrolled in a research study. Similarly, at the creation of the research study, before the study has begun, the group can be a candidate pool or a selected prospective cohort (e.g., a set of prospects identified as meeting the selection criteria which may not yet have enrolled).

The system can determine the measures of composition of the group for each of the different constraints or measures of diversity used to define the target. For example, if the target is a set of quotas for different participant types or profiles (e.g., defined by age, race, sex, or other attributes), the system can determine the number of people in the assessed group that meet each type or profile. Similarly, if the target is expressed in terms of percentages for different types or profiles, the group composition can also be determined as the percentages for the different types or profiles. In general, the group composition can indicate the amounts of members in different categories and the distribution of different attribute values among the group, in absolute or relative terms.

The process 700 includes determining that the group composition differs from the target composition in a manner that the group composition does not achieve the target level of diversity (706). The system can store user profiles that describe the attributes, history, medical history, and other characteristics of individuals. The system can compare the group composition with the target composition and determine whether the group composition is within a threshold level of the target composition. This can involve comparing the amounts of participating devices or users in different categories to the respective amounts indicated by the target composition data. This may also include generating a diversity score, for the group as a whole or for different categories of participants, and determining whether the difference is less than a predetermined threshold (e.g., less than 5% different, etc.). In many cases, a difference of at least the predetermined magnitude for any one of various categories or groups (e.g., less than the minimum needed for any of group 1, group 2, group 3, etc.) or for any of the predetermined attributes for which diversity is needed (e.g., age, sex, race, diabetes status, location, mental health history, etc.) can trigger the system to take corrective actions to bring the monitoring group back to the composition needed.

Notably, the system can assess diversity for not only the nominal membership of the monitoring group (e.g., the set enrolled or invited to enroll), but also the set of members actually complying with (or predicted to comply with) the requirements of the monitoring program. For example, for a clinical trial, 1000 participants may be enrolled, but only 850 may be complying with the requirements of the study protocol. These requirements may be for data collection (e.g., completing a survey, acquiring sensor data, etc.) or for other actions separate from data collection (e.g., taking a medication, performing a needed amount of exercise, sleeping according to study guidelines, etc.). As a result, the system can assess the composition and diversity of the set of the 850 complying participants to provide a more accurate indicator of the results of the study. Because compliance and attrition can vary for different participant backgrounds and different participant attributes, the system's assessment of the complying set can provide an early indicator where compliance problems for some groups may decrease the effective diversity among the valid, usable data sets for the study. Participants that do not comply with the requirements may be considered withdrawn from participation for the purposes of the calculation showing the diversity status, even if the participants continue to be enrolled and outreach is made to bring them back into compliance.

In many cases, administrators may enroll an appropriately diverse group of participants at the beginning of the study, but poor quality data collected, incomplete data collection, lack of compliance with participant disproportionately affects participants in one or more groups, which can put the entire research study at risk of cancellation. This, of course, risks wasting all of the resources expended on the study, at the servers of the system as well as at all of the many remote devices. The system can compare the collected data for individual participants with the requirements of the monitoring program they participate in to determine compliance, on a repeated or ongoing basis. This then gives the system the ability to determine the composition and diversity status of the subset of the monitoring group that is complying with the requirements.

The system can be a multi-tenant system that manages many different monitoring programs each with their own requirements for diversity and their own target compositions. The system can monitor the compliance of individuals in each monitoring group with respect to the particular requirements of the corresponding monitoring programs. This allows the system to track, in real time or substantially in real time, whether each monitoring program is meeting its own objectives for composition and diversity.

The process 700 includes selecting one or more actions that are configured to adjust the composition of the group to achieve the target level of diversity (708). When the desired diversity level is not met, the system can identify the participant categories or participant attributes that are underrepresented and determine actions to bring levels for those categories or attributes up to the levels needed to meet the target composition. For example, the system can determine that within a monitoring group, a first category is represented by only 7 participants while the target is 10 individuals. In response, the system can search the user profile database and identify at least three additional individuals in the first category that meet the eligibility criteria for the monitoring program. The identified candidates may then be added to monitoring group (e.g., invited to enroll, added as participants, etc.) to bring the composition and diversity level to the needed state.

The selection of actions can include actions determined to increase the compliance with study requirements for participants in specific categories or with specific attributes that are underrepresented. For example, if 10 participants are needed for category 2, but only 8 out of the 10 enrolled participants in that category are complying with the data collection requirements, then the system can select actions that are calculated to increase the compliance of the two non-complying participants and/or to increase future compliance for all participants in that category. The tables shown in FIG. 4 can be used by the system to identify additional elements to add to the monitoring program to increase compliance (e.g., those associated with positive effect on compliance or at least lower negative effects). The system can also change the manner of communicating with those participants, add additional participants for underrepresented categories or take other actions to improve the diversity level.

The process 700 provides output indicating the selected actions (710). This can include providing the output to a device associated with a researcher or other administrator for the monitoring program, for display in a user interface on the administrator's device. The user interface may include interactive controls, and in response to the controls the system can carry out one or more recommended actions to improve the composition and diversity level for the monitoring group toward the target composition.

In addition, the system may carry out the one or more selected actions, in some cases automatically without requiring specific user input or confirmation. In these cases, the system can carry out adjustments to the monitoring groups (e.g., inviting or enrolling new participants in categories that are underrepresented or are effectively underrepresented when compliance is taken into account), adjusting monitoring program elements for unrepresented groups (e.g., adding or substituting interactions, survey elements, configuration data, etc.), changing the form or content of communications to underrepresented groups, and so on. The system can identify and carry out various types of actions to improve the level of diversity among enrolled and complying members of the monitoring group. This includes providing customized support or interaction to customized for the needs or preferences of different groups. Depending on the participant's background, some may respond better to being provided a credit for taxi service, providing a mobile phone, changing manner of interactions in the study, etc. Similarly, the system may broaden inclusion criteria (e.g., remove limitations to joining the monitoring group) to encompass more of people of the needed backgrounds. Similarly, the system can reduce or remove exclusion criteria to similarly encompass more candidates when needed. As discussed further below, various actions can add additional participants to the cohort from underrepresented groups or may communicate with participants to restore compliance with program requirements. In addition, the system may determine a reason that diversity metrics are out of target ranges, such as identifying one or more factors in the study that are resulting in a bias to enrollment, compliance, or retention. For example, for certain groups, one or more requirements may be disproportionately missed, signaling a need to change that requirement or add additional support for those groups. For each of various potential changes, the system can determine a candidate pool or predicted outcome as if the change was carried out, then select the actions with the best results predicted (e.g., scored as providing the least disruption, highest improvement to diversity, etc.)

In addition to assessing effective level of diversity among participants currently complying with program requirements, the system can assess the diversity among the set of participants projected or predicted to comply with the requirements. This can be useful at the creation of a study, to assess how the requirements of a new study may disproportionally affect the compliance or retention of one group over another. Using the analysis of FIG. 4, the system can identify the elements that have the negative effect and propose substitute elements with better outcome profiles and/or recommend additional elements to compensate for the effect. Similarly, the predictions of compliance rates and retention rates for different groups can be used while a study is ongoing, showing that although current compliance is acceptable, historically the compliance or retention by the end of the study may be worse and may remove the diversity level currently seen.

FIGS. 8A-8B are diagrams that illustrate one or more components of the system 200 and a process for assessing and adjusting the composition of groups for a monitoring program 812*a* or the monitoring program 812*a* using a set of profiles 804.

The disclosed systems can be used to achieve number benefits. For example, the computer system 210 can provide numerous benefits to realize and improved program monitoring and distribution system.

Notably, other systems often, if not always, fail to start with an appropriate set of subjects to monitor. That is, these systems are incapable of checking if a set of subjects, such as a set of devices or device users, will provide the overall set of data and the diverse context to be able to capture the variety of data required in the monitoring program. Often these systems are simply provided a pre-selected group subjects or randomly select a group of subjects that are bound to produce, or have an unacceptably high likelihood of producing, unviable results or results that fail one or more other goals of the monitoring program.

In contrast, the computer system 210 can address this issue by selecting a group of subjects to invite or enroll in a monitoring program that are predicted to meet the set goals for the monitoring program. In more detail, the computer system 110 may select a diverse group of subjects to enroll or invite to the monitoring program such that the composition of the group meets certain diversity requirements. By including a diverse group of subjects at the outset of the monitoring program, the computer system 210 can at least improve the likelihood of obtaining viable results from the monitoring program. As an example, many medical studies today fail to produce viable results or produce results having severely limited applicability due to a failure to include or maintain a diverse set of participants. Diversity may refer to diversity among various subject attributes, including both demographic and non-demographic attributes.

The computer system 210 may also take into account other attributes of the subjects when selecting a group of subjects to enroll or invite to a monitoring program. For example, the computer system 210 may take into account historical data, trends in the historical data, and, optionally, trends among certain populations to select subjects that are likely to meet the requirements of the study. The historical data or trends may indicate past or anticipated retention rates for subjects or groups of subjects, past or anticipated compliance rates for subjects or groups of subjects, or past or anticipated data quality obtained from subjects or groups of subjects. For example, the historical data may indicate that a particular subset of subjects is likely to have low compliance with a particular requirement of a monitoring program. In response to this determination, the computer system 210 may avoid enrolling or inviting those subjects to the monitoring program.

However, if those subjects are necessary to achieve certain minimum diversity criteria or other goals for the monitoring program, the computer system 210 can modify the elements of the monitoring program for that particular subset of subjects to improve compliance. Modifying the elements may include modifying or removing requirements of the monitoring program, or adding remedial elements. For example, if the particular subset of subjects is determined by the computer system 210 to generally not have access to a vehicle and, as a result, have low compliance with required medical office visits, the system 210 may add taxi credit to a new version of the monitoring program for those subjects as a remedial measure to improve compliance rates for those subjects with respect to office visits.

In selecting subjects at an outset of a monitoring program or determining how to modify the elements of a monitoring program to improve, the computer system 210 may use various profiles that represent categories of subjects. These profiles may be used to determine how particular subjects are likely to respond to certain monitoring program requirements, and, therefore, to determine if they should be enrolled to the monitoring program or if the monitoring program needs to be adjusted for one or more particular groups of subjects. These profiles may additionally or alternatively be used to improve the diversity of a monitored group or to determine if a monitored group has a sufficient diversity. For example, the computer system 110 may identify the profiles corresponding to a monitoring group and use the profiles to determine if there is sufficient diversity, at the outset or predicted diversity at completion of the monitoring program. If diversity is insufficient, the computer system 210 may use the profiles to identify unrepresented or underrepresented profiles, and proceed to enroll or invite subjects from categories represented by those unrepresented or underrepresented profiles.

By selecting at the outset of a monitoring program a group of subjects that will likely provide the overall set of data and the diverse context to be able to capture the variety of data needed for the monitoring program, the computer system 210 is able to significantly reduce computational inefficiencies. Notably, this selection improves the likelihood of obtaining viable results for the monitoring program as a whole, which greatly reduces. As such, the computer system 210 is able to significantly reduce the computational load on the system and the remote devices and the CPU hours of the system and the remote devices.

As shown in FIG. 8A, in response to receiving instructions 802 from the client device 204, the computer system 210 may access the profiles 804 from the database 212 and use the accessed profiles 804 to determine adjustments to make to the monitoring program 812a or to a group composition selected for the monitoring program 812a.

The instructions 802 may also include other information. For example, the instructions 802 may indicate an initial monitoring group 808a. That is, the instructions 802 may include or point to an initial list of devices and/or persons that have been invited to, selected for, or enrolled in the monitoring program.

The instructions 802 may also or alternatively include or otherwise indicate the elements of the monitoring program 812a. In response to receiving the instructions 802, the computer system 210 may generate the monitoring program 812a, may select an existing monitoring program that includes the elements in the instructions 802, or may update an existing monitoring program to include the elements in the instructions 802.

The instructions 802 may include data that the computer system 210 uses to initiate a monitoring program 812a. Specifically, the instructions 802 may include an indication of the specific monitoring program that should be selected for a new monitoring program (e.g., from a list of available monitoring programs).

Alternatively, the computer system 210 may select the initial monitoring group 808a from a candidate pool of devices and/or users based on the instructions 802. As an example, the instructions 802 may include criteria, such as diversity criteria, for a monitoring program that is to be performed. The computer system 210 may use this criteria to select devices and/or people for the monitoring program to place into the initial monitoring group. As an example, the instructions 802 may include diversity criteria indicating an exact or minimum number of devices or persons there needs to be in the monitoring program that are associated with specific profiles. Specifically, the monitoring instructions 802 may indicate that the monitoring group 808a must include at least one device assigned to Profile 1, and at least one device assigned to profile 2. Similarly, the instructions 802 may indicate exact, minimum, and/or maximum percentages that represent the population of devices or persons associated with specific profiles in the monitoring group 808a. For example, the monitoring instructions 802 may indicate that at least 50% of the devices in the monitoring group 808a should be assigned to Profile 1 and that at least 25% of the devices in the monitoring group 808a should be assigned to Profile 2.

Each of the profiles in the profiles 804 may correspond to a subgroup of devices and/or persons. Specifically, each profile may correspond to a subgroup or a distinct (e.g., non-overlapping) subgroup of devices and/or persons that share at least one of the same key attributes, similar attributes, or demonstrate the same or similar behaviors. That is, each profile may represent a category of devices and/or candidates. As will be discussed in more detail with respect to FIGS. 9A-9B, the computer system 210 can generate the profiles using previously observed outcomes (e.g., behaviors) and/or attributes attributed candidates for inclusion in the monitoring group. The computer system 210 may generate the profiles using one or more machine learning models, such as one or more clustering algorithms.

The profiles 804 may be previously generated and stored in the database 212. Alternatively, the profiles 804 may be generated or updated in response to the computer system 210 receiving instructions 802 from the client device 204. For example, in response to receiving the instructions, the computer system 210 may generate the profiles 804 or may update the profiles 804 using the most recently available monitoring data.

A profile distribution 806 indicates example information that defines a number of example profiles. The information in the profile distribution 806 may include criteria for determining if a device or person is eligible for assignment to the profile, e.g., inclusion criteria. For example, the criteria for Profile 1 indicates that a subject must be between the ages of 17-25 and belong to Race A to be eligible. The information may also include outcome information (e.g., anticipated behaviors such as retention, compliance, and quality of data) associated with subjects (e.g., devices and/or persons) associated with the profile. As will be discussed in more detail with respect to FIGS. 9A-9B, this outcome information may be determined for each of the profiles by analyzing outcome information associated with previous subjects or current subjects in a category of subjects corresponding to each of the profiles. As an example, 75% of the subjects in Profile 1 do not have access to a vehicle and 25% of the subjects are more likely to respond to SMS message when compared to an email message. The profile distribution may also contain various other data such as a population percentage that the subjects of each of the profiles represent of the total candidate pool. For example, 3.0% of the subjects in the candidate pool are associated with Profile 1. The candidate pool may include all subjects that have previously or are currently enrolled in a monitoring program. Alternatively, the candidate pool may include all active subjects, e.g., those that are currently enrolled in a monitoring program or are available for enrollment in a monitoring program.

In some cases, a subject may be associated (e.g., assigned to) multiple profiles. For example, a subject may meet the inclusion criteria for multiple profiles and, therefore, be associated with the multiple profiles.

In some cases, a subject is associated with only a single profile. For example, if a subject has been assigned to a first profile, they may be prevented from being assigned to a second profile.

The computer system 210 may reassign subjects to different profiles (e.g., determine that they belong to different categories of subjects) over time based on the monitored actions of the subjects. For example, a particular subject may initially demonstrate a smartphone compliance rate below 60% over the first three monitoring programs they participate in, and, as a result, be assigned by the computer system 210 to a first profile of the profiles 804. However, if over the next three monitoring programs they improve their overall compliance rate to 75%, the computer system 210 can reassign the subject to a second profile of the profiles 804.

The computer system 210 may use the profile distribution 806 to adjust the monitoring group (810). The computer system 210 may use the profile distribution 806 to adjust the initial monitoring group 808a at the outset of the monitoring program for the monitoring program 812a. In more detail, the computer system 210 may use the profile distribution 806 to identify categories of devices or persons that are underrepresented in the initial monitoring group 808a. For example, the computer system 210 may use the profile distribution 806 and the initial monitoring group 808a to determine that a device corresponding to Profile 5 should be added to the monitoring group 808. The computer system 210 may make this determination based on diversity reasons, e.g., in order to have at least one device from each profile or from each profile in one or more subsets of profiles. The computer system 210 may make this determination based on one or more determinations or predications. For example, the computer system 210 may use the profile distribution 806 to select a Profile 5 device based on the higher study completion rate of the profile 5 subjects in order to boost efficiency, increase likelihood that study will be successful (e.g., if an analysis of the initial monitoring group reveals that there is a higher than acceptable chance of study failure), etc. As another example, the computer system 210 may determine to add a Profile 5 device based on the percentage of the candidate pool. Specifically, the computer system 210 may add devices associated with unrepresented or underrepresented profiles for each profile that corresponds to at least threshold percent (e.g., 3%) of the candidate pool. Accordingly, the computer system 210 may determine to add a Profile 5 subject to the monitoring group 808 based on the Profile 5 population meeting the threshold percent.

After determining to add a Profile 5 subject to the monitoring group 808, the computer system 210 may automatically enroll a Profile 5 subject in the monitoring program, or may generate and send an invitation to a Profile subject to enroll in the monitoring program. As an example, the computer system 210 may take into consideration one or more factors to determine which subject to enroll or invite to the monitoring program. These factors may include, for example, the retention rates associated with the subject, the compliance rates associated with the subject, quality of data previously obtained from the subject or otherwise associated with the subject, the experience of the subject (e.g., number of monitoring program the subject has previously participated in), the activity level of the subject (e.g., how recent the subject has participated in a monitoring program), invitation acceptance rate of the subject, trends in factors (e.g., trends in the retention rates, compliance rates, activity level, etc. of the subject), etc. For example, a subject that has participated in at least one monitoring program over the last year and has a retention rate of 78% may be selected by the computer system 210 for enrollment over a subject that has not participated in at least one monitoring program over the last year and/or has a retention rate less than 70% despite both subjects corresponding to Profile 5.

After determining to add a Profile 5 subject to the monitoring group 808, the computer system 210 may generate and send a recommendation to the researcher 202 to enroll a Profile 5 subject or to send an enrollment invitation to a Profile 5 subject. The recommendation may include multiple subjects recommended by the computer system 210. The multiple subjects may be arranged in an order that corresponds to a recommendation order, such that the subject that the computer system 210 recommends most is shown first or highest in a list of subjects. The computer system 210 may wait to receive a response from the researcher, e.g., wait to receive a response from the client device 204, to enroll or invite one or more of the recommended subjects. Alternatively, the computer system 210 may wait for a predetermined amount of time after transmitting the recommendation to the client device 204. If a response is not received by this point, the computer system 210 can automatically enroll a Profile 5 subject in the monitoring program, or generate and send an invitation to a Profile subject to enroll in the monitoring program.

The computer system 210 may also use the profile distribution to adjust the monitoring program 812a (814). That is, the computer system 210 can determine adjustments to make to the monitoring program 812a using information in the profile distribution 806 corresponding to profiles associated with subjects in the monitoring group 808. The adjustments may include one or more changes to elements of the monitoring program 812a. As an example, these adjustments may include one or more of the following: modifications to the inclusion criteria for the monitoring program; modifications to the exclusion criteria for the monitoring program; modifications to the type, source, schedule, or frequency of data collection; modifications to the type, source, schedule, or frequency of data requests; modifications to monitoring program events or other requirements; modifications to communication methods, content, schedule, and/or frequency; and/or the addition of support features.

The adjustments may correspond to particular profiles of the profiles 804. For example a first set of adjustments may be particular to the Profile 1 subjects while a second set of adjustments may be particular to the Profile 2 subjects. That is, the computer system 210 may customize the monitoring program 812a for one or more profiles, e.g., based on the information contained in or associated with the profiles as indicated by the profile distribution 806. As shown, the computer system 210 uses the profile distribution 806 to customize the monitoring program 812 for the Profile 1 devices and the Profile 2 devices. Specifically, for the Profile 1 devices, the computer system 210 adjusts the monitoring program 812 to provide a weekly transportation credit to those Profile 1 devices based on, for example, the profile distribution 806 indicating that 75% of Profile 1 subjects do not have a vehicle and the monitoring program 812 requiring weekly medical office visits. Similarly, the computer system 210 adjusts the monitoring program 812 for the Profile 2 devices to update the communication channel from email to voice call based on the profile distribution 806 indicating that Profile 2 subjects are 60% more likely to respond to voice call over email and SMS message.

The computer system 210 can automatically make the adjustments to the monitoring program 812 or, alternatively, can generate a recommendation that includes the proposed adjustments. The computer system 210 may transmit the recommendation to the client device 204.

The computer system 210 may update the monitoring program for one or more groups of devices to improve efficiency and/or the likelihood of success of the monitoring program. That is, the computer system 210 may update the monitoring program 812a to improve the outcomes of the monitoring program (e.g., improve likelihood of subject compliance, compliance rates, retention rates, and/or quality of data obtained).

The adjustments to the monitoring program 812 may be temporary for the particular monitoring program. Alternatively, the adjustments to the monitoring program 812 may be permanent so as to update the default elements of the monitoring program.

FIG. 8B illustrates the adjustments made by the computer system 210 to the monitoring group 808 and to the monitoring program 812 for different categories of subjects. As shown, the computer system 210 has updated the monitoring group 808a which included a first subgroup 822 of devices that belong to a first category of subjects (e.g., subjects that correspond to Profile 1 of the profiles 804) and a second subgroup 824 of devices that belong to a second category of subjects (e.g., subjects that correspond to Profile 2 of the profiles 804) to the monitoring group 808. The monitoring group 808b includes the first subgroup 822 of devices, the second subgroup 824 of devices, and a third subgroup 826 of devices that belong to a third category of subjects (e.g., subjects that correspond to Profile 5 of the profiles 804).

Based on determinations made using the profile distribution 806 and the monitoring group 808b, the computer system 210 generates customized monitoring programs 812b, 812c, and 812d for each subgroup of devices 822, 824, and 826, respectively. The changes 814 indicate the changes that the computer system 210 made to the initial monitoring program 812a to generate each of the customized monitoring programs 812b, 812c, and 812d. The changes 814 made to the initial monitoring program 812a for the different subgroups of subjects may be made to improve predicted outcomes for the study. For example, the changes 814 may be made by the computer system 210 in an effort to improve retention of the subjects in the different subgroups, improve compliance with the requirements of the monitoring program, improve the likelihood of obtaining a minimally acceptable amount of data (e.g., to get results from the monitoring program that are statistically relevant, or that meet some other viability measure), improve the likelihood of obtaining at least a minimum level of data quality (e.g., to get results from the monitoring program that are statistically relevant, or that meet some other viability measure), etc.

For the subgroup 822 subjects, the changes 814 include a change 832a to message frequency, and an addition of an assistive element 832b to the monitoring program 812 to provide transportation credit 832b. As an example, Profile 1 of the profiles 804 may indicate that the Profile 1 subjects respond better to more frequent communication (e.g., may indicate higher compliance and/or retention rates with more frequent event reminders). The computer system 210 may use this information to increase the default message, e.g., from weekly to daily.

For the subgroup 824 subjects, the changes 814 include a change 834 to the communication channel. As an example, Profile 2 of the profiles 804 may indicate that the Profile 2 subjects demonstrate higher compliance when voice calls are used over other communications channels. The computer system 210 may use the information in Profile 2 to change the default communication channel, e.g., from email to voice call.

For the subgroup 826 subjects, the changes 814 include a change 836 to the communication channel. As an example, Profile 5 of the profiles 804 may indicate that the Profile 5 subjects have significantly lower retention rates when monitoring programs require the subjects to submit test results more than two times a day when compared to the retention rates for Profile 5 subjects when they are required to submit test results two times a day or less frequently. The computer system 210 may use the information in Profile 5 to modify the glucometer reading requirement, e.g., form requiring three readings per day to two readings per day.

Figure 9A:
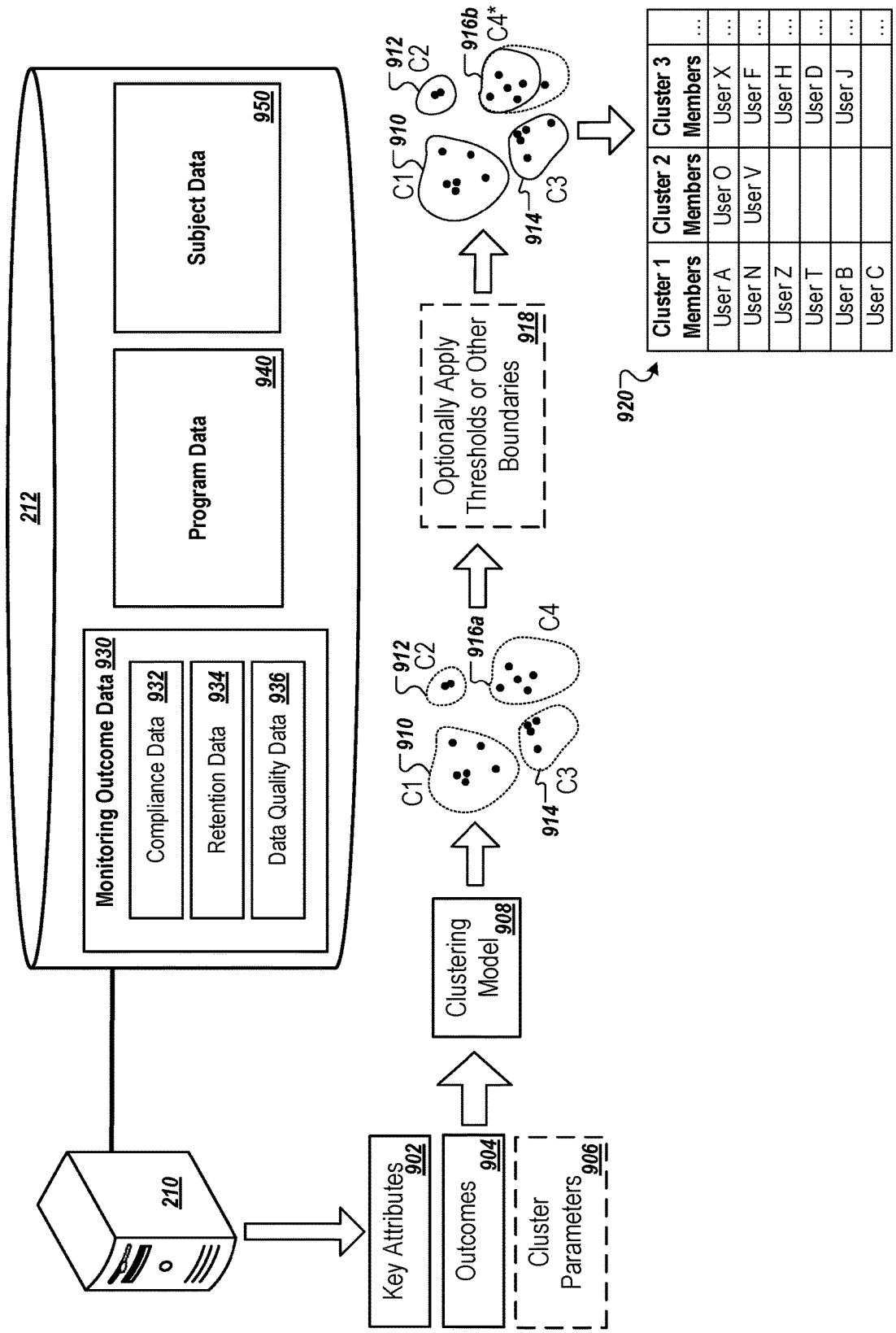
FIGS. 9A-9B are diagrams that illustrate an example system for generating profiles.
Figure 9B:
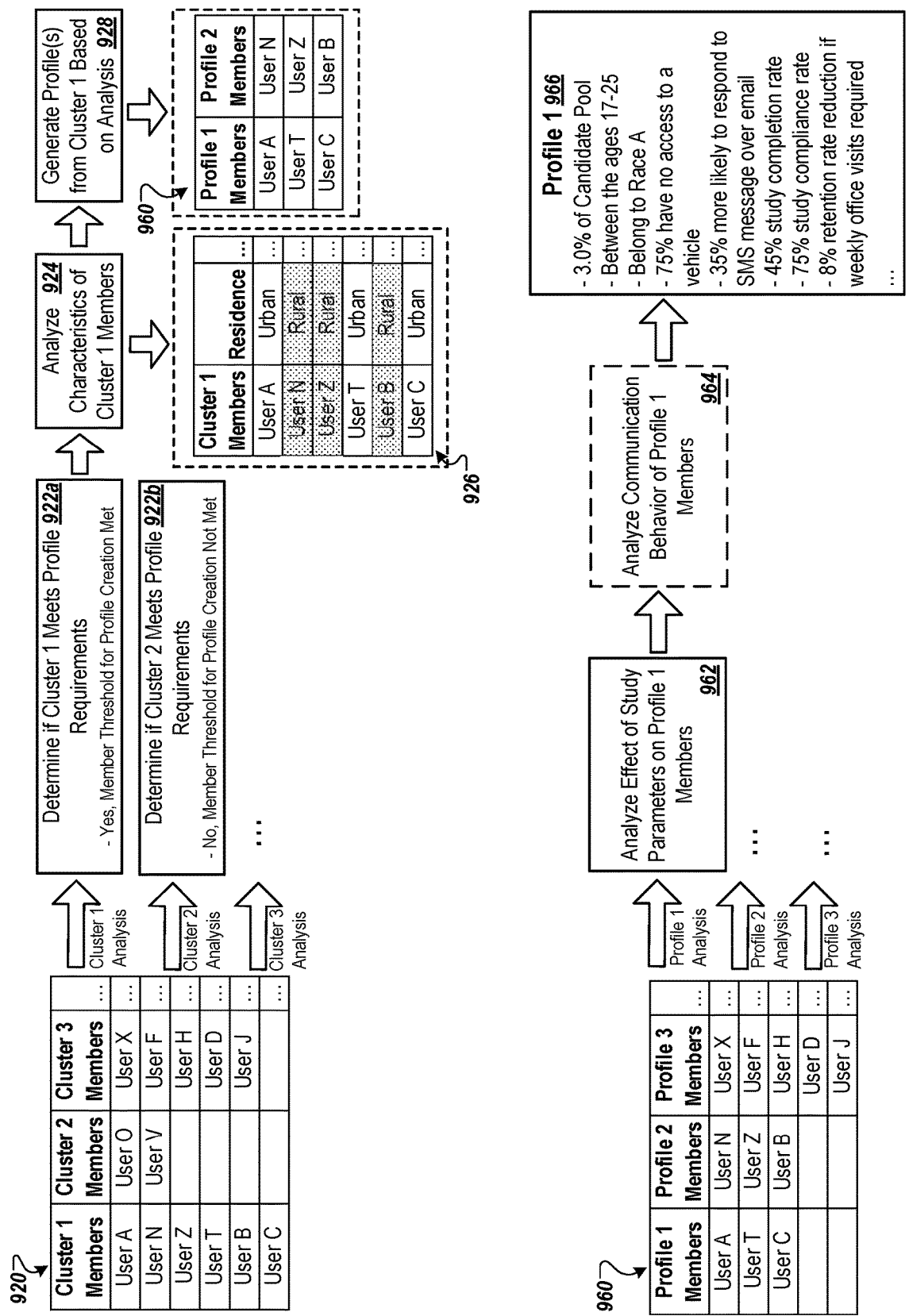

FIGS. 9A-9B are diagrams that illustrate one or more components of the system 200 an example system for generating profiles.

As shown in FIG. 9A, the computer system 210 may generate profiles using outcome data 940, program data 940, and/or subject data 950 stored in the database 212.

The monitoring outcome data 940 may include compliance data 932 (e.g., that indicates previously observed compliance rates for past subjects), retention data 934 (e.g., that indicates previously observed compliance rates for past subjects), and data quality data 936 (e.g., that indicates the quality of data that was obtained from past subjects). The monitoring outcome data 930 may be organized based on the individual subjects. For example, different portions of the compliance data 932, the retention data 934, and the data quality data 936 may correspond to a specific subject. The portion of the compliance data 932 associated with the specific subject may indicate, for example, the overall compliance of the subject across all requirements for all previous monitoring programs or all monitoring programs that are sufficiently recent, the compliance of the subject for particular requirement categories (e.g., smartphone compliance, office visit compliance, etc.) across all previous monitoring programs or all monitoring programs that are sufficiently recent, etc.

The program data 940 may describe the requirements of each monitoring program. For example, the program data 940 may include the default elements of each monitoring program. As was described in more detail with respect to FIGS. 8A-8B, these elements may be removed or modified based on profile data associated with the monitored group. Similarly, elements may be added to monitoring programs based on profile data associated with the monitored group.

More specifically, the program data 940 may include instructions to acquire or request specific data or types of data from subjects, instructions for subjects to perform particular actions, instructions as to the channel of communication and/or the frequency of communication between the computer system 210 and the subjects, instructions to provide accommodations (e.g., taxi credits), etc.

The program data 940 may also include various data packets corresponding to different monitoring programs. These data packets may include, for example, installation files for programs that are to be run on devices to be monitored in a monitoring program.

The subject data 950 may include the attributes, history, behavior, and other tracked data for monitored subjects. As an example, the attribute information in the subject data 950 may include demographic as well as non-demographic information for each of the monitored subjects (e.g., previously monitored subjects or currently monitored subjects), such as race, ethnicity, age, sex, residential area (e.g., city, state, country, etc.), type of residential area (e.g., urban, suburban, or rural), medical conditions, surgeries (e.g., type of surgery and date of surgery), prescriptions, etc. The history information may include information indicating the past monitoring programs that the subject has participated in or completed, and/or the past monitoring programs used. The behavior information may indicate the particular subject's observed responses or compliance with certain monitoring program requirements (e.g., elements). As an example, the behavior information may indicate that the subject is 50% less likely to be retained if the monitoring program requires him to make weekly doctor visits. The behavior information may also include or point to portions of the compliance data 932, the retention data 934, and/or the data quality data 936 associated with that particular subject.

In generating the profiles, the computer system 210 may first use one or more machine learning models to cluster subjects from a set. The set may include, for example, subjects that have previously participated in a monitoring program, have previously completed a monitoring program, are currently participating in a monitoring program, have previously participated in a monitoring program that was held sufficiently recent, or have previously completed a monitoring program that was held sufficiently recent. The computer system 210 may use a clustering model 908 to generate different clusters of subjects or eligible subjects based on certain input.

As shown, the computer system 210 may provide one or more of key attributes 902 or outcomes 904 as input to the clustering model 908. The computer system 210 may optionally provide cluster parameters 906 as input to the clustering model 908. In addition, the clustering model 908 may have access to the monitoring outcome data 930, the program data 940, and/or the subject data 950, or may be provided the monitoring program data 930, the program data 940, and/or the subject data 950 as input.

The key attributes 902 may include a list of types of attributes that the clustering model 908 can use to cluster the subjects. For example, the key attributes 902 may include a list of attribute types that are found in the subject data 950. The key attributes 902 may be selected by the researcher 202, may correspond to a particular monitoring program selected for a monitoring program, and/or may be determined by the computer system 210. For example, a researcher 202 may indicate, for diversity purposes, that the key attributes 902 should include race, ethnicity, and medical conditions of the subjects. Based on this, the clustering model 908 may cluster the subjects based on the key attributes 902 or based in part on the key attributes 902 (e.g., clustering model 908 may also take into account the outcomes 904 or other data in the subject data 950).

The key attributes 902 may additionally or alternatively include a subset of the subject data 950. That is, the key attributes 902 may include a portion of the attribute information in the subject data 950 corresponding to the type of attribute selected. The outcomes 904 may include a list of types of outcomes that the clustering model 908 is to cluster the subjects based on. For example, the outcomes 904 may include a list of outcome types that are found in the monitoring outcome data 930. The outcomes 904 may be selected by the researcher 202, may correspond to a particular monitoring program selected for a monitoring program, and/or may be determined by the computer system 210. For example, a researcher 202 may indicate that subjects should be clustered based on smartphone compliance during monitoring programs. The outcomes 904 may additionally or alternatively include all or a portion of the monitoring outcome data 930. For example, the outcomes 904 may include all or a portion of the compliance data 932, the retention data 934, or the data quality data 936. The cluster parameters 906 may include additional criteria for the clusters. For example, the cluster parameters 906 may specify a minimum cluster size, a maximum cluster size, the number of clusters, a minimum number of clusters, a maximum number of clusters, etc.

The clustering model 908 uses the key attributes 902, the outcomes 904, and/or the cluster parameters 906 to generate the clusters 910, 912, 914, 916*a*. Each of the clusters contain at least one subject of the subject pool. As an example, the key attributes 902 may include medical conditions or a particular set of medical conditions. Based on this, the clustering model 908 may generate the clusters 910, 912, 914, and 916*a* such that each includes subjects that generally have the same or similar medical conditions. As another example, the clustering model 908 may additionally or alternatively cluster subjects in the subject pool based on outcome data associated with the subjects. That is, the clustering model 908 may group subjects that have the same or similar monitoring program compliance rates, monitoring program retention rates, data quality, or health outcomes (e.g., degree of recovery or management of a disease, occurrence of side effects, etc.).

Clustering by the clustering model 908 may be performed in a number of ways. As discussed above, clustering may be primarily based on the attributes of the subjects, such as demographic and/or non-demographic information stored for subjects as part of the subject data 950. In this example, the clustering model 908 may generate clusters of subjects where each cluster includes a group of subjects that have a number of attributes in common (e.g., same ethnicity, same race, same medical conditions, etc.), have a number of similar attributes (e.g., similar or otherwise related medical conditions that fall into the same category of medical conditions, a height that falls within a particular height ranged determined by the clustering model, etc.), have a number of the key attributes 902 in common, and/or have a number of similar attributes of the key attributes 902. In more detail, the clustering model 908 may cluster subjects based on subjects in each of the groups having the highest number of attributes in common or the highest number of the key attributes 902 in common for that particular cluster when compared to the subjects assigned to other clusters.

Another way that the clustering model 908 can generate the clusters 910-916 is by clustering based on the outcome data 930. For example, the clustering model 908 can generate clusters of subjects based on those that perform similarly. In more detail, the clustering model 908 may generate the clusters 910-916 that each correspond to different groups of subjects that have the same or similar retention rates, the same or similar study completion rates, the same or similar compliance rates (e.g., smartphone compliance, office visit compliance, etc.), etc. Accordingly, the computer system 210 can use profiles generated from these clusters to predict how a subject is likely to perform in a current monitoring program if they meet the eligibility criteria for the profiles. Determining on the number of subjects that are assigned to the different profiles, the computer system 210 may determine that more subjects need to be enrolled in the current monitoring program (e.g., due to the profiles indicating a low retention rate and/or completion rate), ideally those that correspond to a profile which indicates a high completion rate, retention rate, and/or compliance rate.

In assigning subjects to clusters, the clustering model 908 may determine a set of attribute values or ranges that serve as criteria for the clusters. For example, the clustering model may determine that the second cluster 912 requires that the subjects belong to Race B, be over thirty-five years old, and have diabetes. Based on subjects O and V meeting these criteria, the clustering model 908 may determine that the second cluster 912 includes subjects O and V. This criteria may be used to generate a profile corresponding to the second cluster 912. For example, the same criteria may be used as eligibility criteria for determining if a corresponding profile is applicable to a subject in a current monitoring program, and/or the criteria may be modified (e.g., by an administrator) before being used as eligibility criteria for determining if a corresponding profile is applicable to a subject in a current monitoring program. Clustering in this manner can be used to achieve clusters of subjects that can be used to meet certain diversity criteria. That is, clusters of subjects can be formed where each cluster includes subjects having particular attributes. Accordingly, in conducting a new monitoring program, profiles generated from these clusters can be used to determine if certain diversity criteria is being met or may be used a substitute for diversity criteria. For example, if it is determined that no subjects in a current monitoring program belong to a first profile corresponding to the cluster 910, then additional subjects should be invited to join the monitoring program in order to improve the diversity of the monitoring program and, thereby, improve the applicability of the results and/or improve the likelihood of the results being valid.

Alternatively, the clustering model 908 may generate a set of attribute values or ranges after determining the clusters from the attributes of the subjects in the determined clusters. For example, after generating the clusters 910-916, the clustering model 908 may determine for each of the clusters eligibility criteria for the cluster using the attributes of subjects assigned to each of the clusters. In more detail, for the second cluster 912, the clustering model 908 may access a subject of the subject data 950 corresponding to the subjects O and V based on the subjects O and V having been assigned to the cluster 912. The clustering model 908 may use this subset of data to generate eligibility criteria for the cluster 912 and/or eligibility criteria for a profile based on the cluster 912. The types of attributes used to generate the criteria may be those that are indicated in the key attributes 902. For example, if the key attributes 902 indicate that clustering should take into account the ethnicity of the subjects, then the ethnicity of the subjects assigned to the cluster 912 should differ from the ethnicity of the subjects assigned to the other clusters. Accordingly, the computer system 210 can access from the subject data 950 the ethnicity data corresponding to the Subjects O and V and use that data to generate the criteria. Additionally or alternatively, the clustering model 908 may determine what attributes of the subjects assigned to the cluster 912 are unique with respect to the other clusters. For example, the clustering model 908 may determine that the cluster 912 is the only cluster to include subjects over thirty-five years old. Accordingly, the clustering model 908 may determine that the criteria corresponding to the cluster 912 should include a requirement of a subject being over thirty-five years old.

Thresholds or other boundaries may be optionally applied to one or more of the generated clusters (918). For example, thresholds or other boundaries set by the researcher 202 may be applied to one or more of the clusters 910, 912, 914, and 916*a*. Applying the thresholds or other boundaries can result in removing clusters, splitting a cluster into two or more new clusters, removing a subject from a cluster or otherwise dissociating the subject with the cluster, etc. As an example, the threshold or other boundaries may include inclusion criteria for the clusters generated by the computer system 210 or set by the researcher 202. The computer system 210 may apply this inclusion criteria to the clusters. As an example, the computer system 210 may apply an inclusion criterion that all subjects in the cluster 916*a* must be older than 30 years of age. As such, the computer system 210 may update the cluster 916*a* to disassociate any subjects that were 30 years of age or younger.

The subjects associated (e.g., assigned to) each of the clusters 910, 912, 914, and 916 may be considered members of their respective clusters. A table 920 includes example members of the first cluster 910, the second cluster 912, and the third cluster 914.

As shown in FIG. 9B, the computer system 210 may use the different clusters to generate profiles. In more detail, the computer system 210 may generate one or more profiles from the clusters. Additionally or alternatively, the computer system 210 may determine that one or more of the clusters are not eligible for profile generation, e.g., due to not meeting eligibility requirements (e.g., minimum member size; minimum subject population representation; minimum diversity level; etc.). For example, the computer system 210 may analyze each of the clusters to determine if they meet certain requirements for profile generation. As an example, a cluster may only be eligible for profile creation if it represents a threshold percentage of the subject pool or eligible subject pool.

In generating the profiles, the computer system 210 may analyze each of the previously determined clusters. For example, the computer system 210 may perform a first analysis on the cluster 910. In this analysis, the computer system 210 may determine if the cluster 910 meets the requirements for a profile (922*a*). Here, the profile requirements include a requirement that the number of members in the cluster meet a member threshold (e.g., at least three members, at least ten members, at least one-hundred members, etc.). The computer system 210 may compare the number of members in the cluster 910 to the member threshold to determine that the member threshold is met, and, therefore, that the cluster 910 meets the profile requirements.

After determining that a cluster meets the profile requirements, the computer system 210 can analyze the characteristics of the cluster's members (924). For example, the computer system 210 may obtain the demographic and non-demographic corresponding to the members of the cluster 910. For example, the computer system 210 may generate a table 926 from subject data obtained from the database 212. After obtaining this information, the computer system 210 may use the information to identify shared or common attributes among the members (e.g., race, religion, ethnicity, sex, residence area, level of education, health conditions, prescriptions, past surgeries, etc.), calculate various statistics for the members (e.g., percentage of members that live in a rural area, percentage of members that have access to a vehicle, etc.), and determine likelihoods of particular outcomes (e.g., likelihood of completing a study, meeting a minimum compliance rate, providing sufficient data for monitoring program/session requirements, etc.) and behaviors (e.g., smartphone compliance, attending medical appointments, responding to reminders, etc.).

The computer system 210 may also identify trends or patterns in the obtained subject data. For example, the computer system 210 may recognize that those cluster 910 members that reside in rural areas tend to have similar and distinct smartphone compliance rates when compared to the cluster 910 members that reside in urban areas.

The computer system may proceed to generate profiles 960 from the cluster based on the analysis results (928). For example, the computer system 210 may use the shared or common attributes among the members to generate inclusion criteria for the profile. Similarly, the computer system 210 can include the calculated statistics and determined likelihoods in the profile(s) corresponding to the cluster 910.

In generating profile(s) from the cluster, the computer system may generate multiple from the cluster. For example, the computer system 210 may generate a first profile corresponding to a first subset of the cluster 910 members and a second profile corresponding to a second subset of the cluster 910 members. The subset of members may be determined by the computer system 210, e.g., based on identified trends or patterns in the subject data. Alternatively, the computer system 210 may determine the subsets based on input from the researcher 202. For example, the researcher 202 may indicate one or more attributes that must be shared among profile members. In more detail, the input from the researcher 202 may indicate that all profile members must share the same residence type. Based on this, the computer system 210 may split the cluster 910 members into a first subgroup corresponding to a first profile for members that reside in urban areas, and a second subgroup corresponding to a second profile for members that reside in rural areas.

If the computer system 210 generates multiple profiles from a single cluster, the computer system 210 may analyze each of the multiple profiles. The computer system 210 may do this to (i) determine if the profiles meet the profile requirements (e.g., computer system 210 may eliminate one of the multiple profiles if it does not meet the member threshold) and (ii) analyze the characteristics of the profile members. The computer system 210 may use the determined shared or common attributes among the profile members to generate inclusion criteria for the profile. Similarly, the computer system 210 may include the resulting statistics and likelihoods in the profiles.

In some cases, in generating the profiles, the computer system 210 uses the clustering model 908 to perform another round of clustering. For example, the computer system 210 may use the clustering model 908 to perform another round of clustering based on a different set of attributes (e.g., a set of attributes other than the key attributes 902) and/or based on the outcomes 904. The computer system 210 may perform this second round of clustering before analyzing the clusters, such that the resulting clusters are analyzed to determine if they meet the cluster requirements.

After generating the profiles 960, the computer system 210 may perform an analysis on each of the profiles. In performing the analysis, the computer system 210 may analyze the effect of study parameters on the profile members (962). For example, the computer system 210 may use the subject data 250 to calculate the effects of different parameters (e.g., monitoring program requirements such as required tests that must be performed by subjects, frequency of tests that must be performed subjects, office visits that subjects must attend, morning office visits, afternoon office visits, etc.) on the outcomes of subjects (e.g., retention rates, compliance rates, sufficient data quality rates, etc.). As an example, based on this analysis, the computer system 210 can determine that Profile 1 subjects are 35% more likely to comply (e.g., respond to) with SMS message over communications sent by email. Similarly, based on this analysis, the computer system 210 can determine that the retention rate of Profile 1 subjects is reduced by 8% when subjects are required to attend weekly office visits.

In some cases, the computer system 210 may analyze the communication behavior of the members of a profile (964). This analysis may be a separate analysis from analyzing the effect of study parameters, or may be part of that analysis. In analyzing the communication behavior, the computer system 210 may determine the preferred communication channel, communication frequency, communication time, communication content, communication vocabulary (e.g., word choice), or communication sentence structure for the profile's members. The computer system 210 may further determine the effects of particular communication attributes (e.g., channel, frequency, time sent, etc.) on the outcomes of the profile's members, e.g., when compared to other communication attributes. For example, the computer system 210 may determine that the Profile 1 subjects prefer communication by SMS text message over email. The computer system 210 may analyze the subject data 250 to determine that, when compared to email, the Profile 1 subjects are 35% more likely to respond to SMS text message.

The computer system 210 may update profiles over time using monitored data. For example, the computer system 210 may reanalyze the effects of study parameters on profile members using updated subject data. The computer system 210 may perform this analysis after a triggering event is detected, such as the passing of a predetermined amount of time, after a threshold amount of monitored data is collected, after a monitoring program ends, etc. Similarly, the computer system 210 may use the clustering model 908 to cluster subjects after a triggering event is detected (e.g., after a predetermined amount of time has passed, after a threshold amount of monitored data is collected, after a threshold number of new subjects have appeared/joined, etc.). The computer system 210 may proceed to analyze the clusters in the manner described above. Additionally or alternatively, the computer system 210 may avoid additional analysis of a cluster (e.g., to improve efficiency, reduce processor load, increase processing speed, etc.) if it is determined that the members for a particular cluster match the membership for a previously determined cluster.

The computer system 210 may reassign users to different profiles overtime. For example, the computer system 210 may reassign users using the clustering model 908 (e.g., if the output of the model indicates that the users now belong to a cluster not associated with their current profile(s)). As another example, the computer system 210 may automatically assign users to profiles and/or reassign users to different profiles if the corresponding subject data indicates that they (i) meet the inclusion criteria for one or more profiles that they are currently not assigned to, and/or (ii) they no longer meet the inclusion criteria for one or more profiles that they are currently assigned to (e.g., current age indicates that they are no longer in a particular age range required for a first profile).

Figure 10:
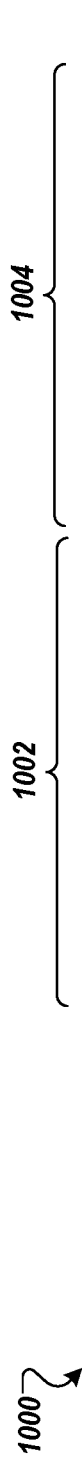
FIG. 10 is a diagram that illustrates an example table that indicates impact scores corresponding to different clusters.

FIG. 10 is a diagram that illustrates an example table 1000 that includes impact scores corresponding to different clusters 1002 and 1004. In more detail, the table 1000 indicates the impact that different study parameters and other elements are anticipated to have on different clusters of subjects 1002 and 1004.

The impact scores may indicate a quantified impact on one or more outcomes of a monitoring program, such as the retention of subjects, compliance of subjects (e.g., overall compliance, or compliance with particular requirements), data quality, etc. An impact on retention of subjects may indicate an anticipated increase or decrease to the retention rate for a group of subjects (e.g., based on stored historical data) that is attributable to one or more particular study parameters or other elements. As another example, an impact on retention may indicate an anticipated increase or decrease to the likelihood of a minimum number or percent of subjects being retained by the end of the monitoring program with respect to those subjects in the cluster or assigned to the corresponding profile.

Similarly, an impact on compliance of subjects may indicate an anticipated increase or decrease to the compliance rate for a group of subjects (e.g., based on stored historical data) that is attributable to one or more particular study parameters or other elements. As another example, an impact on compliance may indicate an anticipated increase or decrease to the likelihood of a minimum acceptable compliance rate for the monitoring program (e.g., for study data viability) with respect to those subjects in the cluster or assigned to the corresponding profile.

An impact on data quality may indicate an anticipated increase or decrease to the data quality (e.g., determined based on whether required or requested data was received, the accuracy of data received, the accuracy of the sensor(s) used to acquire the data, the time spent by a subject to produce the data (e.g., did subject spend the time to read and accurately respond to a set of questions), the quantity of data received, the response time of receiving data after requested, etc.). As another example, an impact on data quality may indicate an anticipated increase or decrease to the likelihood of a minimum acceptable data quality (e.g., for study data viability) being achieved (e.g., by the end of the study) with respect to those subjects in the cluster or assigned to the corresponding profile.

The impact scores may correspond to percentages. For example, a "−1" impact score on retention may indicate that it is anticipated that about 10% (e.g., a value rounded to the nearest decimal place and assigned a positive or negative indicator based on the effect of the parameter) of the cluster 1 subjects will not be retained during the research study (e.g., based on historical data of the subject data 250). The percentages may be particular to the effect. For example, a "+2" impact score on effect of data quality may indicate that it is anticipated that there will be about a 15% increase in data quality as a result of the inclusion of the particular study parameter or element in a monitoring program. In contrast, a "+2" effect on retention may indicate that it is anticipated that there will be about a 10% increase in retention as a result of the inclusion of the particular study parameter or element in a monitoring program.

The impact scores may correspond to percentage ranges. For example, a "−1" may indicate a decrease of 10% or less, a "−2" may indicate a decrease of 25% or less, and a "−3" may indicate a decrease of greater than 25%. The percentage ranges may be set by the researcher 202 or may be determined by the computer system 210. For example, an impact of "1" may indicate small impact as defined by the researcher 202, an impact of "2" may indicate medium impact as defined by the researcher 202, and an impact of "3" may indicate a large impact as defined by the researcher 202. As previously mentioned, the impact scores may be particular to the effect such that percentage ranges differs between effect on compliance, effect on retention, and/or effect on data quality.

The computer system 210 may calculate the impact scores in the table 1000. For example, the computer system 210 may calculate the impact scores when analyzing the effects of study parameters on profile members (962) described above with respect to FIG. 9B.

Instead of impacts on clusters of subjects, the table 1000 may additionally or alternatively indicate the anticipated impact of different study parameters and other elements on different groups of subjects that correspond to particular profiles. For example, the impact information in the table 1000 corresponding to the cluster 1002 may actually correspond to Profile 1 of the profiles 960. Similarly, the impact information in the table 1000 corresponding to the cluster 1004 may actually correspond to Profile 2 of the profiles 960.

Figure 11:
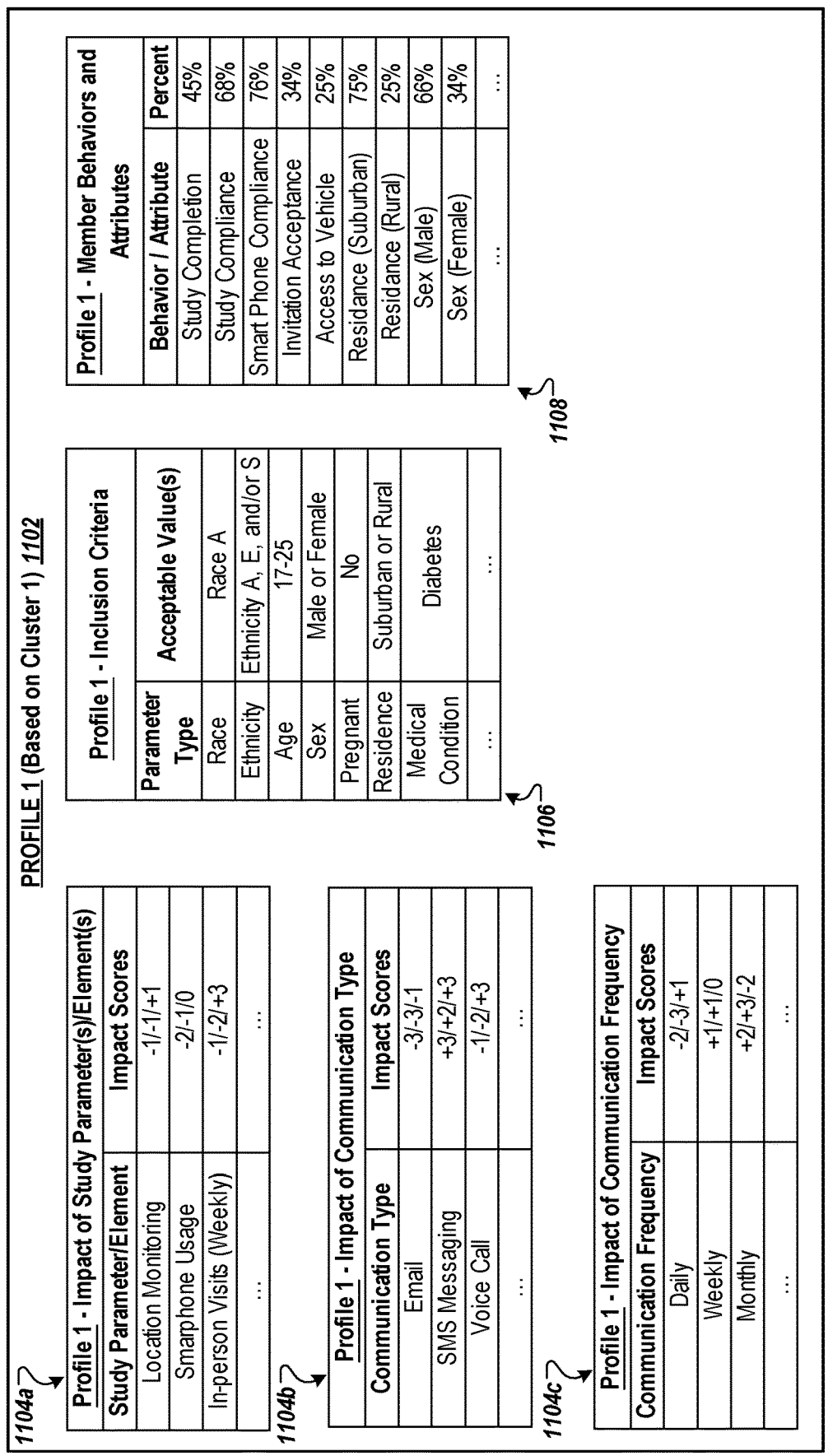
FIG. 11 is a diagram that illustrates an example profile.

FIG. 11 is a diagram that illustrates an example profile 1102.

As shown, the profile 1102 includes a number of tables 1104a, 1104b, and 1104c that indicate the impact of different study parameters or other elements on the compliance, retention, and data quality. The profile 1102 includes a first table 1104a that indicates the anticipated impact of different study parameters and/or other elements on the compliance, retention, and data quality during a given monitoring program. For example, if a monitoring program requires weekly in-person visits, the computer system 210 can anticipate a small reduction to Profile 1 subject retention (e.g., compared to their typical retention rate), a moderate reduction to Profile 1 subject compliance (e.g., compared to their typical compliance rate), and a significant improvement to Profile 1 subject data quality (e.g., compared to their typical data quality provided).

The profile 1102 also includes a second table 1104b that indicates the anticipated impact of different communication types on the compliance, retention, and data quality during a given monitoring program, and a third table 1104c that indicates the anticipated impact of different communication frequencies on the compliance, retention, and data quality during a given monitoring program.

The information in the tables 1104a, 1104b, and 1104c can be determined by the computer system 210. For example, the computer system 210 may calculate the impact scores of the various study parameters and other elements when it analyzes the effect of study parameters on profile members (962) described in more detail above.

The profile 1102 also includes a fourth table 1106 that indicates the inclusion criteria to determine if subjects belong to a category of subjects represented by the profile 1102. The inclusion criteria may include both demographic and non-demographic information. For example, the inclusion criteria in the fourth table 1106 may require that all Profile 1 subjects be between the ages of 17-25 but also require them to being diagnosed with the medical condition, diabetes.

The profile 1102 also includes a fifth table 1108 that includes the determined behaviors and attributes for those subjects associated with the profile 1102. For example, the computer system 210 may determine these behaviors and/or attributes using the subject data 250. The behaviors may include, for example, an overall retention rate (e.g., study completion rate), an overall compliance rate, one or more particular compliance rates (e.g., corresponding to particular requirements of a monitoring program, such as a smart phone compliance rate if a monitoring program requires subjects to use a smart phone and/or collect sensor data with a smart phone), etc. The attributes may include a subset of attributes that are determined to be unusual (e.g., significantly deviate from subject averages). For example, it may be unusual that only 25% of Profile 1 subjects have access to a vehicle (e.g., where 55% of subjects on average have access to a vehicle).

Figure 12:
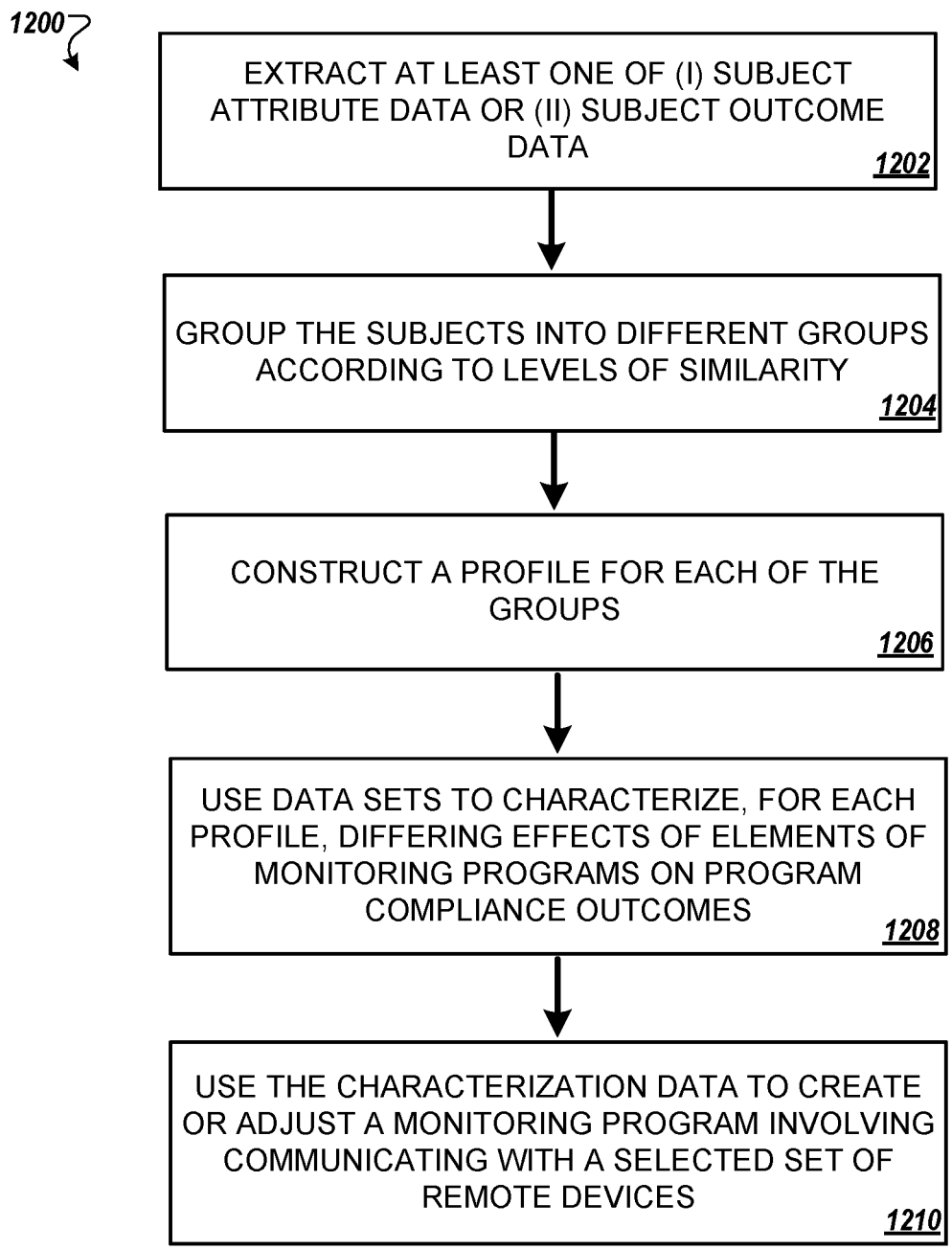
FIG. 12 is a flowchart diagram that illustrates an example process for customizing monitoring programs involving remote devices.

FIG. 12 is a flowchart diagram that illustrates an example process 1200 for customizing monitoring programs involving remote devices. The process 1200 may be performed by one or more computers, such as the computer system 210 shown in various figures including FIG. 2. The operations of the process 1200 may be distributed among one or more servers, one or more client devices, and/or other computing systems. For example, the operations of the process 1200 may be performed by a management and distribution system, such as the system 210, that includes one or more servers, one or more client devices, and/or other computing systems.

The process 1200 includes extracting at least one of (i) subject attribute data or (ii) subject outcome data (1202). Subjects may include at least one of devices or users. For example, a group of subjects selected for a monitoring program may include a diverse set of devices, such as a set of different smartphones. Prior to monitoring the subject devices, the computer system 210 may distribute software for the monitoring program to the subject devices. The subject devices may proceed to install the software. The software may specify the collection of data using sensors of the subject devices or devices connected to the subject devices (e.g., according to a set schedule or in response to receiving particular requests from the computer system 210), provide for a channel of communication between the computer system 210 and the subject devices (e.g., a secure channel of communication, such as an encrypted communication channel), a user interface through which one or more users of the subject devices can interact (e.g., to respond to messages or notifications sent to the subject devices from the computer system 210), etc.

Subjects may additionally or alternatively include a set of users. The users may include users that have participated in one or more previous monitoring programs or monitoring programs. In some cases, the users may include users that are new and have not participated in any monitoring programs or monitoring programs. Prior to monitoring the subjects, the computer system 210 may distribute software for the monitoring program to remote devices that the subject users have access to. The software may be installed in these remote devices and specify, for example, the collection of data of the subject users using sensors of the devices (e.g., according to a set schedule or in response to receiving particular requests from the computer system 210), provide for a channel of communication between the computer system 210 and the devices (e.g., a secure channel of communication, such as an encrypted communication channel), a user interface through which one or more of the subject users can interact with the devices (e.g., to respond to messages or notifications sent to the subject devices from the computer system 210), etc.

Where the subject is a device, extracting subject attribute data describing characteristics of a subject may include, for example, extracting an ID assigned to the subject device, a manufacturer of the device, a model of the device, a software version running on the device, a CPU speed of the device, a memory size of the device, an indication of sensors installed in the device (e.g., fingerprint scanner, GPS unit, Lidar, accelerometer, etc.), etc. Similarly, where the subject is a user, extracting subject attribute data describing characteristics of the subjects may include, for example, extracting a name of the user, an ID assigned to the user, demographic information of the user (e.g., age, race, ethnicity, gender, marital status, income, education, employment, residential state, etc.), non-demographic information of the user (e.g., past surgeries, medical conditions, genetics, lifestyle patterns, environmental factors, access to health care, etc.), an indication of what devices and/or sensors that user has access to, etc. As will be described in more detail below, the computer system 210 may use the attribute data of the subjects to categorize the subjects. As an example, with respect to FIG. 9A, the subject attribute data may be part of the subject data 950.

Extracting the subject outcome data can include extracting subject outcome data including results from monitoring programs that involved the subjects. The results may include, for example, compliance data for the subjects, retention data for the subjects, and data quality data for the subjects. As an example, with respect to FIG. 9A, the subject outcome data may include the compliance data 932, the retention data 934, and the data quality data 936. The computer system 210 may determine the subject outcome data using, for example, monitored results of subjects during the past monitoring programs. The monitored results may be stored, at least initially, as part of the subject data 950. The computer system 210 may extract the relevant information from the subject data 950, such as response times, response content, sensor data, etc., to determine the subject outcome data.

The compliance data may include, for example, compliance rates such as an overall compliance rate for each of the subjects or for each category of subjects with respect to monitoring program requirements of past monitoring programs and/or monitoring programs that the subjects have participated in. However, the compliance data may also or alternatively include compliance rates for particular areas, such as the subjects' compliance with device usage (e.g., smartphone compliance, blood pressure device compliance, heart rate monitor compliance, etc.), with responsiveness (e.g., does the subject on average respond within thirty minutes of receiving a message or notification, within one hour of receiving a message or notification, within one day of receiving a message or notification, etc.; does the subject consistently provide required test results; does the subject consistently perform required tasks; etc.), with office visits (e.g., medical visits scheduled as part of the monitoring program), etc. In determining a compliance rate for a subject, the computer system 210 may average all of the relevant compliance rates (e.g., overall compliance rate, or subject-specific compliance rate) for the subject across their past monitoring programs.

The retention data may include, for example, a retention rate for each of the subject or for each category of subjects over their past monitoring programs. As an example, the computer system 210 may determine a retention rate for each subject using the number of monitoring programs the subject has previously participated in, and the number of monitoring program the subject successfully completed. As an example, the computer system 210 may determine that a subject was not retained in (e.g., did not complete) a particular monitoring program if they stopped responding, if their compliance rate(s) fell below threshold compliance rate(s), if they failed to perform one or more tasks (e.g., perform tests, upload tests results, attend medical office visits, fill out surveys, meet dietary restrictions, perform required exercises, etc.), or if they indicated that they were withdrawing from the monitoring program. The computer system 210 may keep track of the subject retention rates as part of the retention data 934. The computer system 210 may optionally determine and track retention rates of subjects in particular monitoring programs or types of monitoring programs. For example, if a particular subject has participated in three monitoring programs of a monitoring program (e.g., potentially different versions of the monitoring program including customized versions), the computer system 210 may determine and track a retention rate for the subject with respect to this particular monitoring program. The computer system 210 may similarly track the subject's compliance data and data quality data that correspond to this monitoring program.

The data quality data may include, for example, an indication of data quality for each of the subjects or for different categories of subjects. Additionally or alternatively, the data quality data may include data quality rates that indicate, for each of the subjects or for each category of subjects, the percent of data that meets minimum data quality requirements. The computer system 210 may use various factors to determine data quality or which may be used to set minimum data quality requirements. These factors can include response times (e.g., where relatively quick response times and/or relatively long response times may correspond to low data quality), sensor data accuracy (e.g., based on the sensor and/or device used to collect the sensor data), sensor data consistency (e.g., based on the sensor and/or device used to collect the sensor data, and/or the other sensor data values collected using the same sensor and/or device or the same sensor type and/or device type), response content (e.g., text input that is relatively short or that is below a threshold word count may correspond to low data quality; text input that is relatively long or that is above a threshold word count may correspond to high data quality; etc.), etc. The computer system 210 may use one or more algorithms to determine a data quality score or a data quality rate, e.g., for a particular monitoring program and/or across all monitoring programs. As an example, the computer system 210 may calculate a data quality score for each monitoring program of each subject or each category of subjects, and average the data quality scores to obtain an overall data quality score for the subject or the group of subjects.

Extracting at least one of the subject attribute data or the subject outcome data can include extracting at least one of the subject attribute data or the subject outcome data from a database. The database may store data sets for multiple different subjects, such as data sets for different devices and/or data sets for different users. The data sets can include attribute data for the different subjects. For example, where the subject is a device, a corresponding data set may include an ID assigned to the device, make of the device, a model of the device, a software version running on the device, a CPU speed of the device, a memory size of the device, an indication of sensors installed on the device (e.g., fingerprint scanner, GPS unit, Lidar, accelerometer, etc.), etc. The computer system 210 may extract all or a portion of this information from the data sets. Similarly, where the subject is a user, a corresponding data set may include the name of the user, an ID assigned to the user, demographic information of the user (e.g., age, race, ethnicity, gender, marital status, income, education, employment, residential state, etc.), non-demographic information of the user (e.g., past surgeries, medical conditions, genetics, lifestyle patterns, environmental factors, access to health care, etc.), an indication of what devices and/or sensors that user has access to, etc. The computer system 210 may extract all or a portion of this information from the data sets.

The data sets may include results of monitoring performed for the subjects using one or more remote computing devices. For example, the data sets may include an indication of messages sent to the subjects, responses received from the subjects, sensor data received from the subjects, etc. The data sets may additionally include information determined from received data and/or responses, such as subject outcomes. For example, the data sets may include response times, response frequency, message compliance or compliance rates for the user, an indication of user retention or retention rates for the user, indications of data quality, etc.

Extracting at least one of (i) the subject attribute data or (ii) the subject outcome data can include using metadata to identify the data in one or more data sets that should be extracted. For example, the computer system 210 may use an ID or data type to extract attribute data from the database 212. Similarly, the computer system 210 may use a different ID or data type to extract outcome data from the databased 212.

Extracting at least one of (i) the subject attribute data or (ii) the subject outcome data can include parsing through stored, monitored subject data to identify at least one of the subject attribute data or the subject outcome data. For example, the computer system 210 may store the monitored data in the database 212. In response to receiving instructions to start a new monitoring program, receiving instructions to update the profiles or groups, determining that monitoring data has been collected on one or more new subjects, and/or detecting a different event, the computer system 210 may parse through the data sets in the database 212 to identify the subject attribute data and/or the subject outcome data.

The process 1200 includes grouping the subjects into different groups according to levels of similarity (1204). The levels of similarity can be levels of similarity among the attributes of the subjects and/or the monitored outcomes for the subjects. As an example, with respect to FIG. 9A, the computer system 210 may determine or receive an indication of the key attributes 902 and the outcomes 904. The key attributes 902 may include a subset of particular subject attributes extracted by the computer system 210 from the subject data 950. Similarly, the outcomes 904 may include a subset of particular monitored outcomes for the subjects extracted by the computer system 210 from the monitoring outcome data 930. The computer system 210 may proceed to use at least one of the key attributes 902 and the outcomes 904 to group the subjects into different groups.

In grouping the subjects, the computer system 210 may group subjects based on the extracted attributes, the extracted outcomes, or a combination of the attributes and outcomes. As an example, the computer system 210 may use the extracted attributes to identify those subjects that share the same or a similar subset of subject attributes. In grouping the subjects, the computer system may additionally or alternatively identify those subjects that have demonstrated the same or similar outcomes. For example, the computer system 210 may identify those subjects that tend to have similar overall compliance rates (e.g., compliance rate are within a range of multiple ranges of compliance rates), similar device compliance rates, similar retention rates, produce similar data quality, etc. The computer system 210 may then further organize the subjects by those that have similar medical conditions or that share other attributes to identify multiple groups of subjects. For example, the computer system 210 may identify a first group of subjects that have diabetes and a compliance rate above 60%, a second group of subjects that have diabetes and a compliance rate below 60%, a third group of subjects that do not have diabetes and a compliance rate above 60%, and a fourth group of subjects that do not have diabetes and have a compliance rate below 60%.

In grouping the subjects, the computer system 210 may use one or more static or machine learning algorithms. For example, in some implementations, grouping the subjects into different groups according to levels of similarity includes grouping the subjects into different groups using one or more machine learning models. The one or more machine learning models can include a clustering machine learning model. For example, the computer system 210 can provide the key attributes 902 and/or the outcomes 904 to the clustering model 908 as input. The clustering model 908 may proceed to cluster the subjects (e.g., previous monitoring program participants) based on the key attributes 902 and/or the outcomes 904 into multiple groups of subjects. The clustering model 908 can cluster the subjects according to a subset of subject attributes and/or particular outcomes (e.g., desirable outcomes, undesirable outcomes, or certain types of outcomes, such as compliance rates, retention rates, or data quality).

Where a clustering machine learning model is used to group the subjects, the clustering model may be one of following models: a density clustering model, a connectivity clustering model, a centroid clustering model, distribution clustering model, a subpace clustering model, a group clustering model, a graph clustering model, signed-based clustering model, or a neural network model. In some cases, multiple machine learning models are used. As an example, two or more clustering models may be used to group the subjects.

In some implementations, the machine learning model(s) used for grouping subjects are trained (e.g., supervised) using input data sets and expected outputs for those data sets. The data sets may include, for example, subject attribute data and/or subject outcome data. The expected outputs for those data sets may include an indicator for each of the subjects that specifies which group that the subject belongs to. For example, the expected outputs may include values corresponding to subjects that fall within a first range of values corresponding to a first group of subjects, values corresponding to other subjects that fall within a second range of values corresponding to a second group of subjects, etc.

In some implementations, the machine learning model(s) used for grouping subjects are not-trained (e.g., unsupervised). For example, the machine learning model(s) may include an unsupervised k-means clustering algorithm that does not require ground truth in order to group the data points of the input data into distinct subgroups.

The output of the machine learning model may indicate a group that each of the subjects belong to. For example, the output of the machine learning model may include a value for a first subject that falls within a first range of values corresponding to a first group of subjects, and a second value for a second subject that falls within a second range of values corresponding to a second group of subjects. The output of the machine learning model may indicate one or more value ranges or thresholds that define the different groups. As another example, the output of the machine learning model may include a value for each subject, where the value corresponds to a particular group that the subject is placed in. In more detail, the output value may indicate the centroid that each subject was assigned to during grouping (e.g., clustering).

In some implementations, additional input is provided to the machine learning model. For example, with respect to FIG. 9A, the computer system 210 may provide cluster parameters 906 to the clustering model 908. The cluster parameters 906 may define a number of clusters, a minimum or maximum cluster size, a number of clustering iterations, a centroid change threshold, etc.

In some implementations, in grouping the subjects, the machine learning model performs multiple grouping iterations. For example, the machine learning model may be a k-means clustering algorithm that performs multiple clustering iterations until there is no change to the centroids or until the change to the centroids is below a threshold value.

The process 1200 includes constructing a profile for each of the groups (1206). A profile may represent a category of subjects. A profile may be constructed using one of the different groups of subjects. The resulting profile may represent a category of subjects that corresponds to one of the different groups of subjects. For example, after grouping the subjects into the different groups, the computer system 210 may construct corresponding profiles for the different groups. Each profile may be constructed using subject data from one of the different groups of subjects.

In some implementations, a profiles is constructed using two or more groups of subjects of the different groups. For example, the computer system 210 may combine multiple of the different groups of subjects, and used the combined groups to construct the profile such that the profile corresponds to multiple groups of the different groups of subjects.

Similarly, in some implementations, a profile is constructed using only a portion of one of the different groups. For example, the computer system 210 may split a group of subjects into two or more subgroups (e.g., based on input from a researcher or an administrator). The computer system 210 may proceed to use one of these subgroups to construct the profile such that the profile corresponds to the subgroup but does not correspond to all subjects in the larger group of subjects.

The computer system 210 may use subject data corresponding to one or more of the different groups to construct each of the profiles. The computer system 210 may use subject attribute data (e.g., not necessarily limited to the extracted subject attribute data) and subject outcome data (e.g., not necessarily limited to the extracted subject outcome data) to construct the profiles for each of the groups. In more detail, in constructing the profiles, the computer system 210 may use the subject attribute data and/or the subject outcome data to define inclusion criteria for each category of subjects corresponding to one of the different groups. For example, for a particular group of subjects, the computer system 210 may determine based on the attribute data that each subject in the group is over the age of 37, lives in an urban environment, and has been diagnosed with high blood pressure. Based on this, the computer system 210 may, in constructing a profile to represent a category of subjects corresponding to this group, set inclusion criteria for the group to require that subjects be above the age of 35, reside in an urban environment, and be diagnosed with high blood pressure or are observed to have at least 7/10 indicators for high blood pressure (e.g., based on a preliminary test, entry survey, etc.).

The set criteria may include a broader range of values than observed values, e.g., to make the group more inclusive. Alternatively, the set criteria may include a range of values that is the same range as the observed values. Similarly, the set criteria may include a range of values that is less than the observed values, e.g., to make the group more exclusive and/or to account for outliers in the group. Finally, the set criteria may include a combination of different range of values that are greater than, less than, and/or the same as the observed values.

In some implementations, the computer system 210 filters the different groups to identify a subset of groups in the different groups that meet criteria for profile construction. For example, in order to be used for profile construction, each of the different groups may need to include a minimum number of subjects. The groups may also need to meet other profile criteria, such as minimum diversity requirements. The profile criteria may be set by a researcher or an administrator. After determining the subset of groups in the different groups that meet the criteria for profile construction, the computer system 210 may use each of the groups in the subset of groups to construct corresponding profiles.

In some implementations, the inclusion criteria is used to determine which subjects correspond to which profiles. For example, although the subjects were previously assigned to groups, the inclusion criteria may differ from the observed values of the group. Accordingly, the computer system 210 may compare the inclusion criteria against the attribute data and/or outcome data of the subjects to determine or verify which subjects correspond to which profiles. The attribute data and/or outcome data of the subjects used by the computer system 210 used to determine or verify which subjects correspond to which profiles may include attribute data and/or outcome data of active subjects (e.g., subjects that have participated in a monitoring program or monitoring program over the last year, have participated in a monitoring program or monitoring program over the last two years, are listed as active, etc.). In contrast, the attribute data and/or outcome data used to construct the profiles may include attribute data and/or outcome data of all subjects in a subject pool (e.g., for which monitored data has been collected), including active and inactive subjects.

In some implementations, information is added to the profiles that is not used as inclusion criteria. For example, the computer system 210 may include subject attribute data and/or attribute data statistics in the profile. In more detail, the computer system 210 may include the number or percent of subjects in the profile that have a particular attribute (e.g., percent of subjects that have high blood pressure, that are of a first ethnicity, that have a college education, etc.), and/or that demonstrate the same or similar outcomes (e.g., that have a retention rate greater than 75%, that have a retention rate between 50% and 75%, and that have a retention rate less than 50%). The computer system 210 may also determine and include in the profile an indication of the number of subjects in the category of subjects, or a percent of the total or active subject pool that the category of subjects represents. For example, the computer system 210 may compare the number of subjects in a category of subjects represented by a profile to the total number of subjects or to a total number of active subjects to determine that the category of subjects represents 4.2% of the subject pool or of the active subject pool.

The process 1200 includes using data sets to characterize, for each profile, differing effects of elements of monitoring programs on program compliance outcomes (1208). The data sets may be stored in a database by, for example, the computer system 210. The data sets may include monitored subject data over multiple monitoring programs. In determining the different effects of elements of monitoring programs, such as tasks (e.g., tests, appointments, exercises, etc.), message content, message frequency, message time, task or event schedule, etc., on subjects' outcomes, the computer system 210 may use the program data 940 to identify various monitoring program elements and use the monitoring outcome data 930 to identify the effects of those program elements on the different categories of subjects. In more detail, for a particular monitoring program element, the computer system 210 may determine which subjects have encountered that element before and in which past monitoring program(s), and use a portion of the outcome data 930 corresponding to those past monitoring programs and subjects to determine what effect on subject outcomes, if any, the particular element had on those subjects.

For example, if three subjects assigned to a first profile are determined to have encountered the requirement for weekly office visits in one or more prior monitoring programs, the computer system 210 may obtain a portion of the monitoring outcome data 930 corresponding to those monitoring programs for the first profile subjects. The computer system 210 may proceed to use the portion of the outcome data 930 and the corresponding subject data 950 to determine (e.g., to see if there was a deviation or a statistically significant deviation from the first profile subject's typical behavior) if the weekly office visits had a negative, positive, or neutral effect on compliance rates, retention rates, and/or data quality for the first profile subjects, and the magnitude of that effect on those subject outcomes. The computer system 210 may proceed to include the effect (e.g., direction and magnitude) as part of the profile As discussed above, the effect of a monitoring program element on subject outcomes may be in the form of calculated impact scores as shown and described above with respect to FIGS. 10-11. An impact score may be an absolute or relative score. This score may represent a percentage or a percentage range. The percentage or percentage range that the impact score represents may depend on the magnitude of the impact score and/or on the corresponding outcome (e.g., larger percent range for compliance rates than, for example, retention rates which are likely to fluctuate to a lesser degree than compliance rates).

In some implementations, the computer system 210 analyzes the communication behavior of the subjects of a profile. This analysis may be a separate analysis from analyzing the effect of study parameters, or may be part of that analysis. In analyzing the communication behavior, the computer system 210 may determine the preferred communication channel, communication frequency, communication time, communication content, communication vocabulary (e.g., word choice), or communication sentence structure for the profile's subjects. The computer system 210 may further determine the effects of particular communication attributes (e.g., channel, frequency, time sent, etc.) on the outcomes of the profile's subjects, e.g., when compared to other communication attributes. For example, the computer system 210 may determine that the Profile 1 subjects prefer communication by SMS text message over email. The computer system 210 may analyze the subject data 250 to determine that, when compared to email, the Profile 1 subjects are 35% more likely to respond to SMS text message.

The computer system 210 may update profiles over time using monitored data. For example, the computer system 210 may reanalyze the effects of study parameters on profile subjects using updated subject data obtained in one or more ongoing monitoring programs or results from recently completed monitoring programs. The computer system 210 may perform this analysis after a triggering event is detected, such as the passing of a predetermined amount of time, after a threshold amount of monitored data is collected, after a monitoring program ends, etc. Similarly, the computer system 210 may use the clustering model 908 to cluster subjects after a triggering event is detected (e.g., after a predetermined amount of time has passed, after a threshold amount of monitored data is collected, after a threshold number of new subjects have appeared/joined, etc.). The computer system 210 may proceed to analyze the clusters in the manner described above. Additionally or alternatively, the computer system 210 may avoid additional analysis of a cluster (e.g., to improve efficiency, reduce processor load, increase processing speed, etc.) if it is determined that the members for a particular cluster match the membership for a previously determined cluster.

In some implementations, the computer system 210 analyzes the effects of each element of various monitoring programs (or even all monitoring programs) that have been run. Because various monitoring programs and monitoring programs may include all or a portion of the same elements, the computer system 210 does not necessarily need to analyze each and every element of each monitoring program (or version of monitoring program) separately.

In some implementations, the computer system 210 analyzes the effects of only a subset of elements of the monitoring programs that have been run in one or more monitoring programs. For example, the computer system 210 may choose to analyze the effects of only those elements for which sufficient monitored data has been collected on. In more detail, the computer system 210 may choose to only analyze the effects of those elements that have been in at least three monitoring programs, for which there have been at least six months of data collected for, for which at least twenty unique subjects experienced, etc.

In analyzing the effects of the monitoring program elements on subject outcomes, the computer system 210 may extract, for each profile, the relevant information from the database 212, and analyze the extracted data together. That is, instead of analyzing the effects on a subject by subject basis, the computer system 210 may collect, for each of the profiles, all of the relevant subject data and analyze the collected data as a whole. This has the benefit if reducing computational burden by reducing the number of processes the CPU(s) of the computer system 210 need to perform, and further increases efficiency by speeding up the processing time.

After analyzing the effects of the monitoring program elements on subject outcomes, the computer system 210 may update the profiles to include the corresponding analysis results. For example, if it is determined that subjects in a category of subjects represented by Profile 1 are twice as likely to not complete a study if it requires blood to be drawn daily, the computer system 210 may update Profile 1 to include an impact score of −5 (e.g., to represent −50% effect on retention rate) for retention for the monitoring program element, "blood drawn" with a frequency of "daily."

The computer system 210 may organize the different effects of different elements into different categories or hierarchies within the profiles. For example, with respect to FIG. 11, the computer system 210 may organize the data in the table 1104*b* and the table 1104*c* under a communication category.

The process 1200 includes using the characterization data to create or adjust a monitoring program involving communicating with a selected set of remote devices (1210). The computer system 210 may identify the profiles that are present among a monitoring group selected for a monitoring program, compare the elements of the selected monitoring program to the element effect information in the profiles, and, based on the comparison, determine one or more adjustments to the monitoring program for the different categories of subjects. The adjustments made by the computer system 210 may include removing or modifying an element of a monitoring program (e.g., reduce number of tests that user must complete if this is determined to significantly lower retention rates), adjusting communication attributes (e.g., communication channel, frequency, time, content, sentence structure, etc.), or adding an element (e.g., account for subjects not having access to a device, account for subject not having access to transportation by providing transportation credit, etc.). For example, if an element of a monitoring program is anticipated to reduce compliance with subjects assigned to a second profile, the computer system 210 may adjust that element using information in the second profile to mitigate the anticipated reduced compliance.

The computer system 210 can automatically make the adjustments for the one or more groups of subjects enrolled in the monitoring program. For example, if the computer system 210 determines that a particular adjustment should account for an anticipated lower retention rate among Profile 1 subject due to an element of the monitoring program, the computer system 210 may generate a new version of the monitoring program and distribute this new version to only remote devices corresponding to the Profile 1 subjects.

The computer system 210 can generate a recommendation to make one or more adjustments and transmit the recommendation to a researcher or an administrator. The recommendation may include multiple recommended adjustments to the monitoring program, such as one or more recommended adjustments for each unique profile present among the selected subjects for the monitoring program. The recommendation may include the most recommended adjustments, such as the five or ten most recommended adjustments. Similarly, the computer system 210 may generate a recommendation that includes at least two recommendations (e.g., two most recommended adjustments) for each of the profiles present among the selected subjects. The computer system 210 may rank the recommended adjustments, e.g., based on predicted effect at achieving a successful monitoring program (e.g., obtaining viable data). For example, the adjustments predicted by the computer system 210 to have the largest remedial effect (e.g., for expected negative outcomes, such as low retention, low compliance, low data quality, etc.) may be ranked above adjustments that are predicted to have less significant effects. Similarly, adjustments that are predicted by the computer system 210 to have a higher likelihood of producing a remedial effect may be ranked by the computer system 210 above adjustments whose beneficial effect is more speculative.

The computer system 210 may wait for a response from the researcher or administrator before proceeding with the monitoring program. The response may include a confirmation (e.g., if it included one recommended adjustment, or one recommended adjustment for each category of subjects represented in the monitoring group). Alternatively, the response may include one or more selections, e.g., that correspond to adjustments selected by the researcher or administrator. The computer system 210 may use the confirmation or response to generate one or more additional versions of the monitoring program, each specific to a particular category of subjects (e.g., corresponding to a particular profile).

In some implementations, if the computer system 210 does not receive a response within a predetermined amount of time, the computer system may implement one or more recommended adjustments itself. For example, for each profile, the computer system 210 may generate a version of the monitoring program where the most recommended adjustment has been made (e.g., if there are recommended adjustments). If there were no recommended adjustments for a particular category of subjects, the computer system 210 may send the default monitoring program to the remote devices of those subjects.

Using the characterization data to create or adjust the monitoring program may also include using the characterization data to adjust the enrolled subjects. For example, if the characterization data indicates that a subset of the enrolled subjects are predicted to have insufficient compliance rates over a period of time due to the monitoring program requirements (e.g., if the program requirements cannot be adjusted or cannot be adjusted to the extent needed), the computer system 210 may replace the subset of the enrolled subjects with a different set of subjects who are anticipated to produce outcomes that are sufficient with the monitoring program's requirements. The computing system 210 may automatically enroll the other subjects, or may send invitations to the other subjects to enroll.

As another example, the computer system 210 may use the profiles to determine that additional subjects need to be added to the monitoring group due to one or more profiles not being represented. That is, the profiles may be used as a diversity metric. The computer system 210 may, for example, determine that one or more additional subjects should be enrolled or invited to the monitoring program based on the size of the category of subjects that is not represented. For example, the computer system 210 may automatically enroll or generate a recommendation for enrollment of a subject that is in a category of subjects (e.g., corresponding to a particular profile) that represents more than 3%, 5%, or 7% of the subject pool and is not represented in the monitoring group for the current monitoring program. Similarly, certain categories of subjects may be marked as necessary for monitoring program representation for other reasons, such as for meeting diversity criteria required for the monitoring program and/or for obtaining viable results.

Communication with a selected set of remote devices may take place over a communication network such as a wireless internet network (e.g., Wi-Fi), a cellular network (e.g., 5G network), etc. The computer system 210 may form a secure communication channel, such as an encrypted channel between the remote devices and the computer system 210 to protect the transfer of sensitive data such as medical records, medical information, health data, photographs, etc. between the remote devices and the computer system 210.

Prior to starting a monitoring program, the computer system 210 may distribute software to the remote devices. Alternatively, the remote devices may access the software through a website or mobile application. However, the accessed software may be customized to the specific remote device based on it or its user corresponding to a particular subject profile. The software may provide for the configuration of a secure communication channel between a remote device and the computer system 210, and/or for a user interface through which a subject can interact to, for example, respond to messages, provide feedback, provide text input, submit photographs, submit test results, etc. using touch input, keyboard input, voice input, or a combination of different input types.

As previously mentioned, the computer system 210 may customize the monitoring program for different categories of subjects corresponding to different profiles. In doing this, the computer system 210 may generate and distribute different software versions. The different software versions may provide for different and possibly unique interactions between devices of subjects corresponding to a first profile, and devices of subjects corresponding to a second profile. For example, the two different software versions corresponding to the same base monitoring program may provide for a different frequency of data collection, using a different sensor to collect the data, a different channel of communication to send request or message, etc.

In some implementations, the remote devices are the subjects for a monitoring program.

Figure 13:
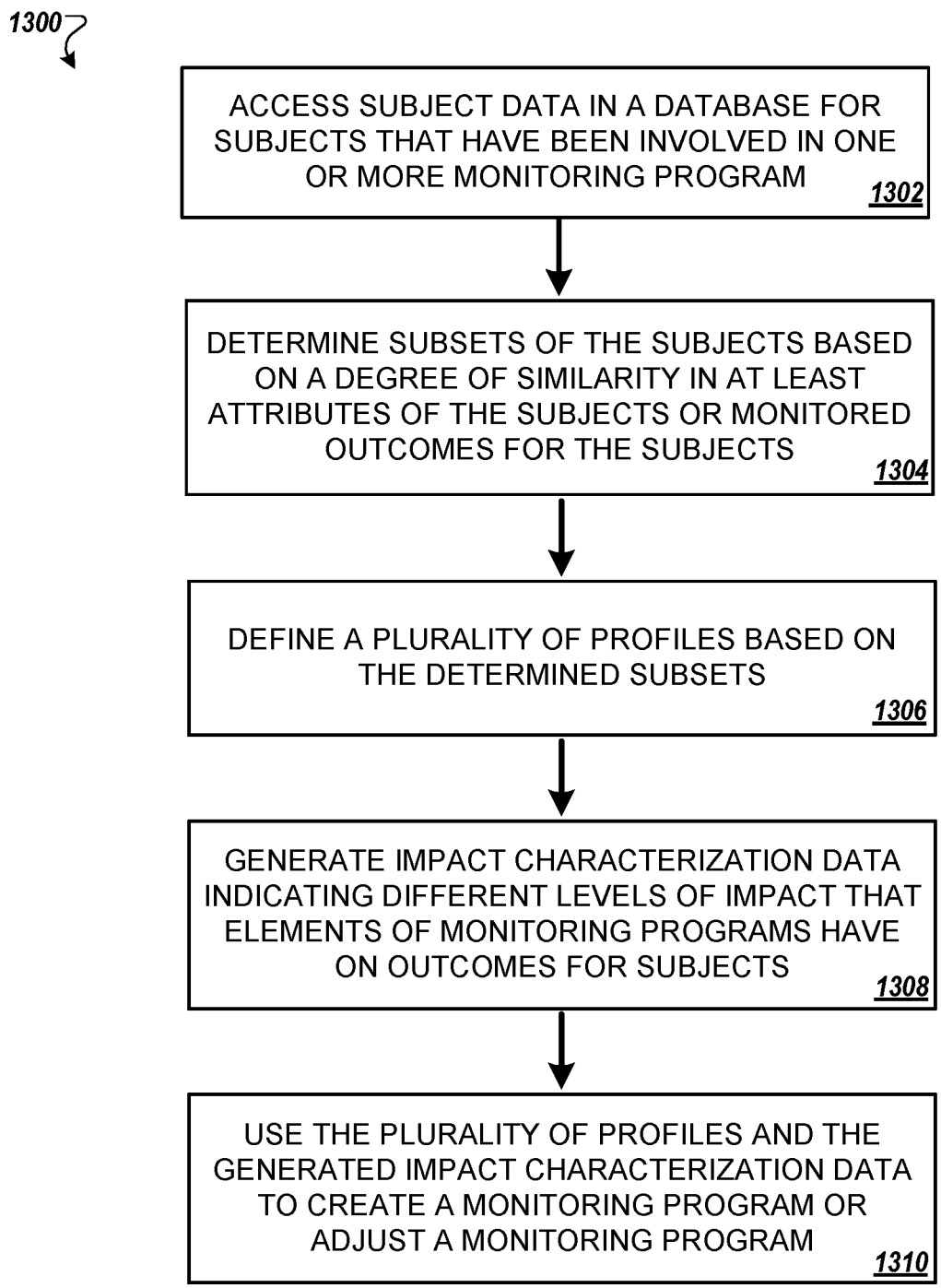
FIG. 13 is a flowchart diagram that illustrates an example process for customizing monitoring programs involving remote devices.

FIG. 13 is a flowchart diagram that illustrates an example process 1200 for assessing and selecting technologies. The process 1300 may be performed by one or more computers, such as the computer system 210 shown in various figures including FIG. 2. The operations of the process 1300 may be distributed among one or more servers, one or more client devices, and/or other computing systems. For example, the operations of the process 1300 may be performed by a management and distribution system, such as the system 210, that includes one or more servers, one or more client devices, and/or other computing systems.

The process 1300 includes accessing subject data in a database for subjects that have been involved in one or more monitoring program (1302). For example, with respect to FIG. 9A, the computer system 210 may access the subject data 950 from the database 212. The subject data 950 may include attributes for subjects in a subject pool that have participated in one or more previous monitoring programs, and/or are currently enrolled in an ongoing monitoring program. The subject data 950 may also include other data, such as historical data, including response times, response content, compliance data, uploaded data, indication of past and/or present monitoring programs that subject has participated in, etc.

The process 1300 includes determining subsets of the subjects based on a degree of similarity in at least attributes of the subjects or monitored outcomes for the subjects (1304). For example, with respect to FIG. 9A, the computer system 210 may use key attributes 902 (e.g., a subset of particular subject attributes selected by the computer system 210 or a researcher) and/or outcomes 904 (e.g., one or more particular outcomes selected by the computer system 210 or a researcher). The computer system 210 may group the subjects using the key attributes 902 and/or the outcomes 904. As an example, the computer system 210 may provide the key attributes 902, the outcomes 904, and subject data for a subject pool to the clustering model 908 as input. The clustering model 908 may proceed to organize the subjects in the subject pool based on the key attributes 902 if that is provided as input, based on the particular outcomes (e.g., data quality, overall compliance rates, compliance rates in a particular category, retention rates, etc.) in the outcomes 904 if that is provided as input the clustering model 908, or based on the key attributes 902 and the outcomes 904 if both are provided as input to the clustering model 908.

The output of the clustering model 908 may include an indication of which cluster each of the subjects in the subject pool belongs to. For example, the output of the clustering model 908 may be an indication of which centroid each subject was assigned to.

The process 1300 includes defining a plurality of profiles based on the determined subsets (1306). For example, the computer system 210 may use each of the groups of the subjects (e.g., the clusters) to a profile that represents a category of subjects. In generating the profiles, the computer system 210 may retrieve information from the subjects in the groups and use the information to define inclusion criteria for the different profiles. The inclusion criteria may be defined by the computer system 210 such that it is mutually exclusive with respect to the inclusion criteria of the other profiles, such that the a subject cannot be assigned to multiple profiles. However, in some cases, a subject may be assigned to multiple profiles.

The process 1300 includes generating impact characterization data indicating different levels of impact that elements of monitoring programs have on outcomes for subjects (1308). The computer system 210 may identify the profiles that are present among a monitoring group selected for a monitoring program, compare the elements of the selected monitoring program to the element effect information in the profiles, and, based on the comparison, determine one or more adjustments to the monitoring program for the different categories of subjects. The adjustments made by the computer system 210 may include removing or modifying an element of a monitoring program (e.g., reduce number of tests that user must complete if this is determined to significantly lower retention rates), adjusting communication attributes (e.g., communication channel, frequency, time, content, sentence structure, etc.), or adding an element (e.g., account for subjects not having access to a device, account for subject not having access to transportation by providing transportation credit, etc.). For example, if an element of a monitoring program is anticipated to reduce compliance with subjects assigned to a second profile, the computer system 210 may adjust that element using information in the second profile to mitigate the anticipated reduced compliance.

The process 1300 includes using the plurality of profiles and the generated impact characterization data to create a monitoring program or adjust a monitoring program (1310). For example, the computer system 210 may customize a monitoring program selected by a researcher to improve the likelihood of viable data being produced as a result of the monitoring program, and/or other goals of the monitoring program being obtained (e.g., such as diversity goals to increase the applicability of the results of the monitoring program). The computer system 210 may create and/or customize a monitoring program for each profile among the enrolled monitoring program subjects. Accordingly, the computer system 210 may first identify what profiles are present among the monitoring group, prior to (i) adjusting the monitoring group and/or (ii) the elements of the monitoring program.

Figure 14:
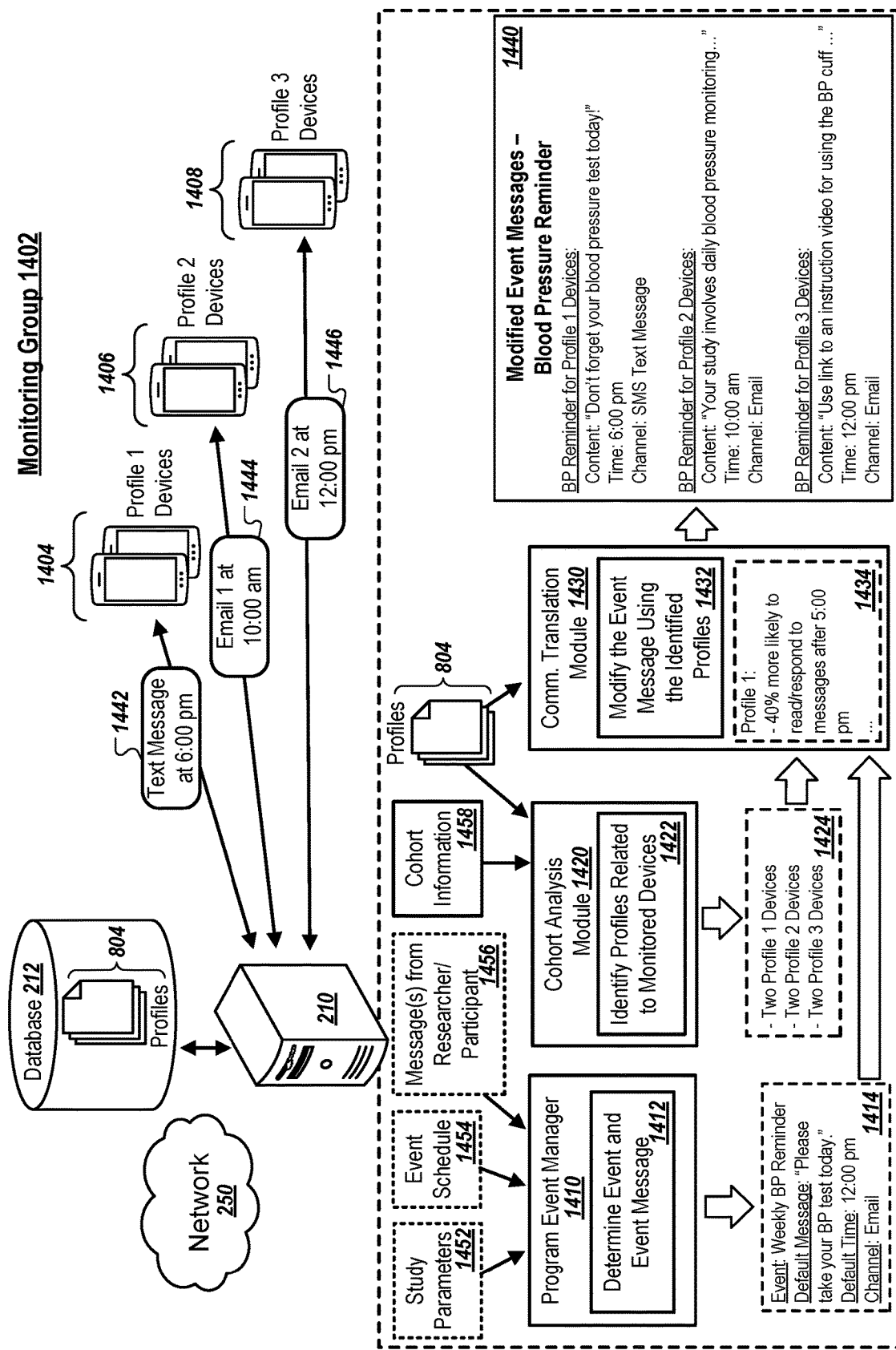
FIG. 14 is a diagram that illustrates an example system for customizing communications for categories of participants.

FIG. 14 is a diagram that illustrates one or more components of the system 200 for customizing communications for categories of participants. For example, the computer system 210 can be used to customize communication for categories of participants.

In more detail, the computer system 210 is configured to manage multiple monitoring programs corresponding to different groups of enrolled subjects. Each of the monitoring programs can have a set of elements that, for example, outline the requirements for the respective monitoring program. The groups of enrolled subjects each include multiple subjects that participate in the same monitoring program or in a monitoring program having the same set of requirements. The subjects within each of the groups can belong to different categories of subjects that interact with the computer system 210 differently or that otherwise have different needs that require adjusted interaction. To promote high compliance with the monitoring programs' requirements among the diverse groups of participants, the computer system 210 can adapt its interactions so that they are tailored to the needs of each category of subjects present among the monitoring program participants.

As an example, the computer system 210 may manage a monitoring program for conducting a clinical trial for a new pharmaceutical. The monitoring program may require obtaining measurements of a physical attribute twice a day for a period of one month. The enrolled subjects of the monitoring program may include a first subgroup of participants that belong to a first category of subjects, and a second subgroup of participants that belong to a second category of subjects. Using information related to the first category, the computer system 210 can determine that the first subgroup responds well to in-application services. In contrast, information related to the second category can indicate that second subgroup responds well to video calls or audio calls, and responds poorly to in-application services. As a result, the computer system can adapt the manner in which it interacts with the different subgroups of participants to achieve high data quality and high compliance with the requirements of the monitoring program. One of the ways this can be done is by converting or translating a message into different forms or styles depending on the information associated with the different categories of subjects. This information may include subject attributes, behaviors associated with the subjects in the categories, and anticipated effects of different monitoring program elements on the actions of the subjects in the categories, and may be stored as part of profiles that represents the different categories of subjects.

With respect to the first subgroup, the computer system 210 may send reminder notifications to devices belonging to participants in the first subgroup, where the reminder notification will be displayed as an in-app notification in an application for the monitoring program. In contrast, the computer system 210 may call the devices belonging to participants in the second subgroup and provided an automated message reminding the participants to provide the measurements.

As illustrated in FIG. 14, the computer system 210 is configured to distribute software for a monitoring program to a monitoring group 1402 that includes multiple devices that are to be monitored. The monitoring program may indicate times when data is to be obtained from, requested from, or sent to the monitored devices in the monitoring group 1402. The monitoring program may also indicate the type of data or the specific data that is to be obtained from, requested from, or sent to the monitored devices in the monitoring group 1402. The data obtained or requested from the monitored devices may include sensor data collected using sensors of the monitored devices or sensor devices electronically connected to the monitored devices in the monitoring group 1402. The data sent to the monitored devices may include messages that request the users of the monitored devices to perform one or more actions. These actions may include a request to perform an action such as a request to take a blood pressure test, a request to permit the access of sensor data, a request to respond to the notification using one or more preselected responses provided in the notification or freestyle responses, etc.

The computer system 210 can adjust the messages that it sends to the monitored devices in the monitoring group 1402 based on profiles 804 associated with the monitored devices. As an example, the computer system 210 may determine one or more categories of users that the users of the monitored devices belong to. The computer system 210 may proceed to access the profiles 804 from the database 212 that represent these categories of users, and use the profiles 804 to customize the messages for the different groups 1404, 1406, and 1408 of monitored devices in the monitoring group 1402. In more detail, if the first group 1404 of the monitored devices are associated with a first profile of the profiles 804 and the second group 1406 of the monitored devices are associated with a second profile of the profiles 804, the computer system 210 may customize and send a first notification 1442 to the first group 1404 of monitored devices having a first set of notification or message attributes, and a second notification 1444 to the second group 1406 of monitored devices having a second set of notification or message attributes that are different from the first set. The computer system 210 may customize the messages to adjust, for example, the time of that the notification is sent, a deadline for providing a response or performing an action associated with a notification, the channel of communication, the formality of the communication such as word choice and sentence structure, the frequency of communication, etc.

The computer system 210 can make these adjustments to achieve one or more goals. For example, the computer system 210 may adjust how to communicate with the different categories of users to achieve improved user retention in the monitoring program, to improve user compliance (e.g., read messages, respond to messages, perform actions requested in messages, etc.), and/or to improve the data quality collected (e.g., obtaining test results at the time requested, obtaining sensor data at the time requested, etc.).

In general, categories of users (or participants) refers to different groupings of users that correspond to particular profiles. That is, each of these profiles may represent a particular category of users. The profiles may specify sets of inclusion criteria (e.g., member parameters) that are used to determine which users belong to which categories of users. In some cases, each user can only belong to a single category of users that corresponds to a single profile. Alternatively, each user can belong to one or more categories of profiles that correspond to one or more profiles. As will be described in more detail below, the computer system 210 may determine whether a user is in a particular category of users by comparing characteristics of the user with the corresponding inclusion criteria for the profile corresponding to the particular category. The user characteristics and inclusion criteria may include, for example, demographic and non-demographic information such as an age or age range, sex, ethnicity race, medical conditions, past surgeries, prescribed medications, etc. Each category of users may also be associated with a particular set of determined effects of message attributes on the outcomes or responses (e.g., behavior) of users in the corresponding category of users. For example, the computer system 210 may determine these effects using data collected from user devices, and, in updating or generating the profiles, may store different subsets of this information in corresponding profiles.

As illustrated in the example of FIG. 14, the computer system 210 may include a program event manager 1410, a cohort analysis module 1420, and a communication translation module 1430. The program event manager 1410, the cohort analysis module 1420, and the communication translation module 1430 can be software modules that each include one or more programs or workflows. These software modules may include or otherwise use various algorithms including, for example, static algorithms and/or machine learning algorithms to perform the tasks described below.

As an example, the program event manager 1410 is configured to determine events and corresponding event messages (1412). In making these determinations, the program event manager 1410 may access or receive, e.g., over the network 250, information that it uses to determine that an event is upcoming or has occurred, and/or to retrieve or generate a message corresponding to the event. This information may include, for example, program parameters 1452, an event schedule 1454, or messages 1456 received from one or more remote devices. This information may also include data received from the devices in the monitored group 1402, such as an indication of response times, sensor data, messages, test results, etc.

As an example, the program event manager 1410 may use the program parameters 1452 for a monitoring program to identify an event or an upcoming event in the monitoring program. The program parameters 1452 may indicate various requirements for a monitoring program. As an example, the program parameters 1452 may indicate that users corresponding to the monitored group 1402 need to take weekly blood pressure (BP) tests and submit the tests results through their respective devices to the computer system 210. The program event manager 1410 may use this information along with other information, such as data indicating the last time users of the monitoring group 1402 devices submitted BP test results or data indicating the last time users of the monitoring group 1402 were required to submit BP test results, to determine a weekly BP test reminder event.

As another example, the program parameters 1452 may indicate one or more tasks that users of the monitoring group 1402 devices need to complete. The program event manager 1410 may use these requirements to determine a first set events that correspond to when the tasks are successfully completed by the users, and a second set of events that correspond to when the users fail to complete the tasks or fail to timely complete the tasks. For example, the program event manager 1410 may determine a noncompliance event if any user—or a user in a particular category of users—does not complete a task within a predetermined time period (e.g., one hour, two hours, 12 hours, or 24 hours) of a set time and/or date for the particular task. With respect to the earlier example, if the program parameters 1452 require users to take weekly BP tests and submit the test results, the program event manager 1410 may determine a non-compliance event if any user corresponding to the monitoring group 1402 of devices fails to submit their tests results within four hours of the set date and time.

In some cases, events determined by the program event manager 1410 are particular to certain categories of users or the criteria for determining a particular event may differ for different categories of users. For example, continuing the earlier example, the computer system 210 may determine a noncompliance event for a first category of users if they do not perform their assigned task within two hours of the set date and/or time. However, the computer system 210 may determine a noncompliance event for second category of users if they do not perform their assigned task within eight hours of the set data and/or time. The program event manager 1410 may make such determinations using, for example, data stored in or with the profiles 804 that indicates the behaviors of users in the corresponding categories of users.

As an example, a profile that represents this example first category of users may indicate that if users do not perform the task within two hours, there is a 95% chance that they will not perform the task after this time period. In contrast, a profile that represents the second category of users may indicate that there is a greater than 50% likelihood of users performing the task after the set time up to eight hours after the set time. Based on this data, the program event manager 1410 may modify the criteria for a noncompliance event such that is differs between users in the first category and users in the second category. Specifically, the program event manager 1410 may update the noncompliance criteria for the second category of users to extend the time until a noncompliance event is triggered from two hours to eight hours.

The program event manager 1410 may additionally or alternatively use an event schedule 1454 for a session or period of a monitoring program or, more generally, the monitoring program as a whole to determine an event and an event message (1412). For example, the event schedule may include dates and times when sensor data should be requested from the monitoring group 1402 devices, when particular messages should be sent to the monitoring group 1402 devices, upcoming deadlines for test results or other data from the monitoring group 1402 devices, upcoming appointments for users of the monitoring group 1402 devices, etc.

In some cases, the program event manager 1410 generates the event schedule 1454 or updates the event schedule 1454 using the program parameters 1452.

The program event manager 1410 may receive messages from a researcher or participant 1456 to transmit. For example, if the messages 1456 include a message from the researcher 202 that includes or is provided with instructions to transmit to the subjects of the monitoring program, the program event manager 1410 may generate an event to transmit the message to all subjects of the monitoring program. Similarly, if the messages 1456 include a message, such as a response, from a participant, the program event manager 1410 may create an event to (i) store the message and/or (ii) to transmit the message to the researcher 202.

The program event manager 1410 may be configured to ping one or more subjects of the study. For example, the program event manager 1410 may generate reminder events and/or reminders that are to be sent to subjects. The reminders may correspond to particular tasks of the monitoring program, such as test reminders (e.g., medical tests), appointment reminders, reminders for upcoming events, etc. The program event manager 1410 may other notification events and/or notifications, such as requests for input or feedback, instructions to perform a task or attend an event, etc.

The program event messages (e.g., notifications) may include particular information. For example, each program event message may include one or more of a program identifier (e.g., that identifies the monitoring program), a session identifier (e.g., that identifies the current monitoring session), an event identifier (e.g., that identifies the type of message), a subject for the event message, indication of recipients (e.g., all subjects, names, phone numbers, email addresses, etc.), or content for the message. The event ID may indicate, for example, that a message is a reminder message, a new task message, an input or feedback request message, etc. The subject for the message may specify the type of data being requested, the specific task the message corresponds to, etc. For example, the subject for a program event message may indicate that the message relates to a blood pressure measure task.

As shown, the program event manager 1410 generates an output 1414. The output 1414 may be a program event message that is generated by the program event manager 1410. Alternatively, the program event message may be a message provided to the program event manager 1410 that the program event manger creates an event for, e.g., an event to transmit the message to the one or more of the monitoring group 1402 devices.

The program event message may include an event subject (e.g., weekly BP reminder), content for the message (e.g., message to "please take your BP test today"), a time that the message is scheduled to be sent (e.g., 12:00 pm), and an indication of the communication channel to be used to send the message (e.g., email). Although the program event message is shown to include these components, a program event message may include more or less components. As an example, a program event message may consist of a program ID, and event ID, and a subject for the message. This information may be enough for the communication translation module 1430, discussed in more detail below, to generate a complete message.

The output 1414 of the program event manager 1410 may be provided to the communication translation module 1430.

A cohort analysis module 1420 may be configured to identify profiles related to monitored devices (1422). The cohort analysis module 1420 may obtain cohort information 1458 corresponding to the monitoring group 1402 and compare this to information in the profiles 804. Specifically, the cohort analysis module 1420 may retrieve subject attributes (e.g., of devices, or of device users) and compare them to inclusion criteria for each of the profiles 804. If a particular subject has attributes that meet the inclusion criteria of a particular profile of the profiles 804, the cohort analysis module 1420 may assign the subject to the particular profile.

In order to improve efficiency and reduce the computational burden, the cohort analysis module 1420 may refer to a list of subjects that have previously been assigned to a particular profile. The cohort analysis module 1420 may use this list to identify subjects in the current monitoring program that have previously been identified with a particular profile of the profiles 804. In some cases, depending on the time that has elapsed since the previous assignment was made and/or on the amount of new data that has been collected with respect to the particular subject since the previous assignment, the cohort analysis module 1420 may reassess what profile(s) the subject should be assigned to.

As shown, the cohort analysis module 1420 generates output 1424. The output may indicate the profiles that are present among the monitoring group 1402 and/or the number of subjects associated with each of the profiles in the monitoring group 1402. For example, the output 1424 may indicate that there are two Profile 1 devices 1404, two Profile 2 devices 1406, and two Profile 3 devices 1408 in the monitoring group 1302 for the current monitoring session.

The cohort analysis module 1420 may provide the output 1424 to the communication translation module 1430.

The communication translation module 1430 is configured to modify program event messages using the identified profiles 1432. For example, the communication translation module 1430 may obtain a program event message (e.g., output 1414) from the program event manager 1410, use the output 1424 of the cohort analysis module 1420 to identify which profiles of the profiles 804 correspond to the monitoring group 1402 devices, and proceed to use those particular profiles to customize the communication for one or more of the groups of profile devices 1404, 1406, and 1408.

In modifying the event messages, the communication translation module 1430 may extract information from the profiles that indicate different effects off communication attributes on outcomes for subjects assigned to those profiles (e.g., compliance rates, data quality, etc.). That is, the communication translation module 1430 may extract information from the profiles indicating the anticipated behavior of subjects assigned to those profiles. This anticipated behavior can be attributed to the subjects in the monitoring group. For example, the communication translation module 1430 may extract information 1434 from a first profile that indicates that Profile 1 subjects are 40% more likely to read/respond to messages sent after 5:00 pm. The communication translation module 1430 can attribute this information to the first profile devices 1404. Similarly, the communication translation module 1430 may extract information from a second profile to attribute to the second profile devices 1406, and information from a third profile to attribute to the third profile devices 1408.

The communication translation module 1430 may use the extracted information for a particular profile to update the communication attributes for a program event message for the group of devices assigned to that particular profile. For example, using the extracted information 1434 for the first profile of the profiles 804, the communication translation module 1430 may update the send time for the program event message 1414 from 12:00 pm to 6:00 pm for Profile 1 devices 1404. The communication translation module 1430 may update the communication attributes for each category of subjects present among the monitoring group 1402. For example, the communication translation module 1430 may proceed to update communication attributes of an event message for each of the first profile devices 1404, the second profile devices 1406, and/or the third profile devices 1408 in the monitoring group 1402.

In updating the communication attributes for a program event message, the communication translation module 1430 may generate different versions of the program event message. For example, the communication translation module 1430 may generate a version of a particular program event message for each of the profiles of the profiles 804 represented among the monitoring group 1402, where each version includes different communication attributes. Each version of the program event message may be different than an incoming program event message received by the communication translation module 1430, or a default event message generated or retrieved by the communication translation module 1430.

As another example, the communication translation module 1430 may generate multiple different versions of a particular program event message for different profiles of the profiles 804 represented among the monitoring group 1402. Here, the communication translation module 1430 may use an incoming event message or a default event message as the event message that is transmitted to one or more groups of subjects. Accordingly, a first version of a particular program event message for a first group of subjects corresponding to a first profile may use the incoming or default communication attributes. In contrast, the communication translation module 1430 may update the incoming or default communication attributes for a second version of the program event message for a second group of subjects corresponding to a second profile.

In updating communication attributes for a program event message or generating a customized program event message, the communication translation module 1430 may utilize a message queue. Incoming program event messages or indication of program event messages may be placed in the queue for the translation module 1430 to process. The communication translation module 1430 may process the event messages in the queue In some implementations, the communication translation module 1430 uses multiple threads to process multiple event messages concurrently. As an example, the communication translation module 1430 may use multiple threads that each pull event messages from a queue or may each pull event messages from a corresponding queue to process. The communication translation module 1430 may use the multiple threads to concurrently generate multiple versions of an event message. For example, the communication translation module 1430 may process one event message at a time, but use multiple threads to update the communication attributes of the event message for different profiles represented in the monitoring group 1402. In more detail, a first thread may be used by the communication translation module 1430 to generate a first version of an event message by updating the communication attributes for the event message in a first way, and a second thread may be used by the communication translation module 1430 to concurrently generate a second version of the event message by updating the communication attributes for the event message in a second way.

Similarly, in some implementations, the communication translation module 1430 may run multiple processes to process multiple event messages in parallel. As an example, the communication translation module 1430 may use multiple processes to process different events pulled a queue, or to process different events pulled from multiple queues (e.g., each corresponding to one of the processes). The communication translation module 1430 may use the multiple processes to generate multiple versions of an event message in parallel. For example, the communication translation module 1430 may each of multiple processes to update the communication attributes for a corresponding version of an event message. In more detail, a first process may be used by the communication translation module 1430 to generate a first version of an event message by updating the communication attributes for the event message in a first way, and a second process may be used by the communication translation module 1430 to generate a second version of the event message in parallel by updating the communication attributes for the event message in a second way.

In some implementation, the communication translation module 1430 processes event messages sequentially. As an example, for a first event message that is first in a queue of event messages, the communication translation module 1430 may modify the communication attributes for each of the subject profiles represented in the monitoring group 1402 before retrieving a second event message and/or modifying the communication attributes for the second event message.

In some implementations, the communication translation module 1430 processes event messages asynchronously.

As will be discussed in more detail below, the communication attributes may include various attributes that define the contents of communication, the means of communication, the time of communication, and the frequency of communication. In more detail, the communication attributes may include attributes that define the content of communication such as word choice/vocabulary (e.g., to account for regions by using certain dialects, to account for level of education, communication trends of groups of subjects as indicated by the profiles, etc.), sentence structure (e.g., formal, informal, semi-formal, etc.) For example, the communication translation module 1430 may modify a message that is to be sent to a group of subjects residing in New York to include the word choice "pop" when asking the subjects how many sweetened carbonated drinks they have had over the last week. In contrast, the communication translation module 1430 may modify the same message that is to be sent to a different group of subjects residing in Virginia to include the word choice "soda" when asking the subjects how many sweetened carbonated drinks they have had over the last week.

In updating the communication attributes for each of the profiles present among the monitoring group 1402, the communication translation module 1430 can generate multiple versions of event messages. For example, the communication translation module 1430 customizes the event message 1414 for each of the profile subjects, thereby generating in this example the three modified event messages 1440.

Each of the event messages in the modified event messages 1440 is designated for one of three groups of devices 1404, 1406, and 1408.

The communication translation module 1430 may use other information extracted from the profiles 804 to generate the modified event messages 1440. Based on the monitoring group 1402 including Profile 1, Profile 2, and Profile 3 subjects, the communication translation module 1430 may, therefore, use other information extracted from the first profile of the profiles 804, from the second profile of the profiles 804, and from the third profile of the profiles 804 to generate the modified event messages 1440 for the blood pressure reminder. This other information may include information that is not a communication attribute but that may be relevant to one or more communication attributes and/or to the particular event message. The other information may include, for example, preferences for the category of subjects represented by the profiles. As an example, a profile may indicate that a first group of subjects are more likely to submit tests in the afternoon. The communication translation module 1430 may extract this information and use it to adjust a send time for an event message corresponding to a reminder to perform a test, such as to take a blood pressure reading.

The communication translation module 1430 may generate customized messages in order to improve one or more particular outcomes. These outcomes may include overall compliance rate for a group of subjects with the requirements of the monitoring program or particular monitoring session for the monitoring program. Similarly, these outcomes may include compliance in a particular area (e.g., smartphone compliance, medical office visit compliance, message response compliance, schedule compliance, test upload compliance, etc.) for a group of subjects with the requirements of the monitoring program or particular monitoring session for the monitoring program. Other outcomes can include data quality, such as a likelihood of sufficient data quality being obtained from a group of subjects in accordance with the requirements of the monitoring program or particular monitoring session for the monitoring program. Similarly, data quality as an outcome can be a level of data quality obtained (e.g., a score for accuracy, precision, completeness, reliability, variance, etc.) from a group of subjects in accordance with the requirements of the monitoring program or particular monitoring session for the monitoring program.

The factors that can be used by the computer system 210 to determine a level of data quality and/or be used by the computer system 210 to determine if sufficient data quality has been obtained may include an indication whether all or a minimum amount of required data was received (e.g., test results, sensor data, user feedback or other input, etc.), the accuracy of the sensor used to obtain data (e.g., may be determined using the make and/or model of the device used to collect sensor data or the make and model of the sensor itself), the amount of time a subject spent generating the data (e.g., if a subject completed a survey too quickly, this may indicate that a subject did not read the questions and, therefore, the data is more likely to have insufficient quality for acceptance), an indication of whether data was received by a set deadline, an indication of the time before or after a goal/deadline the data was received, etc.

By improving the outcomes for different categories of subjects, the computer system 210 can improve the likelihood that one or more goals of the monitoring program are achieved. These goals can include a goal for obtaining viable results. Results of monitoring program may only be viable if, for example, at least a minimum number of participants are retained (e.g., continue in the program for a minimum amount of time or until an end date of the program), the retained subjects are of sufficient diversity (e.g., based on demographic and/or non-demographic diversity factors), the subjects demonstrate sufficient compliance with the monitoring program requirements (e.g., actions to perform, characteristics to maintain, etc.), and/or sufficient data quality and completeness of data collection is obtained from the monitored subjects. Accordingly, by modifying event messages for particular categories of subjects represented by profiles, the communication translation module 1430 can improve the likelihood of obtaining viable results by increasing the likelihood of subjects demonstrating beneficial outcomes (e.g., being more compliance, staying in and/or active in the monitoring program, providing higher quality data, etc.). There are numerous processing benefits from obtaining viable results and/or otherwise successfully meeting the goals for the monitoring program, including an improvement to efficiency through, for example, a reduction in the number of messages being sent and, therefore, a reduction in network bandwidth usage by the computer system 210.

After generating the modified event messages 1440, the computer system 210 can proceed to transmit each of the event messages in the event messages 1440 to one of the groups of devices in the monitoring group 1402. For example, the computer system 210 may transmit a modified version of the event message 1414 for the Profile 1 subjects to the first profile devices 1404 as an SMS text message 1442 at 6:00 pm. Similarly, the computer system 210 may transmit a modified version of the event message 1414 for the Profile 2 subjects to the second profile devices 1406 as a first email 1444 at 10:00 am. Finally, the computer system 210 may transmit a modified version of the event message 1414 for the Profile 3 subjects to the third profile devices 1408 as a second email 1446 at 12:00 μm.

Figure 15:
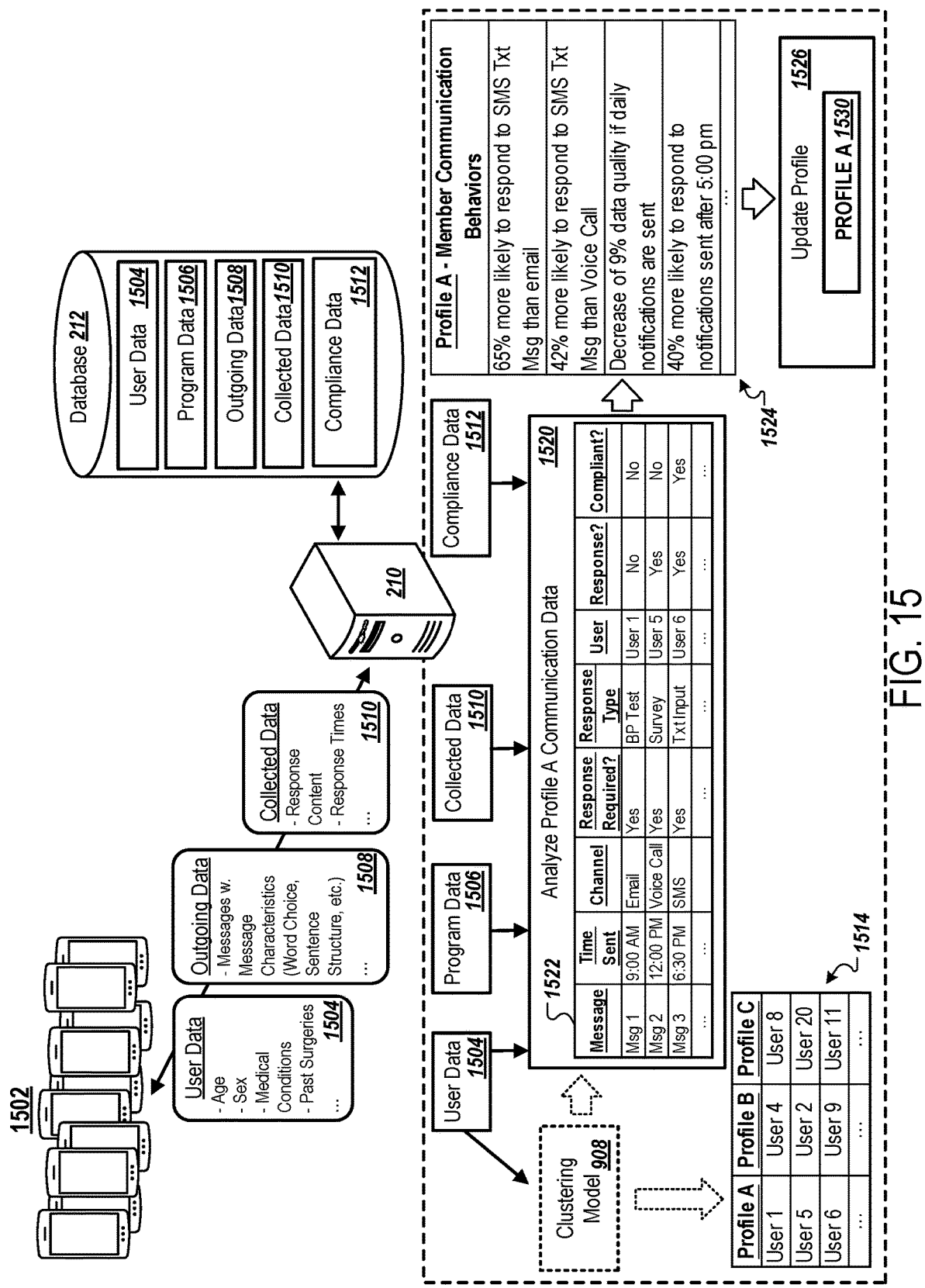
FIG. 15 is a diagram that illustrates an example system for generating profiles that represent different categories of participants.

FIG. 15 is a diagram that illustrates one or more components of the system 200 for generating profiles that represent different categories of participants. For example, the computer system 210 can generate profiles that represent different categories of participants.

In more detail, the computer system 210 can collect information including communication information for different subjects enrolled in various monitoring programs over time. This information may include, for example, information on the messages sent to the subjects, information on the responses received from the subjects, and attributes of the subject. The computer system 210 can use this information to (i) cluster the subjects into different groups, and/or (ii) generate profiles that represent different categories of subjects. In generating the profiles, the computer system 210 can use the collected information to identify behaviors among the subjects in each groups, such as communication behaviors or behaviors related to other interactions. The computer system 210 may use the information and/or the behaviors to determine the impact of various monitoring program elements on subject outcomes for subjects in each of the categories. For example, the computer system may convert the determined communication behaviors related to different communication attributes to impact scores that indicate the effect of the different communication attributes on participant compliance and/or data quality.

As illustrated in FIG. 15, the computer system 210 can distribute and manage a variety of monitoring programs for various devices 1502 over time. The devices 1502 may represent subject devices, devices of subject users, or a combination of subject devices and devices of subject users. In managing these various monitoring programs for the devices 1502, the computer system 210 can track information for various subjects participating in the monitoring program over time, and use this monitored information to determine effects of different communication attributes on subject outcomes. For example, the computer system 210 may identify the effect that different communication attributes have on the compliance and data quality for different categories of subjects. The computer system 210 can incorporate the determined effects into existing profiles that represent categories of subjects, or use the determined effects to generate profiles that represent categories of subjects. As discussed above with respect to FIG. 14, the computer system 210 may later extract these determined effects from the profiles, and use the extracted information to customize interactions between subjects in monitoring groups for ongoing or new monitoring programs in order to improve the likelihood of obtaining desirable subject outcomes.

The monitored information collected by the computer system 210 may include information corresponding to various interactions between the computer system 210 and the subjects of past and ongoing monitoring programs. Specifically, the monitored information may include information sent to the devices 1502, information received from the devices 1502, and information derived from the information received from the devices 1502 during monitoring program managed by the computer system 210. In more detail, this information may include subject data that includes attributes for the subjects, outgoing data 1508 sent by the computer system 210 to the devices 1502, incoming or collected data 1510 received from the devices 1502 and/or derived from information received from the devices 1510, and compliance data 1512 determined from program data 1506 that describes the monitoring programs, the outgoing data 1508, and/or the collected data 1510.

In more detail, the program data 1506 may describe the monitoring programs that are distributed and managed by the computer system 210. The program data 1506 may include, for example, information that identifies the different monitoring programs (or versions of monitoring programs) that have been managed by the computer system 210, start and end dates for different monitoring programs (or sessions, repeats, components, or periods within a monitoring program), an indication of which subjects and/or portion of the devices 1502 were include in the monitoring program, an indication of what software and/or what software configuration was provided to the portion of the devices 1502 in a given monitoring program, etc. The program data 1506 may be arranged in one or more data structures. For example, the program data 1506 may include a data table for each monitoring program. Information can be broken out for different instances or sessions in which that monitoring program was conducted, as well as for sub-studies or continuations of the monitoring program. The columns may indicate various characteristics of the monitoring programs and their variations, such as a start time for the program, an end time for the program, cohort selection criteria uses, requirements for participants, technology items used by participants, the subjects that were in the cohort, and so on.

The program data 1506 can also include the various elements of the monitoring programs. That is, the program data 1506 may include the parameters and requirements for each monitoring program or each version of a monitoring program that was managed by the computer system 210. For example, for a particular monitoring program, the program data 1506 may indicate that Profile A subjects must provide a heart rate reading three times a day, and that Profile B subjects must provide a heart rate reading twice a day along with two glucose test results.

The subject data may include device attribute information, such as the model, manufacturer, CPU model and/or specifications, memory, and/or onboard sensors of at least a portion of the devices 1502. The subject data may additionally or alternatively include user data 1504, such a demographic and non-demographic attribute information of the users of at least a portion of the devices 1502. For example, the user data 1504 may include the age, sex, known medical conditions, and known past surgeries for each of the subject users that have previously participated in a monitoring program or are currently enrolled in a monitoring program. If the subjects for one or more monitoring program are devices, the computer system 210 may still track information for the users of the devices. Similarly, if the subjects for one or more monitoring programs are users, the computer system 210 may still track information for the devices of those users that the computer system 210 communicates with.

The subject data may be organized by the computer system 210 based on the categories of subjects. For example, the portion of the user data 1504 corresponding to a category of subjects represented by a first profile may be stored by the computer system 210 in a first data structure, and a second portion of the user data 1504 corresponding to a category of subjects represented by a second profile may be stored by the computer system in a second data structure.

The computer system 210 may also include in the user data 1504 statistics generated for the different categories of subjects. For example, the computer system 210 may calculate the average age for the subjects in each category of subjects, the percent of subjects that are female and male in each category of subjects, the percent of subjects that suffer from diabetes, the percent of subjects that have had knee surgery, etc. The computer system 210 may identify and/or highlight values that are above a threshold value (e.g., threshold percentage) or that have a relatively high or low value (e.g., 20% higher or lower than the average value for other categories of subjects).

The outgoing data 1508 may include characteristics of messages sent to the devices 1502. For example, the outgoing data 1508 may include an indication of the communication attributes for messages sent to the devices 1502 (e.g., communication channel, word choice, sentence structure, message type, indication of response requested, indication of response type, message content, etc.), transmission times, message sizes, etc.

The outgoing data 1508 may also include information for software distributed to the devices 1502. For example, the outgoing data 1508 may indicate a type of software, a software version, and/or the configuration parameters of the distributed software. The outgoing data 1508 may include software information at, for example, the onset of a new monitoring program when it is distributing software or different versions of the software to different groups of the devices 1502 (e.g., corresponding to different profiles). Additionally or alternatively, the outgoing data 1508 may include software or configuration data sent during the monitoring program. For example, the computer system 210 may distribute new software containing a modified configuration to a group of the devices 1502 corresponding to a particular profile in order to, for example, improve the likelihood of collecting data of sufficient data quality and of those subjects complying with the requirements of the monitoring program.

The outgoing data 1508 may be organized by the computer system 210 based on the categories of subjects. For example, the portion of the outgoing data 1508 corresponding to a category of subjects represented by a first profile may be stored by the computer system 210 in a first data structure, and a second portion of the outgoing data 1508 corresponding to a category of subjects represented by a second profile may be stored by the computer system in a second data structure. The outgoing data 1508 will typically be organized this way as the computer system 210 can, as described in more detail above with respect to FIG. 14, customize the communication attributes of an event message for a particular category of subjects. Accordingly, for a particular event message, the portion of the outgoing data 1508 that corresponds to a particular subject in a first category of subjects will be the same or substantially the same (e.g., the outgoing data 1508 may specify an ID for the recipient device that differs from device to device) as the portion of the outgoing data 1508 corresponding to the other subjects in the first category of subjects.

The collected data 1510 may include information received from the devices 1502 and/or derived from the information received from the devices. For example, the collected data 1510 may include an indication that a message failed to be delivered, an indication that a message was successfully delivered, a response or an indication that a response was received, a time that a response was received, and/or a size of a response. Using the received information, the computer system 210 may determine, for example, the response time for a message by taking the difference between a sent time and a time that a response was received.

The collected data 1510 may be organized by the computer system 210 based on the categories of subjects. For example, the portion of the collected data 1510 corresponding to a category of subject represented by a first profile may be stored by the computer system 210 in a first data structure, and a second portion of the collected data 1510 corresponding to a category of subjects represented by a second profile may be stored by the computer system in a second data structure.

The compliance data 1512 may include information indicating the compliance of different categories of subjects with respect to the elements of the monitoring programs. For example, the computer system 210 may use the program data 1506 and/or the outgoing data 1508 to determine that (i) a message including a survey was sent to subjects in a first category of subjects during a particular monitoring, and (ii) that the message required a response from each of the subject within 24 hours. The computer system 210 may determine the percentage of the first category subjects that were compliant based on the number of compliant responses to the survey message that the computer system 210 received, and may store this percentage in the compliance data 1512 and associate it with the particular message and a first profile that represents the first category of subjects.

The compliance data 1512 may additionally or alternatively include information indicating the compliance for each subject with respect to the elements of the monitoring programs. For example, the computer system 210 may use the program data 1506 and/or the outgoing data 1508 to determine that (i) a message including a survey was sent to a subject in a first category of subjects during a particular monitoring, and (ii) that the message required a response from the subject within 24 hours. The computer system 210 may determine that the subject was not compliant with respect to this particular message if they did not send a response within 24 hours. The computer system 210 may store an indication that the subject was not compliant with respect to this message in the compliance data 1512. The computer system 210 may also associate this indication with the corresponding message and/or the profile that represents the first category of subjects.

The compliance data 1512 may also include information indicating whether subjects or particular categories of subjects were compliant with data quality requirements. For example, the program data 1506 may provide criteria for determining if received data is of sufficient data quality as required for the monitoring program. The computer system 210 may use the criteria to determine if data received from the devices 1502 is of sufficient data quality. For example, based on the program data 1506, the computer system 210 may that the heart rate monitor of one or more of the devices 1502 is observed to not produce results with sufficient accuracy. As such, the computer system 210 may update the monitoring program such that a notification is sent to those devices that includes instructions to use an external heart rate monitor along with updated software that is configured to collect heart rate data from the external heart rate monitor instead of the onboard heart rate monitor of the one or more devices.

In some implementations, once the monitored information is collected, the computer system 210 assigns different portions of the monitored information to different categories of subjects where each category is represented by a particular profile. The computer system 210 may assign different portions of the monitored information by comparing member parameters in the profiles to subject attributes profiles based on comparing attributes of the users to profile member parameters. That is, for each user, the computer system 210 may determine what profile the user is associated with using known attributes of the user and inclusion criteria for the profiles, and proceed to assign the information collected from the user to at least one particular profile of the profiles 804 shown in FIG. 14. The computer system 210 may use the collective information assigned to the profile to identify behaviors that exist among the associated users. For example, the behaviors may indicate a preference for a particular communication channel, communication time, communication frequency, communication formality, etc.

In some implementations, once the monitored information is collected, the computer system 210 provides a portion of the monitored data to the clustering model 908 to determine clusters of subjects. That is, the computer system 210 may use the clustering model 908 to determine the categories of subjects and generate the corresponding profiles as described in more detail above with respect to FIG. 9A-9B. For example, the computer system 210 may provide the clustering module 908 the user data 1504 that includes various user attributes. The clustering model 908 may perform clustering using these different key attributes use these user key attributes to perform the clustering, at least in part, using these attributes. The output of the clustering model 908 may be used to generate a set of profiles 1514 that each include a set of member subjects. As will be discussed in more detail below, the computer system 210 may use the profiles and the indications of their member subjects to determine that the portions of the monitored information, e.g., the portions of the user data 1504, the program data 1506, the collected data 1510, and the compliance data 1512, that correspond to each of the profiles.

In some implementations, the clustering model 908 is a supervised clustering model that is trained using a training set of data. The training set of data may include, for example, a set of user attributes as a training input and a set of expected user groupings as a training output.

In some implementations, the clustering model 908 is not trained. For example, the clustering model 908 may be an unsupervised k-means clustering algorithm In tracking the monitored information, the computer system 210 can store monitored information that the computer system 210 collects in the database 210. The computer system 210 may store the monitored information as it is obtained and/or generated. For example, the computer system 210 may track the attributes of an event message that it distributes to a subset of monitored subjects, record the corresponding responses from those monitored subjects (e.g., if responses are received), and store the attributes and corresponding responses together in the database 212. The computer system 210 may store the monitored information such that it is organized by subject, monitoring program and/or monitoring program session (e.g., portion of or instance of a program, or a sub-study or continuation with a focused sub-group of participants), and/or by category of subject. For example, in sending a blood pressure reminder to a subset of monitored subjects corresponding to a first profile, the computer system 210 may store, in a table or other data structure (e.g., data cube), the attributes of the event message corresponding to the blood pressure reminder (e.g., communication channel, transmission time, message content, indication of message received, indication of transmission error, indication of message type, indication of response type, etc.), data received from the subjects in response to the blood pressure reminder or derived from the received data (e.g., response times, response content, sensor data, test results, etc.), and subject identification data (e.g., subject ID, subject name, subject model, etc.). Other information that may be stored in the table or other data structure may include an indication of the monitoring program or monitoring program session from which the monitored information was obtained, and/or an indication of which categories of subjects the monitored information corresponds to. An indication of a category of subjects can include an indication of a particular cluster of subjects, or an indication of a profile that represents a group of subjects.

Instead of including an indication of the monitoring program or monitoring program session in the table or other data structure, the computer system 112 may generate separate tables—or other data structures—for each monitoring program and/or monitoring program session. The computer system 112 may update these tables over time as new information for the monitoring program and/or monitoring program session is obtained. For example, the computer system 210 may generate a table using tracked information obtained over the duration of a particular research study. The table may include a portion of the outgoing data 1508, the collected data 1510, and/or compliance data 1512 tracked over the duration of the research study.

The computer system 112 may use the monitored information to generate tables—or other data structures—for each category of subjects. For example, the computer system 210 may generate a table 1522 that includes monitored information for all subjects in a first category of subjects represented by a "Profile A." The table 1522 may include a portion of the monitored information tracked, for example, across all past and ongoing monitoring programs for the particular category of subjects. For example, the computer system 210 may generate the table 1522 from the user data 1504, the program data 1506, the collected data 1510, and the compliance data 1512. Specifically, the computer system 210 may generate the table 1522 by extracting a portion of the monitored information that corresponds to the category of subjects represented by a first profile (e.g., Profile A).

As an example, the table 1522 may include rows that each correspond to a particular event message, and columns that correspond to different types of user data 1504, program data 1506, collected data 1510, and/or compliance data 1512. In more detail, for each event message sent by the computer system 210 to a Profile A device of the subject devices 1502, the computer system 210 may update the table 1522 to include a time that the message was sent (e.g., obtained from the outgoing data 1508), a communication channel used to transmit the message (e.g., obtained from the outgoing data 1508), an indication of whether a subject response was required and/or the type of response required (e.g., obtained from the outgoing data 1508 and/or the program data 1506), an indication of the recipient subject (e.g., user) for the message (e.g., obtained from the outgoing data 1508 and/or the user data 1504), an indication of whether a response to the message was received (e.g., obtained from the collected data 1510), an indication of whether the response was compliant with the monitoring program elements (e.g., obtained from the compliance data 1512), etc. The table 1522 may include other information, such as indication of the monitoring program that the computer system 210 was managing (e.g., obtained from the program data 1506). Similarly, the table 1522 may include an indication of the particular monitoring program, such as a name for the monitoring program (e.g., Research Study A) or an ID for the monitoring program (e.g., obtained from the program data 1506).

The computer system 210 may generate the table 1522 in preparation of an analysis 1520 of a portion of the monitored information corresponding to the particular category of subjects (e.g., represented by Profile A). The analysis 1520 may be an analysis to determine the impact of various communication attributes or other elements on subject outcomes, such as subject compliance and data quality, and/or on subject behaviors.

In performing the analysis 1520, the computer system 210 may use one or more algorithms to analyze the table 1522. The algorithms may include static algorithms and/or machine learning algorithms.

As an example, the computer system 210 may use one or more static algorithms to determine, from the table 1522, that first profile subjects are 65% more likely to respond to SMS text message than email based on the percentage of responses received when a message was sent by the text message and the percentage of responses received when a message was sent by email.

The computer system 210 may alternatively or additionally use one or more machine learning models to determine that first profile subjects are 42% more likely to respond to SMS text message than voice call. As an example, the statistics may indicate that first profile subjects are only 35% more likely to respond to SMS text message than voice call. However, the machine learning model may, for example, apply various weights to the data and/or choose to ignore portions of the data in the table 1522 to determine the 42% value. For example, the machine learning model may weigh more recently monitored data more heavily than older data, may ignore data that older than a threshold date, and/or take into account various trends data among the first profile subjects or among subjects in general.

The results 1524 of the analysis generated by the computer system 210 may indicate the determined impacts of different communication attributes on subject outcomes and behavior.

After obtaining the results 1524, the computer system 210 may use the results 1524 to update a profile 1530 that represents the first category of subjects (1526). For example, the computer system 210 may store the results 1524 in the profile 1530. Additionally or alternatively, the computer system 210 may convert the results 1524 to impact scores and/or use the results 1524 to update previously determined impact scores. For example, the computer system 210 may convert percentages in the determined results 1524 to impact scores that indicate the extent of the impact of one or more communication attributes or other monitoring program elements on the subject behaviors and outcomes. In more detail, the computer system 210 may convert the percentages related to SMS text message to an impact score of +5 on compliance (e.g., based on the higher likelihood of the first profile subjects responding to SMS text when compared to other types of communication) and +3 on data quality (e.g., based on the increased quantity of data acquired as a result of first profile subjects responding more often).

The computer system 210 may repeat the described techniques multiple times. For example, the computer system 210 may repeat the analysis 1520 for each category of subjects to update additional corresponding profiles.

Figure 16:
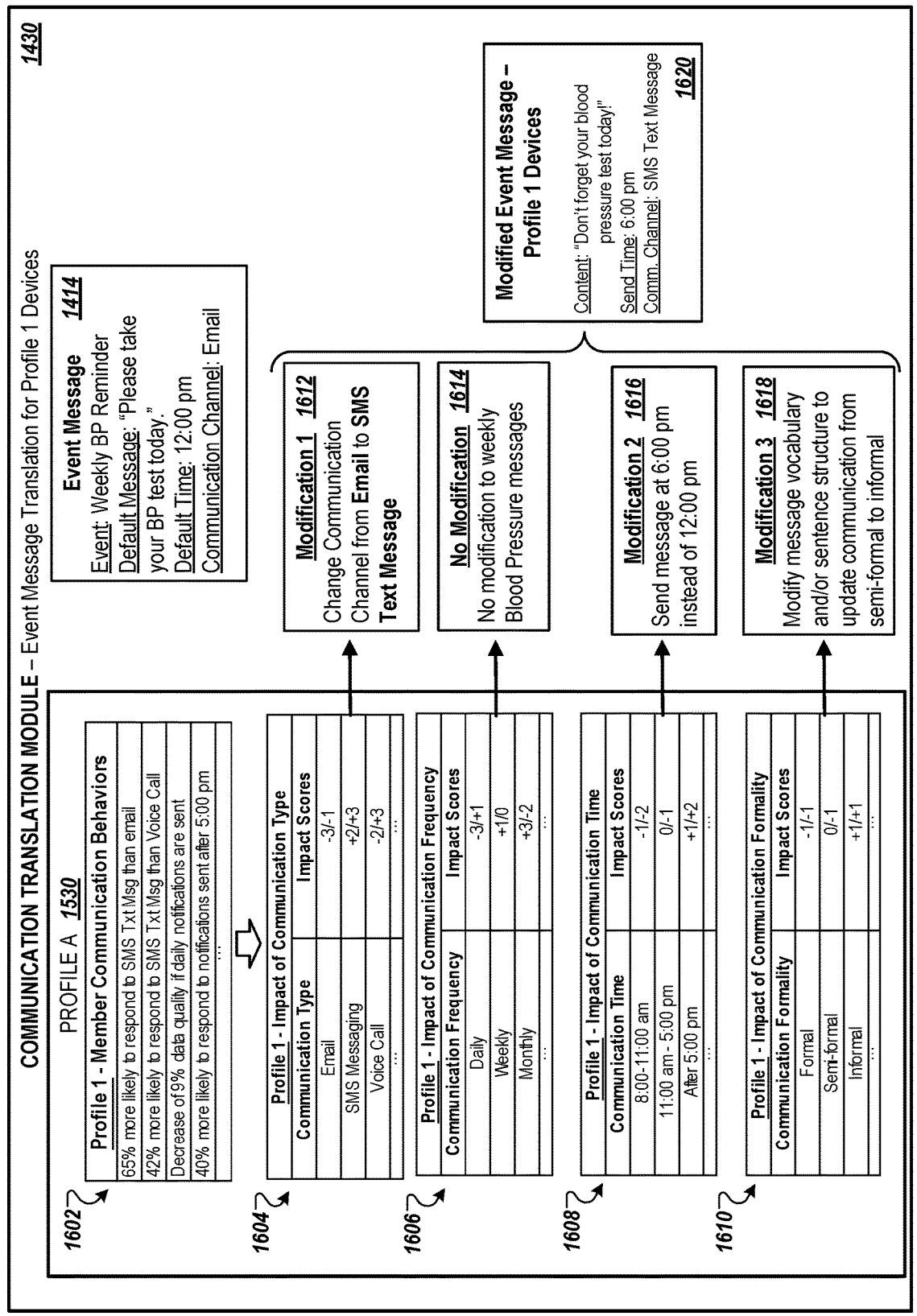
FIG. 16 is a diagram that illustrates an example module for customizing communications for categories of participants.

FIG. 16 is a diagram that illustrates one or more components of the system 200 for customizing communications for categories of participants. For example, the computer system 210 can customize communications for categories of participants using one or more profiles.

In more detail, the computer system 210 may for a particular group of subjects being monitored identify the categories of subjects present among the group of subjects. For example, the computer system 210 can compare attributes of the subjects in the group of subjects to inclusion criteria for different profiles. After identifying a set of profiles associated with the subjects in the group, the computer system 210 can extract impact information from the profiles that indicates the impact of various monitoring program elements on the outcomes and/or on the behaviors of categories of subjects. The computer system 210 can use this impact information to adjust how it interacts with different subgroups of subjects in the group. For example, the computer system 210 may modify messages for the different subgroups, may modify a time that messages are sent to the different subgroups, may modify the frequency that messages are sent to the different subgroups, may modify how a message is to be communicated or displayed to the different subgroups, may modify a vocabulary for the content of messages sent to the different subgroups, and/or may modify a sentence structure for the content of messages sent to the different subgroups.

As illustrated in FIG. 16, the profile 1530 may include information that indicates various anticipated impacts of communication attributes or other monitoring program elements on the outcomes and behaviors of subjects. The computer system 210 can use this information to customize communications for different categories of subjects to account for particular behaviors typically demonstrated by subjects in those categories. Similarly, the computer system 210 can use this information to improve participant outcomes by, for example, increasing the likelihood of sufficient participant compliance and/or increasing the likelihood of obtaining sufficient data quality. By improving the participant compliance and quality of the subject data obtained, the computer system 210 can significantly improve the likelihood that certain monitoring program objectives are met, such as obtaining viable results by the end of the monitoring program.

As shown, the profile 1530 may include various tables 1602, 1604, 1606, 1608, and 1610 that indicate the anticipated behaviors and communication attribute impacts for a particular category of subjects. The computer system 210, specifically the communication translation module 1640 may extract all or a portion of the information included in the tables 1602, 1604, 1606, 1608, and 1610 from the profile 1530 to generate or customize the event message 1414 for the profile 1530 subjects. For example, the communication translation module 1440 may extract the impact information in tables 1604, 1606, 1608, and 1610 in response to receiving the event message 1414 or in response to retrieving the event message 1414 from a queue of messages. As shown, the impact information tables 1604, 1606, 1608, and 1610 may each include impact information for different types of communication attributes. The impact information may include, for example, a communication attribute or communication attribute value, and corresponding impact scores. The impact scores may include, for example, an impact score for subject compliance (e.g., compliance with respect to messages, such as response requirements, test submissions, etc.) shown first next to an impact score for data quality.

As an example, a positive impact score may indicate that the computer system 210 anticipates that compliance or data quality will be improved (e.g., by a particular percentage, certain percentage range, more than a threshold percent, etc.) compared to the average corresponding compliance or data quality for the subjects in a category of subjects represented by the profile 1530. Similarly, a negative impact score may indicate that the computer system 210 anticipates that compliance or data quality will lower compared to the average corresponding compliance or data quality for subjects in a category of subjects represented by the profile 1530.

Although, the profile 1530 includes the impact of a variety of communication attributes, the profile 1530 is not limited to the communication attributes shown. That is, the profile 1530 may include impact determinations for various other communication attributes or other elements that may affect interactions between the computer system 210 and the subjects. For example, the profile 1530 may include a data structure that indicates the impact of changing the configuration of the remote devices such that sensor data is obtained and transmitted to the computer system 210 without user confirmation. If the user agrees to the configuration change, this may increase user compliance as required data can be more easily and/or consistently obtained. Similarly, this may lead to an improvement to data quality due to an increase in the quantity of data and/or to improved consistency by, for example, being able to acquire data at substantially a set time (e.g., a daily time to measure heart rate). Other configuration changes may include that changing the configuration of profile 1530 devices to change a schedule for obtaining sensor data, change a sensor used to collect sensor data, change a notification type or notification setting of the device (e.g., increase sound, turn off silence, turn on banner notification, etc.), increase the frequency or number of event reminders, decrease the frequency or number of event reminders, etc.

In customizing the event message 1414, the communication translation module 1640 may compare the default communication attributes of the event message 1414 to the extracted information to determine if the communication attributes are ideal, acceptable, or require modification. As an example, the communication translation module 1440 may refrain from changing an attribute of an event message (e.g., to reduce CPU load, account for high network traffic, account for a large number of jobs, etc.) if the corresponding impact information indicates that the default attribute (e.g., attribute value) is anticipate to have a positive impact on compliance and/or data quality. This may be the case even if the communication translation module 1440 recognizes that another attribute would have a larger positive impact. Similarly, the communication translation module 1440 may deem a default attribute as acceptable if the anticipated impact is negative, but (i) the anticipated negative impact is negligible when compared to the anticipated impact from one or more other attributes, (ii) the anticipated negative impact has a lesser magnitude than the negative impact of one or more other attributes, and/or (iii) the monitored information for the monitored subjects corresponding to the first profile 1530 demonstrates sufficient compliance and/or data quality such that the anticipated negative impact will not risk the adequacy of the subject compliance and/or data quality.

The communication translation module 1440 may choose to update the communication attributes of the event message 1414 for the profile 1530 subjects to reflect the ideal communication attributes. For example, for each communication attribute of the event message 1414, the communication translation module 1440 may use the impact information in one of the tables 1604, 1606, 1608, or 1610 to identify the communication attribute that has the largest positive impact scores (e.g., average of compliance impact score and data quality impact score, weighted average of compliance impact score and data quality impact score, etc.) and, if the identified communication attribute differs from the default (e.g., incoming attribute) of the event message 1414.

Similarly, the communication translation module 1440 may make determinations as to which impact score is more relevant to the category of subjects and/or the participants in the current monitoring group that are in the category of subjects. For example, in tracking monitored information for the monitoring group 1402 during the current monitoring program, the computer system 210 may recognize that although the Profile 1 participants with the devices 1404 are providing data of sufficient quality, the Profile 1 participants have low compliance with the elements of the monitoring program (e.g., as a result of poor response time, low response frequency, missed tests, missed exercises, etc.). Based on this determination, the computer system 210, specifically the communication translation module 1440 of the computer system 210, may weigh the compliance impact scores in the extracted data more heavily than the data quality impact scores. For example, between a communication attribute that is anticipated to boost compliance by 6% and data quality by 8% and a second communication attribute that is anticipated to boost compliance by 8% and data quality by 6%, the communication translation module 1440 would select the second communication attribute to account for the observed low compliance of subjects of the monitoring group 1402 corresponding to the profile 1530.

As illustrated in FIG. 16 are a number of example determinations 1612, 1614, 1616, and 1618. These determinations may correspond to determinations made by the communication translation module 1440 to modify or not modify a particular communication attribute of the event message 1414. For example, the communication translation module 1440 may make the determination 1612 to change the communication channel from email to SMS text message based on the impact scores in the table 1604 showing that the profile 1530 subjects demonstrate better compliance and data quality with SMS text message than other forms of communication. As another example, the communication translation module 1440 may make the determination 1614 not to modify the communication frequency based on the impact scores in the table 1606 indicating that the default frequency of the event message 1414 was ideal for the profile 1530 subjects. As another example, the communication translation module 1440 may make the determination 1616 to modify the communication time based on the impact scores in the table 1608 indicating that the ideal time for getting a response from the profile 1530 subjects is after 5:00 pm. As another example, the communication translation module 1440 may make the determination 1618 to modify the communication vocabulary and sentence structure based on the impact scores in the table 1610 indicating that better compliance and data quality is obtained by communicating with the profile 1530 subjects in an informal manner.

Although many examples described herein discuss the possibility for modifying or updating the communication attributes for an event message, the communication translation module 1440 may use extracted information in other ways to improve interactions between the computer system 210 and a set of participant subjects in a monitoring group. These improvements to interactions may include the removal or addition of particular communication attributes to event messages. The communication translation module 1440 or another module of the computer system 210 can also change the configuration of software that the computer system 210 previously distributed to participants in the monitoring group 1402. For example, the communication translation module 1440 may update and redistribute reconfigured software for the first profile devices 1404. The reconfigured software may provide for changing characteristics of how incoming messages are presented to users of the first profile devices 1404, such as a modification to the type of notification, to whether a sound accompanies the notification when it is received (or persists until it is acknowledge), to the type of sounds accompanying the notification, to how the notification is presented in an application running on the first profile devices 1404, etc.

Other configuration changes that the computer system 210 may update to improve interactions, such as communications, between the itself and remote devices of a monitoring group may include changes to which sensor(s) are used to collect data, whether data is to be collected using a third-party device with respect to the first profile devices 1404, the frequency of data collection, whether the users of the first profile devices 1404 must approve the transmission of data or a change to the frequency that users of the first profile devices 1404 must approve transmission of data, a change to the time or time span of data collection, etc.

As a result of modifying the event message 1414 for the profile 1530 subjects, the communication translation module 1440 creates a modified event message 1620. The modified event message 1620 represents a customized event message specifically tailored by the communication translation module 1440 for the profile 1530 subjects present in the current monitoring group 1402. After generating the modified event message 1620, the computer system 210 may transmit the message 1620 to the first profile devices 1404 in place of the event message 1414. At any one point, the communication translation module 1440 may be in the process of generating tens, hundreds, or even thousands of customized event messages for various categories of subjects across multiple ongoing monitoring programs that the computer system 210 is managing. Accordingly, in addition to tracking and analyzing the monitored information discussed above, the computer system 210 is continually analyzing and modifying event messages and other interactions between itself and active remote devices to improve the likelihoods of meeting the objectives of these multiple ongoing monitoring programs that may each have tens, hundreds, or even thousands of subjects enrolled.

As discussed above, the computer system 210 can generate the profiles 804 that represent different categories of users based on the observed behaviors of the users. For example, the computer system 210 may generate a profile of the profiles 804 that represents a first category of users who tend to communicate primarily through SMS text message or prefer to communicate through SMS text message. Accordingly, a known behavior associated with this profile is that this category of users tends to respond more positively to messages sent by SMS text message. When the computer system determines that there exists a group of devices among the monitored devices that are associated with this profile, the computer system may update the communication channel to SMS text message for a single, multiple, or all event messages that are to be sent to the monitored devices.

The computer system 210 and/or the communication translation module 1440 may make various other adjustments to interactions between the computer system 210 and various subjects in the monitoring group 1402. For example, the communication translation module 1440 may use information in the profile 1530 to determine that a message should be sent as an automated voice call or as an audio recording (e.g., sent by email, made accessible through an app running on a set of devices, etc.) instead of as a in-app notification or SMS text message. As another example, the communication translation module 1440 may adjust how the content of a message is to be displayed on a group of devices. In more detail, the communication translation module 1440 may send the event message 1414 with instructions for first profile devices 1404 to display the message with a certain font size, with a certain font color, with an audible alert, in an application for the monitoring program, as a banner notification, etc.

Figure 17:
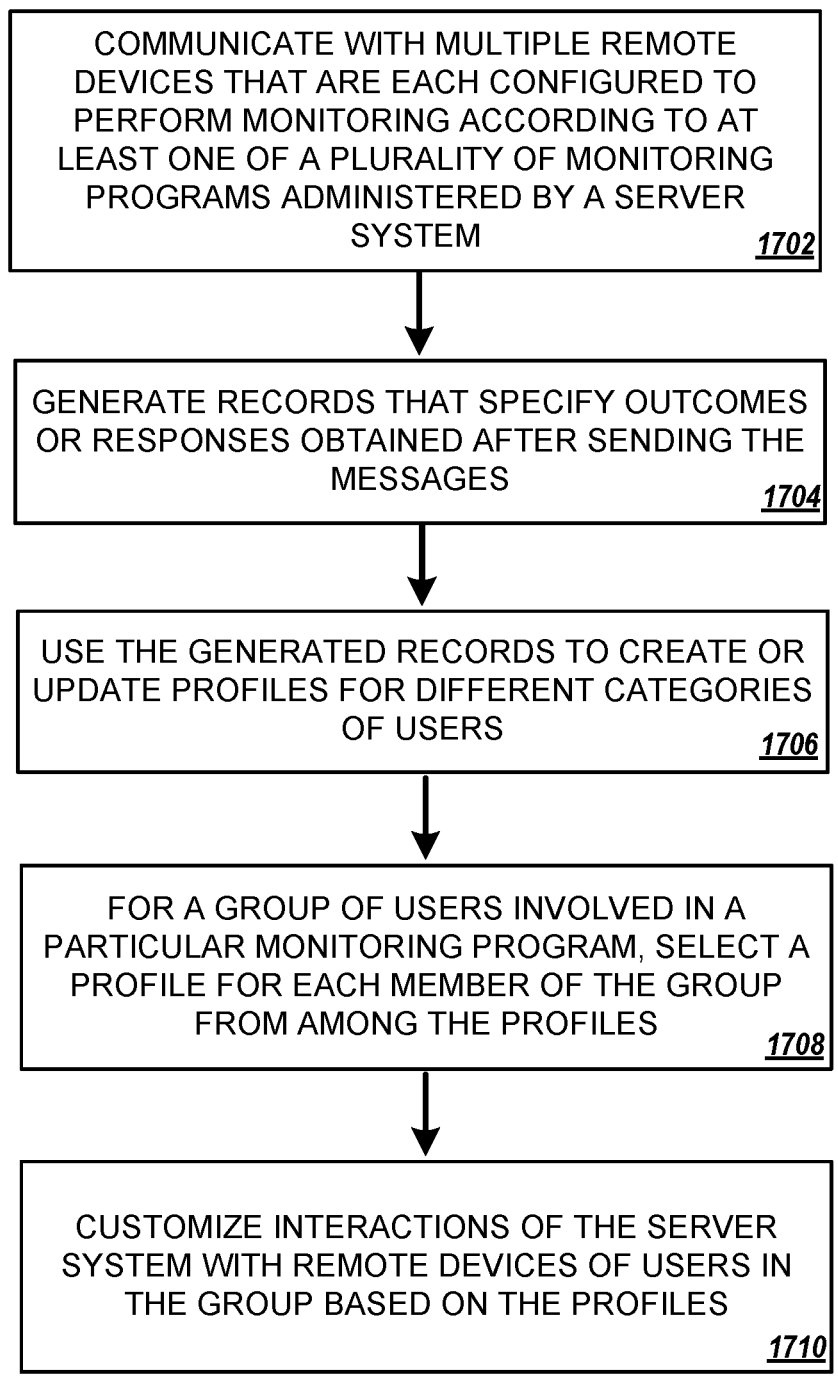
FIG. 17 is a flowchart diagram that illustrates an example process for customizing communications for categories of participants.

In adjusting interactions between the computer system 210 and various subjects in the monitoring group 1402, the computer system 210 and/or the communication translation module 1440 may adjust software running on the different devices in the monitoring group 1402. For example, the computer system 210 may, based on information extract from the profile 1530, send instructions to the first profile devices 1404 to change the sensor that is used to collect particular sensor data, adjust the frequency of sensor collection, adjust a user interface (e.g., layout, font size, theme, etc.) for an application for the monitoring program running on the devices, adjust the type or volume of audible notification alerts, or modify other configuration parameters of the software. Similarly, as another example, the computer system 210 may, based on information extract from the profile 1530, send replacement software to the first profile FIG. 17 is a flowchart diagram that illustrates an example process 1700 for customizing communications for categories of participants. The process 1700 may be performed by one or more computers, such as the computer system 210 shown in various figures including FIG. 14. The operations of the process 1700 may be distributed among one or more servers, one or more client devices, and/or other computing systems. For example, the operations of the process 1700 may be performed by a management and distribution system, such as the computer system 210 that includes one or more servers, one or more client devices, and/or other computing systems.

In the course of managing monitoring programs, the computer system 210 can adapt communications to members of monitoring groups for individuals with different backgrounds. As discussed above, it is often very important for monitoring groups, such as clinical trial cohorts, to include diverse groups of people. In a clinical trial for the safety or efficacy of a pharmaceutical, for example, the clinical trial cohort needs to have sufficiently diverse representation. If the trial indicates successful results for medication, then the cohort used to generate those results would need to have a sufficiently broad base (e.g., at least a minimum level of representation of key attributes or categories of participants) for the results to be extended to all needed groups of people. Diversity can be needed over many different dimensions, e.g., across race, age, sex, location, health status, personal health history, family health history, genetic profile, and more. Each monitoring group can therefore include many sub-groups of individuals, with each sub-group responding differently to different types of messages and other interactions.

The system 210 can use profiles that describe the nature of different categories of participants, whether those profiles correspond specifically to the types of groups needed for diversity in the monitoring program or not (e.g., the profiles may be more fine-grained, and may address combinations of attributes beyond those specifically needed for diversity in the monitoring group). The profiles can include values that indicate the different ways that different messages or interactions affect people in the different categories represented by the profiles. This can take the form of scores or values in a profile indicating the relative effects that different communication or interaction attributes, when present, have on individuals that are in the category corresponding to the profile. These profiles can thus indicate to the system 210 how to tailor communications and interactions to have the best effect for different groups (e.g., the highest likelihood of achieving the result(s) of retention, compliance, high data quality, etc.). The profiles can be used to both selecting content to provide (e.g., which text, images, videos, surveys, etc.) and the manner of presenting the content (e.g., the formatting, layout, color scheme, size, communication channel, etc.).

The system 210 can use the profiles to automatically suggest individual interactions or interaction campaigns (e.g., a series of interactions over time) that indicate, for example, which participants to contact, the manner of contact to initiate, the types of content or specific content to include, formatting and layout of the content, and so on. The information in the profiles enables the system 210 to select interactions that are tailored to the elements and styles that have been observed, through tracking of prior interactions, to promote the desired outcomes (e.g., enrollment in a monitoring program, compliance with monitoring program requirements, high data quality, retention of participants in the programs, etc.). Naturally, as different categories of people have different preferences and capabilities, the profiles will generally indicate that the message attributes that result in high likelihood of desired outcomes are different for different categories. Many different message and interaction characteristics can be adapted. As just a few, the system 210 can adjust tone in messaging (e.g., formal vs. informal), style of content (e.g., photos vs. drawings), reading level or language complexity, etc. The system 210 can personalize the tone of messages to improve success with different groups.

The adaptive communication techniques and the profiles enable the system 210 to recommend and/or even automatically carry out the adaptation of messages based on the cohort composition at any point in time. In some cases, messages are customized for the different categories of participants, so that even within a single cohort of a single monitoring program, a reminder message to one sub-group in the cohort is different than the corresponding reminder message to another sub-group in the cohort. Different messages or interactions is not required, however. For example, the system 210 may use the composition of the cohort to optimize the content of the message across all categories, weighting the values from the different profiles according to their representation in the cohort and generating a single message (e.g., as a composite or a best compromise) having the best overall likelihood of successful outcomes for the cohort as a whole.

The information in the profiles can be used not only to generate and send adaptive communications. It can also be used to analyze the effectiveness or predicted effectiveness of planned messaging. The system 210 can use tracked data about recruitment results, compliance results and retention results (both within an individual study as well as from a general pool of studies) to make the predictions about probability of success of messages having certain characteristics, e.g., a particular mode of delivery, a particular message type, types of imagery used, etc.

The techniques for adapting communication can be used at any phase in the development and carrying out of a monitoring program, e.g., a research study, such as a clinical trial). For example, the adaptive techniques can be used for recruitment of candidates to a monitoring program, to increase a level of conversion from invited candidates to enrolled participants. The techniques can be used at the enrollment phase, to select interactions that will more quickly lead to completion of enrollment requirements and will lead to a higher rate of completing enrollment requirements (e.g., needed consent including electronic consent, entry of participant health data, completion of enrollment forms or surveys, etc.). Once a monitoring program is ongoing, the same techniques can be used to adapt communications to participants in different ways to increase the likelihood of retention of the participants in the study, to increase the likelihood of compliance with program requirements, to maximize data quality, etc. In general, the techniques can be used to adapt communications and interactions, whether initiated by users' devices (e.g., through an application or software module for the monitoring program) or by a server system, at each of the phases discussed above for FIG. 2 (e.g., 232, 234, 236, 238, 240, 242).

The process 1700 includes communicating with multiple remote devices that are each configured to perform monitoring according to at least one of a plurality of monitoring programs administered by a server system (1702). For example, with respect to FIG. 15, the computer system 210 can manage a plurality of monitoring programs for the devices 1502. Each monitoring program may have a set of elements that, for example, define various requirements for the monitoring program. The requirements can include actions that the participants need to perform, which can include data collection actions (e.g., complete a survey, take a physiological measurement, have a blood test, etc.) and may also include other actions (e.g., exercise 30 minutes a day, take a medication twice a day, etc.). The requirements of a study may include, for example, minimum data accuracy, minimum data quantity, required data types (e.g., for particular events), data collection frequency requirements, etc. As an example, a monitoring program may be for a particular study (e.g., a medical study) that has a set of protocols and compliance standards. The protocols may indicate that the blood glucose data needs to be collected. The compliance standards may indicate that the data needs to be collected three times a day from cohort participants of the study for those participants to be compliant (e.g., collected in a manner that the collected data can be used in the study).

In managing the plurality of monitoring programs, the computer system 210 can select who participates in the monitoring program and which devices to communicate with. For example, the computer system 210 can select the cohort for a new study. The computer system 210 can make this determination based on instructions received from an external computing device, such as instructions received from the client device 204 of the researcher 202.

In managing the plurality of monitoring programs, the computer system 210 can determine and distribute software to each of the devices 1502 for the corresponding monitoring program that they are part of. The software distributed may be particular to the categories of subjects. For example, the computer system 210 may distribute different software or different versions of the same software to each of the first profile devices 1404, the second profile devices 1406, and the third profile devices 1408 of the monitoring group 1402. The distributed software can specify various communication attributes (e.g., default message attributes), such as a communication channel to use transferring messages, a type of messages (e.g., request or notification), different request types (e.g., requests for different sensor data, for different responses from a user, etc.), a type of notification (e.g., reminder, instructions for user to perform action immediately, etc.), a communication schedule, etc. The distributed software may specify one or more of these communication attributes through different APIs or different API configurations. For example, each software version distributed may use its own set of API calls and requests, or a different combination of permissible API calls and requests. The distributed software may specify various configuration data. For example, the distributed software may specify hardware settings, software settings, Bluetooth profiles, etc.

The distributed software may allow the computer system 210 to modify one or more of the communication attributes (e.g., message attributes). The communication attributes may include, for example, a message sent time, a required response time, a message frequency, a message type, content vocabulary, content sentence structure, etc. Similarly, the computer system 210 can modify one or more of the communication attributes through software updates or by distributing replacement software to the remote devices. For example, the computer system 210 may send instructions containing updated configuration data to a set of monitored devices. In response to receiving these instructions, the monitored devices can update the configuration settings of the monitoring program related software on these devices to reflect the updated configuration data.

In managing the plurality of monitoring programs, the computer system 210 can collect and process data received from the monitored devices. For example, the computer system 210 may record the time that a response was received, the data size of the response, the extracted content of the response, etc. The computer system 210 may proceed to use this information and, for example, information of the originally sent message to determine if the particular subject is compliant with the requirements of the monitoring program. For example, the monitoring program may require for a particular message that a test result be submitted within 24 hours of the message being sent. If a response from a subject that received the message is not received within the 24 hours, the computer system 210 may determine that the subject was not compliant. If a response is eventually received, the computer system 210 may still record this information and analyze the submission against other requirements for the monitoring program.

In managing the plurality of monitoring programs, the computer system 210 can affirmatively initiate display of information and interaction on the remote, monitored devices. For example, the computer system 210 can generate and send a message (e.g., a set of instructions) to trigger sensor measurement on the recipient devices, cause a survey to be provided and displayed on a user interface of the recipient devices, cause a message to be provided and displayed on a user interface of the recipient device with an audible alert, etc.

Accordingly, in managing the plurality of monitoring programs, the computer system 210 can track various remote devices, distribute software to the remote devices, collect data from the remote devices, and perform compliance monitoring using the collected data to ultimately ensure that the standards for monitoring programs are met across the entire group of remote devices.

Multiple monitoring programs may be conducted concurrently, all administered and managed (e.g., each with their separate objectives, requirements, study protocols, cohorts, and corresponding software and data collection schemes). The multiple monitoring programs can include multiple different monitoring programs and/or different versions of monitoring programs (e.g., including sub-studies that include variations or extensions of an original study, involving a subset of the participants of the original study). The multiple monitoring program can include varying elements, such as different requirements. Similarly, the multiple monitoring program versions, e.g., for different categories of subjects in a particular monitoring program, can also include varying elements, such as different requirements. That is, there may be multiple versions of a monitoring program being managed by the computer system 210 in a monitoring program. Accordingly, in communicating with the remote devices, the computer system 210 may be required to, for example, communicate differently (e.g., communicate in accordance with different sets of communication attributes) with different groups of devices that correspond to different monitoring groups as well as communicate differently with different subgroups of devices that correspond to multiple categories of subjects in those groups of devices.

Communicating can include sending messages with different message attributes to remote devices over a communication network. In sending a message, the computer system 210 may send a message over particular communication channels, such as email, SMS text message, Bluetooth, voice call, etc. Sending messages may additionally or alternatively include the computer system 210 establishing a client-server model between the remote devices and the computer system 210. After this is established, the computer system 210 can communicate with the various remote devices using a request-response messaging pattern. As another example, sending messages can include the computer system 210 sending instructions to the remote devices to trigger sensor data collection. For example, the computer system 210 may send instructions to a particular set of monitored devices to collect sensor data using one or more on-board sensors, or using sensors of device connected to or in communication with the monitored devices.

As an example, the computer system 210 may customize an event message for a first set of remote devices that are or correspond to a first category of subjects, and proceed to customize the event message differently for a second set of remote devices that are or correspond to a second category of subjects. In customizing the event message, the computer system 210 may select a first set of communication attributes to use for the first set of remote devices and a second set of communication attributes to use for the second set of remote devices. After customizing the event message for each of the device groups, the computer system 210 may transmit the customized messages in accordance with their respective communication attributes. The communication attributes may specify, for example, a communication channel, a time to send the message, an indication of whether the message is a request or notification, an indication of the data being requested (e.g., sensor data, test results, survey data, etc.), the content of the message, the vocabulary used in the content of the message, the sentence structure used in the content of the message, a requested response time, etc.

The computer system 210 may send messages to the remote devices as reminders for upcoming events, to request user input or feedback (e.g., to complete a survey, provide feedback on the monitoring program, etc.), to request sensor data (e.g., from one or more sensors of the remote devices), etc. As will be discussed in more detail below, the computer system may use the information corresponding to these sent messages and the data received in response to these messages to generate records corresponding to the remote devices (e.g., subject records).

The communication network may include public and/or private networks. As an example, the communication network may include the internet or a cellular network.

The process 1700 includes generating records that specify outcomes or responses obtained after sending the messages (1704). For example, the computer system 210 may generate records using responses obtained from the remote devices. The responses may include sensor data obtained using the remote devices or external devices in communication with the remote devices (e.g., connected to the remote devices through a wired connection, Bluetooth connection, etc.), user responses (e.g., feedback, survey answers, test answers, etc.), and characteristics for the responses. The characteristics for the responses may include sent/transmission times (e.g., time that the responses were sent from the remote devices), received times (e.g., times that the responses were received at the computer system 210), data creation times (e.g., time that sensor data was obtained, time that user feedback or survey answers were created by the users of the remote devices, etc.), and/or indications of the response data sizes. The computer system 210 may use the response information to generate records for the various monitored subjects. The computer system 210 may proceed to store the generated records in the database 212.

After sending messages, the computer system 210 can check to confirm that the requested data was received at later data. Messages may, for example, include an indication of a deadline that the computer system 210 uses to determine when to check to see if the data was received at a later date and/or if subjects are compliant. For example, a message may not require a contemporaneous response but may indicate that a user must submit a heart rate test by 12:00 pm tomorrow. At 12:00 pm the next day, the computer system 210 may check to determine if the required data was ever received. If the data was received, the computer system 210 may determine that the user was compliant and may record both the determination of compliance and the corresponding data. If the data was not received, the computer system 210 may determine that the user was not compliance and may record an indication that the user was not compliant.

The computer system 210 may additionally or alternatively use determined outcomes to generate records. The computer system 210 may use the messages that it sends to the remote devices, and the received responses or lack of received responses to determine the outcomes. The outcomes may indicate whether a required response was received. For example, the outcomes may indicate whether requested data was received, whether requested responses were received, whether requested data was received in a specified time frame or by a set time, and/or whether requested responses were received in a specified time frame or by a set time. The outcomes may additionally or alternatively indicate whether the responses were compliant, e.g., with the requirements of the corresponding monitoring program. For example, the outcomes may indicate whether a response was received in a specified time frame or by a set time, whether the correct type of data was received from the remote devices, whether the difference between the request time (e.g., message send time) and response time met one or more thresholds (e.g., if difference is below a threshold, the response may be determined by the computer system 210 to be unacceptable as it can be inferred that the user did not spend the necessary time to read and respond to the message; if difference reaches a threshold, the computer system 210 may determine that the user is unresponsive; etc.), whether the received sensor data met quality metrics (e.g., data was sufficiently accurate, sufficiently consistent with other sensor data readings, obtained from a sensor that has characteristics that meet certain sensor criteria, and/or associated with a date that is sufficiently recent), etc.

The responses may also include other information, such as characteristics of users of the remote devices. For example, the responses may include a user ID or device ID that the computer system 210 can use to identify the user and/or device. The responses may also include other subject attributes, such as demographic and non-demographic information. For example, a response may include an indication that the user of a particular remote device is male, is 6' ft tall, resides in an urban environment, has had two surgeries in the last year, and is allergic to peanuts. Alternatively, the subject attributes may be previously acquired and stored in the database 212 (e.g., acquired during user registration). The computer system 210 may use the user ID or device ID to extract all or a portion of the stored subject attributes as needed for record generation.

The outcomes may include indications of different types of outcomes and corresponding binary values. For example, for an outcome corresponding to whether a response to a message was received, the computer system 210 may assign a value of "1" or "yes" to indicate that a response was received or was received in a threshold period of time, or may assign a value of "0" or "no" to indicate that a response was not received or was not received in a threshold period of time.

The computer system 210 may use these determined outcomes to generate the records. For example, the computer system 210 may generate records where each entry corresponds to a particular message sent by the computer system 210 and includes the determined outcomes for the message. The computer system 210 may also include in these records information that describes the corresponding message and/or information that described the response(s) if any were received. For example, with respect to FIG. 15, the computer system 210 may generate the table 1522 that includes multiple entries each corresponding to a particular event message. The table 1522 may include, for example, outcomes in the form of indications as to whether responses to the messages were received and indications as to whether the responses, if received, were compliant.

The records can indicate the characteristics of messages sent to the remote devices and characteristics of users of the devices that received the messages. For example, the records can include all or a portion of the communication attributes (e.g., message attributes) the computer system 210 used to communicate with the remote devices. As shown with respect to FIG. 15, the computer system 210 may use a portion of the communication attributes to generate the table 1522. Specifically, the computer system 210 may extract from the communication attributes the message sent times, the communication channel, the indication whether a response is required, and/or the response type. The characteristics of messages may also include other information such as an address that a message was sent to, an indication whether a message was successfully delivered, an indication of any errors that occurred with message transmission, a message size (e.g., data size, word count, etc.), etc.

As discussed above, the records may also indicate the characteristics of the users of the remote devices. The user characteristics may include, for example, physiological characteristics (e.g., resting heart rate, blood pressure, blood pH, etc.), demographic characteristics (e.g., age, sex, height, etc.), and behavior characteristics (e.g., compliance rate, retention rate, sufficient data quality rate, a user's tendency to prefer certain interactions with the computer system 210 over other interactions, etc.). For example, in generating the table 1522, the computer system 210 may include a name for each recipient user of the messages.

The records may additionally or alternatively indicate characteristics of devices, e.g., where the subjects are devices. The device characteristics may include, for example, a make, a model, a CPU speed, a memory amount, a memory transfer speed, the type of onboard sensors, etc.

The records may be initially organized by user, by event message, by monitoring program, by monitoring program, by researcher (e.g., who initiated or manages the monitoring program), etc. For example, the computer system 210 may generate a data structure, such as a table, for each monitoring program where each entry corresponds to a particular event message that was sent during the monitoring program. The entries in the data structures may be arranged by time (e.g., time sent) and/or by subject (e.g., subject ID).

The computer system 210 may proceed to use the initial data structures to update or generate data structures corresponding to the different categories of subjects. For example, the computer system 210 may access the profiles 804 and extract the inclusion criteria for the different profiles 804. The computer system 210 may use the inclusion criteria to determine what entries of the initial data structures correspond to what categories of subjects. For example, with respect to FIG. 15, the computer system 210 may generate the table 1522 containing entries that correspond to each event message sent to a subset of the remote devices 1502 during a monitoring program. The computer system 210 may proceed to use a user name, user ID, or device ID in the table 1522 to identify a category of subjects that corresponds to each entry. This may include the computer system 210 retrieving from the database 212 a profile of the profiles 804 that is associated with the user name, user ID, or device ID.

However, if, for example, the subject has not been assigned to a category of subjects, the computer system 210 may use the user name, user ID, or device ID to retrieve subject attribute data from the database 212. The computer system 210 may proceed to compare the subject attribute data to the inclusion criteria for the various profiles in the profiles 804 to determine which entries in the table 1522 correspond to which of the profiles 804. The computer system 210 may proceed to generate a new data structure for each category of subjects such that each data structure corresponds to one of the profiles 804.

As another example, the computer system 210 may initially organize the records by category of users. For example, the computer system 210 may generate a data structure for each category of users. The computer system 210 may proceed to update the data structures with new entries as responses are received and analyzed. For example, in response to receiving a response from a remote device, the computer system 210 may determine what category of subjects corresponds to the remote device or what category of subjects does the remote device belong to. Once the category of subjects is determined, the computer system 210 may proceed to update a data structure for the particular category of subjects using information corresponding to the originally sent message, information in the received response, and/or outcomes determined from the other information.

In some implementations, generating records indicating characteristics of the messages sent includes generating records indicating one or more of the following: a time that the messages were sent; a channel of communication that the messages were sent by; content of the messages; an indication of formality associated with the messages; an indication of word choice associated with the messages; an indication of sentence structure associated with the messages; a response time associated with the messages; an indication of compliance associated with the messages; or an indication of data quality associated with the messages. As described in more detail below, the computer system 210 may adjust interactions between itself and the remote devices by adjusting one or more of the characteristics of the messages before sending them, e.g., in order to improve compliance, data quality, or the likelihood of reaching one or more other objectives for the monitoring program.

As an example, the computer system 210 can determine for a particular category of subjects that they demonstrate improved compliance if the message sentence structure is informal. Accordingly, for participants determined to belong to the category of subjects, the communication and translation module 1430 can modify the content of outgoing messages such that they use an informal sentence structure. By doing this, the computer system 210 can improve compliance with respect to those subjects, and, thereby, improve the likelihood of meeting the objectives of the monitoring program. Accordingly, by adjusting the interactions, the computer system 210 can improve the likelihood of reaching monitoring program objectives. This, in turn, reduces the number and/or frequency of messages that need to be sent by reducing the need to extend monitoring programs or the need for repeated monitoring programs, thereby reducing network bandwidth usage while providing a myriad of other computing and processing benefits.

The computer system may also use these message characteristics to generate and/or update profiles. For example, the computer system 210 may cluster the users based on one or more behavioral attributes. The computer system 210 can also or alternatively use the behavioral attributes to generate inclusion criteria for the different categories of subjects. This inclusion criteria may be included in the corresponding profiles.

In some implementations, generating records indicating characteristics of users of the devices that received the messages includes generating records indicating one or more of the following: a demographic attribute of the user; physiological attribute of the user; or a behavioral attribute of the user. The demographic attributes may include, for example, an age of the user, a sex of the user, a race of the user, an ethnicity of the user, an area where the user resides, etc. The physiological attributes may include, for example, a blood pressure for the user, a blood pH for the user, a heart rate for the user, a resting heart rate for the user, a body fat percent for the user, etc. The behavioral attributes may include, for example, compliance rates for the user (e.g., overall compliance rate, compliance rate in a particular monitoring program, compliance rate with respect to a particular task or type of message, etc.), retention rates for the user (e.g., overall retention rate, retention rate with respect to a particular type of monitoring program, retention rate with respect to particular monitoring program elements, etc.), data quality (e.g., overall data quality provided by the user across multiple monitoring programs, data quality provided by the user in a particular monitoring program session or type of monitoring program, data quality provided by the user in monitoring programs having particular elements, etc.), a particular event or behavior associated with the user, etc.

The computer system 210 may use these user characteristics to generate and/or update profiles that represent different categories of subjects. For example, the computer system 210 may cluster the users based on one or more characteristics. The computer system 210 can also or alternatively use the characteristics to generate inclusion criteria for the different categories of subjects. This inclusion criteria may be included in the corresponding profiles.

In some implementations, the computer system 210 records characteristics for devices. The computer system 210 may use these characteristics to generate different profiles the represent different categories of devices.

The process 1700 includes using the generated records to create or update profiles for different categories of users (1706). The computer system 210 may use the generated records to determine categories of users and use the categories of users to generate profiles. For example, the computer system 210 may provide the generated records as input to one or more machine learning models. The one or more machine learning models may be configured to cluster the subjects into different groups using the information in the records. Specifically, the computer system 210 may user the records to cluster the subjects based on compliance rates, response likelihood, response times, etc.

As another example, the computer system 210 may use the generated records to update the profiles for different categories of users. In more detail, as shown in FIG. 15, the computer system 210 may identify a subset of records that correspond to a particular category of subjects and a profile. After identifying the subset of records, the computer system 210 may analyze the records to identify communication trends, patterns, and behaviors among the subjects in the particular category of subjects. For example, the computer system 210 may determine the results 1524 based on an analysis of the table 1522. The computer system 210 may proceed to add the identified communication trends, patterns, and behaviors to the profile 1530. Additionally or alternatively, the computer system 210 may convert the identified communication trends, patterns, and behaviors to impact scores that indicate the impact of particular communication attributes on subject outcomes (e.g., compliance, data quality, etc.) when compared to alternative communication attributes (e.g., impact of email communication channel over SMS text message).

As described above, each profile can include a set of inclusion criteria that defines the category of users corresponding to the profile. Each profile can store data that characterizes effects of message attributes on outcomes or responses for users in the category corresponding to the profile. The effects can include direct effects. For example, a profile may indicate that compliance in taking a test tends to improve 5% when the subjects in the corresponding category of subjects are sent a reminder at least one day before the test. However, the effects can also include indirect effects. For example, the profile may also indicate that by sending positive or encouraging messages to the subjects in the corresponding category of subjects, the compliance of the subjects is anticipated to improve by 7% and the data quality is expected to improve by 4%. That is, the computer system 210 can form the connections between particular monitoring program elements, including particular messages, types of messages, and/or message attributes, to particular subject outcomes (e.g., compliance, data quality, retention, etc.).

The process 1700 includes, for a group of users involved in a particular monitoring program, selecting a profile for each member of the group from among the profiles (1708). For example, with respect to FIG. 14, the computer system 210 may determine for each device in the monitoring group 1402 a corresponding profile of the profiles 804. In more detail, the computer system 210 may look up subject attributes corresponding to the devices in the monitoring group 1402, and compare the subject attributes to the inclusion criteria in the profiles 804 to determine the profiles that the corresponding subjects should be assigned to. Where a subject participating in the monitoring program has previously participated in one or more monitoring programs, the computer system 210 may reduce the processing burden by looking up the profile(s) that the corresponding subject was previously assigned to or otherwise associated with.

The group of users may be a cohort for a research study that corresponds to the monitoring program. The group of users may be selected by a researcher. Alternatively, using inclusion criteria and/or exclusion criteria for the research study, the computer system 210 may identify and enroll the group of users into the cohort. The research study may be a medical study to, for example, study the effects of a new pharmaceutical, to study the general health of persons in different population groups, to study sleep health, to study cardiovascular health, etc.

In some implementations, selecting a profile for each member of the group from among the profiles includes: identifying characteristics for each member of the group; determining that the characteristics satisfy a first set of inclusion criteria of the sets of inclusion criteria defining the categories that correspond to the profiles; and selecting the profile that corresponds to the first set of inclusion criteria. For example, the computer system 210 may extract inclusion criteria from various profiles, and proceed to compare attributes of participants to the inclusion criteria to determine which categories of subjects are present among a monitoring group.

The process 1700 includes customizing interactions of the server system with remote devices of users in the group based on the profiles (1710). For example, as described above with respect to FIG. 16, the communication translation module 1430 may customize event messages or other interactions for different categories of subjects based on information extracted from a corresponding profile. The communication translation module 1430 may first identify an event message that it is planning to distribute to the remote devices of the users in a particular group of a monitoring program. The communication translation module 1430 may then extract from the previously selected profiles, the impact data for different communication attributes. Using the impact data, the computer system 210 can determine (i) if a communication attribute of the event message should be modified for a particular category of subjects, and (ii) how to adjust the communication attribute if it should be modified. For example, the computer system 210 may adjust an event message such that each attribute of the message is the attribute that is anticipated to provide the highest subject compliance and/or the highest data quality. The communication translation module 1430 may do this by updating the communication attributes of an event message for the different categories of subjects present in an ongoing monitoring program.

As an example, the communication translation module 1430 may adjust the attributes of a particular message to change the time the message is sent, change the vocabulary used in the content of the message, change the sentence structure used in the content of the message (e.g., to adjust the formality and/or tone of the message), change a communication channel used to transmit the message (e.g., change from SMS message to voice call), change a response or requested data deadline, change a message frequency, etc.

The server system can customize the interactions using the profiles to select different message attributes to increase a likelihood of a target outcome of the monitoring program. For example, the communication translation module 1430 can for a group of participants enrolled in a monitoring program adjust the outgoing messages to change the communication channel from email to an in-app message displayed in a mobile application running on the remote devices. The communication translation module 1430 can do this to improve the likelihood of getting sufficient participant compliance to complete the monitoring program (e.g., a research study) and sufficient data quality to complete the monitoring program. As such, by adjusting the interactions, the computer system 210 can increase the likelihood of the monitoring program being successfully, and/or the likelihood of not needing to extend the monitoring program or repeating the monitoring program.

In some implementations, customizing the interactions with the remote devices to increase the likelihood of the target outcome comprises customizing interactions with remote devices to increase the likelihood of one or more of the following: retention of users involved in the monitoring program; compliance of users involved in the monitoring program; obtaining sufficient data quality corresponding to users involved in the monitoring program; or obtaining improved data quality corresponding to users involved in the monitoring program. For example, the computer system 210 may customize interactions to meet a threshold compliance rate required for a particular monitoring program or monitoring program session.

The interactions that the computer system 210 and/or the communication translation module 1430 can adjust may include server to client interactions. For example, the computer system can affect how the device interacts with users through adjusting how messages are depicted to the users. In more detail, the computer system 210 may provide instructions to display the message in an application running on a first subgroup of devices. However, for a second subgroup of devices, the computer system 210 may provide different instructions to display a clickable link the application running on a second subgroup of devices. When the second subgroup users click the link, they may be provided a video that communicate the message to those users.

The interactions that the computer system 210 and/or the communication translation module 1430 can adjust may include configuration settings for software installed on the remote devices. The configuration settings may include settings for a mobile application running on the remote devices for the monitoring program. As an example, adjusting the configuration settings may include the computer system 210 sending different instructions to different groups of devices that provides for different ways to display messages, different timing for responding to messages or providing data for messages, different timing for requesting information from the computer system 210, using different sensors to collect data, etc.

In some implementations, customizing interactions of the server system with remote devices of users in the group based on the profiles includes, for each category of users in the group, adjusting a communication to remove, add, or modify one or more message attributes using the stored data of the corresponding profile. For example, for a group of participants in a first category of subjects, the communication translation module 1430 may add a message attribute that provides a response or data deadline. The computer system 210 may make this adjustment based on a profile for the first category of subjects indicating that those subjects are more likely to respond if they are provided a clear deadline.

In some implementations, adjusting the communication to remove, add, or modify one or more message attributes includes adjusting the communication to modify one or more of the following: a time for the communication to take place; a channel of communication; content of a message to be sent in communication; a formality of communication; word choice of message to be sent in communication; or sentence structure of message to be sent in communication. For example, for a group of participants in a first category of subjects, the communication translation module 1430 may adjust the time that messages are sent to devices of the participants. The computer system 210 may make this adjustment based on a profile for the first category of subjects indicating that those subjects are anticipated to demonstrate increased compliance if the messages are received after 2:00 pm.

In some implementations, customizing interactions of the server system with remote devices of users in the group based on the profiles includes: generating updated configuration data for software installed on the remote devices of the users in the group; distributing the updated configuration data to a subset of the remote devices of the users in the group, where the subset of the remote devices corresponds to a particular profile of the profiles; and interacting with subset of the remote devices differently than other remote devices of the users in the group in accordance with the updated configuration data. For example, the computer system 210 may determine new configuration settings for a mobile application corresponding that users installed for a research study. The computer system 210 may determine that a group of participants in the study cohort belong to a first category of users, and extract information from a corresponding profile that indicates that those users tend to provide better data quality if the messages are provided through a video rather than a text-based message. Accordingly, the computer system 210 may update the configuration settings for this group of participants so that messages will be sent be presented by a video message rather than by text on the respective devices.

In some implementations, customizing interactions of the server system with remote devices of users in the group based on the profiles includes: selecting a first set of message attributes for users in the group that belong to a first category of the different categories of users; using the first set of message attributes to generate or modify a first message for the users in the group that belong to the first category; selecting a second set of message attributes for users in the group that belong to a second category of the different categories of users; and using the second set of message attributes to generate or modify a second message for the users in the group that belong to the second category. Here, at least one attribute in the first set of message attributes is not shared in the second set of message attributes, and at least one attribute in the second set of message attributes is not shared in the first set of message attributes. For example, the communication translation module 1430 may use a first profile to determine that a message to be sent at 12:00 pm should be adjusted for a first group of participants to change the sentence structure from formal to informal. Similarly, using a second profile, the communication translation module 1430 may adjust the same message for a second group of participants to change the time sent to 5:00 pm while keeping the formal sentence structure.

In some implementations, the process 1700 includes sending, over the communication network and in accordance with the first set of message attributes, the first message to a first group of remote devices, the first group of remote devices belonging to users in the group that belong to the first category of the different categories of users; and sending, over the communication network and in accordance with the second set of message attributes, the second message to a second group of remote devices, the second group of remote devices belonging to users in the group that belong to the second category of the different categories of users. The computer system 210 may send the two sets of messages in possibly different ways and/or may send the two sets of messages along with instructions for the recipient groups of devices to display the messages in different ways.

In some implementations, the process 1700 includes accessing an event schedule corresponding to the monitoring program; identifying a particular event from the event schedule based on at least one of a time, date, or completed performance of an action; and retrieving or generating a message that corresponds to the event. For example, the computer system 210 may use a schedule to detect a reminder event based on an upcoming deadline event, such as blood pressure test upload date. The computer system 210 may proceed to retrieve data associated with this event and use the data to generate a corresponding reminder message for the event. The communication translation module 1430 can adjust the message for the different categories of subjects present in the monitoring group to improve compliance, data quality, or the likelihood of program success. Customizing interactions of the server system with remote devices of users in the group based on the profiles can include, for each category of users in the group, customizing the message using the stored data of the corresponding profile. For example, the communication translation module 1430 may use information in a profile to adjust one or more communication attributes for the message, or to adjust configuration settings for software running on the remote devices to adjust the display of the message on those devices.

In some implementations, the process 1700 includes detecting an event corresponding to the monitoring program; and retrieving or generating a message that corresponds to the event. For example, the computer system 210 may detect a reminder event based on an upcoming deadline or a schedule including the reminder event. The computer system 210 may proceed to retrieve a default message corresponding to the reminder event that the communication translation module 1430 can customize for the different categories of subjects present among the monitoring group. Customizing interactions of the server system with remote devices of users in the group based on the profiles can include, for each category of users in the group, customizing the message using the stored data of the corresponding profile. For example, the communication translation module 1430 may use information in a profile to adjust one or more communication attributes for the message, or to adjust configuration settings for software running on the remote devices to adjust the display of the message on those devices.

In some implementations, the process 1700 includes receiving, from a remote computing device of a program manager of the monitoring program and over the communication network, a message corresponding to the monitoring program and designated for the users in the group. Here, customizing interactions of the server system with remote devices of users in the group based on the profiles can include, for each category of users in the group, customizing the message using the stored data of the corresponding profile. For example, the computer system 210 may receive a message from a researcher or admin that is to be sent out to all or a subset of users in a monitoring group. The communication translation module 1430 may customize the message or how the message is to be presented on the recipient devices in accordance with information extracted from one or more profiles.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method comprising:
   communicating, by a server system, with multiple remote devices that are each configured to perform monitoring according to at least one of a plurality of monitoring programs administered by the server system, wherein the communicating involves sending messages having different message attributes to remote devices over a communication network;
   generating, by the server system, records that specify outcomes or responses obtained after sending the messages, the records indicating or being associated with (i) message attributes of messages sent to the remote devices and (ii) user attributes, including values for one or more of age, race, ethnicity, or sex, of users of the remote devices that received the messages;
   determining, by the server system, different categories of users, wherein the categories are defined based at least in part on one or more types of user attributes including one or more of age, race, ethnicity, or sex, wherein each category has a corresponding set of inclusion criteria specifying one or more user attributes needed in order for a user to be included in the category;
   using, by the server system, the generated records to create or update category profiles for the different categories of users, the category profiles including a first category profile for a first category of users and a second category profile for a second category of users, wherein each category profile stores data that characterizes effects of different message attributes on outcomes or responses for users that satisfy the inclusion criteria for the category corresponding to the category profile, and wherein the data in each category profile is based on outcomes or responses indicated by the records for a set of multiple users determined to satisfy the inclusion criteria for the category corresponding to the category profile;
   selecting, by the server system, different category profiles for different participants in a particular monitoring program, wherein, for each of the participants, the category profile selected for the participant is one of the category profiles for which the participant satisfies the inclusion criteria for the category corresponding to the category profile; and
   customizing, by the server system, interactions of the server system with remote devices of the participants based on the category profiles selected for the respective participants, wherein the server system customizes the interactions using the selected category profiles to transmit messages that respectively have different message attributes to different remote devices of participants in the particular monitoring program, wherein customizing interactions of the server system with remote devices of the participants based on the category profiles comprises:
      selecting, for a first set of participants that have user attributes that satisfy the inclusion criteria for the first category of users, a first set of message attributes based on the first category profile for the first category, wherein the first set of message attributes specifies aspects of presentation or transmission of content, and the first set of attributes is selected based on values in the first category profile that indicate predicted impact of different message attributes on actions by individuals in the first category;
      using the first set of message attributes to generate or modify a first message for the first set of participants;
      selecting, for a second set of participants that have user attributes that satisfy the inclusion criteria for the second category of users, a second set of message attributes based on the second category profile for the second category, wherein the second set of message attributes specifies aspects of presentation or transmission of content, and the second set of attributes is selected based on values in the second category profile that indicate predicted impact of different message attributes on actions by individuals in the second category; and using the second set of message attributes to generate or modify a second message for the second set of participants, wherein at least one message attribute in the first set of message attributes is not included in the second set of message attributes, and at least one message attribute in the second set of message attributes is not included in the first set of message attributes.

2. The method of claim 1, wherein the user attributes that are indicated by or associated with the records and that are specified in the inclusion criteria specify one or more physiological characteristics or one or more behavioral characteristics.

3. The method of claim 1, wherein customizing interactions of the server system with the remote devices comprises customizing one or more communications presented to the participants so that the one or more communications have different message attributes for users participants in different categories, and wherein, for each of the participants, message attributes for a communication to the participant are selected based on the category profile selected for the participant.

4. The method of claim 3, wherein customizing the one or more communications comprises generating and sending the one or more communications with differences, depending on the category of user, among at least one of: a mode of transmission or presentation of the communication; a communication channel used to provide the communication; content of the communication; a tone of the communication; a sentence structure or language complexity of the communication; or a media type of the communication.

5. The method of claim 1, wherein customizing interactions of the server system with remote devices of the participants based on the category profiles comprises:

generating updated configuration data for software installed on the remote devices of the participants, wherein different sets of updated configuration data are generated for different categories of users, wherein the updated configuration data for each category of users is based on information, in the category profile corresponding to the category, that indicates effects of different communication or interaction attributes on compliance of users in performing one or more actions requested of participants in the monitoring program; and distributing the different sets of updated configuration data to remote devices of the participants, each of the different sets of updated configuration data being transmitted to a different set of remote devices corresponding to users in a category corresponding to the set of updated configuration data, wherein the different sets of updated configuration data cause different changes to the presentation of messages to users, including changes to visual properties of displayed messages or rules for timing of display of messages.

6. The method of claim 1, wherein customizing the interactions of the server system with the remote devices comprises customizing interactions with remote devices to involve content or characteristics determined, based on the category profiles selected for the respective participants, to increase a likelihood of one or more of the following:

retention of participants involved in the particular monitoring program;

compliance of participants involved in the particular monitoring program with requirements of the monitoring program; or collection of data having at least a predetermined level of data quality from participants involved in the particular monitoring program.

7. The method of claim 1, comprising:

accessing an event schedule corresponding to the particular monitoring program;

identifying a particular event from the event schedule based on at least one of a time, date, or completed performance of an action; and retrieving or generating a message that corresponds to the event, wherein customizing interactions of the server system with remote devices of the participants based on the category profiles comprises, for each category of users among the participants, customizing the message using the stored data of the corresponding category profile.

8. The method of claim 1, comprising:

detecting an event corresponding to the particular monitoring program; and retrieving or generating a message that corresponds to the event, wherein customizing interactions of the server system with remote devices of participants based on the category profiles comprises, for each category of users among the participants, customizing the message using the stored data of the corresponding category profile for the category.

9. The method of claim 1, comprising:

sending, over the communication network and in accordance with the first set of message attributes, the first message to remote devices that are each associated with one of the participants in the first set of participants that have user attributes that satisfy the inclusion criteria for the first category; and sending, over the communication network and in accordance with the second set of message attributes, the second message to remote devices that are each associated with one of the participants in the second set of participants that have user attributes that satisfy the inclusion criteria for the second category.

10. A system comprising:

a subject database storing data sets for each of multiple subjects, wherein the data set for a subject comprises results of monitoring performed for the subject using one or more remote devices;

a network interface to receive monitoring data from the remote devices of the subjects; and a server system comprising one or more computers, wherein the server system is configured to manage monitoring of the remote devices, the server system being configured to perform operations comprising:

communicating, by the server system, with multiple remote devices that are each configured to perform monitoring according to at least one of a plurality of monitoring programs administered by the server system, wherein the communicating involves sending messages having different message attributes to remote devices over a communication network;

generating, by the server system, records that specify outcomes or responses obtained after sending the messages, the records indicating or being associated with (i) message attributes of messages sent to the remote devices and (ii) user attributes, including values for one or more of age, race, ethnicity, or sex, of users of the remote devices that received the messages;

determining, by the server system, different categories of users, wherein the categories are defined based at least in part on one or more types of user attributes including one or more of age, race, ethnicity, or sex, wherein each category has a corresponding set of inclusion criteria specifying one or more user attributes needed in order for a user to be included in the category;

using, by the server system, the generated records to create or update category profiles for the different categories of users, the category profiles including a first category profile for a first category of users and a second category profile for a second category of users, wherein each category profile stores data that characterizes effects of different message attributes on outcomes or responses for users that satisfy the inclusion criteria for the category corresponding to the category profile, and wherein the data in each category profile is based on outcomes or responses indicated by the records for a set of multiple users determined to satisfy the inclusion criteria for the category corresponding to the category profile;

selecting, by the server system, different category profiles for different participants in a particular monitoring program, wherein, for each of the participants, the category profile selected for the participant is one of the category profiles for which the participant satisfies the inclusion criteria for the category corresponding to the category profile; and customizing, by the server system, interactions of the server system with remote devices of the participants based on the category profiles selected for the respective participant, wherein the server system customizes the interactions using the selected category profiles to transmit messages with different message attributes to different remote devices of participants in the particular monitoring program, wherein customizing interactions of the server system with remote devices of the participants based on the category profiles comprises:

selecting, for a first set of participants that have user attributes that satisfy the inclusion criteria for the first category of users, a first set of message attributes based on the first category profile for the first category, wherein the first set of message attributes specifies aspects of presentation or transmission of content, and the first set of attributes is selected based on values in the first category profile that indicate predicted impact of different message attributes on actions by individuals in the first category;

using the first set of message attributes to generate or modify a first message for the first set of participants;

selecting, for a second set of participants that have user attributes that satisfy the inclusion criteria for the second category of users, a second set of message attributes based on the second category profile for the second category, wherein the second set of message attributes specifies aspects of presentation or transmission of content, and the second set of attributes is selected based on values in the second category profile that indicate predicted impact of different message attributes on actions by individuals in the second category; and using the second set of message attributes to generate or modify a second message for the second set of participants, wherein at least one message attribute in the first set of message attributes is not included in the second set of message attributes, and at least one message attribute in the second set of message attributes is not included in the first set of message attributes.

11. The system of claim 10, wherein the inclusion criteria for one or more of the category profiles include, in addition to one or more criteria for age, race, ethnicity, or sex, one or more criteria for a physiological attribute or a behavioral attribute.

12. The system of claim 10, wherein customizing interactions of the server system with remote devices of the participants based on the category profiles comprises:

generating updated configuration data for software installed on the remote devices of the participants;

distributing the updated configuration data to a subset of the remote devices of the participants, where the subset of the remote devices is a subset associated with participants that satisfy the inclusion criteria for a particular profile of the category profiles; and interacting with the subset of the remote devices in accordance with the updated configuration data, in a manner that is different from interactions with other remote devices of the participants that do not satisfy the inclusion criteria for the particular profile.

13. One or more non-transitory computer-readable media storing instructions that are operable, when executed by one or more computers of a server system, cause the server system to perform operations comprising:

communicating, by the server system, with multiple remote devices that are each configured to perform monitoring according to at least one of a plurality of monitoring programs administered by the server system, wherein the communicating involves sending messages having different message attributes to remote devices over a communication network;

generating, by the server system, records that specify outcomes or responses obtained after sending the messages, the records indicating or being associated with (i) message attributes of messages sent to the remote devices and (ii) user attributes, including values for one or more of age, race, ethnicity, or sex, of users of the remote devices that received the messages;

determining, by the server system, different categories of users, wherein the categories are defined based at least in part on one or more types of user attributes including one or more of age, race, ethnicity, or sex, wherein each category has a corresponding set of inclusion criteria specifying one or more user attributes needed in order for a user to be included in the category;

using, by the server system, the generated records to create or update category profiles for the different categories of users, the category profiles including a first category profile for a first category of users and a second category profile for a second category of users, wherein each category profile stores data that characterizes effects of different message attributes on outcomes or responses for users that satisfy the inclusion criteria for the category corresponding to the category profile, and wherein the data in each category profile is based on outcomes or responses indicated by the records for a set of multiple users determined to satisfy the inclusion criteria for the category corresponding to the category profile;

selecting, by the server system, different category profiles for different participants in a particular monitoring program, wherein, for each of the participants, the category profile selected for the participant is one of the category profiles for which the participant satisfies the inclusion criteria for the category corresponding to the category profile; and customizing, by the server system, interactions of the server system with remote devices of the participants based on the category profiles selected for the respective participants, wherein the server system customizes the interactions using the selected category profiles to transmit messages that respectively have different message attributes to different remote devices of participants in the particular monitoring program, wherein customizing interactions of the server system with remote devices of the participants based on the category profiles comprises:

selecting, for a first set of participants that have user attributes that satisfy the inclusion criteria for the first category of users, a first set of message attributes based on the first category profile for the first category, wherein the first set of message attributes specifies aspects of presentation or transmission of content, and the first set of attributes is selected based on values in the first category profile that indicate predicted impact of different message attributes on actions by individuals in the first category;

using the first set of message attributes to generate or modify a first message for the first set of participants;

selecting, for a second set of participants that have user attributes that satisfy the inclusion criteria for the second category of users, a second set of message attributes based on the second category profile for the second category, wherein the second set of message attributes specifies aspects of presentation or transmission of content, and the second set of attributes is selected based on values in the second category profile that indicate predicted impact of different message attributes on actions by individuals in the second category; and using the second set of message attributes to generate or modify a second message for the second set of participants, wherein at least one message attribute in the first set of message attributes is not included in the second set of message attributes, and at least one message attribute in the second set of message attributes is not included in the first set of message attributes.

14. The method of claim 1, wherein the particular monitoring program is a health research study;

wherein the participants are participants in a cohort for the health research study; and wherein customizing the interactions of the server system with remote devices comprises sending messages that are customized for the respective participants based on the respective category profiles selected for the participants.

15. The method of claim 1, wherein the particular monitoring program is a health research study;

wherein the participants are participants in a cohort for the health research study; and wherein customizing the interactions of the server system with remote devices of the participants comprises communicating with different participants in the cohort using different message attributes to increase a likelihood of at least one of (i) compliance with one or more requirements of the health research study by the participants or (ii) retention of the participants in the health research study, wherein, for each of the participants, the message attributes used for messages to the participant are determined based on the data in the category profile selected for the participant that characterizes effects of message attributes on outcomes or responses.

16. The method of claim 1, wherein customizing the interactions of the server system with remote devices of the participants comprises using the data in the category profiles that characterizes effects of different message attributes on outcomes or responses to increase a likelihood of a target outcome of the monitoring program.

17. The method of claim 1, wherein customizing, by the server system, interactions of the server system with remote devices includes selectively changing a configuration of the remote devices based on the respective category profiles of the users of the remote devices, wherein the selective change in configuration of the remote devices alters collection of sensor data by at least some of the remote devices.

18. The method of claim 1, wherein, in each of the category profiles, the data that characterizes effects of different message attributes on outcomes or responses comprises scores indicating relative likelihoods of a particular outcome being achieved by a user in the category corresponding to the category profile following a communication having the message attribute provided to the user in the category corresponding to the category profile.

19. The method of claim 1, wherein, in each of the category profiles, the data that characterizes effects of different message attributes on outcomes or responses comprises, for each message attribute of multiple different message attributes, a score based on a rate at which a particular outcome has been achieved by users in the category corresponding to the category profile following communications presented using the message attribute.

20. The method of claim 1, wherein, to provide (i) at least one message attribute in the first set of message attributes that is not included in the second set of message attributes and (ii) at least one message attribute in the second set of message attributes that is not included in the first set of message attributes, the first set of message attributes and the second set of message attributes specify different modes of transmission or presentation of messages, different communication channels used to provide messages, different content of messages, or different sentence structure or language complexity for messages.

21. The method of claim 1, identifying, by the server system, first message text of a message to provide to participants in the particular monitoring program; and based on the first message text, generating, by the server system, message text for each of the selected category profiles, wherein different message text is generated for each of at least some of the selected category profiles by altering, for one or more of the selected category profiles, the first message text based on the effects of different message attributes indicated by the category profile;

wherein customizing, by the server system, interactions of the server system with remote devices of the participants based on the category profiles selected for the respective participants, including providing messages to the remote devices so that each remote device receives the message text that was generated for the category profile selected for the participant associated with the remote device.

22. A method comprising:

communicating, by a server system, with multiple remote devices that are each configured to perform monitoring according to at least one of a plurality of monitoring programs administered by the server system, wherein the communicating involves sending messages with different message attributes to remote devices over a communication network;

generating, by the server system, records that specify outcomes or responses obtained after sending the messages, the records indicating (i) message attributes of messages sent to the remote devices and (ii) user attributes, including one or more of age, race, ethnicity, or sex, of users of the remote devices that received the messages;

determining, by the server system, different categories of users, wherein the categories are defined based at least in part on one or more user attributes including one or more of age, race, ethnicity, or sex, wherein each category has a corresponding set of inclusion criteria specifying the one or more user attributes needed in order for a user to be included in the category;

using, by the server system, the generated records to create or update category profiles for the different categories of users, wherein each category profile stores data that characterizes effects of different message attributes on outcomes or responses for users that satisfy the inclusion criteria for the category corresponding to the category profile, and wherein the data in each category profile is based on outcomes or responses indicated by the records for a set of multiple users determined to satisfy the inclusion criteria for the category corresponding to the category profile;

selecting, by the server system, different category profiles for different participants in a particular monitoring program, wherein, for each of the participants, the selected category profile is one of the category profiles for which the participant satisfies the inclusion criteria for the category corresponding to the category profile; and customizing, by the server system, interactions of the server system with remote devices of the participants based on the category profiles selected for the respective participants, wherein the server system customizes the interactions using the selected category profiles to transmit messages with different message attributes to different remote devices of participants in the particular monitoring program, wherein customizing, by the server system, interactions of the server system with remote devices includes selectively changing a configuration of the remote devices based on the respective category profiles of the users of the remote devices, wherein the selective change in configuration of the remote devices alters collection of sensor data by at least some of the remote devices.

* * * * *